(12) United States Patent
Gong et al.

(10) Patent No.: US 11,046,769 B2
(45) Date of Patent: Jun. 29, 2021

(54) MULTISPECIFIC BINDING CONSTRUCTS AGAINST CHECKPOINT MOLECULES AND USES THEREOF

(71) Applicant: Compass Therapeutics LLC, Brighton, MA (US)

(72) Inventors: Bing Gong, Brighton, MA (US); Rachel Rennard, Stoneham, MA (US); Amanda Frank Oliphant, Boston, MA (US); Cheuk Lun Leung, Quincy, MA (US); Benjamin Jacob Wolf, Seattle, WA (US); Ugur Eskiocak, Somerville, MA (US); Pearl Bakhru, Ashland, MA (US); Diana I. Albu, Windham, NH (US)

(73) Assignee: COMPASS THERAPEUTICS LLC, Brighton, MA (US)

( * ) Notice: Subject to any disclaimer, the term of this patent is extended or adjusted under 35 U.S.C. 154(b) by 0 days.

(21) Appl. No.: 16/682,756

(22) Filed: Nov. 13, 2019

(65) Prior Publication Data

US 2020/0181266 A1 Jun. 11, 2020

Related U.S. Application Data

(60) Provisional application No. 62/760,801, filed on Nov. 13, 2018, provisional application No. 62/855,580, filed on May 31, 2019, provisional application No. 62/898,991, filed on Sep. 11, 2019, provisional application No. 62/931,478, filed on Nov. 6, 2019.

(51) Int. Cl.
   C07K 16/28 (2006.01)
   A61P 35/00 (2006.01)
   A61K 39/00 (2006.01)

(52) U.S. Cl.
   CPC .......... *C07K 16/2818* (2013.01); *A61P 35/00* (2018.01); *C07K 16/2827* (2013.01); *A61K 2039/505* (2013.01); *C07K 2317/31* (2013.01); *C07K 2317/33* (2013.01); *C07K 2317/35* (2013.01); *C07K 2317/565* (2013.01); *C07K 2317/92* (2013.01)

(58) Field of Classification Search
   None
   See application file for complete search history.

(56) References Cited

U.S. PATENT DOCUMENTS

| | | |
|---|---|---|
| 3,710,795 A | 1/1973 | Higuchi |
| 3,773,919 A | 11/1973 | Boswell |
| 4,433,059 A | 2/1984 | Chang |
| 4,444,878 A | 4/1984 | Paulus |
| 4,496,654 A | 1/1985 | Katz |
| 4,863,457 A | 9/1989 | Lee |
| 5,026,773 A | 6/1991 | Steel |
| 5,071,909 A | 12/1991 | Pappin |
| 5,122,458 A | 6/1992 | Post |
| 5,168,062 A | 12/1992 | Stinski |
| 5,273,743 A | 12/1993 | Ahlem |
| 5,342,585 A | 8/1994 | Lebl |
| 5,501,856 A | 3/1996 | Ohtori |
| 5,534,254 A | 7/1996 | Huston |
| 5,582,996 A | 12/1996 | Curtis |
| 5,591,828 A | 1/1997 | Bosslet |
| 5,635,602 A | 6/1997 | Cantor |
| 5,637,481 A | 6/1997 | Ledbetter |
| 5,759,808 A | 6/1998 | Casterman |
| 5,837,242 A | 11/1998 | Holliger |
| 5,837,821 A | 11/1998 | Wu |
| 5,844,094 A | 12/1998 | Hudson |
| 5,864,019 A | 1/1999 | King |
| 5,869,620 A | 2/1999 | Whitlow |
| 5,885,793 A | 3/1999 | Griffiths |
| 5,932,448 A | 8/1999 | Tso |
| 5,959,083 A | 9/1999 | Bosslet |
| 5,989,830 A | 11/1999 | Davis |
| 6,001,329 A | 12/1999 | Buchsbaum |
| 6,005,079 A | 12/1999 | Casterman |
| 6,172,197 B1 | 1/2001 | McCafferty |
| 6,180,370 B1 | 1/2001 | Queen |
| 6,239,259 B1 | 5/2001 | Davis |
| 6,248,516 B1 | 6/2001 | Winter |
| 6,291,158 B1 | 9/2001 | Winter |

(Continued)

FOREIGN PATENT DOCUMENTS

| | | |
|---|---|---|
| EP | 0036676 | 7/1984 |
| EP | 0088046 | 12/1987 |

(Continued)

OTHER PUBLICATIONS

Mariuzza, R.A. etal. 'The Structural Basis of Antigen-Antibody Recognitionl Annu. Rev. Biophys. Biphys. Chem. 16:139-159, 1987.*

Maccallum et al. "Antibody-antigen interactions: contact analysis and binding site topography", Journal of Molecular Biology, 1996. vol. 262, pp. 732-745.*

De Pascalis et al. "Grafting of abbreviated complementarity determining regions containing specificity determining residues essential for ligand contact to engineer a less immunogenic humanzied monoclonal antibody", Journal of Immunology, 2002. vol. 169, pp. 3076-3084.*

Goel et al. 'Plasticity within the Antigen-Combining Site May Manifest as Molecular Mimicry in the Humoral Immune Response.1 J. Immunol. 173(12)7358-7367, 2004.*

(Continued)

*Primary Examiner* — Nora M Rooney
(74) *Attorney, Agent, or Firm* — DT Ward, PC; Donna T. Ward; Samuel A. McMahon

(57) ABSTRACT

The present disclosure relates to compositions and methods for inhibiting tumor evasion by reducing immune checkpoint suppression. In some embodiments, provided herein are compositions that block the interaction between PD-1 and its ligand (e.g., PD-1 and/or PD-L2) while promoting the interaction of the cells on which PD-1 and its ligand are expressed. Also provided are methods of using such compositions.

22 Claims, 34 Drawing Sheets
(34 of 34 Drawing Sheet(s) Filed in Color)
Specification includes a Sequence Listing.

(56) References Cited

U.S. PATENT DOCUMENTS

| | | |
|---|---|---|
| 6,291,159 B1 | 9/2001 | Winter |
| 6,294,353 B1 | 9/2001 | Pack |
| 6,300,064 B1 | 10/2001 | Knappik |
| 6,319,690 B1 | 11/2001 | Little |
| 6,333,396 B1 | 12/2001 | Filpula |
| 6,476,198 B1 | 11/2002 | Kang |
| 6,482,591 B2 | 11/2002 | Lockhart |
| 6,511,663 B1 | 1/2003 | King |
| 6,548,640 B1 | 4/2003 | Winter |
| 6,670,453 B2 | 12/2003 | Frenken |
| 6,743,896 B2 | 6/2004 | Filpula |
| 6,809,185 B1 | 10/2004 | Schoonjans |
| 6,833,441 B2 | 12/2004 | Wang |
| 6,933,368 B2 | 8/2005 | Co |
| 6,946,292 B2 | 9/2005 | Kanda |
| 6,995,259 B1 | 2/2006 | Vargeese |
| 7,129,330 B1 | 10/2006 | Little |
| 7,183,076 B2 | 2/2007 | Arathoon |
| 7,214,775 B2 | 5/2007 | Hanai |
| 7,425,446 B2 | 9/2008 | Kanda |
| 7,521,056 B2 | 4/2009 | Chang |
| 7,527,787 B2 | 5/2009 | Chang |
| 7,534,866 B2 | 5/2009 | Chang |
| 7,566,771 B1 | 7/2009 | Adair |
| 7,635,757 B2 | 12/2009 | Freeman |
| 7,708,992 B2 | 5/2010 | Hanai |
| 7,737,325 B2 | 6/2010 | Kanda |
| 7,790,655 B2 | 9/2010 | Gao |
| 7,943,743 B2 | 5/2011 | Korman |
| 7,947,495 B2 | 5/2011 | Dubridge |
| 7,972,993 B2 | 7/2011 | Slootstra |
| 8,258,082 B2 | 9/2012 | Ladner |
| 8,288,322 B2 | 10/2012 | Ladner |
| 8,551,920 B2 | 10/2013 | Hoet |
| 8,552,154 B2 * | 10/2013 | Freeman ............... A61P 1/16 530/387.1 |
| 8,679,490 B2 | 3/2014 | Dennis |
| 8,697,359 B1 | 4/2014 | Zhang |
| 8,735,331 B2 | 5/2014 | Villa |
| 8,877,688 B2 | 11/2014 | Vasquez |
| 8,981,063 B2 | 3/2015 | Chen |
| 9,073,994 B2 | 7/2015 | Honjo |
| 9,181,327 B2 | 11/2015 | Dimitrov |
| 9,300,829 B2 | 3/2016 | Sohara |
| 9,354,228 B2 | 5/2016 | Vasquez |
| 9,388,510 B2 | 7/2016 | Ladner |
| 9,845,356 B2 | 12/2017 | Freeman |
| 9,861,621 B2 | 1/2018 | Saha |
| 2002/0004587 A1 | 1/2002 | Miller |
| 2002/0076406 A1 | 6/2002 | Leung |
| 2002/0103345 A1 | 8/2002 | Zhu |
| 2003/0207346 A1 | 11/2003 | Arathoon |
| 2003/0211078 A1 | 11/2003 | Heavner |
| 2003/0232410 A1 | 12/2003 | Liljedahl |
| 2004/0219643 A1 | 11/2004 | Winter |
| 2004/0220388 A1 | 11/2004 | Mertens |
| 2004/0242847 A1 | 12/2004 | Fukushima |
| 2005/0003403 A1 | 1/2005 | Rossi |
| 2005/0004352 A1 | 1/2005 | Kontermann |
| 2005/0026157 A1 | 2/2005 | Baltimore |
| 2005/0064474 A1 | 3/2005 | Urnov |
| 2005/0069552 A1 | 3/2005 | Bleck |
| 2005/0079170 A1 | 4/2005 | Le Gall |
| 2005/0100543 A1 | 5/2005 | Hansen |
| 2005/0136049 A1 | 6/2005 | Ledbetter |
| 2005/0136051 A1 | 6/2005 | Scallon |
| 2005/0163782 A1 | 7/2005 | Glaser |
| 2005/0208489 A1 | 9/2005 | Carroll |
| 2005/0266425 A1 | 12/2005 | Zauderer |
| 2006/0040354 A1 | 2/2006 | O'Keefe |
| 2006/0083747 A1 | 4/2006 | Winter |
| 2006/0120960 A1 | 6/2006 | Deyev |
| 2006/0188987 A1 | 8/2006 | Guschin |
| 2006/0204493 A1 | 9/2006 | Huang |
| 2006/0263367 A1 | 11/2006 | Fey |
| 2007/0004909 A1 | 1/2007 | Johnson |
| 2007/0087381 A1 | 4/2007 | Kojima |
| 2007/0128150 A1 | 6/2007 | Norman |
| 2007/0141049 A1 | 6/2007 | Bredehorst |
| 2007/0154901 A1 | 7/2007 | Thogersen |
| 2007/0274985 A1 | 11/2007 | Dubel |
| 2008/0050370 A1 | 2/2008 | Glaser |
| 2008/0069820 A1 | 3/2008 | Fuh |
| 2008/0152645 A1 | 6/2008 | Pardridge |
| 2008/0171855 A1 | 7/2008 | Rossi |
| 2008/0241223 A1 | 10/2008 | Nivaggioli |
| 2008/0241884 A1 | 10/2008 | Shitara |
| 2008/0254512 A1 | 10/2008 | Capon |
| 2008/0260738 A1 | 10/2008 | Moore |
| 2009/0130106 A1 | 5/2009 | Christopherson |
| 2009/0148905 A1 | 6/2009 | Ashman |
| 2009/0155275 A1 | 6/2009 | Wu |
| 2009/0162359 A1 | 6/2009 | Klein |
| 2009/0162360 A1 | 6/2009 | Klein |
| 2009/0175851 A1 | 7/2009 | Klein |
| 2009/0175867 A1 | 7/2009 | Thompson |
| 2009/0232811 A1 | 9/2009 | Klein |
| 2009/0234105 A1 | 9/2009 | Gervay-Hague |
| 2009/0263392 A1 | 10/2009 | Igawa |
| 2009/0274649 A1 | 11/2009 | Qu |
| 2012/0165201 A1 | 6/2012 | Short |
| 2014/0017836 A1 | 1/2014 | Wei |
| 2016/0304607 A1 | 10/2016 | Sadineni |
| 2017/0174773 A1 | 6/2017 | Davis |
| 2017/0247467 A1 | 8/2017 | Amann |
| 2018/0251548 A1 | 9/2018 | Sabzevari |
| 2018/0318417 A1 | 11/2018 | Schuetz |
| 2019/0031785 A1 | 1/2019 | Schuetz |

FOREIGN PATENT DOCUMENTS

| | | |
|---|---|---|
| EP | 0143949 | 10/1988 |
| EP | 0346087 | 12/1989 |
| EP | 0430539 | 6/1991 |
| EP | 488401 | 6/1992 |
| EP | 2330120 | 6/2011 |
| EP | 2522727 | 11/2012 |
| EP | 2742953 | 6/2014 |
| WO | 1984003564 | 9/1984 |
| WO | 1990002809 | 3/1990 |
| WO | 1991010737 | 7/1991 |
| WO | 1992001047 | 1/1992 |
| WO | 1992018619 | 10/1992 |
| WO | 1993009872 | 5/1993 |
| WO | 1993011162 | 6/1993 |
| WO | 1993011236 | 6/1993 |
| WO | 1993023537 | 11/1993 |
| WO | 1994001875 | 1/1994 |
| WO | 1994004678 | 3/1994 |
| WO | 1994009131 | 4/1994 |
| WO | 1994012625 | 6/1994 |
| WO | 1994025591 | 11/1994 |
| WO | 1995009917 | 4/1995 |
| WO | 1995015982 | 6/1995 |
| WO | 1995020401 | 8/1995 |
| WO | 1996027011 | 9/1996 |
| WO | 1996037621 | 11/1996 |
| WO | 1999064460 | 12/1999 |
| WO | 2000001739 | 10/2000 |
| WO | 2002083872 | 4/2002 |
| WO | 2002072635 | 9/2002 |
| WO | 2003104415 | 12/2003 |
| WO | 2004081051 | 9/2004 |
| WO | 2005073384 | 8/2005 |
| WO | 2005118629 | 12/2005 |
| WO | 2006012414 | 2/2006 |
| WO | 2006020258 | 2/2006 |
| WO | 2006106905 | 10/2006 |
| WO | 2007014275 | 2/2007 |
| WO | 2007024715 | 3/2007 |
| WO | 2007044887 | 4/2007 |
| WO | 2007095338 | 8/2007 |
| WO | 2007110205 | 10/2007 |
| WO | 2007137760 | 12/2007 |

(56) References Cited

FOREIGN PATENT DOCUMENTS

| WO | 2008024188 | 2/2008 |
|---|---|---|
| WO | 2008119353 | 10/2008 |
| WO | 2009021754 | 2/2009 |
| WO | 2009036379 | 3/2009 |
| WO | 2009068630 | 6/2009 |
| WO | 2009089004 | 7/2009 |
| WO | 2009103493 | 8/2009 |
| WO | 2010105256 | 9/2010 |
| WO | 2010129304 | 11/2010 |
| WO | 2011034605 | 3/2011 |
| WO | 2011131746 | 10/2011 |
| WO | 2012009568 | 1/2012 |
| WO | 2013060867 | 5/2013 |
| WO | 2014134165 | 9/2014 |
| WO | 2015009856 | 1/2015 |
| WO | 2015103072 | 7/2015 |
| WO | 2015103602 | 7/2015 |
| WO | 2015104406 | 7/2015 |
| WO | 2015119923 | 8/2015 |
| WO | 2015181342 | 12/2015 |
| WO | 2016022630 | 2/2016 |
| WO | 2016023875 | 2/2016 |
| WO | 2016029073 | 2/2016 |
| WO | 2016030455 | 3/2016 |
| WO | 2017174329 | 10/2017 |
| WO | 2020006605 | 1/2020 |

OTHER PUBLICATIONS

Kahn et al. 'Adjustable Locks and Flexible Keys: Plasticity of Epitope-Paratope Interactions in Germline Antibodies.' J. Immunol. 192:5398-5405, 2014.*

Poosarla et al. 'Computational De Novo Design of Antibodies Binding to a Peptide With High Affinity.' Biotech. Bioeng. 114(6): 1331-1342, 2017.*

Thommen, D. S. et al. "Progression of Lung Cancer Is Associated with Increased Dysfunction of T Cells Defined by Coexpression of Multiple Inhibitory Receptors" Cancer Immunology Research; 3(12) Dec. 2015.

Ngiow, S. F. et al. "A Threshold Level of Intratumor CD8þ T-cell PD1 Expression Dictates Therapeutic Response to Anti-PD1" Cancer Research; 75(18) Sep. 15, 2015.

Cong et al., Multiplex Genome Engineering Using CRISPR/Cas Systems, Science 339(6121):819-823, 2013.

Conti et al., Differential distribution of ryanodine receptor type 3 (RyR3) gene product in mammalian skeletal muscles. Biochem J. 316(1):19-23, 1996.

Cornelis., Expressing genes in different *Escherichia coli* compartments. Current Opinion in Biotechnology. Oct. 1, 2000;11(5):450-454.

Creighton, T. (1993). Proteins: Structures and Molecular Properties (2nd ed.). New York, NY: W. H. Freeman and Company.

Cromie et al., Nanobodies and their Use in GPCR Drug Discovery, Cum Top. Med. Chem. 15:2543-2557,2016.

Davis et al., SEEDbodies: fusion proteins based on strand-exchange engineered domain (Seed) CH3 heterodimers in an Fc analogue platform for asymmetric binders or immunofusions and bispecific antibodies. Protein Engineering, Design & Selection. Apr. 1, 2010;23(4):195-202.

De Genst et al., Antibody repertoire development in camelids, Dev. Comp. Immunol. 30: 187-198, 2006.

De Meyer et al., Nanobody-based products as research and diagnostic tools, Trends Biotechnol. 32:263-270, 2014.

Deans et al., Expression of an immunoglobulin heavy chain gene transfected into lymphocytes. Proceedings of the National Academy of Sciences. Mar. 1, 1984;81(5):1292-1296.

Di Niro et al., Characterizing monoclonal antibody epitopes by filtered gene fragment phage display. The Biochemical Journal. Jun. 7, 2005;388(Pt 3):889-894.

DiGiammarino et al., Design and generation of DVD-Ig™ molecules for dual-specific targeting, Methods Mal. Biol. 899:145-156, 2012.

Doering et al., Biosynthesis of glycosyl phosphatidylinositol membrane anchors, J. Biol. Chem. 265(2):611-614, 1990.

Dong et al., B7-H1 pathway and its role in the evasion of tumor immunity. Journal of Molecular Medicine. May 1, 2003;81(5):281-287.

Dooley et al., Antibody repertoire development in cartilaginous fish, Dev. Comp. Immunol. 30:43-56,2006.

Dumoulin et al., A camelid antibody fragment inhibits the formation of amyloid fibrils by human lysozyme, Nature 424 (6950):783-788, 2003.

Duraiswamy et al., Therapeutic PD-1 Pathway Blockade Augments with Other Modalities of Immunotherapy T-Cell Function to Prevent Immune Decline in Ovarian Cancer Cancer Res; 73(23) Dec. 1, 2013: 6900-6912.

Eisenhaber et al., Automated annotation of GPI anchor sites: case study C. elegans, Trends Biochem. Sci. 25(7)340-341, 2000.

Eisenhaber et al., Post-translational GPI lipid anchor modification of proteins in kingdoms of life: analysis of protein sequence data from complete genomes, Protein Engineering 14( 1): 17-25, 2001.

Eisenhaber et al., Prediction of lipid posttranslational modifications and localization signals from protein sequences: big-Pi, NMT and PTSI, Nucleic Acids Res. 31(13):3631-3634, 2003.

Eisenhaber et al., Prediction of potential GPI-modification sites in proprotein sequences, J. Mol. Biol. 292(3):741-758, 1999.

Eisenhaber et al., Sequence properties of GPI-anchored proteins near the omega-site: constraints for the polypeptide binding site of the putative transamidase, Protein Engineering 11(12):1155-1161, 1998.

Engberg et al., Phage-display libraries of murine and human antibody Fab fragments. Antibody Engineering Protocols. 1995;(pp. 355-376). Humana Press.

Eshhar et al., Specific activation and targeting of cytotoxic lymphocytes through chimeric single chains consisting of antibody-binding domains and the gamma or zeta subunits of the immunoglobulin and T-cell receptors, Proc. Natl. Acad. Sci. U.S.A. 90(2):720-724, Jan. 1993.

Etz et al., Bacterial phage receptors, versatile tools for display of polypeptides on the cell surface. Journal of Bacteriology. Dec. 1, 2001;183(246924-6935.

Fatima et al., Development of VHH antibodies against dengue vims type 2 NSI and comparison with monoclonal antibodies for use in immunological diagnosis, PLOS ONE 9(4):e95263, 2014.

Firth et al., Stimulation of stop codon readthrough: frequent presence of an extended 3' RNA structural element, Nucleic Acids Res. 39(15):6679-6691, 2011.

Forbes et al., The Catalogue of Somatic Mutations in Cancer (COSMIC), Curr. Protoc. Hum. Genet. 2008.

Freeman et al., Engagement of the PD-1 immunoinhibitory receptor by a novel B7 family member leads to negative regulation of lymphocyte activation. The Journal of Experimental Medicine. Oct. 2, 2000;192(7):1027-1034.

Freeman G., Structures of PD-1 with its ligands: Sideways and dancing cheek to cheek. Proceedings of the National Academy of Sciences. Jul. 29, 2008;105(30):10275-10276.

Fulton et al., Advanced multiplexed analysis with the FlowMetrixTM system. Clin. Chem. 43(9):1749-1756, 1997.

Garber, Bispecific antibodies rise again, Nature Rev. Druz Discov. 13:799-801, 2014.

Gautheret and Lambert, Direct RNA motif definition and identification from multiple sequence alignments using secondary structure profiles, J. Mol. Biol. 313(5):1003-1011, 2001.

George et al., An analysis of protein domain linkers: their classification and role in protein folding, Protein Eng Des. Sel. 15(11):871-879, 2002.

Ghiotto et al., PD-L1 and PD-L2 differ in their molecular mechanisms of interaction with PD-1. International Immunology. Aug. 1, 2010;22(8):651-660.

Grabherr et al., The baculovirus expression system as a tool for generating diversity by viral surface display. Combinatorial Chemistry & High Throughput Screening. Apr. 1, 2001;4(2):185-192.

(56) References Cited

OTHER PUBLICATIONS

Gronwald et al., Cloning and expression of a cDNA coding for the human platelet-derived growth factor receptor: evidence for more than one receptor class, Proc. Natl. Acad. Sci. U.S.A. 85(10):3435-3439, 1988.
Gruber et al., Efficient tumor cell lysis mediated by a bispecific single chain antibody expressed in Escherichia coli, J. Immunol. 152(11):5368-5374, 1994.
Gunasekaran et al., Enhancing antibody Fc heterodimer formation through electrostatic steering effects: applications to bispecffic molecules and monovalent IgG. Journal of Biological Chemistry. Jun. 18, 2010;285(25):19637-19646.
Hanes et al., Picomolar affinity antibodies from a fully synthetic naive library selected and evolved by ribosome display. Nature Biotechnology. Dec. 2000;18(12):1287-1292.
Harlow, E., & Lane, D. (1988). Antibodies: A laboratory manual. Cold Spring Harbor, NY, NY: Cold Spring Harbor Laboratory.
Harmer & Samuel, The FITC-anti-FITC System Is a Sensitive Alternative to Biotin-Streptavidin in ELISA. J. lmmunol. Methods 122(1):115-121, 1989.
Hasler et al., VNAR single-domain antibodies specific for BAFF inhibit B cell development by molecular mimicry, Mol. Immunol. 75:28-37, 2016.
Haynie, Physics of polypeptide multilayer films. J. Biomed. Mater. Res. B Appl. Biomater. 78(2):243-252, 2006.
Hedhammar et al., Chromatographic methods for protein purification. Stockholm: Royal Institute of Technology, 2006.
Hellen et al., Internal ribosome entry sites in eukaryotic mRNA molecules, Genes Dev. 15(13):1593-612, 2001.
Hey et al., Artificial, non-antibody binding proteins for pharmaceutical and industrial applications, TRENDS Biotechnol. 23(10):514-522, 2005.
Hilpert et al., Cellulose-bound peptide arrays: preparation and applications. Biotechnol. Genet. Engin. Rev. 24:31-106, 2007.
Hollinger et al., 'Diabodies': small bivalent and bispecific antibody fragments, Proc. Natl. Acad. Sci. U.S.A. 90:6444-6448, 1993.
Holt et al., Domain antibodies: proteins for therapy, Trends Biotechnol. 21(11):484-490, 2003.
Hoogenboom., Designing and optimizing library selection strategies for generating high-affinity antibodies. Trends in Biotechnology. Feb. 1, 1997;15(2):62-70.
Semmler et al., De novo sequencing of peptides on single resin beads by MALDI-FTICR tandem mass spectrometry. J. Am. Soc. Mass Spec. 21(2):215-219, 2010.
Shindo, Y. et al., Combination Immunotherapy with 4-1 BB Activation and PD-1 Blockade Enhances Antitumor Efficacy in a Mouse Model of Subcutaneous Tumor Anticancer Research 35: 129-136 (2015).
Shiraishi et al., Short-step chemical synthesis of DNA by use of MMTrS group for protection of 5'—hydroxyl group. Nucleic Acids Symposium Series. Nov. 1, 2007;51(1):129-130.
Sidman et al., Controlled release of macromolecules and pharmaceuticals from synthetic polypeptides based on glutamic acid. Biopolymers: Original Research on Biomolecules. Jan. 1983;22(1):547-556.
Sivakamasundari et al., Expression and Cellular Localization of the Protein Encoded by the IC7 Gene: A Recently Described Component of the MHC, Immunogenetics, vol. 51, Nos. 8-9, Jul. 2000, pp. 723-732.
Smith & Waterman., Comparison of biosequences. Advances in Applied Mathematics. Dec. 1981;2(4):482-489.
Smith and Berg, Homologous recombination between defective neo genes in mouse 3T6 cells, Cold Spring Harbor Symp. Quant. Biol. 49:171-181, 1984.
Southern and Berg, Transformation of mammalian cells to antibiotic resistance with a bacterial gene under control of the SV40 early region promoter, J Mol. Appl. Genet. 1(4):327-341, 1982.
Spiess et al., Alternative molecular formats and therapeutic applications for bispecific antibodies, Mol. Jmmunol. 67:95-106, 2015.

Spiess et al., Sequence of Human Asialoglycoprotein Receptor cDNA, J Biol. Chem. 260( 4): 1979-1982, 1985.
Stephen et al., "SATB1 Expression Governs Epigenetic Repression of PD-1 in Tumor-Reactive T Cells," Immunity. 46:51-64, 2017.
Stijlemans et al., Efficient targeting of conserved cryptic epitopes of infectious agents by single domain antibodies. African trypanosomes as paradigm, J Biol. Chem. 279(2):1256-1261, 2004.
Stocks Intrabodies: production and promise, Drug Discov. Today 9(22):960-966, 2004.
Stoddard, Homing endonuclease structure and function, Q Rev. Biophys. 38(1):49-95, 2005.
Suresh et al., Bispecific monoclonal antibodies from hybrid hybridomas, Methods Enzymol. 121:210-228, 1986.
Sutandy et al. Overview of Protein Microarrays. Curr.Protoc. Protein Sci. 27(1):27.1.1-27.1.16, 2013.
Szymanski et al., Development and validation of a robust and versatile one-plasmid regulated gene expression system, Mol. Therapy 15(7):1340-1347, 2007.
Takemura et al., Construction of a diabody (small recombinant bispecific antibody) using a refolding system, Protein Enz. 13(8):583-588, 2000.
Tashiro et al., Signal sequence trap: a cloning strategy for secreted proteins and type I membrane proteins, Science 261(5121):600-603, 1993.
Thein et al., The polyadenylation site mutation in the alpha-globin gene cluster, Blood 71(2):313-319, 1988.
Tjio et al., Genetics of somatic mammalian cells. II. Chromosomal constitution of cells in tissue culture, J Exp. Med. 108:259-271, 1958.
Todorovska et al., Design and application of diabodies, triabodies and tetrabodies for cancer targeting, J Immunol. Methods 248(1-2):47-66, 2001.
Tutt et al., Trispecific F (ab') 3 derivatives that use cooperative signaling via the TCR/CD3 complex and CD2 to activate and redirect resting cytotoxic T cells. The Journal of Immunology. Jul. 1, 1991;147(1):60-9.
Urnov et al., Genome editing with engineered zinc finger nucleases, Nature Reviews Genetics 11(9):636-656, 2010.
Vagner et al., Rigid linkers for bioactive peptides, Bioconjug. Chem. 17(6): 1545-1550, 2006.
Van Audenhove et al., Nanobodies as Versatile Tools to Understand, Diagnose, Visualize and Treat Cancer, EBioMedicine 8:40-48, 2016.
Van Bockstaele et al., The development of nano bodies for therapeutic applications, Curr. Opin. Investig Drugs 10: 1212-1224, 2009.
Van Kuik-Romeijn et al., Expression of a functional mouse-human chimeric anti-CD19 antibody in the milk of transgenic mice. Transgenic Research. Apr. 1, 2000;9(2):155-159.
Vaughan et al., Of minibody, camel and bacteriophage, Combinatorial Chem. High Throughput Screening 4:417-430, 2001.
Vincke et al., Introduction to heavy chain antibodies and derived Nanobodies, Methods Mal. Biol. 911: 15-26, 2012.
Wei, H. et al., Dual targeting of CD137 co-stimulatory and PD-1 co-inhibitory molecules for ovarian cancer Immunotherapy Oncolmmunology (3); Mar. 2014.
Welch, Michael J & Redvanly, Carol S (2003). Handbook of radiopharmaceuticals : radiochemistry and applications. J. Wiley, New York. ISBN 0471495603.
Wesolowski et al., Single domain antibodies: promising experimental and therapeutic tools in infection and immunity, Med. Microbiol. Jmmunol. 198:157-174, 2009.
Wheeler et al., Intrabody and intrakine strategies for molecular therapy, Mol. Ther. 8(3):355-366, 2003.
Wigler et al., Transformation of mammalian cells with genes from procaryotes and eucaryotes. Cell. Apr. 1, 1979;16 (4):777-785.
Wolf et al., BiTEs: bispecific antibody constructs with unique anti-tumor activity, Drug Discovery Today 10:1237-1244, 2005.
Woychik et al., Requirement for the 3' flanking region of the bovine growth hormone gene for accurate polyadenylation, Proc. Natl. Acad Sci. U.S.A. 81(13):3944-3948, 1984.

(56) References Cited

OTHER PUBLICATIONS

Wranik et al., LUZ-Y, a novel platform for the mammalian cell production of full-length IgG-bispecific antibodies. Journal of Biological Chemistry. Dec. 21, 2012;287(52):43331-43339.
Wright et al., Antibody variable region glycosylation: position effects on antigen binding and carbohydrate structure. The EMBO journal. Oct. 1991;10(10):2717-2723.
Wu et al. Antibody array analysis with label-based detection and resolution of protein size Proteomics. Mol. Cell. Proteomics. 8(2):245-257, 2009.
Wu et al., Simultaneous targeting of multiple disease mediators by a dual-variable-domain immunoglobulin, Nat. Biotechnol. 25(11):1290-1297, 2007.
Wu, Diabodies: molecular engineering and therapeutic applications, Drug News Perspect. 22:453-458,2009.
Xu et al., Production of bispecific antibodies in "knobs-into-holes" using a cell-free expression system. MAbs. Jan. 2, 2015;7(1):231-242.
Yang et al., ELISA microplate: a viable immunocapture platform over magnetic beads for immunoaffinity-LC—MS/MS quantitation of protein therapeutics? Bioanalysis 7(3):307-318, 2015.
Yazaki et al., Tumor targeting of radiometal labeled anti-CEA recombinant T84.66 diabody and t84.66 minibody: comparison to radioiodinated fragments. Bioconjugate Chemistry 12:220-228, 2001.
Yeung et al., Quantitative screening of yeast surface-displayed polypeptide libraries by magnetic bead capture. Biotechnology Progress. 2002;18(2):212-220.
Yokoyama-Kobayashi et al., A signal sequence detection system using secreted protease activity as an indicator, Gene 163(2):193-196, 1995.
Zak, K., et al., Structure of the Complex of Human Programmed Death 1, PD-1, and Its Ligand PD-L1. Structure. Dec. 1, 2015;23(12):2341-2348.
Zapata et al., Engineering linear F(ab')2 fragments for efficient production in *Escherichia coli* and enhanced antiproliferative activity, Protein Ensz. 8(10):1057-1062, 1995.
Zhang et al., Programmable Sequence-Specific Transcriptional Regulation of Mammalian Genome Using Designer TAL Effectors, Nat. Biotechnol. 29(2):149-153, 2011.
Zhao et al., The restriction fold turns to the dark side: a bacterial homing endonuclease with a PD-(D/E)-XK motif, EMBO J. 26(9):2432-42, 2007.
Zhou et al., Photocleavable peptide-conjugated magnetic beads for protein kinase assays by MALDI-TOF MS. Bioconjug. Chem. 21(10):1917-1924, 2010.
Zhu et al., "BET Bromodomain Inhibition Promotes Anti-Tumor Immunity by Suppressing PD-LI Expression," Cell Rep. 16:2829-2837, 2016.
Zhu et al., High Level Secretion of a Humanized Bispecific Diabody from *Escherichia coli*, Nature Biotech. 14:192-196, 1996.
Chen et al., Characterization of germline antibody libraries from human umbilical cord blood and selection of monoclonal antibodies to viral envelope glycoproteins: implications for mechanisms of immune evasion and design of vaccine immunogents, Biochem Biophys Res Commun. 417(4): 1164-1169, 2012.
Gabibov et al., Combinatorial antibody library from multiple sclerosis patients reveals antibodies that cross-react with myelin basic protein and EBV antigen, FASEB Journ. 25: 4211-4221, 2011.
Prabakaran et al., Expressed antibody repertoires in human cord blood cells: 454 sequencing and IMGT/HighV-QUEST analysis of germline gene usage, junctional diversity, and somatic mutations, Immunogenetics 64:337-350 (2012).
Mali et al., RNA-Guided Human Genome Engineering via Cas9, Science 339:823-826, 2013.
Martins et al., Evaluation of a Multiplex Fluorescent Microsphere Immunoassay for the Determination of Epstein-Barr Virus Serologic Status. Am. J. Clin. Pathol. 129(1):34-41, 2008.
Mcconville et al., The structure, biosynthesis and function of glycosylated phosphatidylinositols in the parasitic protozoa and higher eukaryotes, Biochem. J. 294(Pt 2):305-324, 1993.

McHugh et al., Simultaneous detection of antibodies to cytomegalovirus and herpes simplex virus by using flow cytometry and a microsphere-based fluorescence immunoassay. J. Clin. Microbiol. 26(10):1957-1961, 1988.
Merchant et al., An efficient route to human bispecific IgG. Nature Biotechnology. Jul. 1998;16(7):677-681.
Merz & Drapeau. Generating a phage display antibody library against an indentified neuron. J Neurosci Methods Nov. 1995;62(1-2):213-9.
Michael et al., Addition of a short peptide ligand to the adenovirus fiber protein. Gene Therapy. Nov. 1995;2(9):660-668.
Miller et al., A TALE nuclease architecture for efficient genome editing, Nature Biotechnol. 29(2):143-148, 2011.
Milstein and Cuello, Hybrid hybridomas and their use in immunohistochemistry, Nature 305(5934):537-540, 1983.
Mueller et al., Homing endonucleases, in Nucleases 2nd Edition, S. M. Linn, R. S. Lloyd, and R. J. Roberts (Eds) Cold Spring Harbor Laboratory Press:1993, DD. 111-143.
Mujic-Delic et al., GPCR-targeting nanobodies: attractive research tools, diagnostics, and therapeutics, Trends Pharmacol. Sci. 35:247-255, 2014.
Mulligan and Berg, Selection for animal cells that express the *Escherichia coli* gene coding for xanthine-guanine phosphoribosyltransferase, Proc. Natl. Acad. Sci. U.S.A. 78(4):2072-2076, 1981.
Muyldermans et al., Recognition of antigens by single-domain antibody fragments: the superfluous luxury of paired domains, Trends Biochem. Sci. 26:230-235, 2001.
Muyldermans, Nanobodies: natural single-domain antibodies, Ann. Rev. Biochem. 82:775-797, 2013.
Muyldermans, Single domain camel antibodies: current status, J. Biotechnol. 74:277-302, 2001.
Needleman & Wunsch., A General Method Applicable to the Search for Similarities in the Amino Acid Sequences of Two Proteins. Journal of Molecular Biology. Mar. 28, 1970;48(2)443-453.
Nuttall, Overview and discovery of IgNARs and generation of VNARs, Methods Mal. Biol. 911:27-36, 2012.
Okazaki et al., New regulatory co-receptors: inducible co-stimulator and PD-1. Curr Opin Immunol. Dec. 2002;14 (6):779-782.
Oke et al., The Scottish Structural Proteomics Facility: targets, methods and outputs, J. Struct. Fund. Genomics 11(2): 167-180, 2010.
Orkin et al., Thalassemia due to a mutation in the cleavage-polyadenylation signal of the human beta-globin gene, EMBO J 4(2):453-456, 1985.
Papapetrou et al., Gene Insertion Into Genomic Safe Harbors for Human Gene Therapy, Mol. Theravv 24(4):678-684, 2016.
Pearson & Lipman., Improved tools for biological sequence comparison. Proceedings of the National Academy of Sciences. Apr. 1, 1988;85(8):1444-2448.
Pelletier et al., Cap-independent translation of poliovirus mRNA is conferred by sequence elements within the 5' noncoding region, Mol. Cell. Biol. 8(3): 1103-1112, 1988.
Pereboev et al., Phage display of adenovirus type 5 fiber knob as a tool for specific ligand selection and validation. Journal of Virology. Aug. 1, 2001;75(15):7107-7113.
Persic et al., An integrated vector system for the eukaryotic expression of antibodies or their fragments after selection from phage display libraries. Gene. Mar. 10, 1997;187(1):9-18.
Pleschberger et al., Generation of a functional monomolecular protein lattice consisting of an s-layer fusion protein comprising the variable domain of a camel heavy chain antibody, Bioconjugate Chem. 14(2):440-448, 2003.
Pluckthun, Antibodies from *E. coli*, in Rosenberg M. & Moore G.P. (Eds.), The Pharmacology of Monoclonal Antibodies, vol. 113, DD. 269-315, Springer-Verlag, New York, 1994.
Pogson et al., Immunogenomic engineering of a plug-and-(dis)play hybridoma platform, Nature Comm. 7:12535, 2016.
Poljak, Production and structure of diabodies, Structure 2:1121-1123, 1994.
Pollock et al., Transgenic milk as a method for the production of recombinant antibodies. Journal of Immunological Methods. Dec. 10, 1999;231(1-2):147-157.

(56) References Cited

OTHER PUBLICATIONS

Presta., Antibody engineering. Current Opinion in Structural Biology. Aug. 1, 1992;2(4):593-596.
Proudfoot et al., Integrating mRNA processing with transcription, Cell 108(4):501-512, 2002.
Rahbarizadeh et al., Nanobody; an old concept and new vehicle for immunotargeting, Immunol. Invest. 40:299-338, 2011.
Repp et al., Combined Fe-protein-and Fc-glyco-engineering of scFv-Fc fusion proteins synergistically enhances CD 16a binding but does not further enhance NK-cell mediated ADCC, J. Immunol. Methods 373(1-2):67-78, 2011.
Reuter & Matthews, RNAstructure: software for RNA secondary structure prediction and analysis, BMC Bioinformatics 11:129, 2010.
Ridgway et al., 'Knobs-into-holes' engineering of antibody CH3 domains for heavy chain heterodimerization. Protein Engineering, Design and Selection. Jul. 1, 1996;9(7):617-621.
Riechmann et al., Reshaping human antibodies for therapy. Nature. Mar. 1988;332(6162):323-327.
Roberts et al., Chemistry for peptide and protein PEGylation. Advanced Drug Delivery Reviews. Jun. 17, 2002;54 (4):459-476.
Sadelain et al., Safe harbours for the integration of new DNA in the human genome, Nature Reviews 12(1):51-58, 2012.
Sambrook et al., (1989). Molecular Cloning: A Laboratory Manual (2nd ed.). Cold Spring Harbor Press.
Sambrook, J., Fritsch, E., & Maniatis, T. (1989). Molecular Cloning: A Laboratory Manual (2nd ed.). NY: Cold Spring Harbor Laboratory Press.
Sarver et al., Transformation and replication in mouse cells of a bovine papillomavirus—pML2 plasmid vector that can be rescued in bacteria. Proceedings of the National Academy of Sciences. Dec. 1, 1982;79(23):7147-7151.
Schaffitzel et al., Ribosome display: an in vitro method for selection and evolution of antibodies from libraries. Journal of Immunological Methods. Dec. 10, 1999;231(1-2):119-135.
Schek et al., Definition of the upstream efficiency element of the simian vims 40 late polyadenylation signal by using in vitro analyses, Mol. Cell Biol. 12(12):5386-5393, 1992.
Schoonbroodt et al., Oligonucleotide-assisted cleavage and ligation: a novel directional DNA cloning technology to capture cDNAs. Application in the construction of a human immune antibody phage-display library. Nucleic Acids Research. Jan. 1, 2005;33(9):e81.
Schoonooghe et al., Efficient production of human bivalent and trivalent anti-MU CI Fab-scFv antibodies in Pichia vastoris, BMC Biotechnol. 9:70, 2009.
Schroeder, H.W., et al. "Structure and Function of Immunoglobulins" J Allergy Clin Immunol. Feb. 2010; 125(2 0 2): S41-S52. doi:10.1016/j.jaci.2009.09.046.
Schueren et al., Peroxisomal lactate dehydrogenase is generated by translational readthrough in mammals, eLife 3: e03640, 2014.
Scopes, R. (1994). Protein Purification (3rd ed.) (C. R. Cantor, Ed.). New York City, NY: Springer-Verlag.
Sedivy and Sharp, Positive genetic selection for gene disruption in mammalian cells by homologous recombination, Proc. Natl. Acad. Sci. U.S.A. 86(1):227-231, 1989.
Horan & Wheeless, Quantitative Single Cell Analysis and Sorting. Science 198(4313):149-157, 1977.
Houdebine., Antibody manufacture in transgenic animals and comparisons with other systems. Current Opinion in Biotechnology. Dec. 1, 2002;13(6):625-629.
Houseman & Mrksich, Towards quantitative assays with peptide chips: a surface engineering approach. Trends Biotechnol. 20(7):279-281, 2002.
Hudson et al., High avidity scFv multimers; diabodies and triabodies, J. Immunol. Methods 231:177-189, 1999.
Huehls et al., Bispecific T-cell engagers for cancer immunotherapy, Immunol. Cell Biol. 93:290-296,2015.
Huston et al., Engineered antibodies take center stage, Hum. Antibodies 10(3-4):127-142, 2001.

Huston et al., Protein engineering of antibody binding sites: recovery of specific activity in an anti-digoxin single-chain Fv analogue produced in *Escherichia coli*. Proceedings of the National Academy of Sciences. Aug. 1, 1988;85(16):5879-5883.
Hwang et al., Efficient genome editing in zebrafish using a CRISPR-Cas system, Nature Biotechnol. 31(3):227-229, 2013.
Intlekofer and Thompson, At the Bench: Preclinical rationale for CTLA-4 and PD-1 blockade as cancer immunotherapy, J. Leukoc. Biol. 94(1):25-39, 2013.
Ishida et al., Induced expression of PD-1, a novel member of the immunoglobulin gene superfamily, upon programmed cell death. The EMBO journal. Nov. 1992;11(11):3887-3895.
Iwai et al., Involvement of PD-L1 on tumor cells in the escape from host immune system and tumor immunotherapy by PD-L1 blockade. Proceedings of the National Academy of Sciences. Sep. 17, 2002;99(19):12293-12297.
Jacob et al., Peptide-polymer biotherapeutic synthesis on novel cross-linked beads with "spatially tunable" and "isolated" functional sites. Biopolymers 90(4):512-525, 2008.
Jakob et al., Structure reveals function of the dual variable domain immunoglobulin (DVD-Ig™) molecule, MAbs 5:358-363, 2013.
Jiang et al., RNA-guided editing of bacterial genomes using CRISPR-Cas systems, Nature Biotechnol. 31(3):233-239, 2013.
Jinek et al., A programmable dual-RNA-guided DNA endonuclease in adaptive bacterial immunity, Science 337 (6096):816-821, 2012.
Johnson et al., 3-O-Desacyl monophosphoryl lipid A derivatives: synthesis and immunostimulant activities. Journal of Medicinal Chemistry. Nov. 4, 1999;42(22):4640-4649.
Jones et al., Replacing the complementarity-determining regions in a human antibody with those from a mouse. Nature. May 1986;321(6069):522-525.
Jones, MHC class I and class II structures, Curr. Opinion Immunol. 9(1):75-79, 1997.
Ju and Jung, "Aglycosylated full-length IgG antibodies: steps toward next generation immunotherapeutics," Curr. Opin. Biotechnol. 30:128-139, 2014.
Juarez et al., Monoclonal antibodies for the identification and purification of vNAR domains and IgNAR Immunoglobulins from the horn shark Heterodontus francisci, Hybridoma (Larchmt), 30(4):323-329, 2011.
Kaszubska et al., Expression, purification, and characterization of human recombinant thrombopoietin in Chinese hamster ovary cells. Protein Expression and Purification. Mar. 1, 2000;18(2):213-220.
Kawabe et al., Production of scFv-Fc fusion protein using genetically manipulated quails, J. Biosci. Bioeng. 102(4): 297-303, 2006.
Kessler, The digoxigenin: anti-digoxigenin (DIG) technology—a survey on the concept and realization of a novel bioanalyticalindicator system. Mol. Cell. Probes 5(3):161-205, 1991.
Kieke et al., Isolation of anti-T cell receptor scFv mutants by yeast surface display. Protein Engineering. Nov. 1, 1997;10(11)1303-1310.
Kijanka et al., Nanobody-based cancer therapy of solid tumors, Nanomedicine 10:161-174, 2015.
Kim et al., Genome editing with modularly assembled zinc-finger nucleases, Nature Methods 7(2):91; Author Reply 91-2, 2010.
Kinstler et al., Mono-N-terminal poly (ethylene glycol)—protein conjugates. Advanced Drug Delivery Reviews. Jun. 17, 2002;54(4):477-485.
Kipriyanov et al., Bispecific tandem diabody for tumor therapy with improved antigen binding and pharmacokinetics, J. Mol. Biol. 293(1):41-56, Oct. 1999.
Kipriyanov et al., Generation of bispecific and tandem diabodies, Methods Mal. Biol. 317-331, 2002.
Klein et al., Progress in overcoming the chain association issue in bispecific heterodimeric IgG antibodies. MAbs. Nov. 1, 2012;4(6):653-663.
Klemm et al., Fimbrial surface display systems in bacteria: from vaccines to random libraries. Microbiology. Dec. 1, 2000;146(12):3025-3032.
Knappik et al., Fully synthetic human combinatorial antibody libraries (HuCAL) based on modular consensus frameworks and CDRs randomized with trinucleotides, J. Mol. Biol. 296(1):57-86, 2000.

(56) References Cited

OTHER PUBLICATIONS

Kochupurakkal et al., Nourseothricin N-acetyl transferase: a positive selection marker for mammalian cells, PLoS ONE 8(7):e68509, 2013.

Konishi et al., B7-H1 expression on non-small cell lung cancer cells and its relationship with tumor-infiltrating lymphocytes and their PD-1 expression. Clinical Cancer Research. Aug. 1, 2004;10(15):5094-5100.

Konning et al., Camelid and shark single domain antibodies: structural features and therapeutic potential, Curr. Opin. Struct. Biol. 45:10-16, 2017.

Kontermann et al., Bispecific Antibodies. Drug Discovery Today 20:838-847, 2015.

Kostelny et al., Formation of a bispecific antibody by the use of leucine zippers, J. Immunol. 148(5):1547-1553, 1992.

Kovaleva et al., Shark variable new antigen receptor biologics—a novel technology platform for therapeutic drug development, Exvert. Ovin. Biol. Ther. 14:1527-1539, 2014.

Krah et al., Single-domain antibodies for biomedical applications, Immunopharmacol. Immunotoxicol. 38:21-28, 2016.

Kroon, P. et al., Concomitant targeting of programmed death-1 (PD-1) and CD137 improves the efficacy of radiotherapy in a mouse model of human BRAFV600-mutant melanoma Cancer Immunol Immunother (2016) 65:753-763.

Langer et al., Biocompatibility of polymeric delivery systems for macromolecules. Journal of Biomedical Materials Research. Mar. 1981;15(2):267-277.

Lazar-Molnar et al., Crystal structure of the complex between programmed death-1 (PD-1) and its ligand PD-L2. Proceedings of the National Academy of Sciences. Jul. 29, 2008;105(30):10483-10488.

Lee et al., High-affinity human antibodies from phage-displayed synthetic Fab libraries with a single framework scaffold, J. Mol. Biol. 340(5):1073-1093, 2004.

Levitt et al., Definition of an efficient synthetic poly(A) site, Genes Dev. 3(7): 1019-1025, 1989.

Li et al., Reduction of kidney uptake in radiometal labeled peptide linkers conjugated to recombinant antibody fragments. Site-specific conjugation of DOT A-peptides to a Cys-diabody, Bioconiuzate Chem. 13:985-995, 2002.

Lo, B. K. (2004). Antibody engineering: Methods and protocols. Totowa, NJ: Humana Press.

Loughran et al., Evidence of efficient stop codon readthrough in four mammalian genes, Nucleic Acids Res. 42 (14):8928-8938, 2014.

Lusky & Botchan., Inhibition of SV40 replication in simian cells by specific pBR322 DNA sequences. Nature. Sep. 3, 1981;293(5827):79-81.

MacCallum et al., Antibody-antigen interactions: contact analysis and binding site topography. Journal of Molecular Biology. Oct. 11, 1996;262(5):732-745.

Macke et al., RNA Motif, an RNA secondary structure definition and search algorithm, Nucleic Acids Res. 29 (22):4724-4735, 2001.

Abdel-Motal et al., Anti-gpl20 minibody gene transfer to female genital epithelial cells protects against HIV-1 vims challenge in vitro, PLoS ONE 6:e26473, 2011.

Agata et al., Expression of the PD-1 antigen on the surface of stimulated mouse T and B lymphocytes. International Immunology. May 1, 1996;8(5):765-772.

Ali et al., Transferrin Trojan Horses as a Rational Approach for the Biological Delivery of Therapeutic Peptide Domains, J Biol. Chem. 274:24066-24073, 1999.

Almagro, J. C. et al. Humanization of Antibodies Frontiers in Bioscience 2008; 13:1619-33.

Ames et al., Conversion of murine Fabs isolated from a combinatorial phage display library to full length Immunoglobulins. Journal of Immunological Methods. Aug. 18, 1995;184(2):177-186.

Amet et al., Insertion of the designed helical linker led to increased expression of tf-based fusion proteins, Pharm. Res. 26:523-528, 2009.

Anderson et al., Intercellular transfer of a glycosylphosphatidylinositol (GPI)-linked protein: release and uptake of CD4-GPI from recombinant adeno-associated vims-transduced HeLa cells, Proc. Natl. Acad. Sci. U.S.A. 93(12):5894-5898, 11, 1996.

Anderson et al., Intercellular transfer of a glycosylphosphatidylinositol (GPI)-linked protein: release and uptake of CD4-GPI from recombinant adeno-associated virus-transduced HeLa cells, Proc. Natl. Acad. Sci. U.S.A. 93(12):5894-5898, 1996.

Arnau et al., Current strategies for the use of affinity tags and tag removal for the purification of recombinant proteins, Protein Express. Purification 48(1):1-13, 2006.

Ausubel et al., (1991). Current Protocols in Molecular Biology. Wiley.

Ausubel et al., (1993). Current Protocols in Molecular Biology. Wiley.

Ausubel et al., (2001) Current Protocols in Molecular Biology (3rd ed). NY: Cold Spring Harbor Laboratory Press, New York.

Ayoglu et al., Antigen arrays for profiling autoantibody repertoires. Bioanalysis 8(10):1105-1126, 2016.

Ayoglu et al., Autoantibody Profiling in Multiple Sclerosis Using Arrays of Human Protein Fragments. Mol. Cell. Proteomics 12(9):2657-2672, 2013.

Baeuerle et al., BiTE: Teaching antibodies to engage T-cells for cancer therapy, Curr. Opin. Mal. Ther. 11:22-30, 2009.

Baldridge et al., Monophosphoryl Lipid A (MPL) Formulations for the Next Generation of Vaccines. Methods. Sep. 1999;19(1):103-107.

Batt et al., Characterization of the polyomavirus late polyadenylation signal, Mol. Cell Biol. 15(9):4783-4790, 1995.

Bennett et al., Program Death-1 Engagement Upon TCR Activation Has Distinct Effects on Costimulation and Cytokine-Driven Proliferation: Attenuation of ICOS, IL-4, and IL-21, But Not CD28, IL-7, and IL-15 Responses. The Journal of Immunology. Jan. 15, 2003;170(2):711-718.

Berg, J. M., Tymoczko, J. L., & Stryer, L. (2002). Biochemistry (5th ed.). New York, NY: W.H. Freeman.

Bever et al., Development and utilization of camelid VHH antibodies from alpaca for 2,2',4,4'-tetrabrominated diphenvl ether detection, Analytical Chem. 86(15):7875-7882, 2014.

Bever et al., VHH antibodies: emerging reagents for the analysis of environmental chemicals, Anal. Bioanal. Chem. 408(22):5985-6002, 2016.

Binz et al., Engineering novel binding proteins from nonimmunoglobulin domains. Nature biotechnology. Oct. 6, 2005;23(10):1257-1268.

Bird et al., Single-chain antigen-binding proteins, Science 242:423-426, 1989.

Blank et al., Interaction of PD-L1 on tumor cells with PD-1 on tumor-specific T cells as a mechanism of immune evasion: implications for tumor immunotherapy. Cancer Immunology, Immunotherapy. Apr. 1, 2005;54(4):307-314.

Blank, C et al., Contribution of the PD-L1/PD-1 pathway to T-cell exhaustion: an update on implications for chronic infections and tumor evasion. Cancer immunology, immunotherapy. May 1, 2007;56(5):739-745.

Boder et al., Yeast surface display for directed evolution of protein expression, affinity, and stability. Methods in Enzymology. Jan. 1, 2000; 328:430-444.

Bonocora and Shub, A novel group I intron-encoded endonuclease specific for the anticodon region of tRNA(fMet) genes, Mol. Microbial. 39(5): 1299-1306, 2001.

Borrebaeck, C. A. (1995). Antibody engineering. New York, NY: Oxford University Press.

Braeckmans et al., Encoding microcarriers: present and future technologies. Nat. Rev. Drug Discov. 1:447-456, 2002.

Brennan et al., Preparation of bispecitic antibodies by chemical recombination of monoclonal immunoglobulin Gl fragments, Science 229(4708):81-83, 1985.

Brinkman et al., Phage display of disulfide-stabilized Fv fragments. Journal of Immunological Methods. Jan. 1, 1995;182(1):41-50.

Brown et al., Blockade of programmed death-1 ligands on dendritic cells enhances T cell activation and cytokine production. The Journal of Immunology. Feb. 1, 2003;170(3):1257-1266.

(56) References Cited

OTHER PUBLICATIONS

Brunschwig et al., Protein transfer of glycosyl-phosphatidylinositol (GPI)-modified murine B7-I and B7-2 costimulators, J Immunother. 22(5):390-400, 1999.

Burton et al., Human antibodies from combinatorial libraries. Advances in Immunology. Jan. 1, 1994; 57:191-280.

Burton, D.R., & Woof J.M. (1992). Human Antibody Effector Function. In F.J. (Ed), Advances in Immunology (pp. 1-2, 2a, 2b, 3084). ScienceDirect.

Canfield et al., The binding affinity of human IgG for its high affinity Fc receptor is determined by multiple amino acids in the CH2 domain and is modulated by the hinge region. The Journal of Experimental Medicine. Jun. 1, 1991;173(6):1483-1491.

Caras et al., Signal for attachment of a phospholipid membrane anchor in decay accelerating factor, Science 238 (4831)1280-1283, 1987.

Caras et al., Signal peptide for protein secretion directing glycophospholipid membrane anchor attachment, Science 243(4895):1196-1198, 1989.

Carter et al., PD-1: PD-L inhibitory pathway affects both CD4+ and CD8+ T cells and is overcome by IL-2. European Journal of Immunology. Mar. 2002;32(3):634-643.

Chasteen et al., Eliminating helper phage from phage display. Nucleic Acids Research. Dec. 1, 2006;34(21):e145.

Chen, S. et al. Combination of 4-1 BB Agonist and PD-1 Antagonist Promotes Antitumor Effector/Memory CDS T Cells in a Poorly Immunogenic Tumor Model Cancer Immunology Research: Nov. 11, 2014: 149-161.

Chestnut et al., Selective isolation of transiently transfected cells from a mammalian cell population with vectors expressing a membrane anchored single-chain antibody, J Immunol. Methods 193(1):17-27, 1996.

Chevalier and Stoddard, Homing endonucleases: structural and functional insight into the catalysts of intron/intein mobility, Nucleic Acids Res. 29(18):3757-3774, 2001.

Cho et al., Targeted genome engineering in human cells with the Cas9 RNA-guided endonuclease, Nature Biotechnol. 31(3):230-232, 2013.

Chothia et al., Canonical structures for the hypervariable regions of immunoglobulins. Journal of Molecular Biology. Aug. 20, 1987;196(4):901-917.

Chothia et al., Conformations of immunoglobulin hypervariable regions. Nature. Dec. 1989;342(6252):877-883.

Chou et al., Expression of chimeric monomer and dimer proteins on the plasma membrane of mammalian cells, Biotechnol. Bioeng 65(2):160-169, 1999.

Christian et al., Targeting DNA double-strand breaks with TAL effector nucleases, Genetics 186(2):757-761, 2010.

::::hu et al., Increasing the efficiency of homology-directed repair for Crispr-Cas9-induced precise gene editing in mammalian cells, Nature Biotechnol. 33(5):543-548, 2015.

r.:oloma and Morrison, Design and production of novel tetravalent bispecific antibodies, Nature Biotechnol. 15:159-163, 1997.

\* cited by examiner

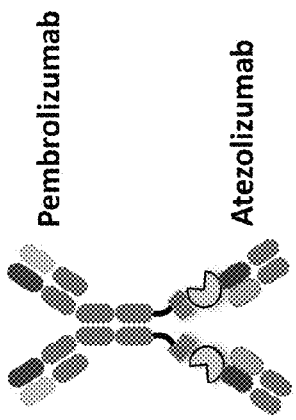

Pembrolizumab_aglyco-IgG1- (G4S)$_4$
— H chain
GTQVQLVQSGVEVKKPGASVKVSCKASGYTFTNYYMYWVRQAPGQGLEWMGGINPSNGGTNFNEKFKNRVTLTTDSSTTTAYMELKSLQFDDTAVYYCA
RRDYRFDMGFDYWGQGTTVTVSSASTKGPSVFPLAPSSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYAST
YRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSD
GSFFLYSKLTVDKSRWQQGNVFSCSVMHEALHNHYTQKSLSLSPGKGGGGSGGGGSGGGGSGGGGS
— L chain
TGEIVLTQSPATLSLSPGERATLSCRASKGVSTSGYSYLHWYQQKPGQAPRLLIYLASYLESGVPARFSGSGSGTDFTLTISSLEPEDFAVYYCQHSRDLPLTFG
GGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGL
SSPVTKSFNRGECLE Atezolizumab_HC Fab-(G4S)$_4$
— H chain
GTEVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARR
HWPGGFDYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTLEGGGGSGGGGSGGGGSGGGGS
— L chain
TGDIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGT
KVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPV
TKSFNRGECLE

FIGURE 3

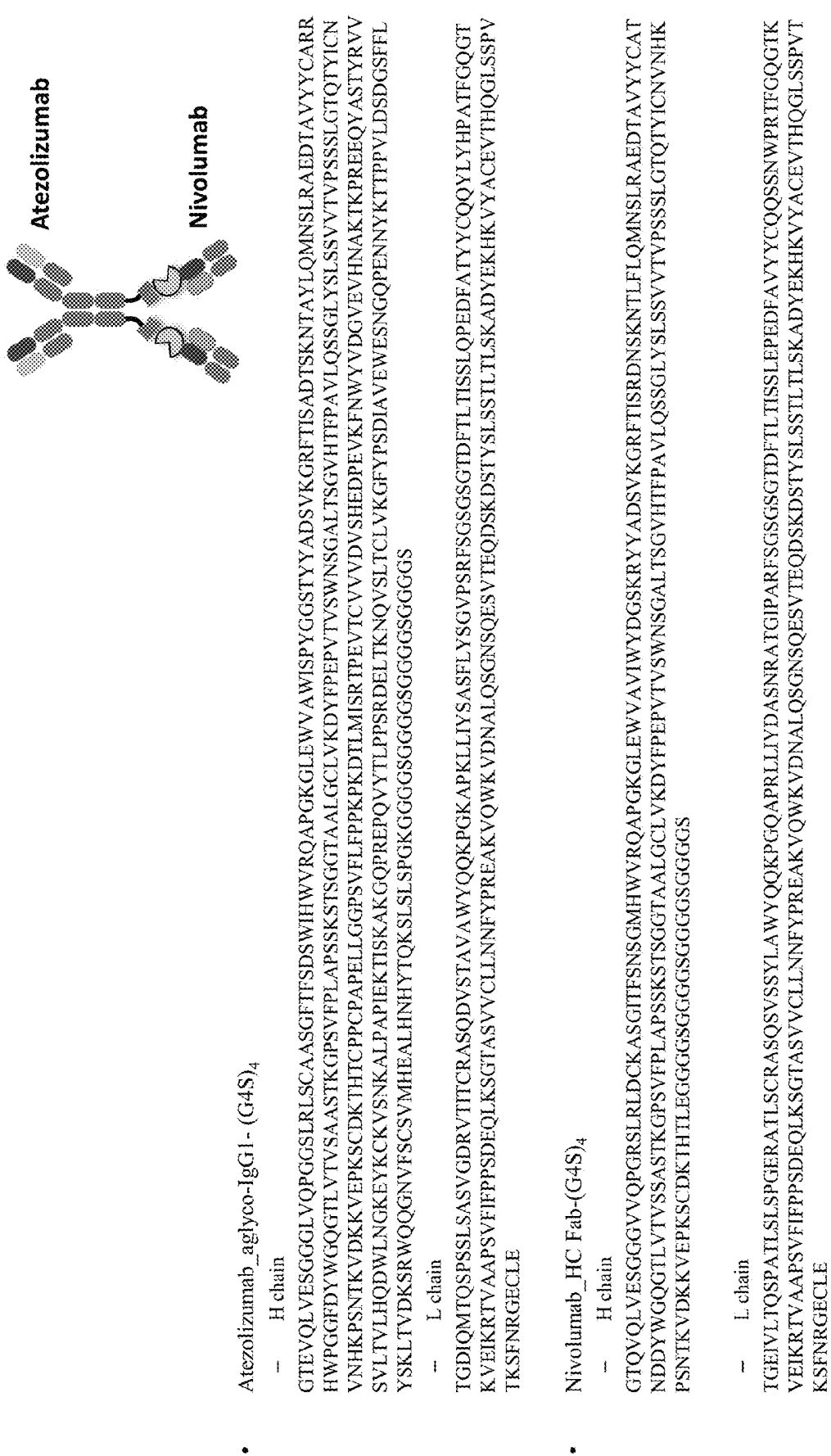

Atezolizumab

Nivolumab

Atezolizumab_aglyco-IgG1-(G4S)4
— H chain
GTEVQLVESGGGLVQPGGSLRLSCAASGFTFSDSWIHWVRQAPGKGLEWVAWISPYGGSTYYADSVKGRFTISADTSKNTAYLQMNSLRAEDTAVYYCARR
HWPGGFDYWGQGTLVTVSAASTKGPSVFPLAPSSKSTSGGTAALGCLVKDYFPEPVTVSWNSGALTSGVHTFPAVLQSSGLYSLSSVVTVPSSSLGTQTYICN
VNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYASTYRVV
SVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGKGGGGSGGGGSGGGGSGGGGS
— L chain
TGDIQMTQSPSSLSASVGDRVTITCRASQDVSTAVAWYQQKPGKAPKLLIYSASFLYSGVPSRFSGSGSGTDFTLTISSLQPEDFATYYCQQYLYHPATFGQGT
KVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPV
TKSFNRGECLE Nivolumab_HC Fab-(G4S)4
— H chain
GTQVQLVESGGGVVQPGRSLRLDCKASGITFSNSGMHWVRQAPGKGLEWVAVIWYDGSKRYYADSVKGRFTISRDNSKNTLFLQMNSLRAEDTAVYYCAT
NDDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHK
PSNTKVDKKVEPKSCDKTHTILEGGGGSGGGGSGGGGSGGGGS
— L chain
TGEIVLTQSPATLSLSPGERATLSCRASQSVSSYLAWYQQKPGQAPRLLIYDASNRATGIPARFSGSGSGTDFTLTISSLEPEDFAVYYCQQSSNWPRTFGQGTK
VEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVT
KSFNRGECLE

FIGURE 6

Figures 17D-17F
Figure 17D
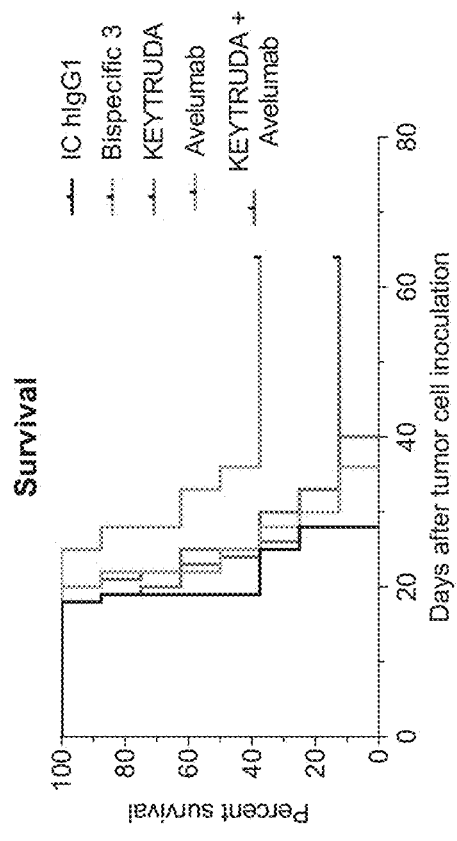
Figure 17E
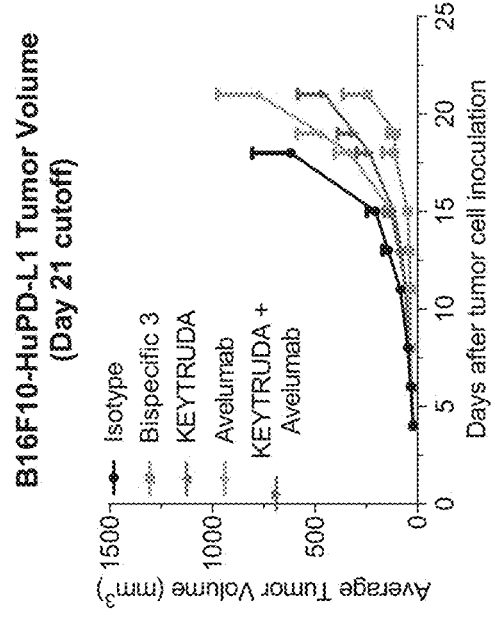
Figure 17F

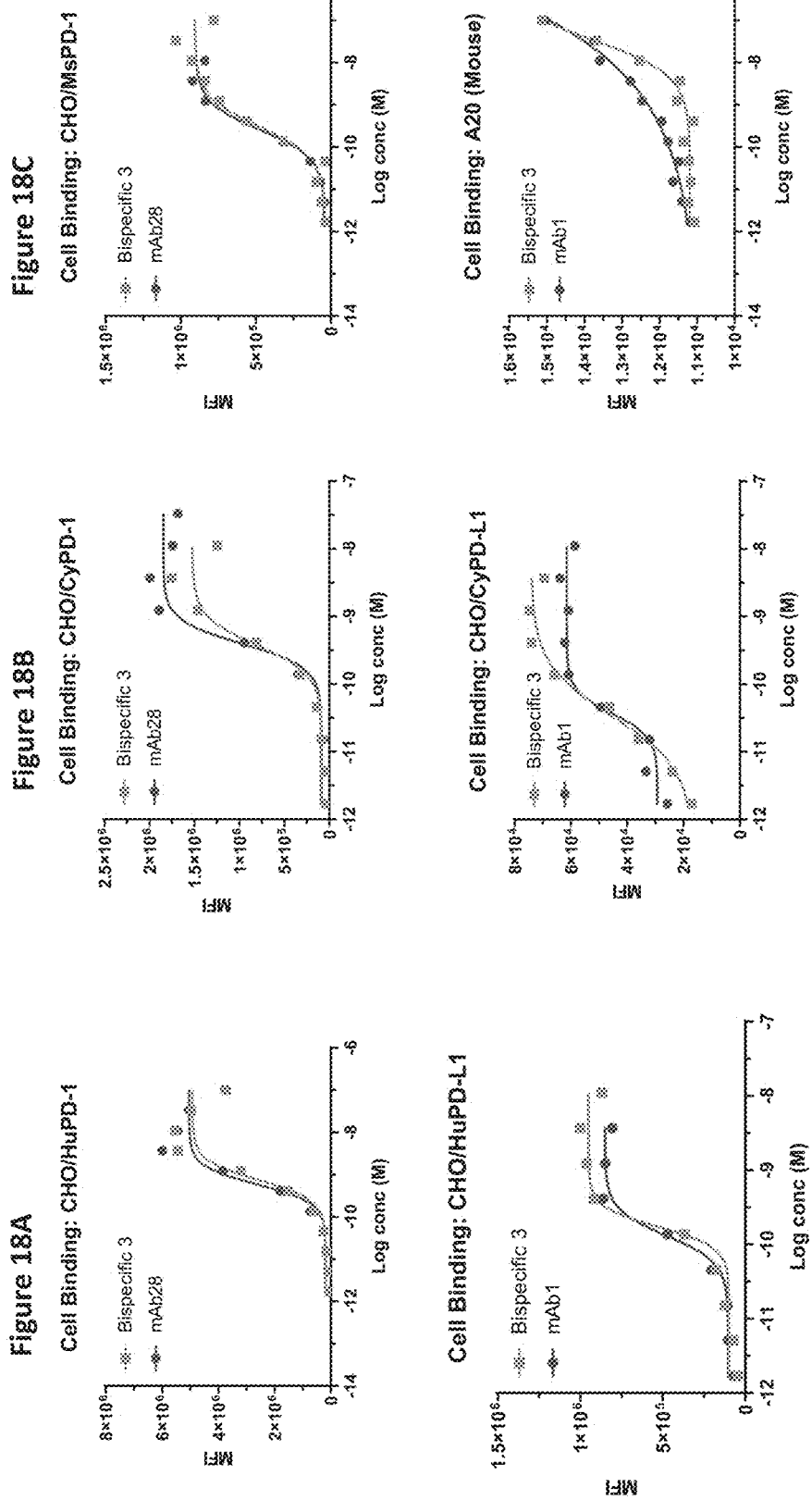

SEQUENCE LISTING

<160> NUMBER OF SEQ ID NOS: 122

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 1

Gly Thr Phe Ser Ser Tyr Ala Ile Asn
1               5

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Phe, Leu or Val
<220> FEATURE:
<221> NAME/KEY: MOD_RES
<222> LOCATION: (9)..(9)
<223> OTHER INFORMATION: Thr or Ala

<400> SEQUENCE: 2

Gly Gly Ile Ile Pro Xaa Xaa Gly Xaa Ala Thr Tyr Ala
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Gly, Phe or Asn

<400> SEQUENCE: 3

Ala Arg Leu Lys Xaa Glu Leu Lys Asp Ala Phe Asp Ile
1               5                   10

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ser, Trp or Gln

<400> SEQUENCE: 4

Arg Ala Ser Gln Xaa Ile Ser Ser Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

```
Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Phe

<400> SEQUENCE: 6

Xaa Gln Ser Tyr Ser Thr Pro Leu Thr
1               5

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Ile Ile Pro Ile Leu Gly Ala Ala Thr Tyr Ala
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Arg Leu Lys Gly Glu Leu Lys Asp Ala Phe Asp Ile
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Ala Ser Gln Ser Ile Ser Ser Tyr Leu Asn
1               5                   10

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Ser Tyr Ser Thr Pro Leu Thr
1               5
```

```
<210> SEQ ID NO 11
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Gly Gly Ile Ile Pro Val Phe Gly Thr Ala Thr Tyr Ala
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Arg Ala Ser Gln Trp Ile Ser Ser Tyr Leu Asn
1               5                   10

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Gln Ile Ser Ser Tyr Leu Asn
1               5                   10

<210> SEQ ID NO 14
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Thr Phe Ser Ser Tyr Ala Phe Ser
1               5

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Gly Ile Ile Pro Ile Phe Gly Ile Ala Asn Tyr Ala
1               5                   10

<210> SEQ ID NO 16
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16
```

Gly Gly Ile Ile Pro Asn Phe Gly Thr Ala Thr Tyr Ala
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ala Arg Leu Lys Gly Glu Leu Lys Gly Ala Gly Asp Ile
1               5                   10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ala Arg Leu Lys Phe Glu Leu Lys Asp Ala Phe Asp Ile
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ala Arg Leu Lys Gly Glu Leu Lys Asp Ala Phe Asp Glu
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Leu Lys Asn Glu Leu Lys Asp Ala Phe Asp Ile
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Gly Val Ile Pro Phe Leu Gly Thr Ala Asn Tyr Ala
1               5                   10

<210> SEQ ID NO 22
<211> LENGTH: 13
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 22

Ala Arg Leu Lys Gly Ile Leu Lys Asp Ala Leu Asp Ile
1               5                   10

<210> SEQ ID NO 23
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Thr Phe Ser Ser Tyr Ala Ile Ser
1               5

<210> SEQ ID NO 24
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Gly Ile Ile Pro Ile Val Gly Ile Ala Asn Tyr Ala
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Ala Arg Leu Lys Gly Glu Phe Lys Asp Ala Phe Asp Ile
1               5                   10

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Arg Ile Ile Pro Leu Phe Gly Thr Ala His Tyr Ala
1               5                   10

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Arg Ile Asn Pro Ile Leu Gly Thr Ala Asn Tyr Ala
1               5                   10
```

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Ala Arg Leu Lys Gly Glu Leu Lys Asp Ala Phe Ser Ile
1               5                   10

<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Arg Ile Ile Pro Ile Phe Gly Thr Ala Asp Tyr Ala
1               5                   10

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Ala Arg Leu Lys Gly Glu Leu Lys Cys Ala Phe Asp Ile
1               5                   10

<210> SEQ ID NO 31
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Gly Ile Ile Pro Ile Leu Gly Thr Ala Thr Tyr Ala
1               5                   10

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Ala Arg Arg Lys Gly Glu Leu Lys Asp Ala Phe Asp Ile
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Ile Ile Pro Ile Val Ala Thr Ala Asn Tyr Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Ile Ile Pro Ile Phe Gly Lys Ala Thr Tyr Ala
1               5                   10

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Met Val Thr Val Ser Ser
        115                 120

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Pro Phe Arg Ser His Ala Val Ser
1               5

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Ala Arg Leu Lys Ser Glu Leu Lys Asp Ala Phe Asp Ile
1               5                   10
```

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Phe Gln Ser Tyr Ser Thr Pro Leu Thr
1               5
```

<210> SEQ ID NO 39
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Gln Gln Ser Tyr Ser Thr Ile Leu Thr
1               5
```

<210> SEQ ID NO 40
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

```
Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Phe Ser Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
        115                 120
```

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

```
Gln Val Gln Leu Val Gln Ser Gly Ala Glu Val Lys Lys Pro Gly Ser
1               5                   10                  15
```

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
            35                  40                  45

Gly Gly Ile Ile Pro Ile Phe Gly Ile Ala Asn Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
            115                 120

<210> SEQ ID NO 42
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
            35                  40                  45

Gly Gly Ile Ile Pro Asn Phe Gly Thr Ala Thr Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Gly Ala Gly Asp Ile Trp Gly Gln
            100                 105                 110

Gly Thr Leu Val Thr Val Ser Ser
            115                 120

<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
            35                  40                  45

Gly Gly Ile Ile Pro Val Phe Gly Thr Ala Thr Tyr Ala Gln Lys Phe
 50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Phe Glu Leu Lys Asp Ala Phe Asp Ile Trp Gly Gln
            100                 105                 110

Gly Thr Leu Val Thr Val Ser Ser
        115                 120

<210> SEQ ID NO 44
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Glu Trp Gly Gln
            100                 105                 110

Gly Thr Leu Val Thr Val Ser Ser
        115                 120

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Ala Ser Thr
        115                 120

<210> SEQ ID NO 46
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Asn Glu Leu Lys Asp Ala Phe Asp Ile Trp Gly Gln
            100                 105                 110

Gly Thr Leu Val Thr Val Ser Ser
        115                 120

<210> SEQ ID NO 47
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Val Ile Pro Phe Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Ile Leu Lys Asp Ala Leu Asp Ile Trp Gly Gln
            100                 105                 110

Gly Thr Leu Val Thr Val Ser Ser
        115                 120

<210> SEQ ID NO 48
<211> LENGTH: 120
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Asp Leu Glu Trp Met
        35                  40                  45

Gly Gly Ile Ile Pro Ile Val Gly Ile Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 49
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Phe Lys Asp Ala Phe Asp Ile Trp Gly Gln
            100                 105                 110

Gly Thr Leu Val Thr Val Ser Ser
        115                 120

<210> SEQ ID NO 50
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Leu Phe Gly Thr Ala His Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
            115                 120

<210> SEQ ID NO 51
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Asn Pro Ile Leu Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Ser Ile Trp Gly Gln
            100                 105                 110

Gly Thr Leu Val Thr Val Ser Ser
            115                 120

<210> SEQ ID NO 52
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Arg Ile Ile Pro Ile Phe Gly Thr Ala Asp Tyr Ala Gln Lys Phe
    50                  55                  60
```

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Gln Ser Gly Ala Glu Val Lys Lys Pro Gly Ser
1               5                   10                  15

Ser Val Lys Val Ser Cys Lys Ala Ser Gly Gly Lys Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Cys Ala Phe Asp Ile Trp Gly Gln
            100                 105                 110

Gly Thr Leu Val Thr Val Ser Ser
        115                 120

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 55
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Leu Gly Ala Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 56
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Val Ala Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 57
<211> LENGTH: 120
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 57

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Asn Trp Val Arg Gln Ala Pro Gly Gln Gly Leu Glu Trp Met
        35                  40                  45

Gly Gly Ile Ile Pro Ile Phe Gly Lys Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Lys Gly Glu Leu Lys Asp Ala Phe Asp Ile Trp Gly Gln
            100                 105                 110

Gly Thr Leu Val Thr Val Ser Ser
        115                 120

<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Gln Ser Gly Ala Glu Val Lys Lys Pro Gly Ser
1               5                   10                  15

Ser Val Lys Val Ser Cys Lys Ala Ser Gly Gly Pro Phe Arg Ser His
            20                  25                  30

Ala Val Ser Trp Val Arg Gln Ala Pro Gly Gln Gly Leu Glu Trp Met
        35                  40                  45

Gly Gly Ile Ile Pro Val Phe Gly Thr Ala Thr Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Lys Ser Glu Leu Lys Asp Ala Phe Asp Ile Trp Gly Gln
            100                 105                 110

Gly Thr Leu Val Thr Val Ser Ser
        115                 120

<210> SEQ ID NO 59
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr

```
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 60
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105

<210> SEQ ID NO 61
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 61

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
                20                  25                  30

Leu Asn Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
```

<210> SEQ ID NO 62
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Phe Gln Ser Tyr Ser Thr Pro Leu
                85                  90                  95

Thr Phe Gly Gly Gly Thr Lys Val Glu Ile Lys
            100                 105

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Ile Leu
                85                  90                  95

Thr Phe Gly Gly Gly Thr Lys Val Glu Ile Lys
            100                 105

<210> SEQ ID NO 64
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Ala Ser Thr Lys Gly Pro Ser Val Phe Pro Leu Ala Pro Ser Ser Lys
1               5                   10                  15

```
Ser Thr Ser Gly Gly Thr Ala Ala Leu Gly Cys Leu Val Lys Asp Tyr
            20              25              30

Phe Pro Glu Pro Val Thr Val Ser Trp Asn Ser Gly Ala Leu Thr Ser
            35              40              45

Gly Val His Thr Phe Pro Ala Val Leu Gln Ser Ser Gly Leu Tyr Ser
            50              55              60

Leu Ser Ser Val Val Thr Val Pro Ser Ser Ser Leu Gly Thr Gln Thr
 65              70              75              80

Tyr Ile Cys Asn Val Asn His Lys Pro Ser Asn Thr Lys Val Asp Lys
                85              90              95

Lys Val Glu Pro Lys Ser Cys Asp Lys Thr His Thr Cys Pro Pro Cys
            100             105             110

Pro Ala Pro Glu Leu Leu Gly Gly Pro Ser Val Phe Leu Phe Pro Pro
            115             120             125

Lys Pro Lys Asp Thr Leu Met Ile Ser Arg Thr Pro Glu Val Thr Cys
130             135             140

Val Val Val Asp Val Ser His Glu Asp Pro Glu Val Lys Phe Asn Trp
145             150             155             160

Tyr Val Asp Gly Val Glu Val His Asn Ala Lys Thr Lys Pro Arg Glu
                165             170             175

Glu Gln Tyr Asn Ser Thr Tyr Arg Val Val Ser Val Leu Thr Val Leu
            180             185             190

His Gln Asp Trp Leu Asn Gly Lys Glu Tyr Lys Cys Lys Val Ser Asn
            195             200             205

Lys Ala Leu Pro Ala Pro Ile Glu Lys Thr Ile Ser Lys Ala Lys Gly
            210             215             220

Gln Pro Arg Glu Pro Gln Val Tyr Thr Leu Pro Pro Ser Arg Asp Glu
225             230             235             240

Leu Thr Lys Asn Gln Val Ser Leu Thr Cys Leu Val Lys Gly Phe Tyr
            245             250             255

Pro Ser Asp Ile Ala Val Glu Trp Glu Ser Asn Gly Gln Pro Glu Asn
            260             265             270

Asn Tyr Lys Thr Thr Pro Pro Val Leu Asp Ser Asp Gly Ser Phe Phe
            275             280             285

Leu Tyr Ser Lys Leu Thr Val Asp Lys Ser Arg Trp Gln Gln Gly Asn
290             295             300

Val Phe Ser Cys Ser Val Met His Glu Ala Leu His Asn His Tyr Thr
305             310             315             320

Gln Lys Ser Leu Ser Leu Ser Pro Gly Lys
            325             330

<210> SEQ ID NO 65

<400> SEQUENCE: 65

000

<210> SEQ ID NO 66

<400> SEQUENCE: 66

000

<210> SEQ ID NO 67

<400> SEQUENCE: 67
```

```
<210> SEQ ID NO 68
<211> LENGTH: 327
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 69
```

<211> LENGTH: 326
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<221> NAME/KEY: MOD_RES
<222> LOCATION: (4)..(4)
<223> OTHER INFORMATION: Ser, Arg, Gly or Asn
<220> FEATURE:
<221> NAME/KEY: MOD_RES
<222> LOCATION: (5)..(5)
<223> OTHER INFORMATION: Asp, Ser, Asn, Ala, Arg or Gly
<220> FEATURE:
<221> NAME/KEY: MOD_RES
<222> LOCATION: (8)..(8)
<223> OTHER INFORMATION: Met or Leu
<220> FEATURE:
<221> NAME/KEY: MOD_RES
<222> LOCATION: (9)..(9)
<223> OTHER INFORMATION: Ser, Leu or Asn

<400> SEQUENCE: 70

Phe Thr Phe Xaa Xaa Tyr Ala Xaa Xaa
1               5

<210> SEQ ID NO 71
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ala Ile Ser Asn Ser Gly Thr Tyr Thr Tyr Tyr Ala
1               5                   10

<210> SEQ ID NO 72
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: Ala, Tyr or Arg

<400> SEQUENCE: 72

Ala Arg Gly Leu Asp Phe Ile Val Gly Xaa Thr Gly Asn Asp Tyr
1               5                   10                  15

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Phe Thr Phe Ser Asp Tyr Ala Met Ser
1               5

<210> SEQ ID NO 74
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74
```

Ala Arg Gly Leu Asp Phe Ile Val Gly Ala Thr Gly Asn Asp Tyr
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Ala Arg Gly Leu Asp Phe Ile Val Gly Tyr Thr Gly Asn Asp Tyr
1               5                   10                  15

<210> SEQ ID NO 76
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Phe Thr Phe Ser Ser Tyr Ala Met Ser
1               5

<210> SEQ ID NO 77
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Phe Thr Phe Ser Ser Tyr Ala Met Leu
1               5

<210> SEQ ID NO 78
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Phe Thr Phe Ser Asn Tyr Ala Leu Ser
1               5

<210> SEQ ID NO 79
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Phe Thr Phe Ser Ala Tyr Ala Met Asn
1               5

<210> SEQ ID NO 80
<211> LENGTH: 9
<212> TYPE: PRT
<213> ORGANISM: Artificial Sequence -continued
<220> FEATURE:
<223> OTHER INFORMATION: Description of Artificial Sequence: Synthetic
      peptide

<400> SEQUENCE: 80

Phe Thr Phe Arg Ser Tyr Ala Met Ser
1               5

<210> SEQ ID NO 81
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Phe Thr Phe Gly Arg Tyr Ala Met Ser
1               5

<210> SEQ ID NO 82
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Phe Thr Phe Asn Ser Tyr Ala Met Ser
1               5

<210> SEQ ID NO 83
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Phe Thr Phe Ser Asn Tyr Ala Met Ser
1               5

<210> SEQ ID NO 84
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Phe Thr Phe Ser Gly Tyr Ala Met Ser
1               5

<210> SEQ ID NO 85
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ala Arg Gly Leu Asp Phe Ile Val Gly Arg Thr Gly Asn Asp Tyr
1               5                   10                  15

<210> SEQ ID NO 86
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 86

Phe Thr Phe Ser Ser Tyr Ala Met Asn
1               5

<210> SEQ ID NO 87
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Ala Thr Gly Asn Asp Tyr Trp
            100                 105                 110

Gly Gln Gly Thr Leu Val Thr Val Ser Ser
        115                 120

<210> SEQ ID NO 88
<211> LENGTH: 122
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp

```
                    100                 105                 110

Gly Gln Gly Thr Leu Val Thr Val Ser Ser
            115                 120

<210> SEQ ID NO 89
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
            115                 120

<210> SEQ ID NO 90
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Leu Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
            115                 120

<210> SEQ ID NO 91
<211> LENGTH: 122
<212> TYPE: PRT
```

```
<213> ORGANISM: Artificial Sequence
<220> FEATURE:
<223> OTHER INFORMATION: Description of Artificial Sequence: Synthetic
      polypeptide

<400> SEQUENCE: 91

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Leu Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
        115                 120

<210> SEQ ID NO 92
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ala Tyr
            20                  25                  30

Ala Met Asn Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
        115                 120

<210> SEQ ID NO 93
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Val Gln Leu Leu Glu Ser Gly Gly Gly Leu Val Gln Pro Gly Gly
1               5                   10                  15
```

-continued

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
        115                 120

<210> SEQ ID NO 94
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Arg Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
        115                 120

<210> SEQ ID NO 95
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser
        115                 120

<210> SEQ ID NO 96
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Ala Thr Gly Asn Asp Tyr Trp
            100                 105                 110

Gly Gln Gly Thr Leu Val Thr Val Ser Ser
        115                 120

<210> SEQ ID NO 97
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Arg Thr Gly Asn Asp Tyr Trp
            100                 105                 110

Gly Gln Gly Thr Leu Val Thr Val Ser Ser
        115                 120

<210> SEQ ID NO 98
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Arg Thr Gly Asn Asp Tyr Trp
            100                 105                 110

Gly Gln Gly Thr Leu Val Thr Val Ser Ser
        115                 120

<210> SEQ ID NO 99
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Ala Met Ser Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Arg Thr Gly Asn Asp Tyr Trp
            100                 105                 110

Gly Gln Gly Thr Leu Val Thr Val Ser Ser
        115                 120

<210> SEQ ID NO 100
<211> LENGTH: 698
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Leu Trp Val Arg Gln Ala Pro Gly Lys Gly Leu Glu Trp Val
        35                  40                  45

Ser Ala Ile Ser Asn Ser Gly Thr Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
        355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
```

```
                385                 390                 395                 400
Pro Val Leu Asp Ser Asp Gly Ser Phe Phe Leu Tyr Ser Lys Leu Thr
                    405                 410                 415

Val Asp Lys Ser Arg Trp Gln Gln Gly Asn Val Phe Ser Cys Ser Val
                420                 425                 430

Met His Glu Ala Leu His Asn His Tyr Thr Gln Lys Ser Leu Ser Leu
            435                 440                 445

Ser Pro Gly Gly Gly Gly Ser Gly Gly Gly Gly Ser Gly Gly Gly Gly
        450                 455                 460

Ser Gly Gly Gly Gly Ser Gln Val Gln Leu Val Gln Ser Gly Ala Glu
465                 470                 475                 480

Val Lys Lys Pro Gly Ser Ser Val Lys Val Ser Cys Lys Ala Ser Gly
                485                 490                 495

Gly Thr Phe Ser Ser Tyr Ala Ile Asn Trp Val Arg Gln Ala Pro Gly
                500                 505                 510

Gln Gly Leu Glu Trp Met Gly Gly Ile Ile Pro Ile Leu Gly Ala Ala
            515                 520                 525

Thr Tyr Ala Gln Lys Phe Gln Gly Arg Val Thr Ile Thr Ala Asp Glu
        530                 535                 540

Ser Thr Ser Thr Ala Tyr Met Glu Leu Ser Ser Leu Arg Ser Glu Asp
545                 550                 555                 560

Thr Ala Val Tyr Tyr Cys Ala Arg Leu Lys Gly Glu Leu Lys Asp Ala
                565                 570                 575

Phe Asp Ile Trp Gly Gln Gly Thr Leu Val Thr Val Ser Ser Ala Ser
                580                 585                 590

Thr Lys Gly Pro Ser Val Phe Pro Leu Ala Pro Ser Ser Lys Ser Thr
            595                 600                 605

Ser Gly Gly Thr Ala Ala Leu Gly Cys Leu Val Lys Asp Tyr Phe Pro
        610                 615                 620

Glu Pro Val Thr Val Ser Trp Asn Ser Gly Ala Leu Thr Ser Gly Val
625                 630                 635                 640

His Thr Phe Pro Ala Val Leu Gln Ser Ser Gly Leu Tyr Ser Leu Ser
                645                 650                 655

Ser Val Val Thr Val Pro Ser Ser Ser Leu Gly Thr Gln Thr Tyr Ile
                660                 665                 670

Cys Asn Val Asn His Lys Pro Ser Asn Thr Lys Val Asp Lys Lys Val
            675                 680                 685

Glu Pro Lys Ser Cys Asp Lys Thr His Thr
        690                 695

<210> SEQ ID NO 101
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210

<210> SEQ ID NO 102
<211> LENGTH: 687
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
             20                  25                  30

Ala Met Leu Trp Val Arg Gln Ala Pro Gly Lys Gly Leu Glu Trp Val
         35                  40                  45

Ser Ala Ile Ser Asn Ser Gly Thr Tyr Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Asp Phe Ile Val Gly Tyr Thr Gly Asn Asp Tyr Trp
            100                 105                 110

Gly Gln Gly Thr Leu Val Thr Val Ser Ser Ala Lys Thr Thr Pro Pro
        115                 120                 125

Ser Val Tyr Pro Leu Ala Pro Gly Ser Ala Ala Gln Thr Asn Ser Met
130                 135                 140

Val Thr Leu Gly Cys Leu Val Lys Gly Tyr Phe Pro Glu Pro Val Thr
145                 150                 155                 160

Val Thr Trp Asn Ser Gly Ser Leu Ser Ser Gly Val His Thr Phe Pro
                165                 170                 175

Ala Val Leu Glu Ser Asp Leu Tyr Thr Leu Ser Ser Ser Val Thr Val
            180                 185                 190

-continued

```
Pro Ser Ser Pro Arg Pro Ser Glu Thr Val Thr Cys Asn Val Ala His
        195                 200                 205

Pro Ala Ser Ser Thr Lys Val Asp Lys Lys Ile Val Pro Arg Asp Cys
    210                 215                 220

Gly Cys Lys Pro Cys Ile Cys Thr Val Pro Glu Val Ser Ser Val Phe
225                 230                 235                 240

Ile Phe Pro Pro Lys Pro Lys Asp Val Leu Thr Ile Thr Leu Thr Pro
                245                 250                 255

Lys Val Thr Cys Val Val Val Asp Ile Ser Lys Asp Asp Pro Glu Val
            260                 265                 270

Gln Phe Ser Trp Phe Val Asp Asp Val Glu Val His Thr Ala Gln Thr
        275                 280                 285

Gln Pro Arg Glu Glu Gln Phe Ala Ser Thr Phe Arg Ser Val Ser Glu
    290                 295                 300

Leu Pro Ile Met His Gln Asp Trp Leu Asn Gly Lys Glu Phe Lys Cys
305                 310                 315                 320

Arg Val Asn Ser Ala Ala Phe Pro Ala Pro Ile Glu Lys Thr Ile Ser
                325                 330                 335

Lys Thr Lys Gly Arg Pro Lys Ala Pro Gln Val Tyr Thr Ile Pro Pro
            340                 345                 350

Pro Lys Glu Gln Met Ala Lys Asp Lys Val Ser Leu Thr Cys Met Ile
        355                 360                 365

Thr Asp Phe Phe Pro Glu Asp Ile Thr Val Glu Trp Gln Trp Asn Gly
    370                 375                 380

Gln Pro Ala Glu Asn Tyr Lys Asn Thr Gln Pro Ile Met Asn Thr Asn
385                 390                 395                 400

Gly Ser Tyr Phe Val Tyr Ser Lys Leu Asn Val Gln Lys Ser Asn Trp
                405                 410                 415

Glu Ala Gly Asn Thr Phe Thr Cys Ser Val Leu His Glu Gly Leu His
            420                 425                 430

Asn His His Thr Glu Lys Ser Leu Ser His Ser Pro Gly Gly Gly Gly
        435                 440                 445

Ser Gly Gly Gly Gly Ser Gly Gly Gly Ser Gly Gly Gly Gly Ser
450                 455                 460

Gln Val Gln Leu Val Gln Ser Gly Ala Glu Val Lys Lys Pro Gly Ser
465                 470                 475                 480

Ser Val Lys Val Ser Cys Lys Ala Ser Gly Gly Thr Phe Ser Ser Tyr
                485                 490                 495

Ala Ile Asn Trp Val Arg Gln Ala Pro Gly Gln Gly Leu Glu Trp Met
            500                 505                 510

Gly Gly Ile Ile Pro Ile Leu Gly Ala Ala Thr Tyr Ala Gln Lys Phe
        515                 520                 525

Gln Gly Arg Val Thr Ile Thr Ala Asp Glu Ser Thr Ser Thr Ala Tyr
    530                 535                 540

Met Glu Leu Ser Ser Leu Arg Ser Glu Asp Thr Ala Val Tyr Tyr Cys
545                 550                 555                 560

Ala Arg Leu Lys Gly Glu Leu Lys Asp Ala Phe Asp Ile Trp Gly Gln
                565                 570                 575

Gly Thr Leu Val Thr Val Ser Ser Ala Lys Thr Thr Pro Pro Ser Val
            580                 585                 590

Tyr Pro Leu Ala Pro Gly Ser Ala Ala Gln Thr Asn Ser Met Val Thr
        595                 600                 605
```

```
Leu Gly Cys Leu Val Lys Gly Tyr Phe Pro Glu Pro Val Thr Val Thr
    610                 615                 620

Trp Asn Ser Gly Ser Leu Ser Ser Gly Val His Thr Phe Pro Ala Val
625                 630                 635                 640

Leu Glu Ser Asp Leu Tyr Thr Leu Ser Ser Val Thr Val Pro Ser
            645                 650                 655

Ser Pro Arg Pro Ser Glu Thr Val Thr Cys Asn Val Ala His Pro Ala
            660                 665                 670

Ser Ser Thr Lys Val Asp Lys Lys Ile Val Pro Arg Asp Cys Gly
        675                 680                 685

<210> SEQ ID NO 103
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 104
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104
```

```
Gly Thr Gln Val Gln Leu Val Gln Ser Gly Val Glu Val Lys Lys Pro
1               5                   10                  15

Gly Ala Ser Val Lys Val Ser Cys Lys Ala Ser Gly Tyr Thr Phe Thr
            20                  25                  30

Asn Tyr Tyr Met Tyr Trp Val Arg Gln Ala Pro Gly Gln Gly Leu Glu
        35                  40                  45

Trp Met Gly Gly Ile Asn Pro Ser Asn Gly Gly Thr Asn Phe Asn Glu
    50                  55                  60

Lys Phe Lys Asn Arg Val Thr Leu Thr Thr Asp Ser Ser Thr Thr Thr
65                  70                  75                  80

Ala Tyr Met Glu Leu Lys Ser Leu Gln Phe Asp Asp Thr Ala Val Tyr
                85                  90                  95

Tyr Cys Ala Arg Arg Asp Tyr Arg Phe Asp Met Gly Phe Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
    195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
            275                 280                 285

Val His Asn Ala Lys Thr Lys Pro Arg Glu Glu Gln Tyr Ala Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
            340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
    370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
```

```
                    420                 425                 430
Met His Glu Ala Leu His Asn His Tyr Thr Gln Lys Ser Leu Ser Leu
                435                 440                 445

Ser Pro Gly Lys Gly Gly Gly Ser Gly Gly Gly Ser Gly Gly
    450                 455                 460

Gly Gly Ser Gly Gly Gly Ser
465                 470

<210> SEQ ID NO 105
<211> LENGTH: 222
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Thr Gly Glu Ile Val Leu Thr Gln Ser Pro Ala Thr Leu Ser Leu Ser
1               5                   10                  15

Pro Gly Glu Arg Ala Thr Leu Ser Cys Arg Ala Ser Lys Gly Val Ser
            20                  25                  30

Thr Ser Gly Tyr Ser Tyr Leu His Trp Tyr Gln Gln Lys Pro Gly Gln
        35                  40                  45

Ala Pro Arg Leu Leu Ile Tyr Leu Ala Ser Tyr Leu Glu Ser Gly Val
    50                  55                  60

Pro Ala Arg Phe Ser Gly Ser Gly Ser Gly Thr Asp Phe Thr Leu Thr
65                  70                  75                  80

Ile Ser Ser Leu Glu Pro Glu Asp Phe Ala Val Tyr Tyr Cys Gln His
                85                  90                  95

Ser Arg Asp Leu Pro Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys Leu Glu
    210                 215                 220

<210> SEQ ID NO 106
<211> LENGTH: 250
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Gly Thr Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
```

```
                20                  25                  30
Asp Ser Trp Ile His Trp Val Arg Gln Ala Pro Gly Lys Gly Leu Glu
        35                  40                  45

Trp Val Ala Trp Ile Ser Pro Tyr Gly Gly Ser Thr Tyr Tyr Ala Asp
 50                  55                  60

Ser Val Lys Gly Arg Phe Thr Ile Ser Ala Asp Thr Ser Lys Asn Thr
 65                  70                  75                  80

Ala Tyr Leu Gln Met Asn Ser Leu Arg Ala Glu Asp Thr Ala Val Tyr
                85                  90                  95

Tyr Cys Ala Arg Arg His Trp Pro Gly Gly Phe Asp Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Leu Glu Gly Gly Gly Ser Gly Gly Gly Gly Ser
225                 230                 235                 240

Gly Gly Gly Gly Ser Gly Gly Gly Gly Ser
                245                 250

<210> SEQ ID NO 107
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Thr Gly Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Asp Val Ser
            20                  25                  30

Thr Ala Val Ala Trp Tyr Gln Gln Lys Pro Gly Lys Ala Pro Lys Leu
        35                  40                  45

Leu Ile Tyr Ser Ala Ser Phe Leu Tyr Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Gln Gln Tyr Leu Tyr His
                85                  90                  95

Pro Ala Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125
```

```
Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Leu Glu
    210                 215

<210> SEQ ID NO 108
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Gly Thr Gln Val Gln Leu Val Glu Ser Gly Gly Val Val Gln Pro
1               5                   10                  15

Gly Arg Ser Leu Arg Leu Asp Cys Lys Ala Ser Gly Ile Thr Phe Ser
                20                  25                  30

Asn Ser Gly Met His Trp Val Arg Gln Ala Pro Gly Lys Gly Leu Glu
            35                  40                  45

Trp Val Ala Val Ile Trp Tyr Asp Gly Ser Lys Arg Tyr Tyr Ala Asp
        50                  55                  60

Ser Val Lys Gly Arg Phe Thr Ile Ser Arg Asp Asn Ser Lys Asn Thr
65                  70                  75                  80

Leu Phe Leu Gln Met Asn Ser Leu Arg Ala Glu Asp Thr Ala Val Tyr
                85                  90                  95

Tyr Cys Ala Thr Asn Asp Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270
```

-continued

```
Phe Asn Trp Tyr Val Asp Gly Val Glu Val His Asn Ala Lys Thr Lys
        275                 280                 285

Pro Arg Glu Glu Gln Tyr Ala Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
                355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Gly Gly
                435                 440                 445

Gly Ser Gly Gly Gly Gly Ser Gly Gly Gly Gly Ser Gly Gly Gly Gly
        450                 455                 460

Ser
465

<210> SEQ ID NO 109
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Thr Gly Glu Ile Val Leu Thr Gln Ser Pro Ala Thr Leu Ser Leu Ser
1               5                   10                  15

Pro Gly Glu Arg Ala Thr Leu Ser Cys Arg Ala Ser Gln Ser Val Ser
                20                  25                  30

Ser Tyr Leu Ala Trp Tyr Gln Gln Lys Pro Gly Gln Ala Pro Arg Leu
        35                  40                  45

Leu Ile Tyr Asp Ala Ser Asn Arg Ala Thr Gly Ile Pro Ala Arg Phe
    50                  55                  60

Ser Gly Ser Gly Ser Gly Thr Asp Phe Thr Leu Thr Ile Ser Ser Leu
65                  70                  75                  80

Glu Pro Glu Asp Phe Ala Val Tyr Tyr Cys Gln Gln Ser Ser Asn Trp
                85                  90                  95

Pro Arg Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
        130                 135                 140

Glu Ala Lys Val Gln Trp Lys Val Asp Asn Ala Leu Gln Ser Gly Asn
```

```
145             150             155             160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
            195                 200                 205

Lys Ser Phe Asn Arg Gly Glu Cys Leu Glu
        210                 215

<210> SEQ ID NO 110
<211> LENGTH: 472
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gly Thr Gln Val Gln Leu Gln Gln Ser Gly Ala Glu Leu Val Lys Pro
1               5                   10                  15

Gly Ala Ser Val Lys Met Ser Cys Lys Ala Phe Gly Tyr Thr Phe Thr
                20                  25                  30

Thr Tyr Pro Ile Glu Trp Met Lys Gln Asn His Gly Lys Ser Leu Glu
            35                  40                  45

Trp Ile Gly Asn Phe His Pro Tyr Asn Asp Asp Thr Lys Tyr Asn Glu
        50                  55                  60

Lys Phe Lys Gly Lys Ala Lys Leu Thr Val Glu Lys Ser Ser Thr Thr
65                  70                  75                  80

Val Tyr Leu Glu Leu Ser Arg Leu Thr Ser Asp Asp Ser Ala Val Tyr
                85                  90                  95

Tyr Cys Ala Arg Glu Asn Tyr Gly Ser His Gly Gly Phe Val Tyr Trp
            100                 105                 110

Gly Gln Gly Thr Leu Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285
```

Val His Asn Ala Lys Thr Lys Pro Arg Glu Glu Gln Tyr Ala Ser Thr
290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
            325                 330                 335

Ile Glu Lys Thr Ile Ser Lys Ala Lys Gly Gln Pro Arg Glu Pro Gln
        340                 345                 350

Val Tyr Thr Leu Pro Pro Ser Arg Asp Glu Leu Thr Lys Asn Gln Val
    355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
            405                 410                 415

Val Asp Lys Ser Arg Trp Gln Gln Gly Asn Val Phe Ser Cys Ser Val
        420                 425                 430

Met His Glu Ala Leu His Asn His Tyr Thr Gln Lys Ser Leu Ser Leu
    435                 440                 445

Ser Pro Gly Lys Gly Gly Gly Ser Gly Gly Gly Ser Gly Gly
450                 455                 460

Gly Gly Ser Gly Gly Gly Ser
465                 470

<210> SEQ ID NO 111
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Thr Gly Glu Asn Val Leu Thr Gln Ser Pro Ala Ile Met Ser Ala Ser
1               5                   10                  15

Pro Gly Glu Lys Val Thr Met Thr Cys Arg Ala Ser Ser Ser Val Ile
            20                  25                  30

Ser Ser Tyr Leu His Trp Tyr Gln Gln Lys Ser Gly Ala Ser Pro Lys
        35                  40                  45

Leu Trp Ile Tyr Ser Thr Ser Asn Leu Ala Ser Gly Val Pro Asp Arg
    50                  55                  60

Phe Ser Gly Ser Gly Ser Gly Thr Ser Tyr Ser Leu Thr Ile Ser Ser
65                  70                  75                  80

Val Glu Ala Glu Asp Ala Ala Thr Tyr Tyr Cys Gln Gln Tyr Asn Gly
                85                  90                  95

Tyr Pro Leu Thr Phe Gly Ala Gly Thr Lys Leu Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys Leu Glu
    210                 215

<210> SEQ ID NO 112
<211> LENGTH: 470
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Gly Thr Glu Val Gln Leu Val Glu Ser Gly Gly Gly Leu Val Gln Pro
1               5                   10                  15

Gly Gly Ser Leu Arg Leu Ser Cys Ala Ala Ser Gly Phe Thr Phe Ser
            20                  25                  30

Asp Ser Trp Ile His Trp Val Arg Gln Ala Pro Gly Lys Gly Leu Glu
        35                  40                  45

Trp Val Ala Trp Ile Ser Pro Tyr Gly Gly Ser Thr Tyr Tyr Ala Asp
    50                  55                  60

Ser Val Lys Gly Arg Phe Thr Ile Ser Ala Asp Thr Ser Lys Asn Thr
65                  70                  75                  80

Ala Tyr Leu Gln Met Asn Ser Leu Arg Ala Glu Asp Thr Ala Val Tyr
            85                  90                  95

Tyr Cys Ala Arg Arg His Trp Pro Gly Gly Phe Asp Tyr Trp Gly Gln
        100                 105                 110

Gly Thr Leu Val Thr Val Ser Ala Ala Ser Thr Lys Gly Pro Ser Val
    115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
        180                 185                 190

Ser Ser Ser Leu Gly Thr Gln Thr Tyr Ile Cys Asn Val Asn His Lys
    195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Ala Ser Thr Tyr Arg
    290                 295                 300

Val Val Ser Val Leu Thr Val Leu His Gln Asp Trp Leu Asn Gly Lys

```
                305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
            355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys Gly Gly Gly Gly Ser Gly Gly Gly Gly Ser Gly Gly Gly Gly
            450                 455                 460

Ser Gly Gly Gly Gly Ser
465                 470

<210> SEQ ID NO 113
<211> LENGTH: 245
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

Gly Thr Gln Val Gln Leu Val Glu Ser Gly Gly Val Val Gln Pro
1               5                   10                  15

Gly Arg Ser Leu Arg Leu Asp Cys Lys Ala Ser Gly Ile Thr Phe Ser
            20                  25                  30

Asn Ser Gly Met His Trp Val Arg Gln Ala Pro Gly Lys Gly Leu Glu
        35                  40                  45

Trp Val Ala Val Ile Trp Tyr Asp Gly Ser Lys Arg Tyr Tyr Ala Asp
    50                  55                  60

Ser Val Lys Gly Arg Phe Thr Ile Ser Arg Asp Asn Ser Lys Asn Thr
65                  70                  75                  80

Leu Phe Leu Gln Met Asn Ser Leu Arg Ala Glu Asp Thr Ala Val Tyr
                85                  90                  95

Tyr Cys Ala Thr Asn Asp Asp Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190
```

```
Thr Gln Thr Tyr Ile Cys Asn Val Asn His Lys Pro Ser Asn Thr Lys
            195                 200                 205

Val Asp Lys Lys Val Glu Pro Lys Ser Cys Asp Lys Thr His Thr Leu
    210                 215                 220

Glu Gly Gly Gly Ser Gly Gly Gly Ser Gly Gly Gly Ser
225                 230                 235                 240

Gly Gly Gly Gly Ser
                245

<210> SEQ ID NO 114
<211> LENGTH: 288
<212> TYPE: PRT
<213> ORGANISM: Homo sapiens

<400> SEQUENCE: 114

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80

Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285

<210> SEQ ID NO 115
<211> LENGTH: 290
<212> TYPE: PRT
<213> ORGANISM: Homo sapiens
```

<400> SEQUENCE: 115

```
Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290
```

<210> SEQ ID NO 116
<211> LENGTH: 273
<212> TYPE: PRT
<213> ORGANISM: Homo sapiens

<400> SEQUENCE: 116

```
Met Ile Phe Leu Leu Leu Met Leu Ser Leu Glu Leu Gln Leu His Gln
1               5                   10                  15

Ile Ala Ala Leu Phe Thr Val Thr Val Pro Lys Glu Leu Tyr Ile Ile
            20                  25                  30

Glu His Gly Ser Asn Val Thr Leu Glu Cys Asn Phe Asp Thr Gly Ser
        35                  40                  45

His Val Asn Leu Gly Ala Ile Thr Ala Ser Leu Gln Lys Val Glu Asn
    50                  55                  60
```

Asp Thr Ser Pro His Arg Glu Arg Ala Thr Leu Leu Glu Glu Gln Leu
 65                  70                  75                  80

Pro Leu Gly Lys Ala Ser Phe His Ile Pro Gln Val Gln Val Arg Asp
                 85                  90                  95

Glu Gly Gln Tyr Gln Cys Ile Ile Ile Tyr Gly Val Ala Trp Asp Tyr
            100                 105                 110

Lys Tyr Leu Thr Leu Lys Val Lys Ala Ser Tyr Arg Lys Ile Asn Thr
        115                 120                 125

His Ile Leu Lys Val Pro Glu Thr Asp Glu Val Glu Leu Thr Cys Gln
130                 135                 140

Ala Thr Gly Tyr Pro Leu Ala Glu Val Ser Trp Pro Asn Val Ser Val
145                 150                 155                 160

Pro Ala Asn Thr Ser His Ser Arg Thr Pro Glu Gly Leu Tyr Gln Val
                165                 170                 175

Thr Ser Val Leu Arg Leu Lys Pro Pro Gly Arg Asn Phe Ser Cys
            180                 185                 190

Val Phe Trp Asn Thr His Val Arg Glu Leu Thr Leu Ala Ser Ile Asp
        195                 200                 205

Leu Gln Ser Gln Met Glu Pro Arg Thr His Pro Thr Trp Leu Leu His
210                 215                 220

Ile Phe Ile Pro Phe Cys Ile Ile Ala Phe Ile Phe Ile Ala Thr Val
225                 230                 235                 240

Ile Ala Leu Arg Lys Gln Leu Cys Gln Lys Leu Tyr Ser Ser Lys Asp
                245                 250                 255

Thr Thr Lys Arg Pro Val Thr Thr Thr Lys Arg Glu Val Asn Ser Ala
                260                 265                 270

Ile

<210> SEQ ID NO 117
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Asp Tyr Lys Asp Asp Asp Asp Lys
1               5

<210> SEQ ID NO 118
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 118

His His His His His His
1               5

<210> SEQ ID NO 119
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 119

Tyr Pro Tyr Asp Val Pro Asp Tyr Ala
1               5

<210> SEQ ID NO 120
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Gly Ser
1

<210> SEQ ID NO 121
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(30)
<223> OTHER INFORMATION: This sequence may encompass 1-6 "Gly Gly Gly
      Gly Ser" repeating units

<400> SEQUENCE: 121

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 122
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

Gly Thr Lys Ser Ser Tyr Ala Ile Ser
1               5
```

MULTISPECIFIC BINDING CONSTRUCTS AGAINST CHECKPOINT MOLECULES AND USES THEREOF

CROSS-REFERENCE TO RELATED APPLICATIONS

This application claims the benefit of priority under 35 U.S.C. § 119(e) of U.S. Provisional Application No. 62/760,801, filed on Nov. 13, 2018; U.S. Provisional Application No. 62/855,580, filed on May 31, 2019; U.S. Application No. 62/898,991, filed on Sep. 11, 2019; and U.S. Application No. 62/931,478, filed on Nov. 6, 2019. The foregoing applications are incorporated herein by reference in their entireties.

SEQUENCE LISTING

The instant application contains a sequence listing which has been submitted electronically in ASCII format and is hereby incorporated by reference in its entirety. Said ASCII copy, created on Nov. 26, 2019, is named 1848492-0002-007-101_SL.txt and is 122,235 bytes in size.

BACKGROUND

Cancer is one of the leading causes of death in both the United States and worldwide. While common treatments such as surgery, radiation, chemotherapy, hormone therapy, targeted therapies, and immunotherapy have decreased the rates of cancer-related deaths during the $20^{th}$ century, there were 14.1 million new cancer cases diagnosed and 8.2 million cancer deaths worldwide as of 2012. Even with improved overall cancer survival rates during the $20^{th}$ century, cancer is still responsible for one in seven deaths worldwide. See American Cancer Society, Global Cancer Facts & FIGS. $3^{rd}$ Edition, Atlanta: American Cancer Society; 2015.

In recent years, an increasing body of evidence suggests that the immune system operates as a significant barrier to tumor formation and progression. The principle that naturally-occurring T cells with anti-tumor potential or activity exist in a patient with cancer has rationalized the development of immunotherapeutic approaches in oncology. Immune cells, such as T cells, macrophages, and natural killer cells, can exhibit anti-tumor activity and effectively control the occurrence and growth of malignant tumors. Tumor-specific or -associated antigens can induce immune cells to recognize and eliminate malignancies (Chen & Mellman, (2013) *Immunity* 39(1):1-10). In spite of the existence of tumor-specific immune responses, malignant tumors often evade or avoid immune attack through a variety of immunomodulatory mechanisms resulting in the failure to control tumor occurrence and progression (Motz & Coukos, (2013) *Immunity* 39(1):61-730). Indeed, an emerging hallmark of cancer is the exploitation of these immunomodulatory mechanisms and the disablement of anti-tumor immune responses, resulting in tumor evasion and escape from immunological killing (Hanahan and Weinberg (2011) *Cell* 144(5):646-674).

Novel approaches in the immunotherapy of cancer involve counteracting these immune evasion and escape mechanisms and inducing the endogenous immune system to reject tumors. However, there remains a need for novel therapeutics that effectively counteract immune evasion, particularly in cancer therapeutics.

SUMMARY OF THE DISCLOSURE

The present disclosure is based, in part, on novel multispecific and multivalent constructs targeting both PD-1 and PD-L1, such as a bispecific and tetravalent construct. As demonstrated herein, these multispecific constructs have improved in vitro and in vivo potency as compared to combinations of individual antibodies, as well as compared to clinical checkpoint blockade agents. Also provided herein are novel monoclonal anti-PD-1 antibodies and antigen-binding fragments thereof, and novel monoclonal anti-PD-L1 antibodies and antigen-binding fragments thereof, for use in such multispecific and multivalent constructs. Some of these novel monoclonal anti-PD-1 antibodies and novel monoclonal anti-PD-L1 antibodies share a common light chain, thereby allowing for the generation of multispecific and multivalent constructs having surprising excellent drug-like properties (DLPs) and ease of manufacturability, as well as affinities similar to their parental antibodies. The present disclosure is also based, in part, on the discovery that blocking the interaction between PD-1 expressed by an immune cell and its ligand (e.g., PD-L1 or PD-L2) expressed on a second cell, while bridging the immune cell and the second cell (e.g., another immune cell, or a tumor cell that expresses a PD-1 ligand) strongly enhance, for example, T cell proliferation, IFNγ production and secretion, and the cytolytic activity of T cells. Thus, provided herein are compositions that block the interaction between PD-1 and its ligand while promoting the interaction of (bridging) the cells on which PD-1 and its ligand (PD-L1 or PD-L2) are expressed. As exemplified herein, such compositions of the present disclosure with the capacity to "block and bridge" provide superior anti-tumor efficacy (as measured, e.g., by IFNγ production and secretion and in vivo activity) as compared to, e.g., a cocktail having a stoichiometric amount of agents that separately bind the receptor and ligand; or a single agent that binds either the receptor or the ligand. It was also found that the multispecific and multivalent constructs targeting both PD-1 and PD-L1 described herein cause loss of expression of PD-1 on the cell surface, in a valency-dependent fashion. This loss of PD-1 expression was not observed when a combination of the parental antibodies were used in stoichiometrically equivalent amounts. Accordingly, the multispecific and multivalent constructs targeting both PD-1 and PD-L1 described herein provide novel immunotherapeutic agents with increased potency and efficacy for use in the treatment of cancer.

In some embodiments, any of the multispecific antigen-binding constructs disclosed herein binds to at least two different receptors or epitopes (e.g., PD-1 and PD-L1), wherein the two different receptors or epitopes bound by the multispecific antigen-binding construct are expressed on the surface of the same cell. For example, in some embodiments, the multispecific antigen-binding construct simultaneously binds to PD-1 and PD-L1, wherein the PD-1 and PD-L1 are expressed on the surface of the same cell. In some embodiments, any of the multispecific antigen-binding constructs disclosed herein binds to at least two different receptors or epitopes (e.g., PD-1 and PD-L1), wherein the two different receptors or epitopes bound by the multispecific antigen-binding construct are expressed on the surface of two different cells. For example, in some embodiments, the multispecific antigen-binding construct simultaneously binds to PD-1 expressed on the surface of a first cell and to a PD-1 ligand, e.g., PD-L1 or PD-L2, expressed on the surface of a second cell.

In some embodiments, the disclosure provides for a multispecific antigen-binding construct comprising at least two antigen-binding arms, wherein a first arm binds PD-1 expressed by an immune cell, and a second arm binds a PD-1 ligand which is expressed by a second cell, wherein the multispecific antigen-binding construct blocks the interaction of PD-1 and PD-1 ligand. In some embodiments, the PD-1 ligand is PD-L2. In some embodiments, the PD-1 ligand is PD-L1. In some embodiments, the immune cell is a T cell. In some embodiments, the T cell is a CD8+ T cell. In some embodiments, the immune cell is a natural killer (NK) cell. In some embodiments, the immune cell is a macrophage. In some embodiments, the second cell is a second immune cell. In some embodiments, the second immune cell is any one or more of a T cell, a B cell, a macrophage, a myeloid-derived suppressor cell, a dendritic cell, or a mesenchymal stromal cell. In some embodiments, the second immune cell is a regulatory T cell. In some embodiments, the second cell is a tumor cell. In some embodiments, the tumor cell is selected from the group consisting of a hematological cancer, a lymphoma, a myeloma, a leukemia, a neurological cancer, melanoma, breast cancer, a prostate cancer, a colorectal cancer, lung cancer, head and neck cancer, a gastrointestinal cancer, liver cancer, pancreatic cancer, a genitourinary cancer, a bone cancer, renal cancer, and a vascular cancer. In some embodiments, both arms have a $K_D$ of at least $1\times10^{-7}$ M, at least $1\times10^{-8}$ M, at least $1\times10^{-9}$ M, or at least $1\times10^{-10}$ M. In some embodiments, the binding of one arm to its target does not block the binding of the other arm to its target. In some embodiments, the first arm and second arm bind to their respective targets and both arms remain bound concurrently. In some embodiments, binding of the first arm and the second arm to their respective targets can bridge the immune cell and the second cell together. In some embodiments, the bridging of the immune cell and the second cell is determined by flow cytometry. In some embodiments, the first arm is an antagonist of PD-1.

In some embodiments of the multispecific antigen-binding constructs, the first arm binds to PD-1 and comprises: (a) a heavy chain variable region comprising (i) a CDRH1 comprising SEQ ID NO: 70 (FTFX$_1$X$_2$YAX$_3$X$_4$, wherein X$_1$=S, R, G, or N; X$_2$=D, S, N, A, R, or G; X$_3$=M or L; X$_4$=S, L, or N); (ii) a CDRH2 comprising SEQ ID NO: 71 (SAISNSGTYTYYA); and (iii) a CDRH3 comprising SEQ ID NO: 72 (ARGLDFIVGX$_5$TGNDY, wherein X$_5$=A, Y, or R); and (b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the CDRH1 of the first arm comprises SEQ ID NO: 73 (FTFSDYAMS), CDRH2 of the first arm comprises SEQ ID NO: 71 (SAISNSGTYTYYA) and CDRH3 of the first arm comprises SEQ ID NO: 74 (ARGLDFIVGATGNDY). In some embodiments, the CDRH1 of the first arm comprises SEQ ID NO: 73 (FTFSDYAMS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 76 (FTFSSYAMS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 77 (FTFSSYAML), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 78 (FTFSNYALS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 79 (FTFSAYAMN), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 80 (FTFRSYAMS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 81 (FTFGRYAMS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 82 (FTFNSYAMS), CDRH2 of the first arm comprises SEQ ID NO: 71 (SAISNSGTYTYYA) and CDRH3 of the first arm comprises SEQ ID NO: 75 (ARGLDFIVGYTGNDY). In some embodiments, the CDRH1 of the first arm comprises SEQ ID NO: 83 (FTFSNYAMS), CDRH2 of the first arm comprises SEQ ID NO: 71 (SAISNSGTYTYYA) and CDRH3 of the first arm comprises SEQ ID NO: 74 (ARGLDFIVGATGNDY). In some embodiments, the CDRH1 of the first arm comprises SEQ ID NO: 84 (FTFSGYAMS), CDRH2 of the first arm comprises SEQ ID NO: 71 (SAISNSGTYTYYA) and CDRH3 of the first arm comprises SEQ ID NO: 85 (ARGLDFIVGRTGNDY). In some embodiments, the CDRH1 of the first arm comprises SEQ ID NO: 86 (FTFSSYAMN), CDRH2 of the first arm comprises SEQ ID NO: 71 (SAISNSGTYTYYA) and CDRH3 of the first arm comprises SEQ ID NO: 85 (ARGLDFIVGRTGNDY). In some embodiments, the CDRH1 of the first arm comprises SEQ ID NO: 80 (FTFRSYAMS), CDRH2 of the first arm comprises SEQ ID NO: 71 (SAISNSGTYTYYA) and CDRH3 of the first arm comprises SEQ ID NO: 85 (ARGLDFIVGRTGNDY).

In some embodiments, the CDRL1 of the first arm comprises SEQ ID NO: 9 (RASQSISSYLN), CDRL2 of the first arm comprises SEQ ID NO: 5 (AASSLQS) and CDRL3 of the first arm comprises SEQ ID NO: 10 (QQSYSTPLT).

In some embodiments, the heavy chain variable region of the first arm comprises an amino acid sequence that is at least 90% identical to SEQ ID NO: 87. In some embodiments, the heavy chain variable region of the first arm comprises an amino acid sequence that is at least 90% identical to SEQ ID NO: 88. In some embodiments, the heavy chain variable region of the first arm comprises an amino acid sequence that is at least 90% identical to SEQ ID NO: 89. In some embodiments, the heavy chain variable region of the first arm comprises an amino acid sequence that is at least 90% identical to SEQ ID NO: 90. In some embodiments, the heavy chain variable region of the first arm comprises an amino acid sequence that is at least 90% identical to SEQ ID NO: 91. In some embodiments, the heavy chain variable region of the first arm comprises an amino acid sequence that is at least 90% identical to SEQ ID NO: 92. In some embodiments, the heavy chain variable region of the first arm comprises an amino acid sequence that is at least 90% identical to SEQ ID NO: 93. In some embodiments, the heavy chain variable region of the first arm comprises an amino acid sequence that is at least 90% identical to SEQ ID NO: 94. In some embodiments, the heavy chain variable region of the first arm comprises an amino acid sequence that is at least 90% identical to SEQ ID NO: 95. In some embodiments, the heavy chain variable region of the first arm comprises an amino acid sequence that is at least 90% identical to SEQ ID NO: 96. In some embodiments, the heavy chain variable region of the first arm comprises an amino acid sequence that is at least 90% identical to SEQ ID NO: 97. In some embodiments, the heavy chain variable region of the first arm comprises an amino acid sequence that is at least 90% identical to SEQ ID NO: 98. In some embodiments, the heavy chain variable region of the first arm comprises an amino acid sequence that is at least 90% identical to SEQ ID NO: 99. In some embodiments, the light chain variable region of the first arm comprises an amino acid sequence that is at least 90% identical to SEQ ID NO: 59.

In some embodiments, the second arm is an antagonist of the PD-1 ligand. In some embodiments, the second arm is an antagonist of PD-L2. In some embodiments, the second arm is an antagonist of PD-L1. In some embodiments, the second arm binds to PD-L1 and comprises: a. a heavy chain variable region comprising (i) a CDRH1 comprising SEQ ID NO: 1 (GTFSSYAIN); (ii) a CDRH2 comprising SEQ ID NO: 2 (GGIIPX$_1$X$_2$GX$_3$ATYA, wherein X$_1$ is V or I; X$_2$ is F, L, or V; and X$_3$ is T or A); and (iii) a CDRH3 comprising SEQ ID NO: 3 (ARLKX$_1$ELKDAFDI, wherein X$_1$ is G, F, or N); and b. a light chain variable region comprising: (i) a CDRL1 comprising SEQ ID NO: 4 (RASQX$_1$ISSYLN, wherein X$_1$ is S, W, or Q); (ii) a CDRL2 comprising SEQ ID NO: 5 (AASSLQS); and (iii) a CDRL3 comprising SEQ ID NO: 6 (X$_1$QSYSTPLT, wherein X$_1$ is Q or F).

In some embodiments, the CDRH1 of the second arm comprises SEQ ID NO: 1 (GTFSSYAIN), CDRH2 of the second arm comprises SEQ ID NO: 7 (GGIIPILGAATYA) and CDRH3 of the second arm comprises SEQ ID NO: 8 (ARLKGELKDAFDI). In some embodiments, the CDRH1 of the second arm comprises SEQ ID NO: 1 (GTFSSYAIN), CDRH2 of the second arm comprises SEQ ID NO: 7 (GGIIPILGAATYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT). In some embodiments, the CDRH1 of the second arm comprises SEQ ID NO: 1 (GTFSSYAIN), CDRH2 of the second arm comprises SEQ ID NO: 11 (GGIIPVFGTATYA) and CDRH3 of the second arm comprises SEQ ID NO: 8 (ARLKGELKDAFDI). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 12 (RASQWISSYLN); CDRL2 of the second arm comprises SEQ ID NO: 5 (AASSLQS); and CDRL3 of the second arm comprises SEQ ID NO: 10 (QQSYSTPLT). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 13 (RASQQISSYLN); CDRL2 of the second arm comprises SEQ ID NO: 5 (AASSLQS); and CDRL3 of the second arm comprises SEQ ID NO: 10 (QQSYSTPLT). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 15 (GGIIPIFGIANYA) and CDRH3 of the second arm comprises SEQ ID NO: 8 (ARLKGELKDAFDI). In some embodiments, the CDRH1 of the second arm comprises SEQ ID NO: 1 (GTFSSYAIN), CDRH2 of the second arm comprises SEQ ID NO: 15 (GGIIPIFGIANYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 16 (GGIIPNFGTATYA) and CDRH3 of the second arm comprises SEQ ID NO: 17 (ARLKGELKGAGDI). In some embodiments, the CDRH1 of the second arm comprises SEQ ID NO: 1 (GTFSSYAIN), CDRH2 of the second arm comprises SEQ ID NO: 16 (GGIIPNFGTATYA), CDRH3 of the second arm comprises SEQ ID NO: 17 (ARLKGELKGAGDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), and CDRH3 of the second arm comprises SEQ ID NO: 18 (ARLKFELKDAFDI). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 18 (ARLKFELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), and CDRH3 of the second arm comprises SEQ ID NO: 19 (ARLKGELKDAFDE). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 19 (ARLKGELKDAFDE), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), and CDRH3 of the second arm comprises SEQ ID NO: 20 (ARLKNELKDAFDI). In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 20 (ARLKNELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 21 (GGVIPFLGTANYA), and CDRH3 of the second arm comprises SEQ ID NO: 22 (ARLKGILKDALDI). In some embodiments, the CDRH1 of the second arm comprises SEQ ID NO: 1 (GTFSSYAIN), CDRH2 of the second arm comprises SEQ ID NO: 21 (GGVIPFLGTANYA), CDRH3 of the second arm comprises SEQ ID NO: 22 (ARLKGILKDALDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 29 (GRIIPIFGTADYA), and CDRH3 of the second arm comprises SEQ ID NO: 8 (ARLKGELKDAFDI). In some embodiments, the CDRH1 of the second arm comprises SEQ ID NO: 1 (GTFSSYAIN), CDRH2 of the second arm comprises SEQ ID NO: 29 (GRIIPIFGTADYA), CDRH3 of the second arm comprises SEQ ID NO: 8 (ARLKGELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 31 (GGIIPILGTATYA), and CDRH3 of the second arm comprises SEQ ID NO: 32 (ARRKGELKDAFDI). In some embodiments, the CDRH1 of the second arm comprises SEQ ID NO: 1 (GTFSSYAIN), CDRH2 of the second arm comprises SEQ ID NO: 31 (GGIIPILGTATYA), CDRH3 of the second arm comprises SEQ ID NO: 32 (ARRKGELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 33 (GGIIPIVATANYA), and CDRH3 of the second arm comprises SEQ ID NO: 32 (ARRKGELKDAFDI). In some embodiments, the CDRH1 of the second arm comprises SEQ ID NO: 1 (GTFSSYAIN), CDRH2 of the second arm comprises SEQ ID NO: 33 (GGIIPIVATANYA), CDRH3 of the second arm comprises SEQ ID NO: 32 (ARRKGELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 34 (GGIIPIFGKATYA), and CDRH3 of the second arm comprises SEQ ID NO: 32 (ARRKGELKDAFDI). In some embodiments, the CDRH1 of the second arm comprises SEQ ID NO: 1 (GTFSSYAIN), CDRH2 of the second arm comprises SEQ ID NO: 34 (GGIIPIFGKATYA), CDRH3 of the second arm comprises SEQ ID NO: 32 (ARRKGELKDAFDI), CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 10 (QQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 38 (FQSYSTPLT).

In some embodiments, the CDRH1 of the second arm comprises SEQ ID NO: 1 (GTFSSYAIN), CDRH2 of the second arm comprises SEQ ID NO: 11 (GGIIPVFGTATYA), CDRH3 of the second arm comprises SEQ ID NO: 8 (ARLKGELKDAFDI); CDRL1 of the second arm comprises SEQ ID NO: 9 (RASQSISSYLN); CDRL2 of the second arm comprises SEQ ID NO: 5 (AASSLQS); and CDRL3 of the second arm comprises SEQ ID NO: 39 (QQSYSTILT).

In some embodiments, the second arm comprises: a. a heavy chain variable region comprising (i) a CDRH1 comprising SEQ ID NO: 14 (GTFSSYAFS), (ii) a CDRH2 comprising SEQ ID NO: 11 (GGIIPVFGTATYA) and (iii) a CDRH3 comprising SEQ ID NO: 8 (ARLKGELKDAFDI); and b. a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 23 (GTFSSYAIS), (ii) a CDRH2 comprising SEQ ID NO: 24 (GGIIPIVGIANYA), and (iii) a CDRH3 comprising SEQ ID NO: 8 (ARLKGELKDAFDI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 23 (GTFSSYAIS), (ii) a CDRH2 comprising SEQ ID NO: 11 (GGIIPVFGTATYA), and (iii) a CDRH3 comprising SEQ ID NO: 25 (ARLKGEFKDAFDI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 23 (GTFSSYAIS), (ii) a CDRH2 comprising SEQ ID NO: 26 (GRIIPLFGTAHYA), and (iii) a CDRH3 comprising SEQ ID NO: 8 (ARLKGELKDAFDI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 23 (GTFSSYAIS), (ii) a CDRH2 comprising SEQ ID NO: 27 (GRINPILGTANYA), and (iii) a CDRH3 comprising SEQ ID NO: 28 (ARLKGELKDAFSI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 23 (GTFSSYAIS), (ii) a CDRH2 comprising SEQ ID NO: 11 (GGIIPVFGTATYA), and (iii) a CDRH3 comprising SEQ ID NO: 30 (ARLKGELKCAFDI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 122 (GTKSSYAIS), (ii) CDRH2 comprising SEQ ID NO: 11 (GGIIPVFGTATYA), and (iii) a CDRH3 comprising SEQ ID NO: 30 (ARLKGELKCAFDI). In some embodiments, the second arm further comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm comprises a heavy chain variable region comprising (i) a CDRH1 comprising SEQ ID NO: 36 (GPFRSHAVS), (ii) a CDRH2 comprising SEQ ID NO: 11 (GGIIPVFGTATYA), and (iii) a CDRH3 comprising SEQ ID NO: 37 (ARLKSELKDAFDI). In some embodiments, the second arm comprises a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments, the second arm that binds PD-L1 comprises a heavy chain variable region comprising an amino acid sequence that is at least 90% identical to any one of SEQ ID NOs: 35, 40, 41, 42, 43, 44, 45, 46, 47, 48, 49, 50, 51, 52, 53, 54, 55, 56, 57, or 58 and a light chain variable region comprising an amino acid sequence that is at least 90% identical to any one of SEQ ID NOs: 59, 60, 61, 62, or 63.

In some embodiments, the heavy chain variable region of the second arm comprises an amino acid sequence that is at least 90% identical to SEQ ID NO: 35 (QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKGELKDAFDIWGQGTMV TVSS). In some embodiments, the heavy chain variable region of the second arm comprises an amino acid sequence that is at least 90% identical to SEQ ID NO: 40 (QVQLVQSGAEVKKPGSSVKVSCKASGGTFSSYAFSWVRQAPGQGLEWMGGIIPVFGTATYAQKFQGRVTITADESTSTAYMELSSLRSEDTAVYYCARLKGELKDAFDIWGQGTLVT VSS). In some embodiments, the heavy chain variable region of the second arm comprises an amino acid sequence that is at least 90% identical to SEQ ID NO: 41 (QVQLVQSGAEVKKPGSSVKVSCKASGGTFSSYAINWVRQAPGQGLEWMGGIIPIFGIAN YAQKFQGRVTITADESTSTAYMELSSLRSEDTAVYYCARLKGELKDAFDIWGQGTLVT VSS). In some embodiments, the heavy chain variable region of the second arm comprises an amino acid sequence that is at least 90% identical to SEQ ID NO: 42 (QVQLVQSGAEVKKPGSSVKVSCKASGGTFSSYAINWVRQAPGQGLEWMGGIIPNFGTA TYAQKFQGRVTITADESTSTAYMELSSLRSEDTAVYYCARLKGELKGAGDIWGQGTLV TVSS). In some embodiments, the heavy chain variable region of the second arm comprises an amino acid sequence that is at least 90% identical to SEQ ID NO: 43 (QVQLVQSGAEVKKPGSSVKVSCKASGGTFSSYAINWVRQAPGQGLEWMGGIIPVFGTA TYAQKFQGRVTITADESTSTAYMELSSLRSEDTAVYYCARLKFELKDAFDIWGQGTLVT VSS). In some embodiments, the heavy chain variable region of the second arm comprises an amino acid sequence that is at least 90% identical to SEQ ID NO: 44 (QVQLVQSGAEVKKPGSSVKVSCKASGGTFSSYAINWVRQAPGQGLEWMGGIIPVFGTA TYAQKFQGRVTITADESTSTAYMELSSLRSEDTAVYYCARLKGELKDAFDEWGQGTLV TVSS). In some embodiments, the heavy chain variable region of the second arm comprises an amino acid sequence that is at least 90% identical to SEQ ID NO: 45 (QVQLVQSGAEVKKPGSSVKVSCKASGGTFSSYAINWVRQAPGQGLEWMGGIIPVFGTA TYAQKFQGRVTITADESTSTAYMELSSLRSEDTAVYYCARLKGELKDAFDIWGQGTLVT AST). In some embodiments, the heavy chain variable region of the second arm comprises an amino acid sequence that is at least 90% identical to SEQ ID NO: 46 (QVQLVQSGAEVKKPGSSVKVSCKASGGTFSSYAINWVRQAPGQGLEWMGGIIPVFGTA TYAQKFQGRVTITADESTSTAYMELSSLRSEDTAVYYCARLKNELKDAFDIWGQGTLVT VSS). In some embodiments, the heavy chain variable region of the second arm comprises an amino acid sequence that is at least 90% identical to SEQ ID NO: 47 (QVQLVQSGAEVKKPGSSVKVSCKASGGTFSSYAINWVRQAPGQGLEWMGGVIPFLGT ANYAQKFQGRVTITADESTSTAYMELSSLRSEDTAVYYCARLKGILKDALDIWGQGTLV TVSS). In some embodiments, the heavy chain variable region of the second arm comprises an amino acid sequence that is at least 90% identical to SEQ ID NO: 48 (QVQLVQSGAEVKKPGSSVKVSCKASGGTFSSYAISWVRQAPGQDLEWMGGIIPIVGIAN YAQKFQGRVTITADESTSTAYMELSSLRSEDTAVYYCARLKGELKDAFDIWGQGTLVT VSS). In some embodiments, the heavy chain variable region of the second arm comprises an amino acid sequence that is at least 90% identical to SEQ ID NO: 49 (QVQLVQSGAEVKKPGSSVKVSCKASGGTFSSYAISWVRQAPGQGLEWMGGIIPVFGTA TYAQKFQGRVTITADESTSTAYMELSSLRSEDTAVYYCARLKGEFKDAFDIWGQGTLVT VSS). In some embodiments, the heavy chain variable region of the second arm comprises an amino acid sequence that is at least 90% identical to SEQ ID NO: 50 (QVQLVQSGAEVKKPGSSVKVSCKASGGTFSSYAISWVRQAPGQGLEWMGRIIPLFGTA HYAQKFQGRVTITADESTSTAYMELSSLRSEDTAVYY- CARLKGELKDAFDIWGQGTLV TVSS). In some embodiments, the heavy chain variable region of the second arm comprises an amino acid sequence that is at least 90% identical to SEQ ID NO: 51 (QVQLVQS-GAEVKKPGSSVKVSCK-ASGGTFSSYAISWVRQAPGQGLEWMGRINPILGTA NYAQKFQGRVTITADESTSTAYMELSSLRSEDTAVYY-CARLKGELKDAFSIWGQGTLVT VSS). In some embodiments, the heavy chain variable region of the second arm comprises an amino acid sequence that is at least 90% identical to SEQ ID NO: 52 (QVQLVQS-GAEVKKPGSSVKVSCK-ASGGTFSSYAINWVRQAPGQGLEWMGRIIPIFGTA DYAQKFQGRVTITADESTSTAYMELSSLRSEDTAVYY-CARLKGELKDAFDIWGQGTLV TVSS). In some embodiments, the heavy chain variable region of the second arm comprises an amino acid sequence that is at least 90% identical to SEQ ID NO: 53 (QVQLVQS-GAEVKKPGSSVKVSCK-ASGGKFSSYAISWVRQAPGQGLEWMGGIIPVFGTA TYAQKFQGRVTITADESTSTAYMELSSLRSEDTAVYY-CARLKGELKCAFDIWGQGTLVT VSS). In some embodiments, the heavy chain variable region of the second arm comprises an amino acid sequence that is at least 90% identical to SEQ ID NO: 54 (QVQLVQS-GAEVKKPGSSVKVSCK-ASGGTFSSYAINWVRQAPGQGLEWMGGIIPILGTA TYAQKFQGRVTITADESTSTAYMELSSLRSEDTAVYY-CARRKGELKDAFDIWGQGTLVT VSS). In some embodiments, the heavy chain variable region of the second arm comprises an amino acid sequence that is at least 90% identical to SEQ ID NO: 55 (QVQLVQS-GAEVKKPGSSVKVSCK-ASGGTFSSYAINWVRQAPGQGLEWMGGIIPILGAA TYAQKFQGRVTITADESTSTAYMELSSLRSEDTAVYY-CARLKGELKDAFDIWGQGTLVT VSS). In some embodiments, the heavy chain variable region of the second arm comprises an amino acid sequence that is at least 90% identical to SEQ ID NO: 56 (QVQLVQS-GAEVKKPGSSVKVSCK-ASGGTFSSYAINWVRQAPGQGLEWMGGIIPIVATA NYAQKFQGRVTITADESTSTAYMELSSLRSEDTAVYY-CARRKGELKDAFDIWGQGTLV TVSS). In some embodiments, the heavy chain variable region of the second arm comprises an amino acid sequence that is at least 90% identical to SEQ ID NO: 57 (QVQLVQS-GAEVKKPGSSVKVSCK-ASGGTFSSYAINWVRQAPGQGLEWMGGIIPIFGKA TYAQKFQGRVTITADESTSTAYMELSSLRSEDTAVYY-CARRKGELKDAFDIWGQGTLVT VSS). In some embodiments, the heavy chain variable region of the second arm comprises an amino acid sequence that is at least 90% identical to SEQ ID NO: 58 (QVQLVQS-GAEVKKPGSSVKVSCKASGGPFR-SHAVSWVRQAPGQGLEWMGGIIPVFGT ATYAQKFQGRVTITADESTSTAYMELSSLRSED-TAVYYCARLKSELKDAFDIWGQGTLV TVSS). In some embodiments, the light chain variable region of the second arm comprises an amino acid sequence that is at least 90% identical to SEQ ID NO: 59 (DIQMTQSPSSL-SASVGDRVTITCRASQSISSYLNWYQQKPGKAPKLLI-YAASSLQSGVPS RFSGSGSGTDFTLTISSLQPEDFA-TYYCQQSYSTPLTFGGGTKVEIK). In some embodiments, the light chain variable region of the second arm comprises an amino acid sequence that is at least 90% identical to SEQ ID NO: 60 (DIQMTQSPSSL-SASVGDRVTITCRASQWIS-SYLNWYQQKPGKAPKLLIYAASSLQSGVP SRFSGSGSGTDFTLTISSLQPEDFATYYCQQSYS-TPLTFGGGTKVEIK). In some embodiments, the light chain variable region of the second arm comprises an amino acid sequence that is at least 90% identical to SEQ ID NO: 61 (DIQMTQSPSSLSASVGDRVTITCRASQQIS-SYLNWYQQKPGKAPKLLIYAASSLQSGVPS RFSGSGSGTDFTLTISSLQPEDFATYYCQQSYS-TPLTFGGGTKVEIK). In some embodiments, the light chain variable region of the second arm comprises an amino acid sequence that is at least 90% identical to SEQ ID NO: 62 (DIQMTQSPSSLSASVGDRVTITCRASQSIS-SYLNWYQQKPGKAPKLLIYAASSLQSGVPS RFSGSGSGTDFTLTISSLQPEDFATYYCFQSYS-TPLTFGGGTKVEIK). In some embodiments, the light chain variable region of the second arm comprises an amino acid sequence that is at least 90% identical to SEQ ID NO: 63 (DIQMTQSPSSLSASVGDRVTITCRASQSIS-SYLNWYQQKPGKAPKLLIYAASSLQSGVPS RFSGSGSGTDFTLTISSLQPEDFATYYCQQSYS-TILTFGGGTKVEIK).

In some embodiments of any of the aspects described herein, the construct is a bispecific antibody. In some embodiments, the bispecific antibody is an antagonist of both PD-1 and PD-1 ligand. In some embodiments, the construct comprises a common light chain. In some embodiments, one or both of the arms is an aptamer. In some embodiments, one or both of the arms is a protein other than an antibody. In some embodiments, the construct comprises at least two bispecific antibodies. In some embodiments, one of the at least two bispecific antibodies ismonovalent for PD-1. In some embodiments, one of the at least two bispecific antibodies ismonovalent for PD-1 ligand. In some embodiments, at least one of the arms is a bivalent antibody specific for PD-1. In some embodiments, at least one of the arms is a bivalent antibody specific for PD-L1. In some embodiments, at least one of the arms is a bivalent antibody specific for PD-1, and at least one of the arms is a bivalent antibody specific for PD-L1. In some embodiments, at least one of the arms is bivalent for PD-1. In some embodiments, at least one of the arms is bivalent for PD-L1. In some embodiments, at least one of the arms is bivalent for PD-1, and at least one of the arms is bivalent for PD-L1. In some embodiments, the bispecific antibody binds two different epitopes on PD-1. In some embodiments, the bispecific antibody binds two different epitopes on the PD-1 ligand.

In some embodiments, any of the multispecific antigen-binding constructs disclosed herein comprises at least two monospecific antibodies. In some embodiments, at least one of the monospecific antibodies is an anti-PD-1 antibody. In some embodiments, the anti-PD-1 antibody is a bivalent anti-PD-1 antibody. In some embodiments, at least one of the monospecific antibodies is an anti-PD-L1 antibody. In some embodiments, the anti-PD-1 antibody is a bivalent anti-PD-L1 antibody. In some embodiments, the construct comprises a bivalent anti-PD-1 antibody and a bivalent anti-PD-L1 antibody. In some embodiments, the construct is a fusion construct in which a polypeptide comprising the variable heavy chain of the anti-PD-1 antibody is fused to a polypeptide comprising the variable heavy chain of the anti-PD-L1 antibody. In some embodiments, the polypeptide comprising the variable heavy chain of the anti-PD-1 antibody is fused to the polypeptide comprising the variable heavy chain of the anti-PD-L1 antibody by means of a linker. In some embodiments, the fusion construct comprises a common light chain. In some embodiments, the N-terminal variable heavy chain of the fusion construct binds to PD-1 in the presence of the common light chain, and the C-terminal variable heavy chain of the fusion construct binds to PD-L1 in the presence of the common light chain. In some embodiments, the N-terminal variable heavy chain of the fusion construct binds to PD-L1 in the presence of the common light chain, and the C-terminal variable heavy chain of the fusion construct binds to PD-1 in the presence of the common light chain.

In some aspects and embodiments, the disclosure provides for a multispecific antigen-binding construct comprising at least two units of antigen-binding, wherein a first unit of antigen-binding binds PD-1, and a second unit of antigen-binding binds a PD-1 ligand. In some embodiments, the first unit of antigen-binding binds PD-1 expressed by an immune cell. In some embodiments, the second unit of antigen-binding binds PD-1 expressed by a second cell. In some embodiments, the multispecific antigen-binding construct blocks the interaction of PD-1 and a PD-1 ligand, such as PD-L1 or PD-L2. In some embodiments, the multispecific antigen-binding construct blocks the interaction of PD-1 and a PD-1 ligand, such as PD-L1 or PD-L2. In some embodiments, the multispecific antigen-binding construct comprises at least two units of antigen-binding that bind PD-1. In some embodiments, the multispecific antigen-binding construct comprises two units of antigen-binding that bind PD-1. In some embodiments, the multispecific antigen-binding construct comprises at least two units of antigen-binding that bind a PD-1 ligand, such as PD-L1 or PD-L2. In some embodiments, the multispecific antigen-binding construct comprises two units of antigen-binding that bind a PD-1 ligand, such as PD-L1 or PD-L2. In some embodiments, the multispecific antigen-binding construct comprises at least four units of antigen-binding, wherein two units of antigen-binding bind PD-1 and two units of antigen-binding bind a PD-1 ligand, such as PD-L1 or PD-L2. In some embodiments, the multispecific antigen-binding construct comprises four units of antigen-binding, wherein two units of antigen-binding bind PD-1 and two units of antigen-binding bind a PD-1 ligand, such as PD-L1 or PD-L2. In some embodiments, each unit of antigen-binding is capable of binding independently to its cognate antigen, i.e., PD-1 or a PD-1 ligand, such as PD-L1 or PD-L2. In some embodiments, the multispecific antigen-binding construct promotes loss of PD-1 expression from a cell. In some embodiments, the loss of PD-1 expression is due to PD-1 shedding. In some embodiments, the multispecific antigen-binding construct blocks interaction of PD-1 and the PD-1 ligand, such as PD-L1 or PD-L2. In some embodiments, the multispecific antigen-binding construct comprises a common light chain. For example, at least two units of antigen-binding comprise a common light chain.

In some embodiments, the first unit of antigen-binding binds PD-1 and comprises:
  (a) a heavy chain variable region comprising (i) a CDRH1 comprising SEQ ID NO: 70 (FTFX$_1$X$_2$YAX$_3$X$_4$, wherein X$_1$=S, R, G, or N; X$_2$=D, S, N, A, R, or G; X$_3$=M or L; X$_4$=S, L, or N); (ii) a CDRH2 comprising SEQ ID NO: 71 (SAISNSGTYTYYA); and (iii) a CDRH3 comprising SEQ ID NO: 72 (ARGLDFIVGX$_5$TGNDY, wherein X$_5$=A, Y, or R); and
  (b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some such embodiments, the first unit of antigen-binding binds PD-1 and comprises:
  (a) a CDRH1 comprising SEQ ID NO: 73 (FTFSDYAMS), a CDRH2 comprising SEQ ID NO: 71 (SAISNSGTYTYYA), and a CDRH3 comprising SEQ ID NO: 74 (ARGLDFIVGATGNDY);
  (b) a CDRH1 comprising SEQ ID NO: 73 (FTFSDYAMS), a CDRH2 comprising SEQ ID NO: 71 (SAISNSGTYTYYA), and a CDRH3 comprising SEQ ID NO: 75 (ARGLDFIVGYTGNDY);
  (c) a CDRH1 comprising SEQ ID NO: 76 (FTFSSYAMS), a CDRH2 comprising SEQ ID NO: 71 (SAISNSGTYTYYA), and a CDRH3 comprising SEQ ID NO: 75 (ARGLDFIVGYTGNDY);
  (d) a CDRH1 comprising SEQ ID NO: 77 (FTFSSYAML), a CDRH2 comprising SEQ ID NO: 71 (SAISNSGTYTYYA), and a CDRH3 comprising SEQ ID NO: 75 (ARGLDFIVGYTGNDY);
  (e) a CDRH1 comprising SEQ ID NO: 78 (FTFSNYALS), a CDRH2 comprising SEQ ID NO: 71 (SAISNSGTYTYYA), and a CDRH3 comprising SEQ ID NO: 75 (ARGLDFIVGYTGNDY);
  (f) a CDRH1 comprising SEQ ID NO: 79 (FTFSAYAMN), a CDRH2 comprising SEQ ID NO: 71 (SAISNSGTYTYYA), and a CDRH3 comprising SEQ ID NO: 75 (ARGLDFIVGYTGNDY);
  (g) a CDRH1 comprising SEQ ID NO: 80 (FTFRSYAMS), a CDRH2 comprising SEQ ID NO: 71 (SAISNSGTYTYYA), and a CDRH3 comprising SEQ ID NO: 75 (ARGLDFIVGYTGNDY);
  (h) a CDRH1 comprising SEQ ID NO: 81 (FTFGRYAMS), a CDRH2 comprising SEQ ID NO: 71 (SAISNSGTYTYYA), and a CDRH3 comprising SEQ ID NO: 75 (ARGLDFIVGYTGNDY);
  (i) a CDRH1 comprising SEQ ID NO: 82 (FTFNSYAMS), a CDRH2 comprising SEQ ID NO: 71 (SAISNSGTYTYYA), and a CDRH3 comprising SEQ ID NO: 75 (ARGLDFIVGYTGNDY);
  (j) a CDRH1 comprising SEQ ID NO: 83 (FTFSNYAMS), a CDRH2 comprising SEQ ID NO: 71 (SAISNSGTYTYYA), and a CDRH3 comprising SEQ ID NO: 74 (ARGLDFIVGATGNDY);
  (k) a CDRH1 comprising SEQ ID NO: 84 (FTFSGYAMS), a CDRH2 comprising SEQ ID NO: 71 (SAISNSGTYTYYA), and a CDRH3 comprising SEQ ID NO: 85 (ARGLDFIVGRTGNDY);
  (l) a CDRH1 comprising SEQ ID NO: 86 (FTFSSYAMN), a CDRH2 comprising SEQ ID NO: 71 (SAISNSGTYTYYA) and a CDRH3 comprising SEQ ID NO: 85 (ARGLDFIVGRTGNDY); or
  (m) a CDRH1 comprising SEQ ID NO: 80 (FTFRSYAMS), a comprising SEQ ID NO: 71 (SAISNSGTYTYYA), and a CDRH3 comprising SEQ ID NO: 85 (ARGLDFIVGRTGNDY).

In some embodiments, the first unit of antigen-binding binds PD-1 and comprises:
  (a) a heavy chain variable region comprising an amino acid sequence that is at least 90% identical to SEQ ID NO: 87;
  (b) a heavy chain variable region comprising an amino acid sequence that is at least 90% identical to SEQ ID NO: 88;
  (c) a heavy chain variable region comprising an amino acid sequence that is at least 90% identical to SEQ ID NO: 89;

(d) a heavy chain variable region comprising an amino acid sequence that is at least 90% identical to SEQ ID NO: 90;

(e) a heavy chain variable region comprising an amino acid sequence that is at least 90% identical to SEQ ID NO: 91;

(f) a heavy chain variable region comprising an amino acid sequence that is at least 90% identical to SEQ ID NO: 92;

(g) a heavy chain variable region comprising an amino acid sequence that is at least 90% identical to SEQ ID NO: 93;

(h) a heavy chain variable region comprising an amino acid sequence that is at least 90% identical to SEQ ID NO: 94;

(i) a heavy chain variable region comprising an amino acid sequence that is at least 90% identical to SEQ ID NO: 95;

(j) a heavy chain variable region comprising an amino acid sequence that is at least 90% identical to SEQ ID NO: 96;

(k) a heavy chain variable region comprising an amino acid sequence that is at least 90% identical to SEQ ID NO: 97;

(l) a heavy chain variable region comprising an amino acid sequence that is at least 90% identical to SEQ ID NO: 98; or (m) a heavy chain variable region comprising amino acid sequence that is at least 90% identical to SEQ ID NO: 99.

In some embodiments, the first unit of antigen-binding binds PD-1 and comprises a light chain variable region comprising an amino acid sequence that is at least 90% identical to SEQ ID NO: 59.

In some embodiments, the second unit of antigen-binding binds PD-L2. In some embodiments, the second unit of antigen-binding binds PD-L1. In some embodiments, the second unit of antigen-binding binds PD-L1 and comprises:

a. a heavy chain variable region comprising (i) a CDRH1 comprising SEQ ID NO: 1 (GTFSSYAIN); (ii) a CDRH2 comprising SEQ ID NO: 2 (GGIIPX$_1$X$_2$GX$_3$ATYA, wherein X$_1$ is V or I; X$_2$ is F, L, or V; and X$_3$ is T or A); and (iii) a CDRH3 comprising SEQ ID NO: 3 (ARLKX$_1$ELKDAFDI, wherein X$_1$ is G, F, or N); and b. a light chain variable region comprising: (i) a CDRL1 comprising SEQ ID NO: 4 (RASQX$_1$ISSYLN, wherein X$_1$ is S, W, or Q); (ii) a CDRL2 comprising SEQ ID NO: 5 (AASSLQS); and (iii) a CDRL3 comprising SEQ ID NO: 6 (X$_1$QSYSTPLT, wherein X$_1$ is Q or F).

In some such embodiments, the second unit of antigen-binding binds PD-L1 and comprises:

(a) a CDRH1 comprising SEQ ID NO: 1 (GTFSSYAIN), a CDRH2 comprising SEQ ID NO: 7 (GGIIPILGAATYA), and a CDRH3 comprising SEQ ID NO: 8 (ARLKGELKDAFDI);

(b) a CDRH1 comprising SEQ ID NO: 1 (GTFSSYAIN), a CDRH2 comprising SEQ ID NO: 7 (GGIIPILGAATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(c) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(d) a CDRH1 comprising SEQ ID NO: 1 (GTFSSYAIN), a CDRH2 comprising SEQ ID NO: 11 (GGIIPVFGTATYA) and a CDRH3 comprising SEQ ID NO: 8 (ARLKGELKDAFDI);

(e) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 12 (RASQWISSYLN); a CDRL2 comprising SEQ ID NO: 5 (AASSLQS); and a CDRL3 comprising SEQ ID NO: 10 (QQSYSTPLT);

(f) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 13 (RASQQISSYLN); a CDRL2 comprising SEQ ID NO: 5 (AASSLQS); and a CDRL3 comprising SEQ ID NO: 10 (QQSYSTPLT);

(g) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(h) a CDRH1 comprising SEQ ID NO: 1 (GTFSSYAIN), a CDRH2 comprising SEQ ID NO: 15 (GGIIPIFGIANYA), and a CDRH3 comprising SEQ ID NO: 8 (ARLKGELKDAFDI);

(i) a CDRH1 comprising SEQ ID NO: 1 (GTFSSYAIN), a CDRH2 comprising SEQ ID NO: 15 (GGIIPIFGIANYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (CQQSYSTPLTF);

(j) a CDRH1 comprising SEQ ID NO: 1 (GTFSSYAIN), a CDRH2 comprising SEQ ID NO: 16 (GGIIPNFGTATYA), and a CDRH3 comprising SEQ ID NO: 17 (ARLKGELKGAGDI);

(k) a CDRH1 comprising SEQ ID NO: 1 (GTFSSYAIN), a CDRH2 comprising SEQ ID NO: 16 (GGIIPNFGTATYA), a CDRH3 comprising SEQ ID NO: 17 (ARLKGELKGAGDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(l) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 18 (ARLKFELKDAFDI);

(m) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 18 (ARLKFELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(n) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 19 (ARLKGELKDAFDE);

(o) a CDRH1 comprising SEQ ID NO: 1 (GTFSSYAIN), a CDRH2 comprising SEQ ID NO: 11

(GGIIPVFGTATYA), a CDRH3 comprising SEQ ID NO: 19 (ARLKGELKDAFDE), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (p) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 20 (ARLKNELKDAFDI);
- (q) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 20 (ARLKNELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (r) a CDRH1 comprising SEQ ID NO: 1 (GTFSSYAIN), a CDRH2 comprising SEQ ID NO: 21 (GGVIPFLGTANYA), and a CDRH3 comprising SEQ ID NO: 22 (ARLKGILKDALDI);
- (s) a CDRH1 comprising SEQ ID NO: 1 (GTFSSYAIN), a CDRH2 comprising SEQ ID NO: 21 (GGVIPFLGTANYA), a CDRH3 comprising SEQ ID NO: 22 (ARLKGILKDALDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (t) a CDRH1 comprising SEQ ID NO: 1 (GTFSSYAIN), a CDRH2 comprising EQ ID NO: 29 (GRIIPIFGTADYA), and a CDRH3 comprising SEQ ID NO: 8 (ARLKGELKDAFDI);
- (u) a CDRH1 comprising SEQ ID NO: 1 (GTFSSYAIN), a CDRH2 comprising SEQ ID NO: 29 (GRIIPIFGTADYA), a CDRH3 comprising SEQ ID NO: 8 (ARLKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (v) a CDRH1 comprising SEQ ID NO: 1 (GTFSSYAIN), a CDRH2 comprising SEQ ID NO: 31 (GGIIPILGTATYA), and a CDRH3 comprising SEQ ID NO: 32 (ARRKGELKDAFDI);
- (w) a CDRH1 comprising SEQ ID NO: 1 (GTFSSYAIN), a CDRH2 comprising SEQ ID NO: 31 (GGIIPILGTATYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (x) a CDRH1 comprising SEQ ID NO: 1 (GTFSSYAIN), a CDRH2 comprising SEQ ID NO: 33 (GGIIPIVATANYA), and a CDRH3 comprising SEQ ID NO: 32 (ARRKGELKDAFDI);
- (y) a CDRH1 comprising SEQ ID NO: 1 (GTFSSYAIN), a CDRH2 comprising SEQ ID NO: 33 (GGIIPIVATANYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (z) a CDRH1 comprising SEQ ID NO: 1 (GTFSSYAIN), a CDRH2 comprising SEQ ID NO: 34 (GGIIPIFGKATYA), and a CDRH3 comprising SEQ ID NO: 32 (ARRKGELKDAFDI);
- (aa) a CDRH1 comprising SEQ ID NO: 1 (GTFSSYAIN), a CDRH2 comprising SEQ ID NO: 34 (GGIIPIFGKATYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (bb) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 38 (FQSYSTPLT);
- (cc) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 39 (QQSYSTILT);
- (dd) a CDRH1 comprising SEQ ID NO: 14 (GTFSSYAFS), a CDRH2 comprising SEQ ID NO: 11 (GGIIPVFGTATYA) and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (ee) a CDRH1 comprising SEQ ID NO: 23 (GTFSSYAIS), a CDRH2 comprising SEQ ID NO: 24 (GGIIPIVGIANYA), and a CDRH3 comprising SEQ ID NO: 8 (ARLKGELKDAFDI);
- (ff) a CDRH1 comprising SEQ ID NO: 23 (GTFSSYAIS), a CDRH2 comprising SEQ ID NO: 24 (GGIIPIVGIANYA), and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (gg) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 25 (ARLKGEFKDAFDI);
- (hh) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 25 (ARLKGEFKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (ii) a CDRH1 comprising SEQ ID NO: 23 (GTFSSYAIS), a CDRH2 comprising SEQ ID NO: 26 (GRIIPLFGTAHYA), and a CDRH3 comprising SEQ ID NO: 8 (ARLKGELKDAFDI);
- (jj) a CDRH1 comprising SEQ ID NO: 23 (GTFSSYAIS), a CDRH2 comprising SEQ ID NO: 26 (GRIIPLFGTAHYA), and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);
- (kk) a CDRH1 comprising SEQ ID NO: 23 (GTFSSYAIS), a CDRH2 comprising SEQ ID NO: 27 (GRINPILGTANYA), and a CDRH3 comprising SEQ ID NO: 28 (ARLKGELKDAFSI);
- (ll) a CDRH1 comprising SEQ ID NO: 23 (GTFSSYAIS), a CDRH2 comprising SEQ ID NO: 27 (GRINPILGTANYA), and a CDRH3 comprising SEQ ID NO: 28 (ARLKGELKDAFSI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(mm) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 30 (ARLKGELKCAFDI);

(nn) a CDRH1 comprising SEQ ID NO: 23 (GTFSSYAIS), a CDRH2 comprising SEQ ID NO: 11 (GGIIPVFGTATYA), and a comprising SEQ ID NO: 30 (ARLKGELKCAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(oo) a CDRH1 comprising SEQ ID NO: 36 (GPFRSHAVS), a CDRH2 comprising SEQ ID NO: 11 (GGIIPVFGTATYA), and a CDRH3 comprising SEQ ID NO: 37 (ARLKSELKDAFDI); or (pp) a CDRH1 comprising SEQ ID NO: 36 (GPFRSHAVS), a CDRH2 comprising SEQ ID NO: 11 (GGIIPVFGTATYA), and a CDRH3 comprising SEQ ID NO: 37 (ARLKSELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT).

In some such embodiments, the second unit of antigen-binding binds PD-L1 and comprises and comprises a heavy chain variable region comprising an amino acid sequence that is at least 90% identical to any one of SEQ ID NOs: 35, 40, 41, 42, 43, 44, 45, 46, 47, 48, 49, 50, 51, 52, 53, 54, 55, 56, 57, or 58, and a light chain variable region comprising an amino acid sequence that is at least 90% identical to any one of SEQ ID NOs: 59, 60, 61, 62, or 63.

In some embodiments, the second unit of antigen-binding binds PD-L1 and comprises a heavy chain variable region comprising:

(a) an amino acid sequence that is at least 90% identical to SEQ ID NO: 35;
(b) an amino acid sequence that is at least 90% identical to SEQ ID NO: 40;
(c) an amino acid sequence that is at least 90% identical to SEQ ID NO: 41;
(d) an amino acid sequence that is at least 90% identical to SEQ ID NO: 42;
(e) an amino acid sequence that is at least 90% identical to SEQ ID NO: 43;
(f) an amino acid sequence that is at least 90% identical to SEQ ID NO: 44;
(g) an amino acid sequence that is at least 90% identical to SEQ ID NO: 45;
(h) an amino acid sequence that is at least 90% identical to SEQ ID NO: 46;
(i) an amino acid sequence that is at least 90% identical to SEQ ID NO: 47;
(j) an amino acid sequence that is at least 90% identical to SEQ ID NO: 48;
(k) an amino acid sequence that is at least 90% identical to SEQ ID NO: 49;
(l) an amino acid sequence that is at least 90% identical to SEQ ID NO: 50;
(m) an amino acid sequence that is at least 90% identical to SEQ ID NO: 51;
(n) an amino acid sequence that is at least 90% identical to SEQ ID NO: 52;
(o) an amino acid sequence that is at least 90% identical to SEQ ID NO: 53;
(p) an amino acid sequence that is at least 90% identical to SEQ ID NO: 54;
(q) an amino acid sequence that is at least 90% identical to SEQ ID NO: 55;
(r) an amino acid sequence that is at least 90% identical to SEQ ID NO: 56;
(s) an amino acid sequence that is at least 90% identical to SEQ ID NO: 57; or
(t) an amino acid sequence that is at least 90% identical to SEQ ID NO: 58;

In some embodiments, the second unit of antigen-binding binds PD-L1 and comprises a light chain variable region comprising:

(a) an amino acid sequence that is at least 90% identical to SEQ ID NO: 59;
(b) an amino acid sequence that is at least 90% identical to SEQ ID NO: 60;
(c) an amino acid sequence that is at least 90% identical to SEQ ID NO: 61;
(d) an amino acid sequence that is at least 90% identical to SEQ ID NO: 62; or
(e) an amino acid sequence that is at least 90% identical to SEQ ID NO: 63.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 100 or 102, and a light chain amino acid sequence that is at least 85%, identical to the amino acid sequence of SEQ ID NO: 101 or 103.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 100 and a light chain amino acid sequence that is at least 85%, identical to the amino acid sequence of SEQ ID NO: 101.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 102 and a light chain amino acid sequence that is at least 85%, identical to the amino acid sequence of SEQ ID NO: 103.

In some embodiments, the construct does not comprise an Fc domain. In some embodiments, the first arm or second arm, or both, comprises a heavy chain comprising one or more immunoglobulin Fc modifications. In some embodiments, the immunoglobulin Fc domain of the heavy chain comprises one or more amino acid mutations that promote heterodimerization of the first and second arms. In some embodiments, the mutation is present in a CH3 domain of the heavy chain. In some embodiments, the multispecific antigen-binding construct is produced in a quadroma cell. In some embodiments, the construct comprises one or more immunoglobulin constant region modifications. In some embodiments, the immunoglobulin constant region comprises one or more amino acid mutations that promote heterodimerization of antibodies. In some embodiments, one or more mutations is present in the light chain constant region of one arm and one or more mutations is present in the heavy chain constant region of another arm. In some embodiments, the bispecific antibody is of a format selected from the group consisting of a bispecific IgG, bispecific antibody fragment, bispecific fusion protein, appended IgG, and bispecific antibody conjugate. In some embodiments, the Fc region has reduced effector function. In some embodiments, the Fc region enhances half-life of the construct.

In some embodiments, the construct comprises a heavy chain amino acid sequence that is at least 85%, identical to the amino acid sequence of SEQ ID NO: 100 or 102. In some embodiments, the construct comprises a light chain amino acid sequence that is at least 85%, identical to the amino acid sequence of SEQ ID NO: 101 or 103. In some embodiments, the construct comprises a heavy chain amino acid sequence that is at least 85% identical to the amino acid sequence of SEQ ID NO: 100, and wherein the construct comprises a light chain amino acid sequence that is at least 85% identical to the amino acid sequence of SEQ ID NO: 101. In some embodiments, the construct comprises a heavy chain amino acid sequence that is at least 85% identical to the amino acid sequence of SEQ ID NO: 102, and wherein the construct comprises a light chain amino acid sequence that is at least 85% identical to the amino acid sequence of SEQ ID NO: 103.

In some embodiments, any of the multispecific antigen-binding constructs disclosed herein are aglycosylated. In some embodiments, the multispecific antigen-binding construct is capable of binding human PD-1. In some embodiments, the multispecific antigen-binding construct is capable of binding murine PD-1. In some embodiments, the multispecific antigen-binding construct is capable of binding cynomolgus monkey PD-1. In some embodiments, the multispecific antigen-binding construct is capable of binding human, murine and cynomolgus monkey PD-1 with similar affinity.

In some embodiments, any of the multispecific antigen-binding constructs disclosed herein is capable of reducing PD-1 levels on a cell. In some embodiments, the multispecific antigen-binding construct is capable of inducing PD-1 degradation. In some embodiments, the multispecific antigen-binding construct is capable of reducing PD-1 expression. In some embodiments, the multispecific antigen-binding construct is capable of reducing PD-1 cell surface expression. In some embodiments, the multispecific antigen-binding construct is capable of reducing PD-1 cell surface expression by inducing shedding of PD-1 from the cell surface. In some embodiments, the multispecific antigen-binding construct is capable of binding both PD-1 and PD-L1 and reducing PD-1 levels on a cell. In some embodiments, the multispecific antigen-binding construct is capable of binding both PD-1 and PD-L1 and inducing PD-1 degradation. In some embodiments, the multispecific antigen-binding construct is capable of binding both PD-1 and PD-L1 and reducing PD-1 expression. In some embodiments, the multispecific antigen-binding construct is capable of inducing shedding of PD-1 from an immune cell. In some embodiments, the multispecific antigen-binding construct is capable of binding both PD-1 and PD-L1 and inducing PD-1 shedding from an immune cell. In some embodiments, the multispecific antigen-binding construct is capable of sequestering PD-L1, such that PD-L1 cannot bind CD80. In some embodiments, the multispecific antigen-binding construct is capable of sequestering PD-L1, such that PD-L1 cannot bind CD80, and wherein CD80 is free to bind CD28. In some embodiments, the cell is an immune cell, such as a T cell. In some embodiments, the immune cell (e.g., T cell) is a tumor infiltrating lymphocyte (TIL). In some embodiments, engagement of a multispecific antigen-binding molecule described herein to PD-1 expressed by an immune cell in the tumor microenvironment results in the downregulation of PD-1 by the immune cell. In some embodiments, the immune cell is a T cell. In some embodiments, the immune cell (e.g., T cell) is a tumor infiltrating lymphocyte (TIL).

In some embodiments, any of the multispecific antigen-binding constructs disclosed herein is capable of inducing at least 5%, 10%, 15%, 20%, 25%, 30%, 35%, 40%, 45%, 50%, 55%, 60%, 65%, 70%, 75%, 80%, 85%, 90%, 95% or 99% greater interferon-gamma levels (e.g., as measured in a *Staphylococcus aureus* Enterotoxin A ("SEA") assay) as compared to a reference antigen-binding construct (e.g., pembrolizumab or atezolizumab) or to a reference combination of antigen-binding constructs (e.g., a composition comprising the PD-1 and PD-L1 arms of the multispecific antigen-binding construct, wherein the PD-1 and PD-L1 arms in the composition are not conjugated to one another). In some embodiments, the multispecific antigen-binding construct is capable of inducing at least 5%, 10%, 15%, 20%, 25%, 30%, 35%, 40%, 45%, 50%, 55%, 60%, 65%, 70%, 75%, 80%, 85%, 90%, 95% or 99% greater interleukin-2 levels (e.g., as measured in a SEA assay) as compared to a reference antigen-binding construct (e.g., pembrolizumab or atezolizumab) or to a reference combination of antigen-binding constructs (e.g., a composition comprising the PD-1 and PD-L1 arms of the multispecific antigen-binding construct, wherein the PD-1 and PD-L1 arms in the composition are not conjugated to one another).

In some embodiments, the multispecific antigen-binding construct induces at least 5%, 10%, 15%, 20%, 25%, 30%, 35%, 40%, 45%, 50%, 55%, 60%, 65%, 70%, 75%, 80%, 85%, 90%, 95%, 99%, 200%, 300%, 400%, or 500% more killing of tumor cells (e.g., leukemia cells, lymphoma cells, melanoma, or breast cancer cells), as compared to a reference antigen-binding construct (e.g., pembrolizumab or atezolizumab) or to a reference combination of antigen-binding constructs (e.g., a composition comprising the PD-1 and PD-L1 arms of the multispecific antigen-binding construct, wherein the PD-1 and PD-L1 arms in the composition are not conjugated to one another).

In some embodiments, the multispecific antigen-binding construct is capable of extending the survival of a subject suffering from a cancer (e.g., leukemia, lymphoma, melanoma, and/or breast cancer) by at least 5%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, or 500% longer than a subject administered a reference antigen-binding construct (e.g., pembrolizumab or atezolizumab) or a reference combination of antigen-binding constructs (e.g., a composition comprising the PD-1 and PD-L1 arms of the multispecific antigen-binding construct, wherein the PD-1 and PD-L1 arms in the composition are not conjugated to one another). In some embodiments, the multispecific antigen-binding construct is capable of inducing at least 5%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, or 500% more shedding of PD-1 from an immune cell as compared to an untreated immune cell or as compared to an immune cell treated with reference antigen-binding construct (e.g., pembrolizumab or atezolizumab) or a reference combination of antigen-binding constructs (e.g., a composition comprising the PD-1 and PD-L1 arms of the multispecific antigen-binding construct, wherein the PD-1 and PD-L1 arms in the composition are not conjugated to one another). In some embodiments, the multispecific antigen-binding construct is capable of reducing PD-1 levels at least 5%, 10%, 15%, 20%, 25%, 30%, 35%, 40%, 45%, 50%, 55%, 60%, 65%, 70%, 75%, 80%, 85%, 90%, 95%, 99%, 100%, 200%, 300%, 400%, or 500% (e.g., by causing PD-1 shedding from the cell surface and/or inducing PD-1 degradation and/or reducing PD-1 expression) as compared to an untreated immune cell or to an immune cell treated with a reference antigen-binding construct (e.g., pembrolizumab or atezolizumab) or a reference combination of antigen-binding constructs (e.g., a composition comprising the PD-1 and PD-L1 arms of the multispecific antigen-binding construct, wherein the PD-1 and PD-L1 arms in the composition are not conjugated to one another).

In some embodiments, engagement of a multispecific antigen-binding molecule described herein to PD-1 expressed by a cell results in the downregulation and/or loss of cell-surface expression of PD-1 by the cell. Such downregulation or loss of cell-surface expression can be due to, in part, for example, shedding of extracellular PD-1 from the surface of the immune cell. In some embodiments, the cell is an immune cell, such as a T cell. In some embodiments, the immune cell (e.g., T cell) is a tumor infiltrating lymphocyte (TIL). In some embodiments, engagement of a multispecific antigen-binding molecule described herein to PD-1 expressed by an immune cell in the tumor microenvironment results in the downregulation of PD-1 by the immune cell. In some embodiments, the immune cell is a T cell. In some embodiments, the immune cell (e.g., T cell) is a tumor infiltrating lymphocyte (TIL).

In some aspects, the disclosure provides for a method for treating a proliferative disorder in a subject in need thereof, comprising administering to the subject a therapeutically effective amount of any of the multispecific antigen-binding constructs disclosed herein, thereby treating the proliferative disorder in the subject. In some embodiments, the proliferative disorder is cancer. In some embodiments, the cancer is selected from the group consisting of a hematological cancer, a neurological cancer, melanoma, breast cancer, lung cancer, head and neck cancer, a gastrointestinal cancer, liver cancer, pancreatic cancer, a genitourinary cancer, a bone cancer, and a vascular cancer. In some embodiments, the disclosure provides for a method of enhancing an immune response in a subject in need thereof, comprising administering to the subject a therapeutically effective amount of any of the multispecific antigen-binding constructs disclosed herein, thereby enhancing the immune response in the subject. In some embodiments, the enhanced immune response includes any one or more of enhanced T cell function, enhanced NK cell function, or enhanced macrophage function. In some embodiments, the enhancement of T cell function is greater upon administration of the multispecific antigen-binding construct, as compared to an agent that binds either PD-1 or a PD-1 ligand, or a cocktail comprising an agent that binds PD-1 and an agent that binds a PD-1 ligand. In some embodiments, the T cell function is any one or more of increased IFNγ production from T cells, enhanced T cell survival, increased T cell proliferation, or rescue from an exhausted T cell phenotype. In some embodiments, the enhanced T cell function is greater upon administration of the multispecific antigen-binding construct, as compared to an agent that binds either PD-1 or a PD-1 ligand, or a cocktail comprising an agent that binds PD-1 and an agent that binds a PD-1 ligand. In some embodiments, the multispecific antigen-binding construct is administered subcutaneously, intravenously, intradermally, intraperitoneally, orally, intramuscularly or intracranially. In some embodiments, the multispecific antigen-binding construct binds to PD-1 and to PD-L1 expressed on the surface of the same cell in the subject. In some embodiments, the multispecific antigen-binding construct binds to PD-1 expressed on the surface of a first cell in the subject, and wherein the multispecific antigen-binding construct binds to PD-L1 expressed on the surface of a second cell in the subject.

In some embodiments, the disclosure provides for an anti-PD1 antibody or antigen-binding fragment thereof, wherein the anti-PD-1 antibody or antigen-binding fragment comprises: (a) a heavy chain variable region comprising (i) a CDRH1 comprising SEQ ID NO: 70 (FTFX$_1$X$_2$YAX$_3$X$_4$, wherein X$_1$=S, R, G, or N; X$_2$=D, S, N, A, R, or G; X$_3$=M or L; X$_4$=S, L, or N); (ii) a CDRH2 comprising SEQ ID NO: 71 (SAISNSGTYTYYA); and (iii) a CDRH3 comprising SEQ ID NO: 72 (ARGLDFIVGX$_5$TGNDY, wherein X$_5$=A, Y, or R); and (b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT). In some embodiments, the anti-PD-1 antibody or antigen-binding fragment comprises: (a) a heavy chain variable region comprising (i) a CDRH1 comprising the amino acid sequence of any one of SEQ ID NOs: 73, 76, 77, 78, 79, 80, 81, 82, 83, 84, or 86; (ii) a CDRH2 comprising the amino acid sequence of SEQ ID NO: 71; and (iii) a CDRH3 comprising the amino acid sequence of any one of SEQ ID NOs: 74, 75, or 85; and (b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT). In some embodiments, the heavy chain variable region comprises an amino acid sequence that is at least 85% identical to the amino acid sequence of any one of SEQ ID NOs: 87, 88, 89, 90, 91, 92, 93, 94, 95, 96, 97, 98, or 99. In some embodiments, the light chain variable region comprises an amino acid sequence that is at least 85% identical to the amino acid sequence of SEQ ID NO: 59.

In some embodiments, the disclosure provides for an anti-PD-L1 antibody or antigen-binding fragment thereof, wherein the anti-PD-L1 antibody or antigen-binding fragment comprises: a. a heavy chain variable region comprising (i) a CDRH1 comprising SEQ ID NO: 1 (GTFSSYAIN); (ii) a CDRH2 comprising SEQ ID NO: 2 (GGIIPX$_1$X$_2$GX$_3$ATYA, wherein X$_1$ is V or I; X$_2$ is F, L, or V; and X$_3$ is T or A); and (iii) a CDRH3 comprising SEQ ID NO: 3 (ARLKX$_1$ELKDAFDI, wherein X$_1$ is G, F, or N); and b. a light chain variable region comprising: (i) a CDRL1 comprising SEQ ID NO: 4 (RASQX$_1$ISSYLN, wherein X$_1$ is S, W, or Q); (ii) a CDRL2 comprising SEQ ID NO: 5 (AASSLQS); and (iii) a CDRL3 comprising SEQ ID NO: 6 (X$_1$QSYSTPLT, wherein X$_1$ is Q or F). In some embodiments, the anti-PD-L1 antibody or antigen-binding fragment comprises: (a) a heavy chain variable region comprising (i) a CDRH1 comprising the amino acid sequence of any one of SEQ ID NOs: 1, 14, 23, 36, or 122; (ii) a CDRH2 comprising the amino acid sequence of any one of SEQ ID NOs: 11, 15, 16, 21, 24, 26, 27, 29, 31, 33, or 34; and (iii) a CDRH3 comprising the amino acid sequence of any one of SEQ ID NOs: 8, 17, 18, 19, 20, 22, 25, 28, 30, 32, or 37; and (b) a light chain variable region comprising: (i) a CDRL1 comprising the amino acid sequence of any one of SEQ ID NOs: 9, 12, or 13; (ii) a CDRL2 comprising the amino acid sequence of SEQ ID NO: 5; and (iii) a CDRL3 comprising the amino acid sequence of any one of SEQ ID NOs: 10, 38 or 39. In some embodiments, the heavy chain variable region comprises an amino acid sequence that is at least 85% identical to the amino acid sequence of any one of SEQ ID NOs: 40, 41, 42, 43, 44, 45, 46, 47, 48, 49, 50, 51, 52, 53, 54, 55, 56, 57, 58, or 35. In some embodiments, the light chain variable region comprises an amino acid sequence that is at least 85% identical to the amino acid sequence of any one of SEQ ID NOs: 59, 60, 61, 62, or 63.

In some embodiments, the disclosure provides for a method for treating a proliferative disorder in a subject in need thereof, comprising administering to the subject a therapeutically effective amount of any of the antibodies or antigen-binding constructs disclosed herein, thereby treating the proliferative disorder in the subject. In some embodiments, the proliferative disorder is cancer. In some embodiments, the cancer is selected from the group consisting of a hematological cancer, a neurological cancer, melanoma, breast cancer, lung cancer, head and neck cancer, a gastrointestinal cancer, liver cancer, pancreatic cancer, a genitourinary cancer, a bone cancer, and a vascular cancer.

In some embodiments, the disclosure provides for a method of enhancing an immune response in a subject in need thereof, comprising administering to the subject a therapeutically effective amount of any of the antibodies or antigen-binding constructs disclosed herein, thereby enhancing the immune response in the subject.

In some embodiments, any of the methods described herein can involve detecting the presence or absence of PD-1 expression by one or more cells (or a population of cells, such as TILs) before and/or after contact with a multispecific antigen-binding molecule described herein. For example, any of the methods described herein can involve detecting the presence or absence of PD-1 expression by one or more cells (or a population of cells, such as TILs) before and/or after administration of a multispecific antigen-binding molecule described herein to a subject (e.g., a cancer patient). Such methods are useful, e.g., determining a therapeutically effective amount of the molecule for use in treatment of a given patient or patient population. Methods of detecting the presence, reduction in expression, and/or absence of PD-1 expression are known to those of skill in the art, for example, using flow cytometry, Western blotting, ELISA, etc.

In another aspect, the disclosure features a method comprising measuring the level of PD-1 expression by one or more cells (or a population of cells, such as TILs) before and/or after contact with a multispecific antigen-binding molecule described herein. In some embodiments, the method comprises measuring the level of PD-1 expression by one or more cells (or a population of cells, such as TILs) before and/or after administration of a multispecific antigen-binding molecule described herein to a subject (e.g., a cancer patient).

In yet another aspect, the disclosure features a method comprising measuring the level of PD-1 expression by one or more cells (or a population of cells, such as TILs) before and/or after contact with a multispecific antigen-binding molecule described herein. For example, any of the methods described herein can involve measuring the level of PD-1 expression by one or more cells (or a population of cells, such as TILs) before and/or after administration of a multispecific antigen-binding molecule described herein to a subject (e.g., a cancer patient). Such methods are useful for, among other things, detecting or measuring a biological effect of a molecule described herein on the subject. In some embodiments, a reduction in the level of PD-1 expression by an immune cell (e.g., TILs isolated from a patient) following treatment with a multispecific antigen-binding molecule described herein indicates that the molecule has had a biological effect in the subject. In some embodiments, a reduction in the level of PD-1 expression by an immune cell (e.g., TILs isolated from a patient) following treatment with a multispecific antigen-binding molecule described herein indicates that the patient should receive one or more doses of the molecule, or otherwise continue on a therapy comprising the molecule.

In yet another aspect, the disclosure features methods for determining whether a biological effect has occurred in a patient or population of patients treated with a multispecific antigen-binding molecule described herein. The method comprises detecting the presence or amount of PD-1 expression by one or more test immune cells (e.g., effector immune cells, such as those in the tumor microenvironment) obtained from a patient or patients who have been administered a multispecific antigen-binding molecule described herein, wherein a reduced level of PD-1 expression (e.g., cell surface expression) of PD-1 by the one or more immune cells relative to a control expression level (e.g., the expression level of PD-1 by immune cells of the same histological type as the test immune cells prior to administration of the molecule) indicates that a biological effect has occurred in the patient or population of patients. In some embodiments, the method comprises administering the multispecific antigen-binding molecule prior to the detecting. In some embodiments, the method comprises administering a multispecific antigen-binding molecule to the patient or population of patients in whom the occurrence of a biological effect has been determined. In some embodiments, control PD-1 expression level is approximately the median or average expression level of PD-1 by immune cells of the same histological type in a population of subjects who have not been diagnosed as having a cancer. In some embodiments, control PD-1 expression level is approximately the median or average expression level of PD-1 by immune cells of the same histological type in a population of subjects who have not been administered a multispecific antigen-binding molecule described herein and/or an agent that binds to and/or inhibits PD-1.

In yet another aspect, the disclosure features a method for reducing the expression of PD-1 by one or more immune cells in a subject (e.g., a cancer patient), the method comprising administering a multispecific antigen-binding molecule described herein to a subject to thereby reduce the expression of PD-1 by one or more immune cells in the subject. In some embodiments, the method comprises determining whether a reduction in PD-1 expression by one or more immune cells in the patient has occurred. In some embodiments, the method comprises obtaining from the subject a biological sample (e.g., a tumor biopsy) comprising one or more immune cells (e.g., after administration of the molecule to the subject). In some embodiments, the method comprises measuring the level of PD-1 expression by one or more immune cells in the biological sample.

In yet another aspect, the disclosure features a method for inhibiting binding between PD-L1 and CD80 in a subject (e.g., a cancer patient), the method comprising administering a multispecific antigen-binding molecule described herein to a subject to thereby inhibit binding between PD-L1 and CD80 in the subject.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3 shows a schematic and amino acid sequence for a PembrolizumabxAtezolizumab bispecific. Separate sequences are given for the Pembrolizumab_aglyco-IgG1-(G4S)$_4$ heavy chain (H chain; SEQ ID NO: 104) and light chain (L chain; SEQ ID NO: 105) and for the Atezolizumab_FabH-(G4S)$_4$ heavy chain (H chain; SEQ ID NO: 106) and light chain (L chain; SEQ ID NO: 107).

FIG. 6 shows a schematic and amino acid sequence for an Atezolizumab xNivolumab bispecific. Separate sequences are given for the Atezolizumab_aglyco-IgG1-(G4S)$_4$ heavy chain (H chain; SEQ ID NO: 112) and light chain (L chain; SEQ ID NO: 107) and Nivolumab_HC Fab-(G4S)$_4$ heavy chain (H chain; SEQ ID NO: 113) and light chain (L chain; SEQ ID NO: 109).

FIG. 10A shows that Bispecific 3 increased the specific killing of K562-A2-CMV-PDL1 tumor antigen target cells by CMV specific T-cells at low concentrations of 0.001 through 0.01 nM, as compared to both KEYTRUDA and the combination of mAb1 and mAb28, indicating that Bispecific 3 can be used to mediate antigen-specific killing of target cells at lower doses. FIG. 10B shows that Bispecific 3 was more effective than either KEYTRUDA or the combination of mAb1 and mAb28 in the specific killing of Raji-A2-CMV-PDL1 cell tumor antigen target cells by CMV specific T-cells at low concentrations of 0.001 nM, again indicating that Bispecific 3 can be used to mediate antigen-specific killing of target cells at lower doses.

FIGS. 12A-12B demonstrate that only Bispecific 3 results in internalization and subsequent degradation or loss of expression of PD-1, when compared to isotype control, KEYTRUDA, mAb1 and mAb28, Atezolizumab, or Atezolizumab and KEYTRUDA. Additionally, as shown in FIG. 12C, when the anti-PD-L1 antibody, mAb1, was added at 50 nM to wells 5 minutes before adding Bispecific 3, the ability of Bispecific 3 to drive PD-1 internalization was lost. This suggests that both arms of Bispecific 3 should be engaged to drive PD-1 loss of expression and/or internalization and/or degradation. FIG. 12D shows that treatment with Bispecific 3 increases the amount of PD-1 in the supernatant when both binding arms of the bispecific are engaged concurrently. This effect is lost when the PD-L1 targeting arm is blocked by mAb1. This suggests that Bispecific 3 increases shedding of PD-1 into the supernatant. FIG. 12E demonstrates that the valency of the binding arms influences the degree of the loss of PD-1 expression. Bispecific 5 was made having a first N-terminal Fab binding PD-L1 based on the VH and VL sequences of mAb1 and having a second N-terminal Fab binding PD-1 based on the VH and VL sequences of mAb28. In other words, Bispecific 5 has one monovalent arm binding PD-L1 and one monovalent arm binding PD-1, as compared to Bispecific 3, which has bivalent arms binding PD-L1 and bivalent arms binding PD-1. As shown, loss of PD-1 expression starts to occur at higher doses of Bispecific 5 (bivalent) versus Bispecific 3 (tetravalent), suggesting that the increased valency of Bispecific 3 is responsible for this difference. FIG. 12F demonstrates that pretreatment with Batimastat, a broad-spectrum inhibitor of multiple MMPs and ADAMs, sheddases or proteases responsible for cleaving proteins off the plasma membrane of cells, greatly reduces the amount of cell-associated PD-1 loss, suggesting that PD-1 loss or shedding is due to cleavage by an MMP or ADAM protease. FIG. 12G suggests that Bispecific 3 drives loss of cell-surface PD-1 expression primarily when it binds to PD-1 and PD-L1 that are in the trans configuration, i.e., are being expressed by different cells.

FIG. 13A depicts a schematic of the experimental protocol.

FIG. 13B demonstrates that both Bispecific 3 and the combination mAb1 and mAb28 groups had significant delays in tumor growth as compared to both the isotype and KEYTRUDA groups. In addition, at day 24, there was a significant divergence between the Bispecific 3 group and the group treated with a combination of mAb1 and mAb28, with Bispecific 3 causing a greater delay in tumor growth as compared to the combination. The No T cell transfer group had tumors that grew more aggressively than any group containing T cells. In this model, KEYTRUDA gave no benefit in delaying KACP tumor growth as compared to the isotype control.

FIGS. 14A and 14B are graphs illustrating that, while each of the different treatment groups resulted in a delay in average tumor growth as compared to untreated mice, treatment with T cells and Bispecific 3 resulted in the greatest delay in average tumor growth over time. The No T cell transfer group had tumors that grew more aggressively than any group containing T cells. In this model, KEYTRUDA gave no benefit in delaying K562-A2-CMV-PD-L1 tumor growth as compared to the isotype control.

FIG. 15A is a graph showing that treatment of an EMT-6 syngeneic tumor model with Bispecific 3 resulted in a greater delay in tumor growth as compared to the control treatment. FIG. 15B is a graph showing that treatment of an MB49 syngeneic tumor model with Bispecific 3 resulted in a greater delay in tumor growth as compared to the control treatment.

FIG. 16A shows that both KEYTRUDA and Bispecific 1 treatment effectively controlled tumor growth in the MC38-hPD-L1 tumor mice as compared to control-treated mice. FIG. 16B is a survival graph and illustrates that Bispecific 1 increased the survival of MC38-PD-L1 tumor mice as compared to control-treated mice.

FIGS. 17A-17F illustrate in vivo results using Bispecific 3 in a B16F10-hPD-L1 model. FIG. 17A is a series of graphs each showing the effect of different treatments on tumor growth measured at a 15-day cutoff in B16F10-HuPD-L1 mice. Different groups of mice (n=8) were treated with Bispecific 3, KEYTRUDA, Avelumab, KEYTRUDA+Avelumab combination, or isotype control antibodies. FIG. 17A shows individual tumor volume traces for each group. Metastases were identified in multiple mice that died prior to the tumor-sizing cutoff. FIG. 17B shows differences in mean tumor volume across treatment groups, demonstrating that by 15 days after tumor cell inoculation, Bispecific 3 treatment delayed average tumor growth significantly longer than any of the other treatments tested in B16F10-HuPD-L1 mice. **, $P<0.0001$; , $P<0.01$, *, $P<0.05$, Two-way ANOVA and Tukey's multiple comparisons test. FIG. 17B is a graph comparing the effect of different treatments on tumor volume measured at a 15-day cutoff in B16F10-HuPD-L1 mice. Metastases were identified in multiple mice that died prior to the tumor-sizing cutoff. As shown in FIG. 17B, Bispecific 3 treatment delayed average tumor growth significantly longer than any of the other treatments tested in B16F10-hPD-L1 mice. FIG. 17C is a survival graph and illustrates that treatment with Bispecific 3 increased the survival of B16F10-hPD-L1 tumor mice as compared to survival with any of the other treatments tested. FIG. 17D shows that by 21 days after tumor cell inoculation, Bispecific 3 treatment continued to delay average tumor growth significantly better than treatment with KEYTRUDA in B16F10-hPD-L1 mice. FIG. 17E is a survival graph and illustrates that treatment with Bispecific 3 increased the survival of B16F10-HuPD-L1 tumor mice as compared to survival with any of the other treatments tested. FIG. 17F provides a Table showing the number of tumor-free mice for each of the different treatment groups. The group treated with Bispecific 3 had 3 mice that were tumor-free, while the combination of KEYTRUDA and avelumab had 1 mouse that was tumor-free.

FIGS. 18A-18D demonstrate that Bispecific 3 has drug-like properties (DLP's) similar to a well-behaved monoclonal antibody and maintains parental PD-1 and PD-L1 binding. FIG. 18A shows that Bispecific 3 shows similar binding to CHO cells expressing human PD-1 as parental clone mAb28 (top) and to CHO cells expressing human PD-L1 as parental clone mAb1 (bottom). FIG. 18B shows that Bispecific 3 shows similar binding to CHO cells expressing cynomolgus PD-1 as parental clone mAb28 (top) and to CHO cells expressing cynomolgus PD-L 1 as parental clone mAb1 (bottom). FIG. 18C shows that Bispecific 3 shows similar binding to CHO cells expressing mouse PD-1 as parental clone mAb28 (top) and to CHO cells expressing mouse PD-L1 as parental clone mAb1 (bottom). FIG. 18D shows a size-exclusion chromatography trace of Bispecific 3 after Protein A chromatography (top) demonstrating a single peak with greater than 98% purity and a differential scanning fluorimetry (DSF) trace of Bispecific 3 (bottom) demonstrating that the molecule has high thermal stability.

DETAILED DESCRIPTION

Figure 1:
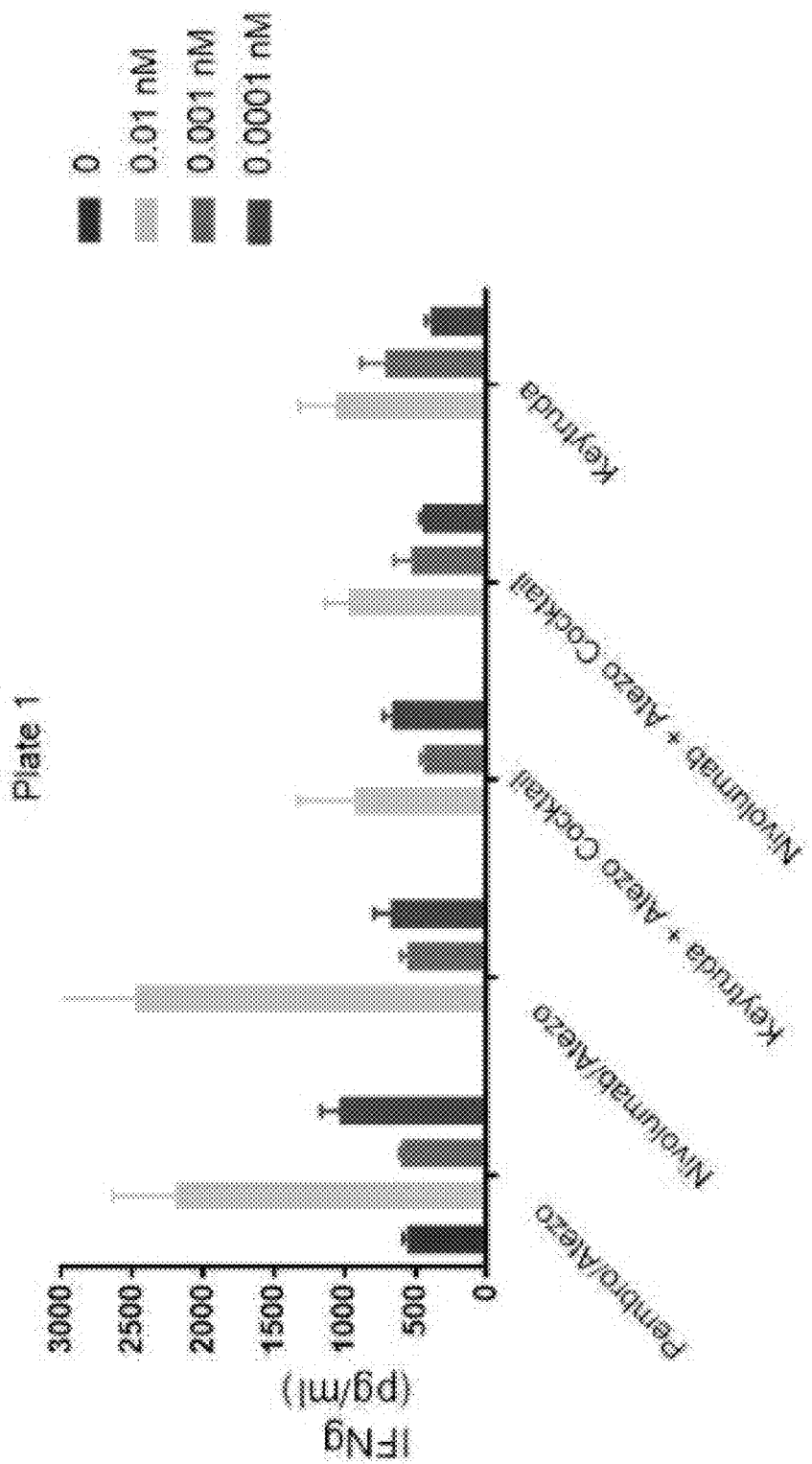
FIG. 1 shows the induction of interferon-gamma (IFNγ) in a mixed lymphocyte reaction (MLR) assaytreated with various antibody cocktails or bispecific antibodies including a PembrolizumabxAtezolizumab bispecific, a NivolumabxAtezolizumab bispecific, a cocktail of KEYTRUDA and Atezolizumab, and a cocktail of Nivolumab and Atezolizumab, as compared to KEYTRUDA alone. The results show the concentration of IFNγ as pg/mL at the final concentrations of antibodies tested, as indicated.

Unless otherwise defined, all terms of art, notations and other scientific terminology used herein are intended to have the meanings commonly understood by those of skill in the art to which this disclosure pertains. In some cases, terms with commonly understood meanings are defined herein for clarity and/or for ready reference, and the inclusion of such definitions herein should not necessarily be construed to represent a difference over what is generally understood in the art. The techniques and procedures described or referenced herein are generally well understood and commonly employed using conventional methodologies by those skilled in the art, such as, for example, the widely utilized molecular cloning methodologies described in Sambrook et al., *Molecular Cloning: A Laboratory Manual* 2nd ed. (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the singular forms "a," "an," and "the" include the plural referents unless the context clearly indicates otherwise.

In the specification and claims, the term "about" is used to modify, for example, the quantity of an ingredient in a composition, concentration, volume, process temperature, process time, yield, flow rate, pressure, and like values, and ranges thereof, employed in describing the embodiments of the disclosure. The term "about" refers to variation in the numerical quantity that can occur, for example, through typical measuring and handling procedures used for making compounds, compositions, concentrates or use formulations; through inadvertent error in these procedures; through differences in the manufacture, source, or purity of starting materials or ingredients used to carry out the methods, and like proximate considerations. The term "about" also encompasses amounts that differ due to aging of a formulation with a particular initial concentration or mixture, and amounts that differ due to mixing or processing a formulation with a particular initial concentration or mixture. Where modified by the term "about" the claims appended hereto include equivalents to these quantities. If there are uses of the term which are not clear to persons of ordinary skill given the context in which it is used, "about" will mean up to plus or minus 10% of the particular value.

With regard to the binding of an antigen-binding protein/region/arm to a target molecule, the terms "specific binding," "specifically binds to," "specific for," "selectively binds," and "selective for" a particular antigen (e.g., a polypeptide target) or an epitope on a particular antigen mean binding that is measurably different from a non-specific or non-selective interaction. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

The term "epitope" means a component of an antigen capable of specific binding to an antigen-binding protein. Epitopes frequently consist of surface-accessible amino acid residues and/or sugar side chains and can have specific three-dimensional structural characteristics, as well as specific charge characteristics. Conformational and non-conformational epitopes are distinguished in that the binding to the former but not the latter is lost in the presence of denaturing solvents. An epitope can comprise amino acid residues that are directly involved in the binding, and other amino acid residues, which are not directly involved in the binding. The epitope to which an antigen-binding protein binds can be determined using known techniques for epitope determination such as, for example, testing for antigen-binding protein binding to antigen variants with different point-mutations.

Percent "identity" between a polypeptide sequence and a reference sequence, is defined as the percentage of amino acid residues in the polypeptide sequence that are identical to the amino acid residues in the reference sequence, after aligning the sequences and introducing gaps, if necessary, to achieve the maximum percent sequence identity. Alignment for purposes of determining percent amino acid sequence identity can be achieved in various ways that are within the skill in the art, for instance, using publicly available computer software such as BLAST, BLAST-2, ALIGN, MEGALIGN (DNASTAR), CLUSTALW, or CLUSTAL OMEGA software. In some embodiments, alignment is performed using the CLUSTAL OMEGA software. Those skilled in the art can determine appropriate parameters for aligning sequences, including any algorithms needed to achieve maximal alignment over the full length of the sequences being compared.

The term "capable of" as used herein means that an agent or method (e.g., any of the multispecific antigen-binding constructs or methods disclosed herein) has the ability to achieve a specified property in the appropriate context (as would be understood by the skilled worker), but is not required to be associated with that property at any particular moment in time. For example, any of the multispecific antigen-binding constructs disclosed herein may be capable of binding PD-1 and/or PD-L1 when administered to cells expressing PD-1 and/or PD-L1, but the constructs would not be expected to bind PD-1 and/or PD-L1 when the constructs are in a composition devoid of PD-1 or PD-L1 protein.

A "conservative substitution" or a "conservative amino acid substitution," refers to the substitution of one or more amino acids with one or more chemically or functionally similar amino acids. Conservative substitution tables providing similar amino acids are well known in the art. Polypeptide sequences having such substitutions are known as "conservatively modified variants," or "variants." Such conservatively modified variants are in addition to and do not exclude polymorphic variants, interspecies homologs, and alleles. Some examples of conservative substitutions can be found, for example, in Creighton, *Proteins: Structures and Molecular Properties* 2nd ed. (1993) W. H. Freeman & Co., New York, N.Y.

A polypeptide disclosed herein can comprise an amino acid sequence which is not naturally occurring. Such variants necessarily have less than 100% sequence identity or similarity with the starting molecule. In certain embodiments, the variant will have an amino acid sequence from about 75% to less than 100% amino acid sequence identity or similarity with the amino acid sequence of the starting (e.g., naturally-occurring or wild-type) polypeptide, more preferably from about 80% to less than 100%, more preferably from about 85% to less than 100%, more preferably from about 90% to less than 100% (e.g., 91%, 92%, 93%, 94%, 95%, 96%, 97%, 98%, 99%) and most preferably from about 95% to less than 100%, e.g., over the length of the variant molecule.

An "antibody," as used herein, can refer to an intact antibody (e.g., an intact immunoglobulin) and antibody portion, for example, an antigen-binding portion. Antigen-binding portions comprise at least one antigen-binding domain. One example of an antigen-binding domain is an antigen-binding domain formed by a $V_H$-$V_L$ dimer. Antibodies and antigen-binding portions can be described by the antigen to which they specifically bind. For example, a PD-L1 antibody, or anti-PD-L1 antibody, is an antibody that specifically binds to PD-L1.

The $V_H$ and $V_L$ regions can be further subdivided into regions of hypervariability (hypervariable regions (HVRs), also called complementarity determining regions (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen-binding, and confer antigen specificity and binding affinity to the antibody. (See Kabat et al. (1991) *Sequences of Proteins of Immunological Interest* 5th ed., Public Health Service, National Institutes of Health, Bethesda, Md.)

CDRs are involved in antigen binding and confer antigen specificity and binding affinity to the antibody. There are three CDRs in each of the variable domains of the heavy chain and the light chain, which are designated CDR1, CDR2 and CDR3, for each of the variable domains. The term "CDR set" as used herein refers to a group of three CDRs that occur in a single heavy or light chain variable domain capable of binding a target antigen. The exact boundaries of these CDRs have been defined differently according to different systems. The three heavy chain CDRs can be referred to as CDRH1, CDRH2, and CDRH3, and the three light chain CDRs can be referred to as CDRL1, CDRL2, and CDRL3.

The system described by Kabat, also referred to as "numbered according to Kabat," "Kabat numbering," "Kabat definitions," and "Kabat labeling," provides an unambiguous residue numbering system applicable to any variable domain of an antibody, and provides precise residue boundaries defining the three CDRs of each chain. (Kabat et al., Sequences of Proteins of Immunological Interest, National Institutes of Health, Bethesda, Md. (1987) and (1991), the contents of which are incorporated by reference in their entirety. These CDRs are referred to as Kabat CDRs and comprise about residues 24-34 (CDR1), 50-56 (CDR2) and 89-97 (CDR3) in the light chain variable domain, and 31-35 (CDR1), 50-65 (CDR2) and 95-102 (CDR3) in the heavy chain variable domain. When the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. The "EU index as in Kabat" refers to the residue numbering of the human IgG1 EU antibody.

Other CDR numbering systems are also used in the art (see, for example, Table A). Chothia and coworkers found that certain sub-portions within Kabat CDRs adopt nearly identical peptide backbone conformations, despite having great diversity at the level of amino acid sequence. (Chothia et al. (1987) J. Mol. Biol. 196: 901-917; and Chothia et al. (1989) Nature 342: 877-883). These sub-portions were designated as L1, L2, and L3 or H1, H2, and H3 where the "L" and the "H" designates the light chain and the heavy chains regions, respectively. These CDRs can be referred to as "Chothia CDRs," "Chothia numbering," or "numbered according to Chothia," and comprise about residues 24-34 (CDR1), 50-56 (CDR2) and 89-97 (CDR3) in the light chain variable domain, and 26-32 (CDR1), 52-56 (CDR2) and 95-102 (CDR3) in the heavy chain variable domain. Mol. Biol. 196:901-917 (1987).

The system described by MacCallum, also referred to as "numbered according to MacCallum," or "MacCallum numbering" comprises about residues 30-36 (CDR1), 46-55 (CDR2) and 89-96 (CDR3) in the light chain variable domain, and 30-35 (CDR1), 47-58 (CDR2) and 93-101 (CDR3) in the heavy chain variable domain. MacCallum et al. ((1996) J. Mol. Biol. 262(5):732-745).

The system described by AbM, also referred to as "numbering according to AbM," or "AbM numbering" comprises about residues 24-34 (CDR1), 50-56 (CDR2) and 89-97 (CDR3) in the light chain variable domain, and 26-35 (CDR1), 50-58 (CDR2) and 95-102 (CDR3) in the heavy chain variable domain.

The IMGT (INTERNATIONAL IMMUNOGENETICS INFORMATION SYSTEM) numbering of variable regions can also be used, which is the numbering of the residues in an immunoglobulin variable heavy or light chain according to the methods of the IIMGT, as described in Lefranc, M.-P., "The IMGT unique numbering for immunoglobulins, T cell Receptors and Ig-like domains", The Immunologist, 7, 132-136 (1999), and is expressly incorporated herein in its entirety by reference. As used herein, "IMGT sequence numbering" or "numbered according to IMTG," refers to numbering of the sequence encoding a variable region according to the IMGT. For the heavy chain variable domain, when numbered according to IMGT, the hypervariable region ranges from amino acid positions 27 to 38 for CDR1, amino acid positions 56 to 65 for CDR2, and amino acid positions 105 to 117 for CDR3. For the light chain variable domain, when numbered according to IMGT, the hypervariable region ranges from amino acid positions 27 to 38 for CDR1, amino acid positions 56 to 65 for CDR2, and amino acid positions 105 to 117 for CDR3.

In some embodiments of the constructs and antigen-binding arms described herein, the CDRs recited herein comprise about residues 24-34 (CDR1), 49-56 (CDR2) and 89-97 (CDR3) in the light chain variable domain, and 27-35 (CDR1), 49-60 (CDR2) and 93-102 (CDR3) in the heavy chain variable domain, when numbered according to Chothia numbering. In some embodiments, CDR2 in the light chain variable domain can comprise amino acids 49-56, when numbered according to Chothia numbering.

TABLE A

| | CDR Definitions | | | | | |
|---|---|---|---|---|---|---|
| | CDRH1 | CDRH2 | CDRH3 | CDRL1 | CDRL2 | CDRL3 |
| Kabat | 31-35 | 50-65 | 95-102 | 24-34 | 50-56 | 89-97 |
| Alternative CDRs numbered according to Chothia | 27-35 | 49-60 | 93-102 | 24-34 | 50-56 | 89-97 |
| Chothia | 26-32 | 52-56 or 50-56 | 95-102 | 24-34 | 50-56 | 89-97 |
| MacCallum | 30-35 | 47-58 | 93-101 | 30-36 | 46-55 | 89-96 |
| AbM | 26-35 | 50-58 | 95-102 | 24-34 | 50-56 | 89-97 |
| IMGT | 27-38 | 56-65 | 105-117 | 27-38 | 56-65 | 105-117 |

Preferred methods and materials are described herein, although methods and materials similar or equivalent to those described herein can also be used in the practice or testing of the presently disclosed methods and compositions. All publications, patent applications, patents, and other references mentioned herein are incorporated by reference in their entirety.

Various aspects of the invention are described in further detail below. Additional definitions are set out throughout the specification.

The immune system has the capability of recognizing and eliminating tumor cells; however, tumors can use multiple strategies to evade immunity. Recent studies have shown that inhibitory immune checkpoint molecules promote cancer progression through various antitumor inhibitory mechanisms. Blockade of immune checkpoints is one of the approaches to activating or reactivating therapeutic antitumor immunity. Various ligands have been described for a number of cognate inhibitory immune checkpoint receptors. Reviewed in, e.g., Nair & Elkord, Immunology & Cell Biology (2018), 96:21-33; and Jenkins et al., British J. of Cancer (2017), 118:9-16.

The Programmed Death 1 (PD-1) protein is an inhibitory member of the extended CD28/CTLA-4 family of T cell regulators (Okazaki et al. (2002) Curr Opin Immunol 14: 391779-82; Bennett et al. (2003) J. Immunol. 170:711-8). Other members of the CD28 family include CD28, CTLA-4, ICOS and BTLA. PD-1 is suggested to exist as a monomer, lacking the unpaired cysteine residue characteristic of other CD28 family members. PD-1 is expressed on activated B cells, T cells, and monocytes.

The PD-1 gene encodes a 55 kDa type I transmembrane protein (Agata et al. (1996) Int Immunol. 8:765-72). Although structurally similar to CTLA-4, PD-1 lacks the MYPPY motif that is important for B7-1 and B7-2 binding. Two ligands for PD-1 have been identified, PD-L1 (B7-H1) and PD-L2 (B7-DC), that have been shown to downregulate T cell activation upon binding to PD-1 (Freeman et al. (2000) J. Exp. Med. 192:1027-34; Carter et al. (2002) Eur. J. Immunol. 32:634-43). Both PD-L1 and PD-L2 are B7 homologs that bind to PD-1, but do not bind to other CD28 family members. PD-L1 is abundant in a variety of human cancers (Dong et al. (2002) *Nat. Med.* 8:787-9).

PD-1 is known as an immunoinhibitory protein that negatively regulates TCR signals (Ishida, Y. et al. (1992) *EMBO J.* 11:3887-3895; Blank, C. et al. (Epub 2006 Dec. 29) *Immunol. Immunother.* 56(5):739-745). The interaction between PD-1 and PD-L1 can act as an immune checkpoint, which can lead to, e.g., a decrease in tumor infiltrating lymphocytes, a decrease in T-cell receptor mediated proliferation, and/or immune evasion by cancerous cells (Dong et al. (2003) *J. Mol. Med.* 81:281-7; Blank et al. (2005) *Cancer Immunol. Immunother.* 54:307-314; Konishi et al. (2004) *Clin. Cancer Res.* 10:5094-100). Immune suppression can be reversed by inhibiting the local interaction of PD-1 with PD-L1 or PD-L2; the effect is additive when the interaction of PD-1 with PD-L2 is blocked as well (Iwai et al. (2002) *Proc. Nat'l. Acad. Sci.* USA 99:12293-7; Brown et al. (2003) *J. Immunol.* 170:1257-66).

PD-L1, also known as cluster of differentiation 274 (CD274) or B7 homolog 1 (B7-H1) is a 40 kDa type 1 transmembrane protein that plays a role in suppressing the immune system during particular events such as pregnancy, tissue allografts, autoimmune disease and other disease states such as hepatitis. By way of example, human PD-L1 comprises the amino acid sequence of SEQ ID NO: 115 (UniProt Q9NZQ7). Normally the immune system reacts to foreign antigens that are associated with exogenous or endogenous danger signals, which triggers a proliferation of antigen-specific CD8+ T cells and/or CD4+ helper cells. In cancer, PD-L1 expressed on cancer cells binds to its ligand PD-1 on immune effector cells, for example, T cells. The binding of PD-L1 to PD-1 transmits an inhibitory signal that reduces the proliferation of antigen-specific T-cells in lymph nodes, while simultaneously reducing apoptosis in regulatory T cells (anti-inflammatory, suppressive T cells). The PD-1/PD-L1 interaction also induces apoptosis of tumor-specific T cells, promotes the differentiation of CD4$^+$ T cells into Foxp3$^+$ regulatory T cells, and promotes resistance of tumor cells to cytotoxic T lymphocyte (CTL) attack, thus allowing tumors to evade the host immune system.

The present disclosure relates to compositions and methods for inhibiting tumor evasion by reducing immune checkpoint suppression that results from the interaction between PD-1 and its ligand (e.g., PD-L1 and/or PD-L2). In particular, provided herein are compositions comprising novel multispecific and multivalent constructs, such as a bispecific and tetravalent construct, that block the interaction between PD-1 and its ligand (e.g., PD-1 and/or PD-L2) while promoting the interaction of (bridging) the cells on which PD-1 and its ligand are expressed. Such compositions of the present disclosure with the capacity to "block and bridge" have increased potency in vitro and in vivo and strongly enhance, for example, T cell proliferation, IFNγ production and/or secretion, the cytolytic activity of T cells, and/or rescue T cells from functional exhaustion, to provide superior anti-tumor efficacy (a biological effect which can be manifested by various means, including, but not limited to, e.g., a decrease in tumor volume, a decrease in the number of tumor cells, a decrease in tumor cell proliferation, and/or a decrease in tumor cell survival), as compared to combinations of individual antibodies, as well as compared to clinical checkpoint blockade agents. Also provided herein are novel monoclonal anti-PD-1 antibodies and antigen-binding fragments thereof, and novel monoclonal anti-PD-L1 antibodies and antigen-binding fragments thereof, for use in such multispecific and multivalent constructs. Some of these novel monoclonal anti-PD-1 antibodies and novel monoclonal anti-PD-L1 antibodies share a common light chain, thereby allowing for the generation of multispecific and multivalent constructs having excellent drug-like properties and manufacturability, as well as affinities similar to their parental antibodies.

Accordingly, the disclosure provides a multispecific antigen-binding construct comprising at least two antigen-binding arms or units of antigen-binding, wherein a first arm or unit of antigen-binding binds PD-1 expressed by an immune cell, and a second arm or unit of antigen-binding binds one or more PD-1 ligands (e.g., PD-L1 and/or PD-L2) which is expressed by a second cell. In some embodiments, the multispecific antigen-binding construct blocks the interaction of PD-1 and its ligand. In some embodiments, the multispecific antigen-binding construct bridges the cells on which PD-1 and its ligand are expressed to promote the interaction and/or efficacy of the immune cell that expresses PD-1. In some embodiments, at least one of the antigen-binding arms is bivalent for PD-1. In some embodiments, at least one of the antigen-binding arms is bivalent for PD-L1. In some embodiments, at least one of the antigen-binding arms is bivalent for PD-1, and at least one of the antigen-binding arms is bivalent for PD-L1. In some embodiments, the multispecific antigen-binding construct comprises at least two units of antigen-binding that bind PD-1. In some embodiments, the multispecific antigen-binding construct comprises two units of antigen-binding that bind PD-1. In some embodiments, the multispecific antigen-binding construct comprises at least two units of antigen-binding that bind a PD-1 ligand, such as PD-L1 or PD-L2. In some embodiments, the multispecific antigen-binding construct comprises two units of antigen-binding that bind a PD-1 ligand, such as PD-L1 or PD-L2. In some embodiments, the multispecific antigen-binding construct comprises at least four units of antigen-binding, wherein two units of antigen-binding bind PD-1 and two units of antigen-binding bind a PD-1 ligand, such as PD-L1 or PD-L2. In some embodiments, the multispecific antigen-binding construct comprises four units of antigen-binding, wherein two units of antigen-binding bind PD-1 and two units of antigen-binding bind a PD-1 ligand, such as PD-L1 or PD-L2. In some embodiments of any of the aspects described herein, the construct is a bispecific antibody. In some embodiments, the bispecific antibody is an antagonist of both PD-1 and PD-1 ligand. In some embodiments, the construct comprises a common light chain. In some embodiments, one or both of the antigen-binding arms is an aptamer. In some embodiments, one or both of the antigen-binding arms is a protein other than an antibody. In some embodiments, the construct comprises at least two antibodies. In some embodiments, at least one of the antigen-binding arms is a bivalent antibody specific for PD-1. In some embodiments, at least one of the antigen-binding arms is a bivalent antibody specific for PD-L1. In some embodiments, at least one of the antigen-binding arms is a bivalent antibody specific for PD-1, and at least one of the antigen-binding arms is a bivalent antibody specific for PD-L1, such that the construct is tetravalent. In some embodiments, the bispecific antibody binds two different epitopes on PD-1. In some embodiments, the bispecific antibody binds two different epitopes on the PD-1 ligand. Also provided herein, in some aspects, are novel isolated antibodies and antigen-binding portions thereof that specifically bind PD-L1 or PD-1. In some embodiments, these novel isolated antibodies and antigen-binding portions thereof, such as CDRs, variable heavy chains, and/or variable light chains, that specifically bind PD-L1 or PD-1 can be used in one or more arms or units of antigen-binding of the multispecific antigen-binding constructs described herein.

Accordingly, as described herein, the disclosed multispecific antigen-binding constructs include bispecific, tri specific, tetraspecific, or multispecific antibodies or antigen-binding portions thereof. The described multispecific constructs are preferably bivalent for at least one, preferably both, antigen-binding arm(s), i.e., are bispecific and trivalent, or bispecific and tetravalent molecules. The multispecific constructs described herein can, in various aspects and embodiments, comprise one or more antibodies and/or antigen-binding portions thereof. For example, an antigen-binding arm can comprise a variable heavy and/or variable light chain, or complementarity determining regions (CDRs) thereof, of a given antibody to PD-1 and/or a given antibody to PD-L1. Accordingly, in some embodiments of any of the aspects described herein, the first antigen-binding arm, second antigen-binding arm, first unit of antigen-binding, second unit of binding, or any combination thereof, can comprise an antibody or an antigen-binding portion thereof. In some embodiments of any of the aspects described herein, the first antigen-binding arm, second antigen-binding arm, first unit of antigen-binding, second unit of binding, or any combination thereof, is an antibody or an antigen-binding portion thereof.

A. PD-L1 Antagonists

In some aspects and embodiments, the disclosure provides for anti-PD-L1 antagonists. In some embodiments, the anti-PD-L1 antagonist is any of the anti-PD-L1 antibodies or antigen-binding molecules disclosed herein. In some embodiments, the anti-PD-L1 antibody or antigen-binding molecule is not a part of a multispecific antigen-binding construct, i.e., the anti-PD-L1 antibody or antigen-binding molecule is not a part of a protein construct that binds to multiple epitopes. In some embodiments, the anti-PD-L1 antibody or antigen-binding portion can be combined with a different antibody or antigen-binding portion to form a multispecific antigen-binding construct. In some embodiments, the multispecific antigen-binding construct is capable of binding an epitope on PD-L1 and an epitope on another protein. In some embodiments, the epitope on the other protein is on PD-1.

Accordingly, in some aspects, provided herein are antibodies or antigen-binding portions thereof that specifically bind PD-L1. In some aspects, the antibody or antigen-binding portion thereof that specifically binds PD-L1 comprises (a) a heavy chain variable region comprising (i) a CDRH1 comprising SEQ ID NO: 1 (GTFSSYAIN); (ii) a CDRH2 comprising SEQ ID NO: 2 (GGIIPX$_1$X$_2$GX$_3$ATYA, wherein X$_1$ is V or I; X$_2$ is F, L, or V; and X$_3$ is T or A); and (iii) a CDRH3 comprising SEQ ID NO: 3 (ARLKX$_1$ELKDAFDI, wherein X$_1$ is G, F, or N); and (b) a light chain variable region comprising: (i) a CDRL1 comprising SEQ ID NO: 4 (RASQX$_1$ISSYLN, wherein X$_1$ is S, W, or Q); (ii) a CDRL2 comprising SEQ ID NO: 5 (AASSLQS); and (iii) a CDRL3 comprising SEQ ID NO: 6 (X$_1$QSYSTPLT, wherein X$_1$ is Q or F).

In some embodiments of these aspects and all such aspects described herein, CDRH1 comprises SEQ ID NO: 1 (GTFSSYAIN), CDRH2 comprises SEQ ID NO: 7 (GGIIPILGAATYA) and CDRH3 comprises SEQ ID NO: 8 (ARLKGELKDAFDI). In some embodiments of these aspects and all such aspects described herein, CDRH1 comprises SEQ ID NO: 1 (GTFSSYAIN), CDRH2 comprises SEQ ID NO: 7 (GGIIPILGAATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb1.

In some embodiments of these aspects and all such aspects described herein, CDRH1 comprises SEQ ID NO: 1 (GTFSSYAIN), CDRH2 comprises SEQ ID NO: 11 (GGIIPVFGTATYA) and CDRH3 comprises SEQ ID NO: 8 (ARLKGELKDAFDI). In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 12 (RASQWISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb2. In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 13 (RASQQISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb3.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb4. Another representative antibody having such heavy and light chain variable CDR regions is mAb24.

In some embodiments of these aspects and all such aspects described herein, CDRH1 comprises SEQ ID NO: 14 (GTFSSYAFS), CDRH2 comprises SEQ ID NO: 11 (GGIIPVFGTATYA) and CDRH3 comprises SEQ ID NO: 8 (ARLKGELKDAFDI). In some embodiments of these aspects and all such aspects described herein, CDRH1 comprises SEQ ID NO: 14 (GTFSSYAFS), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb5.

In some embodiments of these aspects and all such aspects described herein, CDRH1 comprises SEQ ID NO: 1 (GTFSSYAIN), CDRH2 comprises SEQ ID NO: 15 (GGIIPIFGIANYA) and CDRH3 comprises SEQ ID NO: 8 (ARLKGELKDAFDI). In some embodiments of these aspects and all such aspects described herein, CDRH1 comprises SEQ ID NO: 1 (GTFSSYAIN), CDRH2 comprises SEQ ID NO: 15 (GGIIPIFGIANYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb6.

In some embodiments of these aspects and all such aspects described herein, CDRH1 comprises SEQ ID NO: 1 (GTFSSYAIN), CDRH2 comprises SEQ ID NO: 16 (GGIIPNFGTATYA) and CDRH3 comprises SEQ ID NO:

17 (ARLKGELKGAGDI). In some embodiments of these aspects and all such aspects described herein SEQ ID NO: 1 (GTFSSYAIN), CDRH2 comprises SEQ ID NO: 16 (GGIIPNFGTATYA), CDRH3 comprises SEQ ID NO: 17 (ARLKGELKGAGDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb7.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), and CDRH3 comprises SEQ ID NO: 18 (ARLKFELKDAFDI). In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 18 (ARLKFELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb8.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), and CDRH3 comprises SEQ ID NO: 19 (ARLKGELKDAFDE). In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 19 (ARLKGELKDAFDE), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb9.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), and CDRH3 comprises SEQ ID NO: 20 (ARLKNELKDAFDI). In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 20 (ARLKNELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb10.

In some embodiments of these aspects and all such aspects described herein, CDRH1 comprises SEQ ID NO: 1 (GTFSSYAIN), CDRH2 comprises SEQ ID NO: 21 (GGVIPFLGTANYA), and CDRH3 comprises SEQ ID NO: 22 (ARLKGILKDALDI). In some embodiments of these aspects and all such aspects described herein, CDRH1 comprises SEQ ID NO: 1 (GTFSSYAIN), CDRH2 comprises SEQ ID NO: 21 (GGVIPFLGTANYA), CDRH3 comprises SEQ ID NO: 22 (ARLKGILKDALDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb11.

In some embodiments of these aspects and all such aspects described herein, CDRH1 comprises SEQ ID NO: 23 (GTFSSYAIS), CDRH2 comprises SEQ ID NO: 24 (GGIIPIVGIANYA), and CDRH3 comprises SEQ ID NO: 8 (ARLKGELKDAFDI). In some embodiments of these aspects and all such aspects described herein, CDRH1 comprises SEQ ID NO: 23 (GTFSSYAIS), CDRH2 comprises SEQ ID NO: 24 (GGIIPIVGIANYA), CDRH3 comprises SEQ ID NO: 8 (ARLKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb12.

In some embodiments of these aspects and all such aspects described herein, CDRH1 comprises SEQ ID NO: 23 (GTFSSYAIS), CDRH2 comprises SEQ ID NO: 11 (GGIIPVFGTATYA), and CDRH3 comprises SEQ ID NO: 25 (ARLKGEFKDAFDI). In some embodiments of these aspects and all such aspects described herein, CDRH1 comprises SEQ ID NO: 23 (GTFSSYAIS), CDRH2 comprises SEQ ID NO: 11 (GGIIPVFGTATYA), CDRH3 comprises SEQ ID NO: 25 (ARLKGEFKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb13.

In some embodiments of these aspects and all such aspects described herein, CDRH1 comprises SEQ ID NO: 23 (GTFSSYAIS), CDRH2 comprises SEQ ID NO: 26 (GRIIPLFGTAHYA), and CDRH3 comprises SEQ ID NO: 8 (ARLKGELKDAFDI). In some embodiments of these aspects and all such aspects described herein, CDRH1 comprises SEQ ID NO: 23 (GTFSSYAIS), CDRH2 comprises SEQ ID NO: 26 (GRIIPLFGTAHYA), CDRH3 comprises SEQ ID NO: 8 (ARLKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb14.

In some embodiments of these aspects and all such aspects described herein, CDRH1 comprises SEQ ID NO: 23 (GTFSSYAIS), CDRH2 comprises SEQ ID NO: 27 (GRINPILGTANYA), and CDRH3 comprises SEQ ID NO: 28 (ARLKGELKDAFSI). In some embodiments of these aspects and all such aspects described herein, CDRH1 comprises SEQ ID NO: 23 (GTFSSYAIS), CDRH2 comprises SEQ ID NO: 27 (GRINPILGTANYA), CDRH3 comprises SEQ ID NO: 28 (ARLKGELKDAFSI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb15.

In some embodiments of these aspects and all such aspects described herein, CDRH1 comprises SEQ ID NO: 1 (GTFSSYAIN), CDRH2 comprises SEQ ID NO: 29 (GRIIPIFGTADYA), and CDRH3 comprises SEQ ID NO: 8 (ARLKGELKDAFDI). In some embodiments of these aspects and all such aspects described herein, CDRH1 comprises SEQ ID NO: 1 (GTFSSYAIN), CDRH2 comprises SEQ ID NO: 29 (GRIIPIFGTADYA), CDRH3 comprises SEQ ID NO: 8 (ARLKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb16.

In some embodiments of these aspects and all such aspects described herein, CDRH1 comprises SEQ ID NO: 23 (GTFSSYAIS), CDRH2 comprises SEQ ID NO: 11 (GGIIPVFGTATYA), and CDRH3 comprises SEQ ID NO:

30 (ARLKGELKCAFDI). In some embodiments of these aspects and all such aspects described herein, CDRH1 comprises SEQ ID NO: 23 (GTFSSYAIS), CDRH2 comprises SEQ ID NO: 11 (GGIIPVFGTATYA), CDRH3 comprises SEQ ID NO: 30 (ARLKGELKCAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT).

In some embodiments of these aspects and all such aspects described herein, CDRH1 comprises SEQ ID NO: 122 (GTKSSYAIS), CDRH2 comprises SEQ ID NO: 11 (GGIIPVFGTATYA), and CDRH3 comprises SEQ ID NO: 30 (ARLKGELKCAFDI). In some embodiments of these aspects and all such aspects described herein, CDRH1 comprises SEQ ID NO: 122 (GTKSSYAIS), CDRH2 comprises SEQ ID NO: 11 (GGIIPVFGTATYA), CDRH3 comprises SEQ ID NO: 30 (ARLKGELKCAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb17.

In some embodiments of these aspects and all such aspects described herein, CDRH1 comprises SEQ ID NO: 1 (GTFSSYAIN), CDRH2 comprises SEQ ID NO: 31 (GGIIPILGTATYA), and CDRH3 comprises SEQ ID NO: 32 (ARRKGELKDAFDI). In some embodiments of these aspects and all such aspects described herein, CDRH1 comprises SEQ ID NO: 1 (GTFSSYAIN), CDRH2 comprises SEQ ID NO: 31 (GGIIPILGTATYA), CDRH3 comprises SEQ ID NO: 32 (ARRKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb18.

In some embodiments of these aspects and all such aspects described herein, CDRH1 comprises SEQ ID NO: 1 (GTFSSYAIN), CDRH2 comprises SEQ ID NO: 33 (GGIIPIVATANYA), and CDRH3 comprises SEQ ID NO: 32 (ARRKGELKDAFDI). In some embodiments of these aspects and all such aspects described herein, CDRH1 comprises SEQ ID NO: 1 (GTFSSYAIN), CDRH2 comprises SEQ ID NO: 33 (GGIIPIVATANYA), CDRH3 comprises SEQ ID NO: 32 (ARRKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb19.

In some embodiments of these aspects and all such aspects described herein, CDRH1 comprises SEQ ID NO: 1 (GTFSSYAIN), CDRH2 comprises SEQ ID NO: 34 (GGIIPIFGKATYA), and CDRH3 comprises SEQ ID NO: 32 (ARRKGELKDAFDI). In some embodiments of these aspects and all such aspects described herein, CDRH1 comprises SEQ ID NO: 1 (GTFSSYAIN), CDRH2 comprises SEQ ID NO: 34 (GGIIPIFGKATYA), CDRH3 comprises SEQ ID NO: 32 (ARRKGELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb20.

In some embodiments of these aspects and all such aspects described herein, CDRH1 comprises SEQ ID NO: 36 (GPFRSHAVS), CDRH2 comprises SEQ ID NO: 11 (GGIIPVFGTATYA), and CDRH3 comprises SEQ ID NO: 37 (ARLKSELKDAFDI). In some embodiments of these aspects and all such aspects described herein, CDRH1 comprises SEQ ID NO: 36 (GPFRSHAVS), CDRH2 comprises SEQ ID NO: 11 (GGIIPVFGTATYA), CDRH3 comprises SEQ ID NO: 37 (ARLKSELKDAFDI), CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb21.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 38 (FQSYSTPLT). A representative antibody having such heavy and light chain variable CDR regions is mAb22.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 39 (QQSYSTILT). A representative antibody having such heavy and light chain variable CDR regions is mAb23.

In some embodiments of these aspects and all such aspects described herein, CDRH1 comprises SEQ ID NO: 1 (GTFSSYAIN), CDRH2 comprises SEQ ID NO: 11 (GGIIPVFGTATYA), CDRH3 comprises SEQ ID NO: 8 (ARLKGELKDAFDI); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb24.

In each case, where specific sequences are recited, embodiments comprising a sequence having at least 90% (e.g., at least 90%, at least 91%, at least 92%, at least 93%, at least 94%, at least 95%, at least 96%, at least 97%, at least 98%, or at least 99% identical) identity to the recited sequence (e.g., SEQ ID NO: 1-34 and 36-39) are also provided.

The disclosure also provides, in some aspects, an antibody or antigen-binding portion thereof that specifically binds PD-L1, wherein the antibody or antigen-binding portion thereof comprises a heavy chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 35, 40, 41, 42, 43, 44, 45, 46, 47, 48, 49, 50, 51, 52, 53, 54, 55, 56, 57, or 58, and a light chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 59, 60, 61, 62, or 63.

The disclosure also provides, in some aspects, an antibody or antigen-binding portion thereof that specifically binds PD-L1, wherein the antibody or antigen-binding portion thereof comprises a heavy chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 40, 41, 42, 43, 44, 45, 46, 47, 48, 49, 50, 51, 52, 53, 54, 55, 56, 57, or 58 and a light chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 59.

The disclosure also provides, in some aspects, an antibody or antigen-binding portion thereof that specifically binds PD-L1, wherein the antibody or antigen-binding portion thereof comprises a heavy chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 35 and a light chain variable region comprising an amino acid sequence that is at least 90% identical (e.g., at least 90%, at least 91%, at least 92%, at least 93%, at least 94%, at least 95%, at least 96%, at least 97%, at least 98%, or at least 99% identical) to SEQ ID NO: 59, 60, 61, 62, or 63.

Antibodies mAb1-mAb23 are affinity matured antibodies derived from parent antibody mAb24, as described in the Examples. An affinity matured antibody or antigen-binding portion thereof is an antibody or antigen-binding fragment with one or more alterations (e.g., in one or more CDRs or FRs) that result in an improvement in the affinity of an antibody for its antigen, compared to a parent antibody lacking the alteration(s). In some embodiments, an affinity matured antibody has nanomolar or picomolar affinity for PD-L1. In some embodiments, the PD-L1 antibody or antigen-binding portion thereof has a $K_D$ of at least $1\times10^{-7}$ M, at least $1\times10^{-8}$ M, at least $1\times10^{-9}$ M, at least $1\times10^{-10}$ M, at least $1\times10^{-11}$ M, at least $1\times10^{-12}$ M, or at least $1\times10^{-13}$ M.

Table 1 shows the binding affinities ($K_D$) of mAb1, mAb2, mAb3, mAb4, mAb5, mAb6, mAb7, mAb8, mAb9, mAb10, mAb11, mAb12, mAb13, mAb14, mAb15, mAb16, mAb17, mAb18, mAb19, mAb20, mAb21, mAb22, and mAb23 (i.e., affinity matured variants of mAb24) to human PD-L1. The term $K_D$, as used herein, refers to the dissociation equilibrium constant of a particular antibody-antigen interaction. $K_D=k_d/k_a$. The term $k_d$ (sec$^{-1}$), as used herein, refers to the dissociation rate constant of a particular antibody-antigen interaction. The value is also referred to as the $k_{off}$ value. The term $k_a$ (M$^{-1}\times$sec$^{-1}$), as used herein, refers to the association rate constant of a particular antibody-antigen interaction. The value is also referred to as the $k_{on}$ value.

TABLE 1

Binding affinities of mAb1-mAb23 to human PD-L1

| mAb | $K_D$ (nM) | Fold Improvement |
|---|---|---|
| 1 | 4.16 | 1.1 |
| 2 | 2.2 | 2.0 |
| 3 | 0.9 | 4.8 |
| 4 | 4.9 | 0.9 |
| 5 | 27.1 | 0.2 |
| 6 | 35.9 | 0.1 |
| 7 | — | — |
| 8 | 3.7 | 1.2 |
| 9 | 5.4 | 0.8 |
| 10 | 6.3 | 0.7 |
| 11 | 156 | — |
| 12 | 358 | — |
| 13 | 52.3 | 0.1 |
| 14 | — | — |
| 15 | — | — |
| 16 | — | — |
| 17 | — | — |
| 18 | 527 | — |
| 19 | 817 | — |
| 20 | 53.9 | 0.1 |
| 21 | 91.5 | 0.1 |
| 22 | 2.5 | 1.8 |
| 23 | 369 | — |

Table 2 provides cell binding data for mAb1, mAb2, mAb3, mAb4, mAb5, mAb6, mAb7, mAb8, mAb9, mAb10, mAb11, mAb12, mAb13, mAb14, mAb15, mAb16, mAb17, mAb18, mAb19, mAb20, mAb21, mAb22, and mAb23 (i.e., affinity matured variants of mAb24) to human PD-L1 ("huPDL1"), cyno PD-L1, or murine PD-L1 ("muPDL1"). Human or cyno PD-L1 was expressed on HEK cells; murine PD-L1 was expressed on A20 cells. Binding is expressed as an $EC_{50}$ value, which can be estimated from titrating different concentrations of mAb on cells that exogenously express the antigen of interest. Fluorescent tagged secondaries can be used to detect and quantify the mAb binding. The data shown in Table 2 was fit to a 1:1 binding model using built-in functions in GRAPHPAD, which yielded the $EC_{50}$ value.

TABLE 2

Cell binding of mAb1-mAb23 to human, cyno, and murine PD-L1 expressed on cells

| mAb | huPDL1 $EC_{50}$ (nM) | Fold Improvement | cynoPDL1 $EC_{50}$ (nM) | Fold Improvement | muPDL1 $EC_{50}$ (nM) | Fold Improvement |
|---|---|---|---|---|---|---|
| 1 | 0.04 | 3.3 | 0.09 | 3.21 | 0.74 | 5.26 |
| 2 | 0.06 | 2.2 | 0.08 | 3.76 | 2.00 | 1.96 |
| 3 | 0.11 | 1.3 | ND | — | 1.27 | 3.08 |
| 4 | 0.04 | 3.3 | 0.07 | 4.10 | NB | — |
| 5 | 0.09 | 1.5 | 0.39 | 0.74 | NB | — |
| 6 | 0.13 | 1.1 | 0.47 | 0.61 | NB | — |
| 7 | ND | — | NB | — | NB | — |
| 8 | ND | — | 0.08 | 3.42 | NB | — |
| 9 | 0.06 | 2.5 | 0.07 | 4.15 | NB | — |
| 10 | 0.04 | 3.2 | 0.09 | 3.05 | NB | — |
| 11 | 1.37 | 0.1 | NB | — | NB | — |
| 12 | 1.23 | 0.1 | NB | — | NB | — |
| 13 | 1.43 | 1.0 | ND | — | NB | — |
| 14 | 1.54 | 0.1 | NB | — | NB | — |
| 15 | ND | — | NB | — | NB | — |
| 16 | NB | — | NB | — | NB | — |
| 17 | 0.76 | 0.2 | NB | — | NB | — |
| 18 | 0.38 | 0.4 | 0.06 | 4.96 | 0.84 | 4.67 |
| 19 | 1.20 | 0.1 | 0.26 | 1.08 | 2.84 | 1.38 |
| 20 | 0.13 | 1.0 | 0.12 | 2.31 | 2.66 | 1.47 |
| 21 | 0.14 | 1.0 | NB | — | NB | — |
| 22 | 0.18 | 0.8 | 0.32 | 0.89 | NB | — |
| 23 | 0.83 | 0.2 | NB | — | NB | — |

*NB = no binding; ND = not determined; human and cyno PDL1 expressed on HEK cells; murine PDL1 expressed on A20 cells The disclosure also provides an antibody or antigen-binding portion thereof that specifically binds PD-L1, wherein the antibody or antigen-binding portion thereof comprises a heavy chain variable region comprising an amino acid sequence that is at least 90% identical (for example, at least 90%, at least 91%, at least 92%, at least 93%, at least 94%, at least 95%, at least 96%, at least 97%, at least 98% or at least 99% identical) to any one of SEQ ID NOs: 35, 40, 41, 42, 43, 44, 45, 46, 47, 48, 49, 50, 51, 52, 53, 54, 55, 56, 57, or 58, and a light chain variable region comprising an amino acid sequence that is at least 90% identical (for example, at least 90%, at least 91%, at least 92%, at least 93%, at least 94%, at least 95%, at least 96%, at least 97%, at least 98% or at least 99% identical) to any one of SEQ ID NO: 59, 60, 61, 62, or 63. In some embodiments, the heavy chain variable region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from any one of SEQ ID NOs: 35, 40, 41, 42, 43, 44, 45, 46, 47, 48, 49, 50, 51, 52, 53, 54, 55, 56, 57, or 58. In some embodiments, the light chain variable region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from any one of SEQ ID NO: 59, 60, 61, 62, or 63. Tables 3 and 4 provide the sequences for heavy chain variable sequences SEQ ID Nos: 35 and 40-58, and light chain variable sequences SEQ ID Nos: 59-63, respectively.

TABLE 3

Heavy chain anti-PD-L1 variable sequences

| SEQ ID NO | Sequence |
|---|---|
| 35 | QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKGELKDAFDIWGQGTMVTVSS |
| 40 | QVQLVQSGAEVKKPGSSVKVSCKASGGTFSSYAFSWVRQAPGQGLEWMGGIIPVFGTATYAQKFQGRVTITADESTSTAYMELSSLRSEDTAVYYCARLKGELKDAFDIWGQGTLVTVSS |
| 41 | QVQLVQSGAEVKKPGSSVKVSCKASGGTFSSYAINWVRQAPGQGLEWMGGIIPIFGIANYAQKFQGRVTITADESTSTAYMELSSLRSEDTAVYYCARLKGELKDAFDIWGQGTLVTVSS |
| 42 | QVQLVQSGAEVKKPGSSVKVSCKASGGTFSSYAINWVRQAPGQGLEWMGGIIPNFGTATYAQKFQGRVTITADESTSTAYMELSSLRSEDTAVYYCARLKGELKGAGDIWGQGTLVTVSS |
| 43 | QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKFELKDAFDIWGQGTLVTVSS |
| 44 | QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKGELKDAFDEWGQGTLVTVSS |
| 45 | QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKGELKDAFDIWGQGTLVTAST |
| 46 | QVQLVQSGAEVKKPGSSVKVSCKASGGTFSSYAINWVRQAPGQGLEWMGGIIPVFGTATYAQKFQGRVTITADESTSTAYMELSSLRSEDTAVYYCARLKNELKDAFDIWGQGTLVTVSS |
| 47 | QVQLVQSGAEVKKPGSSVKVSCKASGGTFSSYAINWVRQAPGQGLEWMGGVIPFLGTANYAQKFQGRVTITADESTSTAYMELSSLRSEDTAVYYCARLKGILKDALDIWGQGTLVTVSS |
| 48 | QVQLVQSGAEVKKPGSSVKVSCKASGGTFSSYAISWVRQAPGQDLEWMGGIIPIVGIANYAQKFQGRVTITADESTSTAYMELSSLRSEDTAVYYCARLKGELKDAFDIWGQGTLVTVSS |
| 49 | QVQLVQSGAEVKKPGSSVKVSCKASGGTFSSYAISWVRQAPGQGLEWMGGIIPVFGTATYAQKFQGRVTITADESTSTAYMELSSLRSEDTAVYYCARLKGEFKDAFDIWGQGTLVTVSS |

TABLE 3-continued

Heavy chain anti-PD-L1 variable sequences

| SEQ ID NO | Sequence |
|---|---|
| 50 | QVQLVQSGAEVKKPGSSVKVSCKASGGTFSSYAISWVRQAPGQGLEWMGRIIPLFGTAHYAQKFQGRVTITADESTSTAYMELSSLRSEDTAVYYCARLKGELKDAFDIWGQGTLVTVSS |
| 51 | QVQLVQSGAEVKKPGSSVKVSCKASGGTFSSYAISWVRQAPGQGLEWMGRINPILGTANYAQKFQGRVTITADESTSTAYMELSSLRSEDTAVYYCARLKGELKDAFSIWGQGTLVTVSS |
| 52 | QVQLVQSGAEVKKPGSSVKVSCKASGGTFSSYAINWVRQAPGQGLEWMGRIIPIFGTADYAQKFQGRVTITADESTSTAYMELSSLRSEDTAVYYCARLKGELKDAFDIWGQGTLVTVSS |
| 53 | QVQLVQSGAEVKKPGSSVKVSCKASGGKFSSYAISWVRQAPGQGLEWMGGIIPVFGTATYAQKFQGRVTITADESTSTAYMELSSLRSEDTAVYYCARLKGELKCAFDIWGQGTLVTVSS |
| 54 | QVQLVQSGAEVKKPGSSVKVSCKASGGTFSSYAINWVRQAPGQGLEWMGGIIPILGTATYAQKFQGRVTITADESTSTAYMELSSLRSEDTAVYYCARRKGELKDAFDIWGQGTLVTVSS |
| 55 | QVQLVQSGAEVKKPGSSVKVSCKASGGTFSSYAINWVRQAPGQGLEWMGGIIPILGAATYAQKFQGRVTITADESTSTAYMELSSLRSEDTAVYYCARLKGELKDAFDIWGQGTLVTVSS |
| 56 | QVQLVQSGAEVKKPGSSVKVSCKASGGTFSSYAINWVRQAPGQGLEWMGGIIPIVATANYAQKFQGRVTITADESTSTAYMELSSLRSEDTAVYYCARRKGELKDAFDIWGQGTLVTVSS |
| 57 | QVQLVQSGAEVKKPGSSVKVSCKASGGTFSSYAINWVRQAPGQGLEWMGGIIPIFGKATYAQKFQGRVTITADESTSTAYMELSSLRSEDTAVYYCARRKGELKDAFDIWGQGTLVTVSS |
| 58 | QVQLVQSGAEVKKPGSSVKVSCKASGGPFRSHAVSWVRQAPGQGLEWMGGIIPVFGTATYAQKFQGRVTITADESTSTAYMELSSLRSEDTAVYYCARLKSELKDAFDIWGQGTLVTVSS |

TABLE 4

Light chain variable sequences

| SEQ ID NO | Sequence |
|---|---|
| 59 | DIQMTQSPSSLSASVGDRVTITCRASQSISSYLNWYQQKPGKAPKLLIYAASSLQSGVPSRFSGSGSGTDFTLTISSLQPEDFATYYCQQSYSTPLTFGGGTKVEIK |
| 60 | DIQMTQSPSSLSASVGDRVTITCRASQWISSYLNWYQQKPGKAPKLLIYAASSLQSGVPSRFSGSGSGTDFTLTISSLQPEDFATYYCQQSYSTPLTFGGGTKVEIK |
| 61 | DIQMTQSPSSLSASVGDRVTITCRASQQISSYLNWYQQKPGKAPKLLIYAASSLQSGVPSRFSGSGSGTDFTLTISSLQPEDFATYYCQQSYSTPLTFGGGTKVEIK |
| 62 | DIQMTQSPSPSSLSASVGDRVTITCRASQSISSYLNWYQQKPGKAPKLLIYAASSLQSGVPSRFSGSGSGTDFTLTISSLQPEDFATYCFQSYSTPLTFGGGTKVEIK |
| 63 | DIQMTQSPSSLSASVGDRVTITCRASQSISSYLNWYQQKPGKAPKLLIYAASSLQSGVPSRFSGSGSGTDFTLTISSLQPEDFATYYCQQSYSTILTFGGGTKVEIK |

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63, wherein the heavy and light chain CDR residues are numbered according to Kabat.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63, wherein the heavy and light chain CDR residues are numbered according to Chothia.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63, wherein the heavy and light chain CDR residues are numbered according to MacCallum.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63, wherein the heavy and light chain CDR residues are numbered according to AbM.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 35, 40, 41, 42, 43, 44, 45, 46, 47, 48, 49, 50, 51, 52, 53, 54, 55, 56, 57, or 58, and light chain CDRs of any of the light chain variable regions of SEQ ID NOs: 59, 60, 61, 62, or 63, wherein the heavy and light chain CDR residues are numbered according to IMGT.

B. PD-1 Antagonists

In some aspects and embodiments, the disclosure provides for anti-PD-1 antagonists. In some embodiments, the anti-PD-1 antagonist is any of the anti-PD-1 antibodies or antigen-binding molecules disclosed herein. In some embodiments, the anti-PD-1 antibody or antigen-binding molecule is not a part of a multispecific antigen-binding construct, i.e., the anti-PD-1 antibody or antigen-binding molecule is not a part of a protein construct that binds to multiple epitopes. In some embodiments, the anti-PD-1 antibody or antigen-binding portion can be combined with a different antibody or antigen-binding portion to form a multispecific antigen-binding construct. In some embodiments, the multispecific antigen-binding construct is capable of binding an epitope on PD-1 and an epitope on another protein. In some embodiments, the epitope on the other protein is on PD-L1.

In some embodiments, any of the multispecific antigen-binding constructs disclosed herein comprises a PD-1 antagonist. In some embodiments, the PD-1 antagonist is an "inhibitory receptor." As used herein, an "inhibitory receptor" refers generally to an immune checkpoint molecule that, when bound by a cognate ligand, causes suppression or inhibition of an immune response, such as those known to enhance tumor evasion. However, in some instances as used herein, "inhibitory receptor" refers specifically to PD-1.

PD-1 is an immune checkpoint inhibitory receptor that contains an "Immunoreceptor Tyrosine-based Inhibition Motif" or "ITIM", comprising a conserved sequence of amino acids (S/I/V/L)xYxx(I/V/L) where x is any amino acid. Methods for assaying whether PD-1 activity has been inhibited are known in the art and can be readily designed by those of skill in the art. Such assays include, for example, testing the effects of any downstream signaling pathway(s) of PD-1 in vitro or in vivo. After PD-1 interacts with its ligand, the ITIM motif becomes phosphorylated by enzymes of, e.g., the Src kinase family, allowing them to recruit other enzymes, e.g., the phosphotyrosine phosphatases SHP-1 and SHP-2, or the inositol-phosphatase called SHIP. These phosphatases have been shown to decrease the activation of molecules involved in cell signaling. See, e.g., Barrow & Trowsdale (2006) Eur J Immunol. 36 (7): 1646-53. Thus, the phosphorylation state of the ITIM motif within PD-1 can be assessed using known methods in the art. Also, the presence of downstream factors, such as phosphotyrosine phosphatases can also be examined. Moreover, various cell-based assays and kits that detect the presence of downstream factors (e.g., nuclear factor of activated T-cells—NFAT—as a measure of PD-1 inhibition) as a proxy for PD-1 activity state are known in the art. In other examples, simple binding assays can be used to determine whether the construct of the present disclosure can block binding PD-1 and its ligand, as discussed above.

Accordingly, in some aspects, provided herein are antibodies or antigen-binding portions thereof that specifically bind PD-1. In some aspects, the antibody or antigen-binding portion thereof that specifically binds PD-1 comprises (a) a heavy chain variable region comprising (i) a CDRH1 comprising SEQ ID NO: 70 (FTFX$_1$X$_2$YAX$_3$X$_4$, wherein X$_1$=S, R, G, or N; X$_2$=D, S, N, A, R, or G; X$_3$=M or L; X$_4$=S, L, or N); (ii) a CDRH2 comprising SEQ ID NO: 71 (SAISNSGTYTYYA); and (iii) a CDRH3 comprising SEQ ID NO: 72 (ARGLDFIVGX$_5$TGNDY, wherein X$_5$=A, Y, or R); and (b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some embodiments of these aspects and all such aspects described herein, CDRH1 comprises SEQ ID NO: 73 (FTFSDYAMS), CDRH2 comprises SEQ ID NO: 71 (SAISNSGTYTYYA) and CDRH3 comprises SEQ ID NO: 74 (ARGLDFIVGATGNDY). In some embodiments of these aspects and all such aspects described herein, CDRH1 comprises SEQ ID NO: 73 (FTFSDYAMS); CDRH2 comprises SEQ ID NO: 71 (SAISNSGTYTYYA); CDRH3 comprises SEQ ID NO: 74 (ARGLDFIVGATGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb25.

In some embodiments of these aspects and all such aspects described herein, CDRH1 comprises SEQ ID NO: 73 (FTFSDYAMS), CDRH2 comprises SEQ ID NO: 71

(SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 73 (FTFSDYAMS), CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb26.

In some embodiments of these aspects and all such aspects described herein, CDRH1 comprises SEQ ID NO: 76 (FTFSSYAMS), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 76 (FTFSSYAMS), CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb27.

In some embodiments of these aspects and all such aspects described herein, CDRH1 comprises SEQ ID NO: 77 (FTFSSYAML), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 77 (FTFSSYAML), CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb28.

In some embodiments of these aspects and all such aspects described herein, CDRH1 comprises SEQ ID NO: 78 (FTFSNYALS), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 78 (FTFSNYALS); CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb29.

In some embodiments of these aspects and all such aspects described herein, CDRH1 comprises SEQ ID NO: 79 (FTFSAYAMN), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 79 (FTFSAYAMN); CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb30.

In some embodiments of these aspects and all such aspects described herein, CDRH1 comprises SEQ ID NO: 80 (FTFRSYAMS), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 80 (FTFRSYAMS); CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb31.

In some embodiments of these aspects and all such aspects described herein, CDRH1 comprises SEQ ID NO: 81 (FTFGRYAMS), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 81 (FTFGRYAMS); CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb32.

In some embodiments of these aspects and all such aspects described herein, CDRH1 comprises SEQ ID NO: 82 (FTFNSYAMS), CDRH2 comprises SEQ ID NO: 71 (SAISNSGTYTYYA) and CDRH3 comprises SEQ ID NO: 75 (ARGLDFIVGYTGNDY). In some embodiments of these aspects and all such aspects described herein, CDRH1 comprises SEQ ID NO: 82 (FTFNSYAMS); CDRH2 comprises SEQ ID NO: 71 (SAISNSGTYTYYA); CDRH3 comprises SEQ ID NO: 75 (ARGLDFIVGYTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb33.

In some embodiments of these aspects and all such aspects described herein, CDRH1 comprises SEQ ID NO: 83 (FTFSNYAMS), CDRH2 comprises SEQ ID NO: 71 (SAISNSGTYTYYA) and CDRH3 comprises SEQ ID NO: 74 (ARGLDFIVGATGNDY). In some embodiments of these aspects and all such aspects described herein, CDRH1 comprises SEQ ID NO: 83 (FTFSNYAMS); CDRH2 comprises SEQ ID NO: 71 (SAISNSGTYTYYA); CDRH3 comprises SEQ ID NO: 74 (ARGLDFIVGATGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb34.

In some embodiments of these aspects and all such aspects described herein, CDRH1 comprises SEQ ID NO: 84 (FTFSGYAMS), CDRH2 comprises SEQ ID NO: 71 (SAISNSGTYTYYA) and CDRH3 comprises SEQ ID NO: 85 (ARGLDFIVGRTGNDY). In some embodiments of these aspects and all such aspects described herein, CDRH1 comprises SEQ ID NO: 84 (FTFSGYAMS); CDRH2 comprises SEQ ID NO: 71 (SAISNSGTYTYYA); CDRH3 comprises SEQ ID NO: 85 (ARGLDFIVGRTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb35.

In some embodiments of these aspects and all such aspects described herein, CDRH1 comprises SEQ ID NO: 86 (FTFSSYAMN), CDRH2 comprises SEQ ID NO: 71 (SAISNSGTYTYYA) and CDRH3 comprises SEQ ID NO: 85 (ARGLDFIVGRTGNDY). In some embodiments of these aspects and all such aspects described herein, CDRH1 comprises SEQ ID NO: 86 (FTFSSYAMN); CDRH2 comprises SEQ ID NO: 71 (SAISNSGTYTYYA); CDRH3 comprises SEQ ID NO: 85 (ARGLDFIVGRTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb36.

In some embodiments of these aspects and all such aspects described herein, CDRH1 comprises SEQ ID NO: 80 (FTFRSYAMS), CDRH2 comprises SEQ ID NO: 71 (SAISNSGTYTYYA) and CDRH3 comprises SEQ ID NO: 85 (ARGLDFIVGRTGNDY). In some embodiments of these aspects and all such aspects described herein, CDRH1 comprises SEQ ID NO: 80 (FTFRSYAMS), CDRH2 comprises SEQ ID NO: 71 (SAISNSGTYTYYA); CDRH3 comprises SEQ ID NO: 85 (ARGLDFIVGRTGNDY); CDRL1 comprises SEQ ID NO: 9 (RASQSISSYLN); CDRL2 comprises SEQ ID NO: 5 (AASSLQS); and CDRL3 comprises SEQ ID NO: 10 (QQSYSTPLT). A representative antibody having such heavy and light chain variable CDR regions is mAb37.

In each case, where specific sequences are recited, embodiments comprising a sequence having at least 85%, (e.g., at least 85%, at least 90%, at least 91%, at least 92%, at least 93%, at least 94%, at least 95%, at least 96%, at least 97%, at least 98%, or at least 99% identical) identity to the recited sequence (e.g., SEQ ID NO: 5, 9, 10, or 71-86) are also provided.

The disclosure also provides, in some aspects, an antibody or antigen-binding portion thereof that specifically binds PD-1, wherein the antibody or antigen-binding portion thereof comprises a heavy chain variable region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to any one of SEQ ID NO: 87-99, and a light chain variable region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 59. In some embodiments, the heavy chain variable region comprises an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 90, and a light chain variable region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 59. Table 7 provides the sequences for heavy chain variable sequences SEQ ID Nos: 87-99, and Table 4 provides light chain variable sequence SEQ ID NO: 59, respectively. In some embodiments, the heavy chain variable region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from any one of SEQ ID NOs: 87-99. In some embodiments, the light chain variable region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from SEQ ID NO: 59.

Antibodies mAb26-mAb37 are affinity matured antibodies derived from parent antibody mAb25, as described in the Examples. An affinity matured antibody or antigen-binding portion thereof is an antibody or antigen-binding fragment with one or more alterations (e.g., in one or more CDRs or FRs) that result in an improvement in the affinity of an antibody for its antigen, compared to a parent antibody lacking the alteration(s). In some embodiments, an affinity matured antibody has nanomolar or picomolar affinity for PD-1. In some embodiments, the PD-1 antibody or antigen-binding portion thereof has a $K_D$ of at least $1\times10^{-7}$M, at least $1\times10^{-8}$M, at least $1\times10^{-9}$M, at least $1\times10^{-10}$ M, at least $1\times10^{-11}$ M, at least $1\times10^{-12}$M, or at least $1\times10^{-13}$ M.

Tables 5 and 6 provide cell binding data for mAb25, mAb26, mAb27, mAb28, mAb29, mAb30, mAb31, mAb32, mAb33, mAb34, mAb35, mAb36, and mAb37 (i.e., affinity matured variants of mAb25) to human PD-1 ("huPD-1"), cyno PD-1 ("cyPD-1"), or murine PD-1 ("muPD-1"). Human, cyno, or murine PD-1 was expressed on CHO cells. Binding is expressed as an $EC_{50}$ value, which can be estimated from titrating different concentrations of mAb on cells that exogenously express the antigen of interest. Fluorescent tagged secondaries can be used to detect and quantify the mAb binding. The data shown in Table 5 was fit to a 1:1 binding model using built-in functions in GRAPH-PAD, which yielded the $EC_{50}$ value.

TABLE 5

Binding affinities of mAb25-mAb37 to human PD-1

| mAb | $K_D$ (nM) | Fold improvement over Parent |
|---|---|---|
| mAb25 | 240 | |
| mAb26 | 10 | 24 |
| mAb27 | 2.3 | 104 |
| mAb28 | 5.6 | 43 |
| mAb29 | 8.6 | 28 |
| mAb30 | 3.1 | 77 |
| mAb31 | 5.5 | 44 |
| mAb32 | 2.1 | 114 |
| mAb33 | 7 | 34 |
| mAb34 | 7.2 | 33 |
| mAb35 | 9 | 27 |
| mAb36 | 7.7 | 31 |
| mAb37 | 14 | 17 |

TABLE 6

Cell binding of mAb25-mAb37 to human, cyno, and murine PD-1 expressed on cells

| mAb | huPD-1 EC$_{50}$ (nM) | Fold improvement over Parent | cyPD-1 EC$_{50}$ (nM) | Fold improvement over Parent | muPD-1 EC$_{50}$ (nM) |
|---|---|---|---|---|---|
| mAb25 | 0.915 | | 8.59 | | NB |
| mAb26 | 3.74 | 0.2 | 1.54 | 5.6 | 17.9 |
| mAb27 | 1.75 | 0.5 | 1.53 | 5.6 | 6.14 |
| mAb28 | 3.94 | 0.2 | 1.48 | 5.8 | 0.814 |
| mAb29 | 1.27 | 0.7 | 1.73 | 5.0 | 2.14 |
| mAb30 | 2.77 | 0.3 | 2.05 | 4.2 | 4.05 |
| mAb31 | 1.71 | 0.5 | 1.9 | 4.5 | 1.87 |
| mAb32 | 1.51 | 0.6 | 1.29 | 6.7 | 2.8 |
| mAb33 | 1.04 | 0.9 | 1.33 | 6.5 | 10.4 |
| mAb34 | 3.87 | 0.2 | 1.33 | 6.5 | 20.5 |
| mAb35 | 1.64 | 0.6 | 2.66 | 3.2 | PF |
| mAb36 | 1.01 | 0.9 | 1.19 | 7.2 | PF |
| mAb37 | 0.75 | 1.2 | 1.09 | 7.9 | 0.942 |

*NB = no binding;
PF = poor fit; human, cyno, murine PD-1 expressed on CHO cells

TABLE 7

Heavy chain anti-PD-1 variable sequences

| SEQ ID NO | Sequence |
|---|---|
| 87 | EVQLLESGGGLVQPGGSLRLSCAASGFTFSDYAMSWVRQAPGKGLEWVSAISNSGTYTYYADSVKGRFTISRDNSKNTLYLQMNSLRAEDTAVYYCARGLDFIVGATGNDYWGQGTLVTVSS |
| 88 | EVQLLESGGGLVQPGGSLRLSCAASGFTFSDYAMSWVRQAPGKGLEWVSAISNSGTYTYYADSVKGRFTISRDNSKNTLYLQMNSLRAEDTAVYYCARGLDFIVGYTGNDYWGQGTLVTVSS |
| 89 | EVQLLESGGGLVQPGGSLRLSCAASGFTFSSYAMSWVRQAPGKGLEWVSAISNSGTYTYYADSVKGRFTISRDNSKNTLYLQMNSLRAEDTAVYYCARGLDFIVGYTGNDYWGQGTLVTVSS |
| 90 | EVQLLESGGGLVQPGGSLRLSCAASGFTFSSYAMLWVRQAPGKGLEWVSAISNSGTYTYYADSVKGRFTISRDNSKNTLYLQMNSLRAEDTAVYYCARGLDFIVGYTGNDYWGQGTLVTVSS |
| 91 | EVQLLESGGGLVQPGGSLRLSCAASGFTFSNYALSWVRQAPGKGLEWVSAISNSGTYTYYADSVKGRFTISRDNSKNTLYLQMNSLRAEDTAVYYCARGLDFIVGYTGNDYWGQGTLVTVSS |
| 92 | EVQLLESGGGLVQPGGSLRLSCAASGFTFSAYAMNWVRQAPGKGLEWVSAISNSGTYTYYADSVKGRFTISRDNSKNTLYLQMNSLRAEDTAVYYCARGLDFIVGYTGNDYWGQGTLVTVSS |
| 93 | EVQLLESGGGLVQPGGSLRLSCAASGFTFRSYAMSWVRQAPGKGLEWVSAISNSGTYTYYADSVKGRFTISRDNSKNTLYLQMNSLRAEDTAVYYCARGLDFIVGYTGNDYWGQGTLVTVSS |
| 94 | EVQLLESGGGLVQPGGSLRLSCAASGFTFGRYAMSWVRQAPGKGLEWVSAISNSGTYTYYADSVKGRFTISRDNSKNTLYLQMNSLRAEDTAVYYCARGLDFIVGYTGNDYWGQGTLVTVSS |
| 95 | EVQLLESGGGLVQPGGSLRLSCAASGFTFNSYAMSWVRQAPGKGLEWVSAISNSGTYTYYADSVKGRFTISRDNSKNTLYLQMNSLRAEDTAVYYCARGLDFIVGYTGNDYWGQGTLVTVSS |
| 96 | EVQLLESGGGLVQPGGSLRLSCAASGFTFSNYAMSWVRQAPGKGLEWVSAISNSGTYTYYADSVKGRFTISRDNSKNTLYLQMNSLRAEDTAVYYCARGLDFIVGATGNDYWGQGTLVTVSS |
| 97 | EVQLLESGGGLVQPGGSLRLSCAASGFTFSGYAMSWVRQAPGKGLEWVSAISNSGTYTYYADSVKGRFTISRDNSKNTLYLQMNSLRAEDTAVYYCARGLDFIVGRTGNDYWGQGTLVTVSS |
| 98 | EVQLLESGGGLVQPGGSLRLSCAASGFTFSSYAMNWVRQAPGKGLEWVSAISNSGTYTYYADSVKGRFTISRDNSKNTLYLQMNSLRAEDTAVYYCARGLDFIVGRTGNDYWGQGTLVTVSS |
| 99 | EVQLLESGGGLVQPGGSLRLSCAASGFTFRSYAMSWVRQAPGKGLEWVSAISNSGTYTYYADSVKGRFTISRDNSKNTLYLQMNSLRAEDTAVYYCARGLDFIVGRTGNDYWGQGTLVTVSS |

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59, wherein the heavy and light chain CDR residues are numbered according to Kabat.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59, wherein the heavy and light chain CDR residues are numbered according to Chothia.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59, wherein the heavy and light chain CDR residues are numbered according to MacCallum.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59, wherein the heavy and light chain CDR residues are numbered according to AbM.

The disclosure also provides, in some embodiments, an antibody or antigen-binding portion thereof that specifically binds PD-L1, wherein the antibody or antigen-binding portion thereof comprises heavy chain CDRs of any of the heavy chain variable regions of SEQ ID NOs: 87, 88, 89, 90, 91, 92, 93, 94, 95, 96, 97, 98, or 99, and light chain CDRs of the light chain variable region of SEQ ID NO: 59, wherein the heavy and light chain CDR residues are numbered according to IMGT.

C. Multispecific Antigen-Binding Constructs

The present disclosure provides, in some aspects, compositions and methods for enhancing an immune response to tumor cells by inhibiting the interaction between PD-L1 and PD-1, for example, the interaction between PD-L1 expressed on a tumor cell and PD-1 expressed on a T cell. Antibodies or antigen-binding portions thereof that specifically or selectively bind PD-L1 or PD-1 are provided. As used herein, the terms "specifically binds to," "specific for," "selectively binds" and "selective for" PD-L1 or PD-1, or an epitope on PD-L1 or PD-1, mean binding that is measurably different from a non-specific or non-selective interaction. In some embodiments, the antibody or antigen-binding portion thereof specifically binds to human PD-L1 or PD-1 and/or mouse PD-L1 or PD-1. Specific binding can be measured, for example, by determining binding of a molecule compared to binding of a control molecule. Specific binding can also be determined by competition with a control molecule that is similar to the target, such as an excess of non-labeled target. In that case, specific binding is indicated if the binding of the labeled target to a probe is competitively inhibited by the excess non-labeled target.

In some embodiments, any of the multispecific antigen-binding constructs disclosed herein binds to at least two different receptors or epitopes (e.g., PD-1 and PD-L1), wherein the two different receptors or epitopes bound by the multispecific antigen-binding construct are expressed on the surface of the same cell. For example, in some embodiments, the multispecific antigen-binding construct simultaneously binds to PD-1 and PD-L1, wherein the PD-1 and PD-L1 are expressed on the surface of the same cell. In some embodiments, any of the multispecific antigen-binding constructs disclosed herein binds to at least two different receptors or epitopes (e.g., PD-1 and PD-L1), wherein the two different receptors or epitopes bound by the multispecific antigen-binding construct are expressed on the surface of two different cells. For example, in some embodiments, the multispecific antigen-binding construct simultaneously binds to PD-1 expressed on the surface of a first cell and to PD-L1 expressed on the surface of a second cell.

In some embodiments, the multispecific antigen-binding construct is capable of binding human PD-1. In some embodiments, the multispecific antigen-binding construct is capable of binding murine PD-1. In some embodiments, the multispecific antigen-binding construct is capable of binding cynomolgus monkey PD-1. In some embodiments, the multispecific antigen-binding construct is capable of binding human, murine, and cynomolgus monkey PD-1 with similar affinity.

In some aspects and embodiments, the disclosure provides for a multispecific antigen-binding construct comprising at least two units of antigen-binding, wherein a first unit of antigen-binding binds PD-1, and a second unit of antigen-binding binds a PD-1 ligand. In some embodiments, the first unit of antigen-binding binds PD-1 expressed by an immune cell. In some embodiments, the second unit of antigen-binding binds PD-1 expressed by a second cell. In some embodiments, the multispecific antigen-binding construct blocks the interaction of PD-1 and a PD-1 ligand, such as PD-L1 or PD-L2. In some embodiments, the multispecific antigen-binding construct blocks the interaction of PD-1 and a PD-1 ligand, such as PD-L1 or PD-L2. In some embodiments, the multispecific antigen-binding construct comprises at least two units of antigen-binding that bind PD-1. In some embodiments, the multispecific antigen-binding construct comprises two units of antigen-binding that bind PD-1. In some embodiments, the multispecific antigen-binding construct comprises at least two units of antigen-binding that bind a PD-1 ligand, such as PD-L1 or PD-L2. In some embodiments, the multispecific antigen-binding construct comprises two units of antigen-binding that bind a PD-1 ligand, such as PD-L1 or PD-L2. In some embodiments, the multispecific antigen-binding construct comprises at least four units of antigen-binding, wherein two units of antigen-binding bind PD-1 and two units of antigen-binding bind a PD-1 ligand, such as PD-L1 or PD-L2. In some embodiments, the multispecific antigen-binding construct comprises four units of antigen-binding, wherein two units of antigen-binding bind PD-1 and two units of antigen-binding bind a PD-1 ligand, such as PD-L1 or PD-L2. In some embodiments, each unit of antigen-binding is capable of binding independently to its cognate antigen, i.e., PD-1 or a PD-1 ligand, such as PD-L1 or PD-L2. In some embodiments, the multispecific antigen-binding construct promotes loss of PD-1 expression from a cell. In some embodiments, the loss of PD-1 expression is due to PD-1 shedding. In some embodiments, the multispecific antigen-binding construct blocks interaction of PD-1 and the PD-1 ligand, such as PD-L1 or PD-L2. In some embodiments, the multispecific antigen-binding construct comprises a common light chain. For example, at least two units of antigen-binding comprise a common light chain.

In some embodiments, the first unit of antigen-binding binds PD-1 and comprises:
(a) a heavy chain variable region comprising (i) a CDRH1 comprising SEQ ID NO: 70 (FTFX$_1$X$_2$YAX$_3$X$_4$, wherein X$_1$=S, R, G, or N; X$_2$=D, S, N, A, R, or G; X$_3$=M or L; X$_4$=S, L, or N); (ii) a CDRH2 comprising SEQ ID NO: 71 (SAISNSGTYTYYA); and (iii) a CDRH3 comprising SEQ ID NO: 72 (ARGLDFIVGX$_5$TGNDY, wherein X$_5$=A, Y, or R); and
(b) a light chain variable region comprising: (i) a CDRL1 comprising SEQ ID NO: 9 (RASQSISSYLN); (ii) a CDRL2 comprising SEQ ID NO: 5 (AASSLQS); and (iii) a CDRL3 comprising SEQ ID NO: 10 (QQSYSTPLT).

In some such embodiments, the first unit of antigen-binding binds PD-1 and comprises:
(a) a CDRH1 comprising SEQ ID NO: 73 (FTFSDYAMS), a CDRH2 comprising SEQ ID NO: 71 (SAISNSGTYTYYA), and a CDRH3 comprising SEQ ID NO: 74 (ARGLDFIVGATGNDY);
(b) a CDRH1 comprising SEQ ID NO: 73 (FTFSDYAMS), a CDRH2 comprising SEQ ID NO: 71 (SAISNSGTYTYYA), and a CDRH3 comprising SEQ ID NO: 75 (ARGLDFIVGYTGNDY);
(c) a CDRH1 comprising SEQ ID NO: 76 (FTFSSYAMS), a CDRH2 comprising SEQ ID NO: 71 (SAISNSGTYTYYA), and a CDRH3 comprising SEQ ID NO: 75 (ARGLDFIVGYTGNDY);
(d) a CDRH1 comprising SEQ ID NO: 77 (FTFSSYAML), a CDRH2 comprising SEQ ID NO: 71 (SAISNSGTYTYYA), and a CDRH3 comprising SEQ ID NO: 75 (ARGLDFIVGYTGNDY);
(e) a CDRH1 comprising SEQ ID NO: 78 (FTFSNYALS), a CDRH2 comprising SEQ ID NO: 71 (SAISNSGTYTYYA), and a CDRH3 comprising SEQ ID NO: 75 (ARGLDFIVGYTGNDY);
(f) a CDRH1 comprising SEQ ID NO: 79 (FTFSAYAMN), a CDRH2 comprising SEQ ID NO: 71 (SAISNSGTYTYYA), and a CDRH3 comprising SEQ ID NO: 75 (ARGLDFIVGYTGNDY);
(g) a CDRH1 comprising SEQ ID NO: 80 (FTFRSYAMS), a CDRH2 comprising SEQ ID NO: 71 (SAISNSGTYTYYA), and a CDRH3 comprising SEQ ID NO: 75 (ARGLDFIVGYTGNDY);

(h) a CDRH1 comprising SEQ ID NO: 81 (FTFGRYAMS), a CDRH2 comprising SEQ ID NO: 71 (SAISNSGTYTYYA), and a CDRH3 comprising SEQ ID NO: 75 (ARGLDFIVGYTGNDY);

(i) a CDRH1 comprising SEQ ID NO: 82 (FTFNSYAMS), a CDRH2 comprising SEQ ID NO: 71 (SAISNSGTYTYYA), and a CDRH3 comprising SEQ ID NO: 75 (ARGLDFIVGYTGNDY);

(j) a CDRH1 comprising SEQ ID NO: 83 (FTFSNYAMS), a CDRH2 comprising SEQ ID NO: 71 (SAISNSGTYTYYA), and a CDRH3 comprising SEQ ID NO: 74 (ARGLDFIVGATGNDY);

(k) a CDRH1 comprising SEQ ID NO: 84 (FTFSGYAMS), a CDRH2 comprising SEQ ID NO: 71 (SAISNSGTYTYYA), and a CDRH3 comprising SEQ ID NO: 85 (ARGLDFIVGRTGNDY);

(l) a CDRH1 comprising SEQ ID NO: 86 (FTFSSYAMN), a CDRH2 comprising SEQ ID NO: 71 (SAISNSGTYTYYA) and a CDRH3 comprising SEQ ID NO: 85 (ARGLDFIVGRTGNDY); or (m) a CDRH1 comprising SEQ ID NO: 80 (FTFRSYAMS), a comprising SEQ ID NO: 71 (SAISNSGTYTYYA), and a CDRH3 comprising SEQ ID NO: 85 (ARGLDFIVGRTGNDY).

In some embodiments, the first unit of antigen-binding binds PD-1 and comprises:

(a) a heavy chain variable region comprising an amino acid sequence that is at least 90% identical to SEQ ID NO: 87;

(b) a heavy chain variable region comprising an amino acid sequence that is at least 90% identical to SEQ ID NO: 88;

(c) a heavy chain variable region comprising an amino acid sequence that is at least 90% identical to SEQ ID NO: 89;

(d) a heavy chain variable region comprising an amino acid sequence that is at least 90% identical to SEQ ID NO: 90;

(e) a heavy chain variable region comprising an amino acid sequence that is at least 90% identical to SEQ ID NO: 91;

(f) a heavy chain variable region comprising an amino acid sequence that is at least 90% identical to SEQ ID NO: 92;

(g) a heavy chain variable region comprising an amino acid sequence that is at least 90% identical to SEQ ID NO: 93;

(h) a heavy chain variable region comprising an amino acid sequence that is at least 90% identical to SEQ ID NO: 94;

(i) a heavy chain variable region comprising an amino acid sequence that is at least 90% identical to SEQ ID NO: 95;

(j) a heavy chain variable region comprising an amino acid sequence that is at least 90% identical to SEQ ID NO: 96;

(k) a heavy chain variable region comprising an amino acid sequence that is at least 90% identical to SEQ ID NO: 97;

(l) a heavy chain variable region comprising an amino acid sequence that is at least 90% identical to SEQ ID NO: 98; or (m) a heavy chain variable region comprising amino acid sequence that is at least 90% identical to SEQ ID NO: 99.

In some embodiments, the first unit of antigen-binding binds PD-1 and comprises a light chain variable region comprising an amino acid sequence that is at least 90% identical to SEQ ID NO: 59.

In some embodiments, the second unit of antigen-binding binds PD-L2. In some embodiments, the second unit of antigen-binding binds PD-L1. In some embodiments, the second unit of antigen-binding binds PD-L1 and comprises:

a. a heavy chain variable region comprising (i) a CDRH1 comprising SEQ ID NO: 1 (GTFSSYAIN); (ii) a CDRH2 comprising SEQ ID NO: 2 (GGIIPX$_1$X$_2$GX$_3$ATYA, wherein X$_1$ is V or I; X$_2$ is F, L, or V; and X$_3$ is T or A); and (iii) a CDRH3 comprising SEQ ID NO: 3 (ARLKX$_1$ELKDAFDI, wherein X$_1$ is G, F, or N); and b. a light chain variable region comprising: (i) a CDRL1 comprising SEQ ID NO: 4 (RASQX$_1$ISSYLN, wherein X$_1$ is S, W, or Q); (ii) a CDRL2 comprising SEQ ID NO: 5 (AASSLQS); and (iii) a CDRL3 comprising SEQ ID NO: 6 (X$_1$QSYSTPLT, wherein X$_1$ is Q or F).

In some such embodiments, the second unit of antigen-binding binds PD-L1 and comprises:

(a) a CDRH1 comprising SEQ ID NO: 1 (GTFSSYAIN), a CDRH2 comprising SEQ ID NO: 7 (GGIIPILGAATYA), and a CDRH3 comprising SEQ ID NO: 8 (ARLKGELKDAFDI);

(b) a CDRH1 comprising SEQ ID NO: 1 (GTFSSYAIN), a CDRH2 comprising SEQ ID NO: 7 (GGIIPILGAATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(c) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(d) a CDRH1 comprising SEQ ID NO: 1 (GTFSSYAIN), a CDRH2 comprising SEQ ID NO: 11 (GGIIPVFGTATYA) and a CDRH3 comprising SEQ ID NO: 8 (ARLKGELKDAFDI);

(e) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 12 (RASQWISSYLN); a CDRL2 comprising SEQ ID NO: 5 (AASSLQS); and a CDRL3 comprising SEQ ID NO: 10 (QQSYSTPLT);

(f) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 13 (RASQQISSYLN); a CDRL2 comprising SEQ ID NO: 5 (AASSLQS); and a CDRL3 comprising SEQ ID NO: 10 (QQSYSTPLT);

(g) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(h) a CDRH1 comprising SEQ ID NO: 1 (GTFSSYAIN), a CDRH2 comprising SEQ ID NO: 15 (GGIIPIFGIANYA), and a CDRH3 comprising SEQ ID NO: 8 (ARLKGELKDAFDI);

(i) a CDRH1 comprising SEQ ID NO: 1 (GTFSSYAIN), a CDRH2 comprising SEQ ID NO: 15 (GGIIPIFGIANYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(j) a CDRH1 comprising SEQ ID NO: 1 (GTFSSYAIN), a CDRH2 comprising SEQ ID NO: 16 (GGIIPNFGTATYA), and a CDRH3 comprising SEQ ID NO: 17 (ARLKGELKGAGDI);

(k) a CDRH1 comprising SEQ ID NO: 1 (GTFSSYAIN), a CDRH2 comprising SEQ ID NO: 16 (GGIIPNFGTATYA), a CDRH3 comprising SEQ ID NO: 17 (ARLKGELKGAGDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(l) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 18 (ARLKFELKDAFDI);

(m) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 18 (ARLKFELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(n) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 19 (ARLKGELKDAFDE);

(o) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 19 (ARLKGELKDAFDE), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(p) a CDRH1 comprising SEQ ID NO: 1 (GTFSSYAIN), a CDRH2 comprising SEQ ID NO: 11 (GGIIPVFGTATYA), and a CDRH3 comprising SEQ ID NO: 20 (ARLKNELKDAFDI);

(q) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 20 (ARLKNELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(r) a CDRH1 comprising SEQ ID NO: 1 (GTFSSYAIN), a CDRH2 comprising SEQ ID NO: 21 (GGVIPFLGTANYA), and a CDRH3 comprising SEQ ID NO: 22 (ARLKGILKDALDI);

(s) a CDRH1 comprising SEQ ID NO: 1 (GTFSSYAIN), a CDRH2 comprising SEQ ID NO: 21 (GGVIPFLGTANYA), a CDRH3 comprising SEQ ID NO: 22 (ARLKGILKDALDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(t) a CDRH1 comprising SEQ ID NO: 1 (GTFSSYAIN), a CDRH2 comprising EQ ID NO: 29 (GRIIPIFGTADYA), and a CDRH3 comprising SEQ ID NO: 8 (ARLKGELKDAFDI);

(u) a CDRH1 comprising SEQ ID NO: 1 (GTFSSYAIN), a CDRH2 comprising SEQ ID NO: 29 (GRIIPIFGTADYA), a CDRH3 comprising SEQ ID NO: 8 (ARLKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(v) a CDRH1 comprising SEQ ID NO: 1 (GTFSSYAIN), a CDRH2 comprising SEQ ID NO: 31 (GGIIPILGTATYA), and a CDRH3 comprising SEQ ID NO: 32 (ARRKGELKDAFDI);

(w) a CDRH1 comprising SEQ ID NO: 1 (GTFSSYAIN), a CDRH2 comprising SEQ ID NO: 31 (GGIIPILGTATYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(x) a CDRH1 comprising SEQ ID NO: 1 (GTFSSYAIN), a CDRH2 comprising SEQ ID NO: 33 (GGIIPIVATANYA), and a CDRH3 comprising SEQ ID NO: 32 (ARRKGELKDAFDI);

(y) a CDRH1 comprising SEQ ID NO: 1 (GTFSSYAIN), a CDRH2 comprising SEQ ID NO: 33 (GGIIPIVATANYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(z) a CDRH1 comprising SEQ ID NO: 1 (GTFSSYAIN), a CDRH2 comprising SEQ ID NO: 34 (GGIIPIFGKATYA), and a CDRH3 comprising SEQ ID NO: 32 (ARRKGELKDAFDI);

(aa) a CDRH1 comprising SEQ ID NO: 1 (GTFSSYAIN), a CDRH2 comprising SEQ ID NO: 34 (GGIIPIFGKATYA), a CDRH3 comprising SEQ ID NO: 32 (ARRKGELKDAFDI), a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(bb) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 38 (FQSYSTPLT);

(cc) a CDRH1 comprising SEQ ID NO: 1 (GTFSSYAIN), a CDRH2 comprising SEQ ID NO: 11 (GGIIPVFGTATYA), a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 39 (QQSYSTILT);

(dd) a CDRH1 comprising SEQ ID NO: 14 (GTFSSYAFS), a CDRH2 comprising SEQ ID NO: 11 (GGIIPVFGTATYA) and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(ee) a CDRH1 comprising SEQ ID NO: 23 (GTFSSYAIS), a CDRH2 comprising SEQ ID NO: 24

(GGIIPIVGIANYA), and a CDRH3 comprising SEQ ID NO: 8 (ARLKGELKDAFDI);

(ff) a CDRH1 comprising SEQ ID NO: 23 (GTFSSYAIS), a CDRH2 comprising SEQ ID NO: 24 (GGIIPIVGIANYA), and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(gg) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 25 (ARLKGEFKDAFDI);

(hh) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 25 (ARLKGEFKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(ii) a CDRH1 comprising SEQ ID NO: 23 (GTFSSYAIS), a CDRH2 comprising SEQ ID NO: 26 (GRIIPLFGTAHYA), and a CDRH3 comprising SEQ ID NO: 8 (ARLKGELKDAFDI);

(jj) a CDRH1 comprising SEQ ID NO: 23 (GTFSSYAIS), a CDRH2 comprising SEQ ID NO: 26 (GRIIPLFGTAHYA), and a CDRH3 comprising SEQ ID NO: 8 (ARLKGELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(kk) a CDRH1 comprising SEQ ID NO: 23 (GTFSSYAIS), a CDRH2 comprising SEQ ID NO: 27 (GRINPILGTANYA), and a CDRH3 comprising SEQ ID NO: 28 (ARLKGELKDAFSI);

(ll) a CDRH1 comprising SEQ ID NO: 23 (GTFSSYAIS), a CDRH2 comprising SEQ ID NO: 27 (GRINPILGTANYA), and a CDRH3 comprising SEQ ID NO: 28 (ARLKGELKDAFSI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(mm) a CDRH1 comprising SEQ ID NO: 23 (GTFSSYAIS), a CDRH2 comprising SEQ ID NO: 11 (GGIIPVFGTATYA), and a CDRH3 comprising SEQ ID NO: 30 (ARLKGELKCAFDI);

(nn) a CDRH1 comprising SEQ ID NO: 23 (GTFSSYAIS), a CDRH2 comprising SEQ ID NO: 11 (GGIIPVFGTATYA), and a comprising SEQ ID NO: 30 (ARLKGELKCAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT);

(oo) a CDRH1 comprising SEQ ID NO: 36 (GPFRSHAVS), a CDRH2 comprising SEQ ID NO: 11 (GGIIPVFGTATYA), and a CDRH3 comprising SEQ ID NO: 37 (ARLKSELKDAFDI); or (pp) a CDRH1 comprising SEQ ID NO: 36 (GPFRSHAVS), a CDRH2 comprising SEQ ID NO: 11 (GGIIPVFGTATYA), and a CDRH3 comprising SEQ ID NO: 37 (ARLKSELKDAFDI); a CDRL1 comprising SEQ ID NO: 9 (RASQSISSYLN); a CDRL2 comprising SEQ ID NO: 5 (AASSLQS); and a CDRL3 comprising SEQ ID NO: 10 (QQSYSTPLT).

In some such embodiments, the second unit of antigen-binding binds PD-L1 and comprises a heavy chain variable region comprising an amino acid sequence that is at least 90% identical to any one of SEQ ID NOs: 35, 40, 41, 42, 43, 44, 45, 46, 47, 48, 49, 50, 51, 52, 53, 54, 55, 56, 57, or 58, and a light chain variable region comprising an amino acid sequence that is at least 90% identical to any one of SEQ ID NOs: 59, 60, 61, 62, or 63.

In some embodiments, the second unit of antigen-binding binds PD-L1 and comprises a heavy chain variable region comprising:

(a) an amino acid sequence that is at least 90% identical to SEQ ID NO: 35;

(b) an amino acid sequence that is at least 90% identical to SEQ ID NO: 40;

(c) an amino acid sequence that is at least 90% identical to SEQ ID NO: 41;

(d) an amino acid sequence that is at least 90% identical to SEQ ID NO: 42;

(e) an amino acid sequence that is at least 90% identical to SEQ ID NO: 43;

(f) an amino acid sequence that is at least 90% identical to SEQ ID NO: 44;

(g) an amino acid sequence that is at least 90% identical to SEQ ID NO: 45;

(h) an amino acid sequence that is at least 90% identical to SEQ ID NO: 46;

(i) an amino acid sequence that is at least 90% identical to SEQ ID NO: 47;

(j) an amino acid sequence that is at least 90% identical to SEQ ID NO: 48;

(k) an amino acid sequence that is at least 90% identical to SEQ ID NO: 49;

(l) an amino acid sequence that is at least 90% identical to SEQ ID NO: 50;

(m) an amino acid sequence that is at least 90% identical to SEQ ID NO: 51;

(n) an amino acid sequence that is at least 90% identical to SEQ ID NO: 52;

(o) an amino acid sequence that is at least 90% identical to SEQ ID NO: 53;

(p) an amino acid sequence that is at least 90% identical to SEQ ID NO: 54;

(q) an amino acid sequence that is at least 90% identical to SEQ ID NO: 55;

(r) an amino acid sequence that is at least 90% identical to SEQ ID NO: 56;

(s) an amino acid sequence that is at least 90% identical to SEQ ID NO: 57; or (t) an amino acid sequence that is at least 90% identical to SEQ ID NO: 58;

In some embodiments, the second unit of antigen-binding binds PD-L1 and comprises a light chain variable region comprising:

(a) an amino acid sequence that is at least 90% identical to SEQ ID NO: 59;

(b) an amino acid sequence that is at least 90% identical to SEQ ID NO: 60;

(c) an amino acid sequence that is at least 90% identical to SEQ ID NO: 61;

(d) an amino acid sequence that is at least 90% identical to SEQ ID NO: 62; or (e) an amino acid sequence that is at least 90% identical to SEQ ID NO: 63.

In some embodiments, the disclosure provides for a multispecific antigen-binding construct comprising any of the PD-1 antagonists disclosed herein and any of the antagonists of a PD-1 ligand, such as PD-L1, disclosed herein. For example, Bispecific 3 is a multispecific, tetravalent antigen-binding construct that specifically binds human PD-1 and human PD-L1. The construct comprises an anti-PD-1 IgG1 antibody (mAb28) in which the heavy chain of the antibody is a fusion protein further comprising at its C-terminus the heavy chain variable region of an anti-PD-L1 antibody (mAb1), which is connected to the Fc region of the anti-BCMA antibody by way of a poly-GGGS (SEQ ID NO: 120) linker. The light chains for the anti-PD-1 portion and the anti-PD-L1 portions of the construct are identical (SEQ ID NO: 101). Bispecific 3, the structure for which is represented by the illustration in FIG. 13A, comprises the heavy chain sequence recited in SEQ ID NO: 100 and the light chain sequence recited in SEQ ID NO: 101.

In some embodiments, the disclosure provides for a multispecific antibody or antigen-binding portion thereof that specifically binds PD-1 and PD-L1, wherein the antibody or antigen-binding portion thereof comprises a heavy chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 100 or 102 and a light chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 101 or 103.

In some embodiments, the disclosure provides for a multispecific antibody or antigen-binding portion thereof that specifically binds PD-1 and PD-L1, wherein the antibody or antigen-binding portion thereof comprises a heavy chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 100, and a light chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 101. In some embodiments, the heavy chain region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from SEQ ID NO: 100. In some embodiments, the light chain region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from SEQ ID NO: 101.

In some embodiments, the disclosure provides for a multispecific antibody or antigen-binding portion thereof that specifically binds PD-1 and PD-L1, wherein the antibody or antigen-binding portion thereof comprises a heavy chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 102, and a light chain region comprising an amino acid sequence that is at least 85%, (e.g., at least 85%, at least 90%, at least 91%, at least 92%, at least 93%, at least 94%, at least 95%, at least 96%, at least 97%, at least 98%, or at least 99% identical) to SEQ ID NO: 103. In some embodiments, the heavy chain region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from SEQ ID NO: 102. In some embodiments, the light chain region comprises an amino acid sequence that differs by 15 amino acids or less, 14 amino acids or less, 13 amino acids or less, 12 amino acids or less, 11 amino acids or less, 10 amino acids or less, 9 amino acids or less, 8 amino acids or less, 7 amino acids or less, 6 amino acids or less, 5 amino acids or less, 4 amino acids or less, 3 amino acids or less, 2 amino acids or less, or 1 amino acid from SEQ ID NO: 103.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 100 or 102, and a light chain amino acid sequence that is at least 85%, identical to the amino acid sequence of SEQ ID NO: 101 or 103.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 100 and a light chain amino acid sequence that is at least 85%, identical to the amino acid sequence of SEQ ID NO: 101.

Also provided herein, in some aspects and embodiments, is a multispecific antigen-binding construct comprising four units of antigen-binding, wherein two units of antigen-binding bind PD-1 and two units of antigen-binding bind PD-L1, and wherein the construct comprises a heavy chain amino acid sequence that is at least 85%, identical to the amino acid sequence of SEQ ID NO: 102 and a light chain amino acid sequence that is at least 85%, identical to the amino acid sequence of SEQ ID NO: 103.

TABLE 8

Multispecific Heavy Chain Sequences

| SEQ ID NO | Sequence |
| --- | --- |
| 100 | EVQLLESGGGLVQPGGSLRLSCAASGFTFSSYAMLWVRQAPGKG LEWVSAISNSGTYTYYADSVKGRFTISRDNSKNTLYLQMNSLRA EDTAVYYCARGLDFIVGYTGNDYWGQGTLVTVSSASTKGPSVFP LAPSSKSTSGGTAALGCLVKDYFPEPVTVSWNSGALTSGVHTFP AVLQSSGLYSLSSVVTVPSSSLGTQTYICNVNHKPSNTKVDKKV EPKSCDKTHTCPPCPAPELLGGPSVFLFPPKPKDTLMISRTPEV TCVVVDVSHEDPEVKFNWYVDGVEVHNAKTKPREEQYASTYRVV SVLTVLHQDWLNGKEYKCKVSNKALPAPIEKTISKAKGQPREPQ VYTLPPSRDELTKNQVSLTCLVKGFYPSDIAVEWESNGQPENNY KTTPPVLDSDGSFFLYSKLTVDKSRWQQGNVFSCSVMHEALHNH YTQKSLSLSPGGGGSGGGGSGGGGSGGGGSQVQLVQSGAEVKKP GSSVKVSCKASGGTFSSYAINWVRQAPGQGLEWMGGIIPILGAA TYAQKFQGRVTITADESTSTAYMELSSLRSEDTAVYYCARLKGE LKDAFDIWGQGTLVTVSSASTKGPSVFPLAPSSKSTSGGTAALG CLVKDYFPEPVTVSWNSGALTSGVHTFPAVLQSSGLYSLSSVVT VPSSSLGTQTYICNVNHKPSNTKVDKKVEPKSCDKTHT |
| 102 | EVQLLESGGGLVQPGGSLRLSCAASGFTFSSYAMLWVRQAPGKG LEWVSAISNSGTYTYYADSVKGRFTISRDNSKNTLYLQMNSLRA |

TABLE 8-continued

Multispecific Heavy Chain Sequences

| SEQ ID NO | Sequence |
|---|---|
| | EDTAVYYCARGLDFIVGYTGNDYWGQGTLVTVSSAKTTPPSVYP
LAPGSAAQTNSMVTLGCLVKGYFPEPVTVTWNSGSLSSGVHTFP
AVLESDLYTLSSSVTVPSSPRPSETVTCNVAHPASSTKVDKKIV
PRDCGCKPCICTVPEVSSVFIFPPKPKDVLTITLTPKVTCVVVD
ISKDDPEVQFSWFVDDVEVHTAQTQPREEQFASTFRSVSELPIM
HQDWLNGKEFKCRVNSAAFPAPIEKTISKTKGRPKAPQVYTIPP
PKEQMAKDKVSLTCMITDFFPEDITVEWQWNGQPAENYKNTQPI
MNTNGSYFVYSKLNVQKSNWEAGNTFTCSVLHEGLHNHHTEKSL
SHSPGGGGSGGGGSGGGGSGGGGSQVQLVQSGAEVKKPGSSVKV
SCKASGGTFSSYAINWVRQAPGQGLEWMGGIIPILGAATYAQKF
QGRVTITADESTSTAYMELSSLRSEDTAVYYCARLKGELKDAFD
IWGQGTLVTVSSAKTTPPSVYPLAPGSAAQTNSMVTLGCLVKGY
FPEPVTVTWNSGSLSSGVHTFPAVLESDLYTLSSSVTVPSSPRP
SETVTCNVAHPASSTKVDKKIVPRDCG |

TABLE 9

Multispecific Light Chain Sequences

| SEQ ID NO | Sequence |
|---|---|
| 101 | DIQMTQSPSSLSASVGDRVTITCRASQSISSYLNWYQQKPGKAP
KLLIYAASSLQSGVPSRFSGSGSGTDFTLTISSLQPEDFATYYC
QQSYSTPLTFGGGTKVEIKRTVAAPSVFIFPPSDEQLKSGTASV
VCLLNNFYPREAKVQWKVDNALQSGNSQESVTEQDSKDSTYSLS
STLTLSKADYEKHKVYACEVTHQGLSSPVTKSFNRGEC |
| 103 | DIQMTQSPSSLSASVGDRVTITCRASQSISSYLNWYQQKPGKAP
KLLIYAASSLQSGVPSRFSGSGSGTDFTLTISSLQPEDFATYYC
QQSYSTPLTFGGGTKVEIKRADAAPTVSIFPPSSEQLTSGGASV
VCFLNNFYPKDINVKWKIDGSERQNGVLNSWTDQDSKDSTYSMS
STLTLTKDEYERHNSYTCEATHKTSTSPIVKSFNRNEC |

The term "multispecific antigen-binding construct", as used herein refers to bispecific, tri-specific, or multispecific antigen-binding constructs, and antigen-binding portions or fragments thereof. A multispecific antigen-binding construct can be a single multifunctional polypeptide, or it can be a multimeric complex of two or more molecules (e.g., polypeptides and/or aptamers) that are covalently or non-covalently associated with one another. The term "multispecific antigen-binding constructs" includes antibodies (or antigen-binding fragments thereof) that may be linked to or co-expressed with another functional molecule, e.g., another peptide, protein, and/or aptamer. For example, an antibody or fragment thereof can be functionally linked (e.g., by chemical coupling, genetic fusion, non-covalent association or otherwise) to one or more other molecular entities, such as a protein or fragment thereof to produce a bispecific or a multispecific antigen-binding molecule with a second binding specificity. As used herein, the term "multispecific antigen-binding constructs" also includes bispecific, trispecific or multispecific antibodies or antigen-binding fragments thereof. In certain embodiments, an antibody is functionally linked to another antibody or antigen-binding fragment thereof to produce a bispecific antibody with a second binding specificity. Bispecific and multispecific antibodies of the present invention are described elsewhere herein.

As used herein, an antigen-binding "arm" refers to a unit, domain, region, or the like, of the multispecific antigen-binding construct that forms an area of the construct that binds to an antigen. Thus, a "first arm" forms a separate binding area of the multispecific antigen-binding construct from a "second arm" of the construct, each arm forming a unit of antigen binding. Generally, one "arm" (first arm) is distinct from the other "arm" (second arm) in its antigen binding or antigen specificity. Thus, in the example of a bispecific, bivalent antibody, one arm of the antibody binds to antigen A, while the other arm of the antibody binds to antigen B. In some embodiments, in the example of a bispecific, bivalent antibody, one arm of the antibody binds to antigen A, while the other arm of the antibody binds to antigen B or C (cross-reacts with two antigens such as PD-L1 and PD-L2 due to, e.g., similarity in structure). See, e.g., U.S. Pat. No. 9,845,356. Similarly, in the example of a tetravalent bispecific antibody (formed, e.g., by joining two different antibodies), one "arm" refers to the area of the antibody that binds to antigen A (even if two binding sites—of a bivalent antibody—bind to antigen A) and the "other arm" refers to the area of the antibody that binds to antigen B (even if two binding sites—of a bivalent antibody—bind to antigen B). In some embodiments, in the example of a tetravalent bispecific antibody (formed, e.g., by joining two different antibodies), one "arm" refers to the area of the antibody that binds to antigen A (even if two binding sites—of a bivalent antibody—bind to antigen A) and the "other arm" refers to the area of the antibody that binds to antigen B or C (even if two binding sites—of a bivalent antibody—can bind to antigen B or C). See, e.g., U.S. Pat. No. 9,845,356. As would be apparent to those of skill in the art, "first" or "second" can be used interchangeably.

The term "valency," when used to describe an antigen-binding construct or protein or antigen-binding arm, refers to the number of recognition (binding) sites in the antigen-binding construct or protein, regardless of whether those different recognition or binding sites bind to the same epitope. Each recognition site specifically recognizes, and is therefore capable of binding, one epitope (binding site) on an antigen. When an antigen-binding protein comprises more than one recognition site (e.g., when an antigen-binding protein is an IgG, which has two recognition sites in its variable regions), each recognition site can specifically recognize the same epitope on the same antigen, or different epitopes, whether on the same or different antigens. Multi-valency can increase the avidity, i.e., the strength of binding between an antigen-binding arm or construct and the pertinent antigen or target receptor. Avidity is related to both the affinity between an epitope or antigenic determinant and its binding site on the antigen-binding unit, and the actual number of pertinent binding sites present on the antigen-binding unit.

In some embodiments, any of the multispecific antigen-binding constructs disclosed herein comprises a multivalent (e.g., bivalent) antibody or antigen-binding fragment, wherein at least two of the valencies specifically bind PD-1. In some embodiments, any of the multispecific antigen-binding constructs disclosed herein comprises a multivalent (e.g., bivalent) antibody or antigen-binding fragment, wherein at least two of the valencies specifically bind a PD-1 ligand (e.g., PD-L1 or PD-L2). In some embodiments, any of the multispecific antigen-binding constructs disclosed herein comprises a multivalent (e.g., bivalent) antibody or antigen-binding fragment, wherein at least two of the valencies specifically bind PD-L1. In some embodiments, any of the multispecific antigen-binding constructs disclosed herein comprises a first multivalent (e.g., bivalent) antibody or antigen-binding fragment and a second multivalent (e.g., bivalent) antibody or antigen-binding fragment, wherein at least two of the valencies of the first multivalent antibody or antigen-binding fragment specifically bind PD-1, and wherein at least two of the valencies of the second multivalent antibody or antigen-binding fragment specifically bind PD-L1. In some embodiments, any of the multispecific antigen-binding constructs disclosed herein is a tetravalent construct, wherein the tetravalent construct comprises a first bivalent antibody or antigen-binding fragment and a second bivalent antibody or antigen-binding fragment, wherein both valencies of the first bivalent antibody or antigen-binding fragment are specific for the same epitope on PD-1, and wherein both valencies of the second bivalent antibody or antigen-binding fragment are specific for the same epitope on PD-L1. In some embodiments of such tetravalent constructs, the first and second bivalent antibody or antigen-binding fragment or portion thereof use a light chain having the same amino acid sequence. In other words, the tetravalent construct comprises a common light chain. For example, a light chain having the sequence of SEQ ID NO: 101 or SEQ ID NO: 103.

In some embodiments, the first arm is an antagonist of PD-1. In some embodiments, the second arm is an antagonist of a PD-1 ligand—e.g., PD-L1 and/or PD-L2. In some embodiments, the first arm is an antagonist of PD-1, and the second arm is an antagonist of cognate PD-1 ligand—e.g., PD-L1 and/or PD-L2.

The terms "antagonist, "antagonize," and "inhibit" when used to refer to the biological activity of the antigen-binding arm indicate that the antigen-binding arm binds its target (e.g., PD-1) on the respective cell and partially or fully blocks, inhibits, and/or reduces the biological response through PD-1. In some embodiments, inhibition in the presence of the antagonist is observed in a dose-dependent manner. In some embodiments, the measured signal (e.g., biological activity) is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 100% lower than the signal measured with a negative control under comparable conditions. Also disclosed herein, are methods of identifying antagonists suitable for use in the methods of the disclosure. For example, these methods include, but are not limited to, binding assays such as enzyme-linked immuno-absorbent assay (ELISA), FORTE BIO© systems, and radioimmunoassay (RIA). These assays determine the ability of an antagonist to bind the polypeptide of interest (e.g., PD-1 or its ligand) and therefore indicate the ability of the antagonist to inhibit, neutralize or block the activity of the polypeptide of interest. Efficacy of an antagonist can also be determined using functional assays, such as the ability of an antagonist to inhibit the function of the polypeptide. For example, a functional assay may comprise contacting a polypeptide with a candidate antagonist molecule and measuring a detectable change in one or more biological activities normally associated with the polypeptide. The potency of an antagonist is usually defined by its $IC_{50}$ value (concentration required to inhibit 50% of the agonist response). The lower the $IC_{50}$ value the greater the potency of the antagonist and the lower the concentration that is required to inhibit the maximum biological response.

In some embodiments, at least one antigen-binding arm has a $K_D$ of at least $1\times10^{-7}$ M, at least $1\times10^{-8}$ M, at least $1\times10^{-9}$ M, at least $1\times10^{-10}$ M, at least $1\times10^{-11}$ M, at least $1\times10^{-12}$ M, or at least $1\times10^{-13}$ M. In some embodiments, both antigen-binding arms have the same or similar $K_D$. The term "$K_D$" (M), as used herein, refers to the dissociation equilibrium constant of a particular antigen-binding arm/antigen interaction. $K_D=k_d/k_a$. The term "$k_d$" (sec$^{-1}$), as used herein, refers to the dissociation rate constant of a particular antigen-binding arm/antigen interaction. This value is also referred to as the $k_{off}$ value. The term "$k_a$" (M$^{-1}\times$sec$^{-1}$), as used herein, refers to the association rate constant of a particular antigen-binding arm/antigen interaction. This value is also referred to as the $k_{on}$ value.

In some embodiments, the binding of one arm (e.g., the first arm) of the multispecific antigen-binding construct to its target does not block the binding of the other arm (e.g., the second arm) to its target. In some embodiments, the binding of one arm does not sterically hinder the second arm from binding its target. For example, upon the binding of a first arm to PD-1, the second arm is free to bind a ligand of PD-1 (e.g., PD-L1 and/or PD-L2). Thus, in some embodiments, the first arm and second arm bind to their respective targets and both arms remain bound concurrently.

In some embodiments, binding of the first arm and the second arm to their respective targets bridges the immune cell and the second cell together, bringing the two cells in closeproximity. As used herein, "bridge" refers to the joining of two cell types (e.g., one immune cell that expresses PD-1, and a second cell that expresses its ligand—PD-L1), or bringing of the two cells together in close proximity; the two cells need not be in physical contact. Thus, the multispecific antigen-binding construct acts as a connecter (e.g., a bridge) to the two cells, each one expressing PD-1 or either of its ligands.

Methods for determining whether two cells are bridged or connected together by a construct of the present invention are known in the art. For example, in some embodiments, the bridging of the immune cell and the second cell is determined by, e.g., flow cytometry, FRET, immunoprecipitation, microscopy, or fluorescence plate reader.

In some embodiments, binding of the first arm and the second arm of a multispecific construct to their respective targets results in down-regulation and/or shedding of the ectodomain and/or degradation of a target, e.g., PD-1. As used herein, "down-regulation" refers to the process by which a cell decreases the quantity of a cellular component, such as RNA or protein. In the case of cell-surface protein receptors, down-regulation can occur through internalization of the receptor as a consequence of binding to a ligand or any of the constructs described herein. Shedding or ectodomain shedding refers to a process by which cell surface proteins are proteolytically cleaved resulting in the release of their ectodomains into the extracellular milieu. Non-limiting examples of sheddases that regulate ectodomain shedding include members of the disintigrin and metalloproteinase (ADAM) family, such as ADAM8, ADAM9, ADAM 10, ADAM12, ADAM15, ADAM 17, and ADAM 28, and matrix metalloproteinases (MMPs), such as MMP2, MMP3, MMP7, MMP9, and MMP14. It is believed that the distance from the plasma membrane and structure of the cleavage site region are more important than the specific sequence in ectodomain shedding. Protein degradation or proteolysis refers to a set of processes that result in the hydrolysis of one or more of the peptide bonds in a protein, either through catalysis by proteolytic enzymes called proteases, or nonenzymatically, for example at very low or very high pH. In eukaryotic cells, two major pathways—the ubiquitin-proteasome pathway and lysosomal proteolysis—mediate protein degradation. Methods for determining whether a target receptor is down-regulated and/or shedded and/or degraded by a multispecific construct disclosed herein are known in the art, and are described in the Examples, see, for example, FIGS. 12A-12C; e.g., flow cytometry, Western blotting, immunoprecipitation, microscopy, or fluorescence plate reader.

As described herein, the constructs of the present invention can bridge an immune cell that expresses PD-1, and a second cell that expresses its ligand, such as a second immune cell, and/or a cancer or tumor cell. As those of skill in the art would recognize, the type of immune cell depends on the context of the disease to be treated; the particular type of immune cell can be readily determined depending on the disorder under consideration. In some embodiments, the immune cell is a T cell, e.g., regulatory T cells (a.k.a. suppressor T cells), including CD8+ T cells and CD4+ T cells, and subtypes, such as $CD4^+FOXP3^+$ $T_{reg}$ cells, $CD4^+$ $FOXP3^-$ $T_{reg}$ cells, Tr1 cells, Th3 cells, and $T_{reg}17$ cells. In some embodiments, the immune cell is a natural killer (NK) cell. In some embodiments, the immune cell is a B cell. In some embodiments, the immune cell is a macrophage.

Similarly, the type of second cell depends on the disorder under consideration. In some embodiments, the second cell (the cell that expresses a PD-1 ligand) is a second immune cell, e.g., a regulatory immune cell. In some embodiments, the regulatory immune cell is any one or more of a regulatory T cell, a B cell, a macrophage, a myeloid-derived suppressor cell, a dendritic cell, or a mesenchymal stromal cell. In some embodiments, the regulatory immune cell is a regulatory T cell, e.g., CD8+ T cell or CD4+ T cell.

In some embodiments, the second cell is a tumor cell. As used herein, "tumor cell" is sometimes used interchangeably with "cancer cell", but also encompasses non-malignant (non-cancerous) cells exhibiting increased proliferation as compared to a normal cell. In some embodiments, the tumor cell is a cancer that can be treated by blocking the interaction between PD-1 expressed by an immune cell and its ligand (e.g., PD-L1 or PD-L2) expressed on a second cell, while bridging the immune cell and the tumor cell. In some embodiments, the tumor cell is selected from the group consisting of a hematological cancer, a lymphoma, a myeloma, a leukemia, a neurological cancer, melanoma, breast cancer, a prostate cancer, a colorectal cancer, lung cancer, head and neck cancer, a gastrointestinal cancer, liver cancer, pancreatic cancer, a genitourinary cancer, a bone cancer, renal cancer, and a vascular cancer. In some embodiments, the tumor cell is selected from the group consisting of Kaposi's sarcoma, leukemia, acute lymphocytic leukemia, acute myelocytic leukemia, myeloblasts promyelocyte myelomonocytic monocytic erythroleukemia, chronic leukemia, chronic myelocytic (granulocytic) leukemia, chronic lymphocytic leukemia, mantle cell lymphoma, primary central nervous system lymphoma, Burkitt's lymphoma and marginal zone B cell lymphoma, Polycythemia vera Lymphoma, Hodgkin's disease, non-Hodgkin's disease, multiple myeloma, Waldenstrom's macroglobulinemia, heavy chain disease, solid tumors, sarcomas, and carcinomas, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colorectal carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular tumor, lung carcinoma, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, retinoblastoma, nasopharyngeal carcinoma, esophageal carcinoma, basal cell carcinoma, biliary tract cancer, bladder cancer, bone cancer, brain and central nervous system (CNS) cancer, cervical cancer, choriocarcinoma, colorectal cancers, connective tissue cancer, cancer of the digestive system, endometrial cancer, esophageal cancer, eye cancer, head and neck cancer, gastric cancer, intraepithelial neoplasm, kidney cancer, larynx cancer, liver cancer, lung cancer (small cell, large cell), melanoma, neuroblastoma; oral cavity cancer (for example lip, tongue, mouth and pharynx), ovarian cancer, pancreatic cancer, retinoblastoma, rhabdomyosarcoma, rectal cancer; cancer of the respiratory system, sarcoma, skin cancer, stomach cancer, testicular cancer, thyroid cancer, uterine cancer, and cancer of the urinary system.

As described herein, multispecific antigen-binding constructs of the present invention include bispecific, tri specific, tetraspecific, or multispecific antibodies (immunoglobulins) or antigen-binding portions or fragments thereof.

The term "immunoglobulin" refers to a class of structurally related proteins generally comprising two pairs of polypeptide chains: one pair of light (L) chains and one pair of heavy (H) chains. In an "intact immunoglobulin," all four of these chains are interconnected by disulfide bonds. The structure of immunoglobulins has been well characterized. See, e.g., Paul, *Fundamental Immunology* 7th ed., Ch. 5 (2013) Lippincott Williams & Wilkins, Philadelphia, Pa. Briefly, each heavy chain typically comprises a heavy chain variable region ($V_H$) and a heavy chain constant region ($C_H$). The heavy chain constant region typically comprises three domains, $C_{H1}$, $C_{H2}$, and $C_{H3}$. Each light chain typically comprises a light chain variable region ($V_L$) and a light chain constant region. The light chain constant region typically comprises one domain, abbreviated $C_L$. The term "immunoglobulin" (Ig) is sometimes used interchangeably with the term "antibody" herein.

The term "antibody" describes a type of immunoglobulin molecule and is used herein in its broadest sense. An antibody specifically includes intact antibodies (e.g., intact immunoglobulins), and antibody fragments such as antigen-binding fragments of an antibody, as described herein. Thus, "antibody" can refer to an intact antibody as well as an antigen-binding fragment thereof. Antibodies comprise at least one antigen-binding domain. One example of an antigen-binding domain is an antigen binding domain formed by a $V_H$-$V_L$ dimer. Antibodies can be described by the antigen to which they specifically bind. For example, a PD-1 antibody, alternatively referred to as an anti-PD-1 antibody, is an antibody that specifically binds to the inhibitory receptor PD-1.

The $V_H$ and $V_L$ regions can be further subdivided into regions of hypervariability ("hypervariable regions (HVRs);" also called "complementarity determining regions" (CDRs)) interspersed with regions that are more conserved. The more conserved regions are called framework regions (FRs). Each $V_H$ and $V_L$ generally comprises three CDRs and four FRs, arranged in the following order (from N-terminus to C-terminus): FR1-CDR1-FR2-CDR2-FR3-CDR3-FR4. The CDRs are involved in antigen binding, and confer antigen specificity and binding affinity to the antibody. See Kabat et al., *Sequences of Proteins of Immunological Interest* 5th ed. (1991) Public Health Service, National Institutes of Health, Bethesda, Md., incorporated by reference in its entirety.

The light chain from vertebrate species can be assigned to one of two types, called kappa and lambda, based on the sequence of the constant domain.

The heavy chain from vertebrate species can be assigned to one of five different classes (or isotypes): IgA, IgD, IgE, IgG, and IgM. These classes are also designated α, δ, ε, γ, and μ, respectively. The IgG and IgA classes are further divided into subclasses on the basis of differences in sequence and function. Humans express the following subclasses: IgG1, IgG2, IgG3, IgG4, IgA1, and IgA2.

Methods of generating and screening for an antibody against a desired target is well-known in the art. Methods of further modifying antibodies for enhanced properties (e.g., enhanced affinity, chimerization, humanization) as well as generating antigen-binding fragments, as described herein, are also well-known in the art.

The term "chimeric antibody" refers to an antibody in which a component of the heavy and/or light chain is derived from a particular source or species, while the remainder of the heavy and/or light chain is derived from a different source or species.

"Humanized" forms of non-human antibodies are chimeric antibodies that contain minimal sequence derived from the non-human antibody. A humanized antibody is generally a human immunoglobulin (recipient antibody) in which residues from one or more CDRs are replaced by residues from one or more CDRs of a non-human antibody (donor antibody). The donor antibody can be any suitable non-human antibody, such as a mouse, rat, rabbit, chicken, or non-human primate antibody having a desired specificity, affinity, or biological effect. In some instances, selected framework region residues of the recipient antibody are replaced by the corresponding framework region residues from the donor antibody. Humanized antibodies can also comprise residues that are not found in either the recipient antibody or the donor antibody. Such modifications can be made to further refine antibody function. For further details, see Jones et al., (1986) *Nature,* 321:522-525; Riechmann et al., (1988) *Nature,* 332:323-329; and Presta, (1992) *Curr. Op. Struct. Biol.,* 2:593-596, each of which is incorporated by reference in its entirety.

A "human antibody" is one which possesses an amino acid sequence corresponding to that of an antibody produced by a human or a human cell, or derived from a non-human source that utilizes a human antibody repertoire or human antibody-encoding sequences (e.g., obtained from human sources or designed de novo). Human antibodies specifically exclude humanized antibodies.

In some embodiments, an antibody molecule comprises a diabody, and a single-chain molecule, as well as an antigen-binding fragment of an antibody (e.g., Fab, F(ab')$_2$, and Fv). For example, an antibody molecule can include a heavy (H) chain variable domain sequence (abbreviated herein as VH), and a light (L) chain variable domain sequence (abbreviated herein as VL). In some embodiments, an antibody molecule comprises or consists of a heavy chain and a light chain (referred to as a half antibody). In another example, an antibody molecule includes two heavy (H) chain variable domain sequences and two light (L) chain variable domain sequence, thereby forming two antigen binding sites, such as Fab, Fab', F(ab')$_2$, Fc, Fd, Fd', Fv, single chain antibodies (scFv, for example), single variable domain antibodies, diabodies (Dab) (bivalent and bispecific), and chimeric (e.g., humanized) antibodies, which may be produced by the modification of whole antibodies or those synthesized de novo using recombinant DNA technologies. These functional antibody fragments retain the ability to selectively bind with their respective antigen. Antibodies and antibody fragments can be from any class of antibodies including, but not limited to, IgG, IgA, IgM, IgD, and IgE, and from any subclass (e.g., IgA1, IgA2, IgG1, IgG2, IgG3, and IgG4) of antibodies. The preparation of antibody molecules can be monoclonal or polyclonal. An antibody molecule can also be a human, humanized, CDR-grafted, or in vitro generated antibody. The antibody can have a heavy chain constant region chosen from, e.g., IgG1, IgG2, IgG3, or IgG4. The antibody can also have a light chain chosen from, e.g., kappa or lambda. In some embodiments, the antibody comprises an IgG1 heavy chain constant region having an amino acid sequence that is at least 85%, 90%, 91%, 92%, 93%, 94%, 95%, 96%, 97%, 98%, 99%, or 100% identical to SEQ ID NO: 64 (ASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK).

In some embodiments, the antibody comprises an IgG4 heavy chain constant region having an amino acid sequence that is at least 85%, 90%, 91%, 92%, 93%, 94%, 95%, 96%, 97%, 98%, 99%, or 100% identical to SEQ ID NO: 68 (ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPSCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK). In some embodiments, the antibody comprises an IgG4 heavy chain constant region having an amino acid sequence that is at least 85%, 90%, 91%, 92%, 93%, 94%, 95%, 96%, 97%, 98%, 99%, or 100% identical to SEQ ID NO: 69 (ASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG)

Antigen-binding portions or fragments of an antibody molecule are well known in the art, and include, for example: (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv)

a Fv fragment consisting of the VL and VH domains of a single arm of an antibody, (v) a diabody (dAb) fragment, which consists of a VH domain; (vi) a camelid or camelized variable domain; (vii) a single chain Fv (scFv), see e.g., Bird et al. (1988) Science 242:423-426; and Huston et al. (1988) Proc. Natl. Acad. Sci. USA 85:5879-5883); (viii) a single domain antibody. These antibody fragments are obtained using conventional techniques known to those skilled in the art, and the fragments are screened for utility in the same manner as are intact antibodies.

Antibody molecules can also be single domain antibodies. Single domain antibodies can include antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be any of the art, or any future single domain antibodies. Single domain antibodies may be derived from any species including, but not limited to mouse, human, camel, llama, fish, shark, goat, rabbit, and bovine. According to another aspect of the invention, a single domain antibody is a naturally-occurring single-domain antibody known as heavy chain antibody devoid of light chains. Such single domain antibodies are disclosed in WO 9404678, for example. For clarity reasons, this variable domain derived from a heavy chain antibody naturally devoid of light chain is known herein as a VHH or nanobody to distinguish it from the conventional VH of four chain immunoglobulins. Such a VHH molecule can be derived from antibodies raised in Camelidae species, for example in camel, llama, dromedary, alpaca and guanaco. Other species besides Camelidae may produce heavy chain antibodies naturally devoid of light chain; such VHHs are within the scope of the invention.

In some embodiments, the multispecific antigen-binding construct comprises a bispecific antibody. A bispecific antibody has specificity for no more than two antigens, but can have more than two binding sites, as described herein. A bispecific antibody molecule is characterized by a first immunoglobulin variable domain sequence which has binding specificity for a first antigen (e.g., PD-1) and a second immunoglobulin variable domain sequence that has binding specificity for a second antigen (e.g., a PD-1 ligand such as PD-L1 ligand). In some embodiments a bispecific antibody molecule comprises a scFv, or fragment thereof, have binding specificity for a first antigen and a scFv, or fragment thereof, have binding specificity for a second antigen. See, e.g., Kontermann & Brinkmann, (2015), Drug Discovery Today, 20(7):838-47, incorporated by reference in its entirety.

Various formats and methods are known in the art that can be used to generate the multivalent and/or multispecific constructs described herein, such as multivalent and/or multispecific antibody formats of both asymmetric and symmetric architectures. Non-limiting examples of such formats include (i) Fc-less bispecific antibody formats, such as tandem single-chain variable fragments (scFv2, taFv) and triplebodies, including bi-specific T cell engager (BiTE) and bispecific killer cell engagers (BiKE) molecules; bispecific single-domain antibody fusion proteins comprising single-domain antibodies, such as VH or VL domains, VHH, VNAR and Nanobodies; diabodies and diabody derivatives, including tandem diabody and dual-affinity retargeting (DART) proteins; Fab fusion proteins; and other Fc-less fusion proteins, through the use of heterodimerizing peptides or miniantibodies from various proteins, e.g., leucine zippers with a coiled coil structure; (ii) bispecific IgGs with asymmetric architecture, such as asymmetric IgGs with heavy and light chains from two different antibodies; bispecific IgGs with an asymmetric Fc region using knobs-into-holes approaches, electrostatic interactions (steering) to avoid homodimerization of CH3 domains, preferential heavy chain heterodimerization by introducing charge pairs into the hinge region of IgG1 and IgG2, strand-exchange engineered domain (SEED) heterodimers, and bispecific engagement by antibodies based on the T cell receptor (BEAT) technologies; asymmetric Fc and CH3 fusion proteins; (iii) bispecific antibodies with a symmetric architecture, such as appended IgGs by fusion of scFvs, fusion of domain antibodies and scaffold proteins, fusion of Fab arms, and fusion of additional variable heavy and light chain domains; modified IgG molecules; symmetric Fc- and CH3-based bispecific antibodies; and bispecific antibodies using immunoglobulin-derived homodimerization domains. See, for example, "The making of bispecific antibodies," Brinkmann and Kontermann, MABS 2017, Vol. 9:2, pp. 182-212, the contents of which are herein incorporated by reference in its entirety. See also, the"knob in a hole" approach described in, e.g., U.S. Pat. No. 5,731,168; the electrostatic steering Fc pairing as described in, e.g., WO 09/089004, WO 06/106905 and WO 2010/129304; Strand Exchange Engineered Domains (SEED) heterodimer formation as described in, e.g., WO 07/110205; Fab arm exchange as described in, e.g., WO 08/119353, WO 2011/131746, and WO 2013/060867; double antibody conjugate, e.g., by antibody cross-linking to generate a bi-specific structure using a heterobifunctional reagent having an amine-reactive group and a sulfhydryl reactive group as described in, e.g., U.S. Pat. No. 4,433,059; bispecific antibody determinants generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments cross-linked through sulfhdryl reactive groups, as described in, e.g., U.S. Pat. No. 5,273,743; biosynthetic binding proteins, e.g., pair of scFvs cross-linked through C-terminal tails preferably through disulfide or amine-reactive chemical cross-linking, as described in, e.g., U.S. Pat. No. 5,534,254; bifunctional antibodies, e.g., Fab fragments with different binding specificities dimerized through leucine zippers (e.g., c-fos and c-jun) that have replaced the constant domain, as described in, e.g., U.S. Pat. No. 5,582,996; bispecific and oligospecific mono- and oligovalent receptors, e.g., VH-CH1 regions of two antibodies (two Fab fragments) linked through a polypeptide spacer between the CH1 region of one antibody and the VH region of the other antibody typically with associated light chains, as described in, e.g., U.S. Pat. No. 5,591,828; bispecific DNA-antibody conjugates, e.g., crosslinking of antibodies or Fab fragments through a double stranded piece of DNA, as described in, e.g., U.S. Pat. No. 5,635,602; bispecific fusion proteins, e.g., an expression construct containing two scFvs with a hydrophilic helical peptide linker between them and a full constant region, as described in, e.g., U.S. Pat. No. 5,637,481; multivalent and multispecific binding proteins, e.g., dimer of polypeptides having first domain with binding region of Ig heavy chain variable region, and second domain with binding region of Ig light chain variable region, generally termed diabodies (higher order structures are also encompassed creating for bispecifc, trispecific, or tetraspecific molecules, as described in, e.g., U.S. Pat. No. 5,837,242; minibody constructs with linked VL and VH chains further connected with peptide spacers to an antibody hinge region and CH3 region, which can be dimerized to form bispecific/multivalent molecules, as described in, e.g., U.S. Pat. No. 5,837,821; VH and VL domains linked with a short peptide linker (e.g., 5 or 10 amino acids) or no linker at all in either orientation, which can form dimers to form bispecific diabodies; trimers and tetramers, as described in, e.g., U.S. Pat. No. 5,844,094; String of VH domains (or VL domains in family members) connected by peptide linkages with crosslinkable groups at the C-terminus further associated with VL domains to form a series of FVs (or scFvs), as described in, e.g., U.S. Pat. No. 5,864,019; and single chain binding polypeptides with both a VH and a VL domain linked through a peptide linker are combined into multivalent structures through non-covalent or chemical crosslinking to form, e.g., homobivalent, heterobivalent, trivalent, and tetravalent structures using both scFV or diabody type format, as described in, e.g., U.S. Pat. No. 5,869,620. Additional exemplary multispecific and bispecific molecules and methods of making the same are found, for example, in U.S. Pat. Nos. 5,910,573, 5,932,448, 5,959,083, 5,989,830, 6,005,079, 6,239,259, 6,294,353, 6,333,396, 6,476,198, 6,511,663, 6,670,453, 6,743,896, 6,809,185, 6,833,441, 7,129,330, 7,183,076, 7,521,056, 7,527,787, 7,534,866, 7,612,181, US2002004587A1, US2002076406A1, US2002103345A1, US2003207346A1, US2003211078A1, US2004219643A1, US2004220388A1, US2004242847A1, US2005003403A1, US2005004352A1, US2005069552A1, US2005079170A1, US2005100543A1, US2005136049A1, US2005136051A1, US2005163782A1, US2005266425A1, US2006083747A1, US2006120960A1, US2006204493A1, US2006263367A1, US2007004909A1, US2007087381A1, US2007128150A1, US2007141049A1, US2007154901A1, US2007274985A1, US2008050370A1, US2008069820A1, US2008152645A1, US2008171855A1, US2008241884A1, US2008254512A1, US2008260738A1, US2009130106A1, US2009148905A1, US2009155275A1, US2009162359A1, US2009162360A1, US2009175851A1, US2009175867A1, US2009232811A1, US2009234105A1, US2009263392A1, US2009274649A1, EP346087A2, WO0006605A2, WO02072635A2, WO04081051A1, WO06020258A2, WO2007044887A2, WO2007095338A2, WO2007137760A2, WO2008119353A1, WO2009021754A2, WO2009068630A1, WO9103493A1, WO9323537A1, WO9409131A1, WO9412625A2, WO9509917A1, WO9637621A2, WO9964460A1. The contents of the above-referenced applications are incorporated herein by reference in their entireties.

In some embodiments, the multispecific antigen-binding construct of the present invention is a bispecific antibody. Bispecific antibodies according to the present disclosure can be generated against PD-1 and PD-L1, or against PD-1 and PD-L2. The antibody arms of the bispecific antibody can be generated by standard techniques, as disclosed herein. In some embodiments, any known antibodies against PD-1 and its ligand can be used to generate a bispecific antibody according to the present disclosure. For example, such bispecific constructs have been exemplified herein (see, for example, Pembrolizumab (PD-1 antibody) joined with Atezolizumab (PD-L1 antibody) in FIG. 3; Nivolumab (PD-1 antibody) joined with Atezolizumab (PD-L1 antibody) in FIG. 4). As exemplified herein, multispecific antigen-binding constructs (e.g., bispecific antibodies) described herein can be generated using known and/or available antibodies in the art.

In some embodiments, the bispecific antibody is bivalent—e.g., one arm is monovalent for PD-1 while the other arm is monovalent for either PD-L1 or PD-L2, or both—e.g., cross-reacts with both ligands). In some embodiments, the bispecific antibody is tetravalent, such as the novel Bispecific 3 and Bispecific 4 antibodies described herein. For example, as illustrated in FIG. 3, the Pembrolizumab binding arm is bivalent for PD-1, each binding the same epitope on PD-1, while the Atezolizumab binding arm is bivalent for PD-L1, each binding the same epitope on PD-L1. This can also be seen in, for example, the bispecific format in FIG. 8 (the exemplary common light chain bispecific illustrated in the left panel of step 2 of the workflow presented in FIG. 8). The exemplary common light chain bispecific format in FIG. 8 (the format illustrated in the right panel of step 2 of the workflow) represents another example of a tetravalent bispecific format. In contrast to the tetravalent bispecific format in which the first antigen binding arms are joined to the second antigen binding arms on opposite ends of the Fc region, here each Fab of the first antigen binding arms is joined to each Fab of the second antigen binding arm. For example, one a Fab of the first antigen binding arm is linked to a Fab of the second antigen binding arm using a linker, where each antigen binding arm shares a common light chain. See, FIG. 8, the format illustrated in the right panel of step 2 of the workflow.

In some embodiments, the bispecific antibody is tetravalent, wherein one arm is bivalent for PD-1, each binding two different epitopes on PD-1. In some embodiments, the bispecific antibody is tetravalent, wherein one arm is bivalent for a ligand of PD-1 (PD-L1 and/or PD-L2), each binding two different epitopes on a ligand of PD-1. In some embodiments, the bispecific antibody is tetravalent, wherein one arm is bivalent for PD-1, each binding two different but overlapping epitopes on PD-1. In some embodiments, the bispecific antibody is tetravalent, wherein one arm is bivalent for PD-1 ligand (PD-L1 and/or PD-L2), each binding two different but overlapping epitopes on the PD-1 ligand (PD-L1 and/or PD-L2). In some embodiments, the bispecific antibody is tetravalent, wherein one arm is bivalent for PD-1 and each binds the same epitope on PD-1. In some embodiments, the bispecific antibody is tetravalent, wherein one arm is bivalent for a PD-1 ligand (PD-L1 and/or PD-L2), and each binds the same epitope on the PD-1 ligand (PD-L1 and/or PD-L2). In some embodiments, the bispecific antibody is tetravalent, where one arm is bivalent for a same epitope on PD-1; and the other arm is bivalent for a same epitope on a PD-1 ligand (PD-L1 and/or PD-L2).

In some embodiments, the bispecific antibody is an antagonist of both PD-1 and PD-L1. In some embodiments, the bispecific antibody is an antagonist of both PD-1 and PD-L2. In some embodiments, the bispecific antibody is an antagonist of PD-1 and both ligands PD/L1 and PD-L2 (e.g., cross reacts with both ligands).

In certain embodiments, the first antigen-binding arm and the second antigen-binding arm are linked by at least one amino linker amino acid sequence. Optionally, the linker amino acid sequence comprises GGGGSX (SEQ ID NO: 121), wherein x is an integer between and including 1 to 6.

In some embodiments, the multispecific antigen-binding construct does not comprise an immunoglobulin Fc domain.

In some embodiments, the construct comprises an immunoglobulin Fc domain. In some embodiments, the first arm or second arm, or both, of the construct, comprises a heavy chain comprising one or more immunoglobulin Fc modifications. In some embodiments, the immunoglobulin Fc domain of the heavy chain comprises one or more amino acid mutations that, e.g., promote heterodimerization of the first and second arms, promote serum half-life, and/or modify effector function. In some embodiments, the mutation is present in a CH3 domain of the heavy chain. See, e.g., Xu et al., mAbs 7(1): 231-42, 2015.

While traditional Fc fusion proteins and antibodies are examples of unguided interaction pairs, a variety of engineered Fc domains have been designed as asymmetric interaction pairs (Spiess et al., (2015) Molecular Immunology 67(2A): 95-106) to promote heterodimerization, e.g., of a first antigen-binding arm and a second antigen-bind arm. Various methods are known in the art that increase desired pairing of Fc-containing polypeptide chains in a single cell line to produce a preferred asymmetric fusion protein at acceptable yields [see, for example, Klein et al. (2012) mAbs 4:653-663; and Spiess et al. (2015) Molecular Immunology 67(2PartA): 95-106. Methods to obtain desired pairing of Fc-containing polypeptides include, but are not limited to, charge-based pairing (electrostatic steering), "knobs-into-holes" steric pairing, SEEDbody pairing, and leucine zipper-based pairing. See, for example, Ridgway et al. (1996) Protein Eng 9:617-621; Merchant et al. (1998) Nat Biotech 16:677-681; Davis et al. (2010) Protein Eng Des Sel 23:195-202; Gunasekaran et al. (2010); 285:19637-19646; Wranik et al. (2012) J Biol Chem 287:43331-43339; U.S. Pat. No. 5,932,448; WO 1993/011162; WO 2009/089004, and WO 2011/034605.

For example, one means by which interaction between specific polypeptides may be promoted is by engineering protuberance-into-cavity (knob-into-holes) complementary regions such as described in Arathoon et al., U.S. Pat. No. 7,183,076; Carter et al., U.S. Pat. No. 5,731,168; and Kumar et al., WO 2016/164089, incorporated herein by reference in their entireties. "Protuberances" are constructed by replacing small amino acid side chains from the interface of the first polypeptide (e.g., a first interaction pair) with larger side chains (e.g., tyrosine or tryptophan). Complementary "cavities" of identical or similar size to the protuberances are optionally created on the interface of the second polypeptide (e.g., a second interaction pair) by replacing large amino acid side chains with smaller ones (e.g., alanine or threonine). Where a suitably positioned and dimensioned protuberance or cavity exists at the interface of either the first or second polypeptide, it is only necessary to engineer a corresponding cavity or protuberance, respectively, at the adjacent interface.

At neutral pH (7.0), aspartic acid and glutamic acid are negatively charged and lysine, arginine, and histidine are positively charged. These charged residues can be used to promote heterodimer formation and at the same time hinder homodimer formation. Attractive interactions take place between opposite charges and repulsive interactions occur between like charges. In part, protein complexes disclosed herein make use of the attractive interactions for promoting heteromultimer formation (e.g., heterodimer formation), and optionally repulsive interactions for hindering homodimer formation (e.g., homodimer formation) by carrying out site directed mutagenesis of charged interface residues.

For example, the IgG1 CH3 domain interface comprises four unique charge residue pairs involved in domain-domain interactions: Asp356-Lys439', Glu357-Lys370', Lys392-Asp399', and Asp399-Lys409' [residue numbering in the second chain is indicated by (')]. It should be noted that the numbering scheme used here to designate residues in the IgG1 CH3 domain conforms to the EU numbering scheme of Kabat. Due to the 2-fold symmetry present in the CH3-CH3 domain interactions, each unique interaction will be represented twice in the structure (e.g., Asp-399-Lys409' and Lys409-Asp399'). In the wild-type sequence, K409-D399' favors both heterodimer and homodimer formation. A single mutation switching the charge polarity (e.g., K409E; positive to negative charge) in the first chain leads to unfavorable interactions for the formation of the first chain homodimer. The unfavorable interactions arise due to the repulsive interactions occurring between the same charges (negative-negative; K409E-D399' and D399-K409E'). A similar mutation switching the charge polarity (D399K'; negative to positive) in the second chain leads to unfavorable interactions (K409'-D399K' and D399K-K409') for the second chain homodimer formation. But, at the same time, these two mutations (K409E and D399K') lead to favorable interactions (K409E-D399K' and D399-K409') for the heterodimer formation. The electrostatic steering effect on heterodimer formation and homodimer discouragement can be further enhanced by mutation of additional charge residues which may or may not be paired with an oppositely charged residue in the second chain including, for example, Arg355 and Lys360. See, e.g., WO 2016/164089.

Thus, in some embodiments, the multispecific antigen-binding constructs (e.g., bispecific constructs) described herein can comprise a constant domain of an immunoglobulin, including, for example, the Fc portion of an immunoglobulin. For example, a first arm may comprise an amino acid sequence that is derived from an Fc domain of an IgG (IgG1, IgG2, IgG3, or IgG4), IgA (IgA1 or IgA2), IgE, or IgM immunoglobulin. Optionally, a second arm may comprise an amino acid sequence that is derived from an Fc domain of an IgG (IgG1, lgG2, lgG3, or IgG4), IgA (IgA1 or IgA2), IgE, or IgM. Such immunoglobulin domains may comprise one or more amino acid modifications (e.g., deletions, additions, and/or substitutions) that promote heterodimer formation. In some embodiments, a multispecific antigen-binding construct is of the IgG1 isotype. In some embodiments, a multispecific antigen-binding construct is of the IgG1 isotype and comprises a substitution. In some embodiments, a multispecific antigen-binding constructis of the IgG2 isotype. In some embodiments, a multispecific antigen-binding construct is of the IgG3 isotype. In some embodiments, a multispecific antigen-binding construct is of the IgG4 isotype. In some embodiments, a multispecific antigen-binding construct is of the IgG4 isotype and comprises a substitution. In some embodiments, the substitution is at Ser228 when numbered according to EU numbering. In some embodiments, the substitution at Ser228 is S228P. In some embodiments, a first arm and a second arm comprise Fc domains derived from the same immunoglobulin class and subtype. In some embodiments, a first arm and a second arm comprise Fc domains derived from different immunoglobulin classes or subtypes. Similarly, a first arm and/or a second arm (e.g., an asymmetric pair or an unguided interaction pair) comprise a modified constant domain of an immunoglobulin, including, for example, one or more amino acid modifications (e.g., deletions, additions, and/or substitutions) that promote heterodimer formation. Methods of generating Fc modifications having the desired heterodimer formation are known in the art.

In some embodiments, the Fc domain can be modified to enhance serum half-life of the multispecific antigen-binding construct disclosed herein. Fc domains comprising one or more mutations which enhance or diminish antibody binding to the Fc receptor, e.g., at acidic pH as compared to neutral pH, are known in the art. For example, the constructs disclosed herein may comprise a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the construct when administered to an animal. Methods of modifying the Fc domain for desired characteristics, such as enhanced serum half-life are known in the art.

In some embodiments, the constructs described herein comprise an altered heavy chain constant region that has reduced (or no) effector function relative to its corresponding unaltered constant region. Effector functions involving the constant region of the constructs described herein may be modulated by altering properties of the constant or Fc region. Altered effector functions include, for example, a modulation in one or more of the following activities: antibody-dependent cellular cytotoxicity (ADCC), complement-dependent cytotoxicity (CDC), apoptosis, binding to one or more Fc-receptors, and pro-inflammatory responses. Modulation refers to an increase, decrease, or elimination of an effector function activity exhibited by a subject antibody containing an altered constant region as compared to the activity of the unaltered form of the constant region. In particular embodiments, modulation includes situations in which an activity is abolished or completely absent.

An altered constant region with altered FcR binding affinity and/or ADCC activity and/or altered CDC activity is a polypeptide which has either an enhanced or diminished FcR binding activity and/or ADCC activity and/or CDC activity compared to the unaltered form of the constant region. An altered constant region which displays increased binding to an FcR binds at least one FcR with greater affinity than the unaltered polypeptide. An altered constant region which displays decreased binding to an FcR binds at least one FcR with lower affinity than the unaltered form of the constant region. Such variants which display decreased binding to an FcR may possess little or no appreciable binding to an FcR, e.g., 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the binding to the FcR as compared to the level of binding of a native sequence immunoglobulin constant or Fc region to the FcR. Similarly, an altered constant region that displays modulated ADCC and/or CDC activity may exhibit either increased or reduced ADCC and/or CDC activity compared to the unaltered constant region. For example, in some embodiments, any one or more of the antibodies described herein comprising an altered constant region can exhibit approximately 0 to 50% (e.g., less than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%) of the ADCC and/or CDC activity of the unaltered form of the constant region. A multispecific antigen-binding construct described herein comprising an altered constant region displaying reduced ADCC and/or CDC can exhibit reduced or no ADCC and/or CDC activity.

In some embodiments, the multispecific antigen-binding constructs described herein exhibit reduced or no effector function. In some embodiments, the multispecific antigen-binding constructs comprise a hybrid constant region, or a portion thereof, such as a G2/G4 hybrid constant region (see e.g., Burton et al. (1992) *Adv Immun* 51:1-18; Canfield et al. (1991) *J Exp Med* 173:1483-1491; and Mueller et al. (1997) *Mol Immunol* 34(6):441-452).

In some embodiments, the multispecific antigen-binding constructs described herein can contain an altered constant region exhibiting enhanced or reduced complement dependent cytotoxicity (CDC). Modulated CDC activity can be achieved by introducing one or more amino acid substitutions, insertions, or deletions in an Fc region of the antibody. See, e.g., U.S. Pat. No. 6,194,551.

The constructs and antigen-binding arms described herein can comprise, in part, scaffold domains, proteins, or portions, e.g., molecules which do not provide target receptor-binding activity, but which can provide a portion or domain of the construct which provides spatial organization, structural support, a means of linking of multiple receptor-binding units, or other desired characteristics, e.g., improved half-life. Various scaffold technologies and compositions are known in the art and can be readily linked or conjugated to the antigen-binding units described herein. The scaffold domain, protein, or portion can be derived from an antibody or not derived from an antibody. Such scaffold proteins, and domains thereof, are, generally, obtained through combinatorial chemistry-based adaptation of preexisting antigen-binding proteins.

Non-antibody protein scaffolds can be considered to fall into two structural categories, domain-sized constructs (in the range of 6 to 20 kDa), and constrained peptides (in the 2-4 kDa range). Domain-sized non-antibody scaffolds include, but are not limited to, affibodies, affilins, anticalins, atrimers, DARPins, FN3 scaffolds (such as adnectins and centyrins), fynomers, Kunitz domains, pronectins and OBodies. Peptide-sized non-antibody scaffolds include, for example, avimers, bicyclic peptides and cysteine knots. These non-antibody scaffolds and the underlying proteins or peptides on which they are based or from which they have been derived are reviewed by, e.g., Simeon and Chen, Protein Cell 9(1): 3-14 (2018); Vazquez-Lombardi et al., Drug Discovery Today 20: 1271-1283 (2015), and by Binz et al., Nature Biotechnol. 23: 1257-1268 (2005), the contents of each of which are herein incorporated by reference in their entireties. Advantages of using non-antibody scaffolds include increased affinity, target neutralization, and stability. Various non-antibody scaffolds also can overcome some of the limitations of antibody scaffolds, e.g., in terms of tissue penetration, smaller size, and thermostability. Some non-antibody scaffolds can also permit easier construction, not being hindered, for example, by the light chain association issue when bispecific constructs are desired. Methods of constructing constructs on a non-antibody scaffold are known to those of ordinary skill in the art. While not formally on an antibody scaffold, such constructs often include antibody binding domains, whether in the form of single-domain antibodies, scFvs or other antibody binding-domain variants that provide specific target-binding capabilities.

Accordingly, in some embodiments of any of the aspects described herein, a construct can comprise a non-antibody scaffold protein. In some embodiments of any of the aspects described herein, at least one of the receptor-binding units can comprise a non-antibody scaffold protein. One of skill in the art would appreciate that the scaffold portion of a non-antibody scaffold protein can include, in some embodiments, e.g., an adnectin scaffold or a portion derived from human tenth fibronectin type III domain (10Fn3); an anticalin scaffold derived from human lipocalin (e.g., such as those described in, e.g., WO2015/104406); an avimer scaffold or a protein fragment derived from the A-domain of low density-related protein (LRP) and/or very low density lipoprotein receptor (VLDLR); a fynomer scaffold or portion of the SH3 domain of FYN tyrosine kinase; a kunitz domain scaffold or portion of Kunitz-type protease inhibitors, such as a human trypsin inhibitor, aprotinin (bovine pancreatic trypsin inhibitor), Alzheimer's amyloid precursor protein, and tissue factor pathway inhibitor; a knottin scaffold (cysteine knot miniproteins), such as one based on a trypsin inhibitor from *E. elaterium*; an affibody scaffold or all or part of the Z domain of *S. aureus* protein A; a β-Hairpin mimetic scaffold; a Designed ankyrin repeat protein (DARPin) scaffold or artificial protein scaffolds based on ankyrin repeat (AR) proteins; or any scaffold derived or based on human transferrin, human CTLA-4, human crystallin, and human ubiquitin. For example, the binding site of human transferrin for human transferrin receptor can be diversified to create a diverse library of transferrin variants, some of which have acquired affinity for different antigens. See, e.g., Ali et al. (1999) *J. Biol. Chem.* 274:24066-24073. The portion of human transferrin not involved with binding the receptor remains unchanged and serves as a scaffold, like framework regions of antibodies, to present the variant binding sites. The libraries are then screened, as an antibody library is, and in accordance with the methods described herein, against a target antigen of interest to identify those variants having optimal selectivity and affinity for the target antigen. See, e.g., Hey et al. (2005) *TRENDS Biotechnol.* 23(10):514-522.

D. Methods for Producing the Multispecific Antigen-Binding Constructs

The disclosure also features methods for producing any of the multispecific antigen-binding constructs described herein. In some embodiments, methods for producing the construct of the present invention includes methods for preparing an antibody, and/or fragments thereof as described herein. Such methods are well-known in the art, and can include, e.g., immunizing a subject (e.g., a non-human mammal) with an appropriate immunogen. For example, to generate an antibody that binds to PD-1, a skilled artisan can immunize a suitable subject (e.g., a non-human mammal such as a rat, a mouse, a gerbil, a hamster, a dog, a cat, a pig, a goat, a horse, or a non-human primate) with a full-length PD-1 polypeptide such as a full-length human PD-1 polypeptide comprising the amino acid sequence depicted in SEQ ID NO.: 114 (GenBank accession number NP_005009.2; UniProt Q15116), an antigenic fragment thereof, and/or variant thereof. Similarly, to generate an antibody that binds to a ligand of PD-1 (e.g., PD-L1), a skilled artisan can immunize a suitable subject with a full-length PD-L1 polypeptide such as a full-length human PD-L1 polypeptide comprising the amino acid sequence depicted in SEQ ID NO.: 115 (GenBank accession number NP 054862.1, UniProt Q9NZQ7), an antigenic fragment thereof, and/or variant thereof. Similarly, to generate an antibody that binds to PD-L2, a skilled artisan can immunize a suitable subject with a full-length PD-L2 polypeptide such as a full-length human PD-L2 polypeptide comprising the amino acid sequence depicted in SEQ ID NO.: 116 (GenBank accession number NP_079515.2, UniProt Q9BQ51), an antigenic fragment thereof, and/or variant thereof.

As those of skill in the art would recognize, a full-length polypeptide (PD-1, PD-L1, or PD-L2) can be used as an antigen and antibodies can be screened for desired binding properties (e.g., blocks PD-1/ligand interaction; capacity to bridge cells on which PD-1 and its ligand are expressed). As those of skill in the art would also recognize, antigenic fragments of a polypeptide (PD-1, PD-L1, or PD-L2) can be selected based on known structural features of the polypeptide. For example, the PD-1/PD-L1 and PD-1/PD-L2 interactions have been structurally well-characterized (see, e.g., Zak, K., et al. (2015) Structure 23(12):2341-48; Ghiotto, M., et al. (2010) Int'l Immuno. 22(8):651-60; Freeman, G. (2008) PNAS 105(30):10275-76; Lazar-Molnar, E. et al. (2008) PNAS 105:10483-88, incorporated by reference in their entireties). Thus, regions within, e.g., PD-1, PD-L1, and/or PD-L2, based on receptor/ligand interface information available in the art, can be used to design a suitable antigenic fragment having desired binding properties. For example, the PD-1 ectodomain contains a single IgV domain typical of the CD28 family, wherein PD-L1 and PD-L2 are composed of IgV and IgC domains typical of the B7 family. The structures of PD-1, PD-L1 and/or PD-L2 show a 1:1 stoichiometry, with interaction primarily between the faces of the IgV domains. An IgV domain comprises about 120 amino acids organized into nine parallel beta strands (ABCC'C"DEFG) with loops connecting the strands. It has been shown that PD-1 uses the front beta-face (GFCC' strands and CC', CC", and FG loops) to bind to the beta-face of PD-L1 (GFCC') or PD-L2 (AGFC strands and FG loop). Further, six amino acids of the C, F, and G strands of PD-1 form a concave, hydrophobic core that interacts with the F and G strands as well as the FG loop of PD-L2. Eight if 14 residues involved in binding to PD-1 are indentical or highly conserved between PD-L1 and PD-L2. Using such information, those of skill in the art can determine suitable antigenic regions to generate antibodies having desirable properties. For example, those of skill in the art can generate an antibody that cross reacts with both ligands PD-L1 and PD-L2 (see, e.g., U.S. Pat. No. 9,845,356).

A suitable subject (e.g., a non-human mammal) can be immunized with the appropriate antigen along with subsequent booster immunizations a number of times sufficient to elicit the production of an antibody by the mammal. The immunogen can be administered to a subject (e.g., a non-human mammal) with an adjuvant. Adjuvants useful in producing an antibody in a subject include, but are not limited to, protein adjuvants; bacterial adjuvants, e.g., whole bacteria (BCG, *Corynebacterium parvum* or *Salmonella minnesota*) and bacterial components including cell wall skeleton, trehalose dimycolate, monophosphoryl lipid A, methanol extractable residue (MER) of tubercle *bacillus*, complete or incomplete Freund's adjuvant; viral adjuvants; chemical adjuvants, e.g., aluminum hydroxide, and iodoacetate and cholesteryl hemisuccinate. Other adjuvants that can be used in the methods for inducing an immune response include, e.g., cholera toxin and parapoxvirus proteins. See also Bieg et al. (1999) Autoimmunity 31(1):15-24. See also, e.g., Lodmell et al. (2000) Vaccine 18:1059-1066; Johnson et al. (1999) J Med Chem 42:4640-4649; Baldridge et al. (1999) Methods 19:103-107; and Gupta et al. (1995) Vaccine 13(14): 1263-1276.

In some embodiments, the methods include preparing a hybridoma cell line that secretes a monoclonal antibody that binds to the immunogen. For example, a suitable mammal such as a laboratory mouse is immunized with a polypeptide (e.g., PD-1, PD-L1, PD-L2) or antigenic fragment as described above. Antibody-producing cells (e.g., B cells of the spleen) of the immunized mammal can be isolated two to four days after at least one booster immunization of the immunogen and then grown briefly in culture before fusion with cells of a suitable myeloma cell line. The cells can be fused in the presence of a fusion promoter such as, e.g., vaccinia virus or polyethylene glycol. The hybrid cells obtained in the fusion are cloned, and cell clones secreting the desired antibodies are selected. For example, spleen cells of Balb/c mice immunized with a suitable immunogen can be fused with cells of the myeloma cell line PAI or the myeloma cell line Sp2/0-Ag 14. After the fusion, the cells are expanded in suitable culture medium, which is supplemented with a selection medium, for example HAT medium, at regular intervals in order to prevent normal myeloma cells from overgrowing the desired hybridoma cells. The obtained hybridoma cells are then screened for secretion of the desired antibodies, e.g., an antibody that binds to PD-1.

In some embodiments, a skilled artisan can identify an anti-PD-1 antibody from a non-immune biased library as described in, e.g., U.S. Pat. No. 6,300,064 (to Knappik et al.; Morphosys AG) and Schoonbroodt et al. (2005) *Nucleic Acids Res* 33(9):e81.

In some embodiments, the methods described herein can involve, or be used in conjunction with, e.g., phage display technologies, bacterial display, yeast surface display, eukaryotic viral display, mammalian cell display, and cell-free (e.g., ribosomal display) antibody screening techniques (see, e.g., Etz et al. (2001) *J Bacteriol* 183:6924-6935; Cornelis (2000) *Curr Opin Biotechnol* 11:450-454; Klemm et al. (2000) *Microbiology* 146:3025-3032; Kieke et al. (1997) *Protein Eng* 10:1303-1310; Yeung et al. (2002) *Biotechnol Prog* 18:212-220; Boder et al. (2000) *Methods Enzymology* 328:430-444; Grabherr et al. (2001) *Comb Chem High Throughput Screen* 4:185-192; Michael et al. (1995) *Gene Ther* 2:660-668; Pereboev et al. (2001) *J Virol* 75:7107-7113; Schaffitzel et al. (1999) *J Immunol Methods* 231:119-135; and Hanes et al. (2000) *Nat Biotechnol* 18:1287-1292).

Methods for identifying antibodies using various phage display methods are known in the art. In phage display methods, functional antibody domains are displayed on the surface of phage particles which carry the polynucleotide sequences encoding them. Such phage can be utilized to display antigen-binding domains of antibodies, such as Fab, Fv, or disulfide-bond stabilized Fv antibody fragments, expressed from a repertoire or combinatorial antibody library (e.g., human or murine). Phage used in these methods are typically filamentous phage such as fd and M13. The antigen binding domains are expressed as a recombinantly-fused protein to any of the phage coat proteins pIII, pVIII, or pIX. See, e.g., Shi et al. (2010) *JMB* 397:385-396. Examples of phage display methods that can be used to make the immunoglobulins, or fragments thereof, described herein include those disclosed in Brinkman et al. (1995) *J Immunol Methods* 182:41-50; Ames et al. (1995) *J Immunol Methods* 184:177-186; Kettleborough et al. (1994) *Eur J Immunol* 24:952-958; Persic et al. (1997) *Gene* 187:9-18; Burton et al. (1994) *Advances in Immunology* 57:191-280; and PCT publication nos. WO 90/02809, WO 91/10737, WO 92/01047, WO 92/18619, WO 93/11236, WO 95/15982, and WO 95/20401. Suitable methods are also described in, e.g., U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

In some embodiments, the phage display antibody libraries can be generated using mRNA collected from B cells from the immunized mammals. For example, a splenic cell sample comprising B cells can be isolated from mice immunized with a PD-1 polypeptide as described above. mRNA can be isolated from the cells and converted to cDNA using standard molecular biology techniques. See, e.g., Sambrook et al. (1989) "Molecular Cloning: A Laboratory Manual, 2$^{nd}$ Edition," Cold Spring Harbor Laboratory Press, Cold Spring Harbor, N.Y.; Harlow and Lane (1988), supra; Benny K. C. Lo (2004), supra; and Borrebaek (1995), supra. The cDNA coding for the variable regions of the heavy chain and light chain polypeptides of immunoglobulins are used to construct the phage display library. Methods for generating such a library are described in, e.g., Merz et al. (1995) *J Neurosci Methods* 62(1-2):213-9; Di Niro et al. (2005) *Biochem J* 388(Pt 3):889-894; and Engberg et al. (1995) *Methods Mol Biol* 51:355-376.

In some embodiments, a combination of selection and screening can be employed to identify an antibody of interest from, e.g., a population of hybridoma-derived antibodies or a phage display antibody library. Suitable methods are known in the art and are described in, e.g., Hoogenboom (1997) *Trends in Biotechnology* 15:62-70; Brinkman et al. (1995), supra; Ames et al. (1995), supra; Kettleborough et al. (1994), supra; Persic et al. (1997), supra; and Burton et al. (1994), supra. For example, a plurality of phagemid vectors, each encoding a fusion protein of a bacteriophage coat protein (e.g., pIII, pVIII, or pIX of M13 phage) and a different antigen-combining region are produced using standard molecular biology techniques and then introduced into a population of bacteria (e.g., *E. coli*). Expression of the bacteriophage in bacteria can, in some embodiments, require use of a helper phage. In some embodiments, no helper phage is required (see, e.g., Chasteen et al., (2006) *Nucleic Acids Res* 34(21):e145). Phage produced from the bacteria are recovered and then contacted to, e.g., a target antigen bound to a solid support (immobilized). Phage may also be contacted to antigen in solution, and the complex is subsequently bound to a solid support.

A subpopulation of antibodies screened using the above methods can be characterized for their specificity and binding affinity for a particular antigen (e.g., human PD-1) using any immunological or biochemical based method known in the art. For example, specific binding of an antibody to PD-1, may be determined for example using immunological or biochemical based methods such as, but not limited to, an ELISA assay, SPR assays, immunoprecipitation assay, affinity chromatography, and equilibrium dialysis as described above. Immunoassays which can be used to analyze immunospecific binding and cross-reactivity of the antibodies include, but are not limited to, competitive and non-competitive assay systems using techniques such as Western blots, RIA, ELISA (enzyme linked immunosorbent assay), "sandwich" immunoassays, immunoprecipitation assays, immunodiffusion assays, agglutination assays, complement-fixation assays, immunoradiometric assays, fluorescent immunoassays, and protein A immunoassays. Such assays are routine and well known in the art.

It is understood that the above methods can also be used to determine if, e.g., an anti-PD-1 antibody does not bind to full-length, human PD-1 and/or PD-1 proteins.

In embodiments where the selected CDR amino acid sequences are short sequences (e.g., fewer than 10-15 amino acids in length), nucleic acids encoding the CDRs can be chemically synthesized as described in, e.g., Shiraishi et al. (2007) *Nucleic Acids Symposium Series* 51(1):129-130 and U.S. Pat. No. 6,995,259. For a given nucleic acid sequence encoding an acceptor antibody, the region of the nucleic acid sequence encoding the CDRs can be replaced with the chemically synthesized nucleic acids using standard molecular biology techniques. The 5' and 3' ends of the chemically synthesized nucleic acids can be synthesized to comprise sticky end restriction enzyme sites for use in cloning the nucleic acids into the nucleic acid encoding the variable region of the donor antibody. Alternatively, fragments of chemically synthesized nucleic acids, together capable of encoding an antibody, can be joined together using DNA assembly techniques known in the art (e.g. Gibson Assembly).

Any antibody of choice can be further modified to generate an antigen-binding fragment, as described herein, and/or manipulated using known techniques in the art to generate the multispecific antigen-binding constructs as described herein. For example, cross-linking methods can be used to generate a bispecific structure using a heterobifunctional reagent having an amine-reactive group and a sulfhydryl reactive group as described in, e.g., U.S. Pat. No. 4,433,059; bispecific antibody determinants can be generated by recombining half antibodies (heavy-light chain pairs or Fabs) from different antibodies through cycle of reduction and oxidation of disulfide bonds between the two heavy chains, as described in, e.g., U.S. Pat. No. 4,444,878; trifunctional antibodies, e.g., three Fab' fragments can be cross-linked through sulfhdryl reactive groups, as described in, e.g., U.S. Pat. No. 5,273,743. Other methods of generating bispecific constructs, e.g., methods of generating bispecific constructs having common light chains, are described herein. Non-limiting examples of amino acid sequences of common light chains used in the constructs described herein include SEQ ID NOs: 59-63.

E. Expression and Purification of Multispecific Antigen-Binding Constructs

The multispecific antigen-binding constructs thereof described herein can be produced using a variety of techniques known in the art of molecular biology and protein chemistry. For example, a nucleic acid encoding the multispecific antigen-binding construct (as a single multifunctional polypeptide, or as separate molecules of a multimeric complex—e.g., one antigen-binding arm separately from the other antigen-binding arm) can be inserted into an expression vector that contains transcriptional and translational regulatory sequences, which include, e.g., promoter sequences, ribosomal binding sites, transcriptional start and stop sequences, translational start and stop sequences, transcription terminator signals, polyadenylation signals, and enhancer or activator sequences. The regulatory sequences include a promoter and transcriptional start and stop sequences. In addition, the expression vector can include more than one replication system such that it can be maintained in two different organisms, for example in mammalian or insect cells for expression and in a prokaryotic host for cloning and amplification.

Several possible vector systems are available for the expression of cloned heavy chain and light chain polypeptides from nucleic acids in mammalian cells. One class of vectors relies upon the integration of the desired gene sequences into the host cell genome. Cells which have stably integrated DNA can be selected by simultaneously introducing drug resistance genes such as *E. coli* gpt (Mulligan and Berg (1981) *Proc Natl Acad Sci USA* 78:2072) or Tn5 neo (Southern and Berg (1982) *Mol Appl Genet* 1:327). The selectable marker gene can be either linked to the DNA gene sequences to be expressed, or introduced into the same cell by co-transfection (Wigler et al. (1979) *Cell* 16:77). A second class of vectors utilizes DNA elements which confer autonomously replicating capabilities to an extrachromosomal plasmid. These vectors can be derived from animal viruses, such as bovine papillomavirus (Sarver et al. (1982) *Proc Natl Acad Sci USA*, 79:7147), cytomegalovirus, polyoma virus (Deans et al. (1984) *Proc Natl Acad Sci USA* 81:1292), or SV40 virus (Lusky and Botchan (1981) *Nature* 293:79).

The expression vectors can be introduced into cells in a manner suitable for subsequent expression of the nucleic acid. The method of introduction is largely dictated by the targeted cell type, discussed below. Exemplary methods include $CaPO_4$ precipitation, liposome fusion, cationic liposomes, electroporation, viral infection, dextran-mediated transfection, polybrene-mediated transfection, protoplast fusion, and direct microinjection.

Appropriate host cells for the expression of antibodies or antigen-binding fragments thereof include yeast, bacteria, insect, plant, and mammalian cells. Of particular interest are bacteria such as *E. coli*, fungi such as *Saccharomyces cerevisiae* and *Pichia pastoris*, insect cells such as SF9, mammalian cell lines (e.g., human cell lines), as well as primary cell lines.

In some embodiments, an antibody or fragment thereof can be expressed in, and purified from, transgenic animals (e.g., transgenic mammals). For example, an antibody can be produced in transgenic non-human mammals (e.g., rodents) and isolated from milk as described in, e.g., Houdebine (2002) *Curr Opin Biotechnol* 13(6):625-629; van Kuik-Romeijn et al. (2000) *Transgenic Res* 9(2):155-159; and Pollock et al. (1999) *J Immunol Methods* 231(1-2):147-157.

The antibodies and fragments thereof can be produced from the cells by culturing a host cell transformed with the expression vector containing nucleic acid encoding the antibodies or fragments, under conditions, and for an amount of time, sufficient to allow expression of the proteins. Such conditions for protein expression will vary with the choice of the expression vector and the host cell, and will be easily ascertained by one skilled in the art through routine experimentation. For example, antibodies expressed in *E. coli* can be refolded from inclusion bodies (see, e.g., Hou et al. (1998) *Cytokine* 10:319-30). Bacterial expression systems and methods for their use are well known in the art (see Current Protocols in Molecular Biology, Wiley & Sons, and Molecular Cloning—A Laboratory Manual—3rd Ed., Cold Spring Harbor Laboratory Press, New York (2001)). The choice of codons, suitable expression vectors and suitable host cells will vary depending on a number of factors, and may be easily optimized as needed. An antibody (or fragment thereof) described herein can be expressed in mammalian cells or in other expression systems including but not limited to yeast, baculovirus, and in vitro expression systems (see, e.g., Kaszubska et al. (2000) *Protein Expression and Purification* 18:213-220).

Following expression, the antibodies and fragments thereof can be isolated. An antibody or fragment thereof can be isolated or purified in a variety of ways known to those skilled in the art depending on what other components are present in the sample. Standard purification methods include electrophoretic, molecular, immunological, and chromatographic techniques, including ion exchange, hydrophobic, affinity, and reverse-phase HPLC chromatography. For example, an antibody can be purified using a standard anti-antibody column (e.g., a protein-A or protein-G column). Ultrafiltration and diafiltration techniques, in conjunction with protein concentration, are also useful. See, e.g., Scopes (1994) "Protein Purification, $3^{rd}$ edition," Springer-Verlag, New York City, N.Y. The degree of purification necessary will vary depending on the desired use. In some instances, no purification of the expressed antibody or fragments thereof will be necessary.

Methods for determining the yield or purity of a purified antibody or fragment thereof are known in the art and include, e.g., Bradford assay, UV spectroscopy, Biuret protein assay, Lowry protein assay, amido black protein assay, high pressure liquid chromatography (HPLC), mass spectrometry (MS), and gel electrophoretic methods (e.g., using a protein stain such as Coomassie Blue or colloidal silver stain).

F. Modification of the Multispecific Antigen-Binding Constructs

The multispecific antigen-binding constructs can be modified following their expression and purification as a single multifunctional polypeptide, or as separate molecules of a multimeric complex—e.g., one antigen-binding arm separately from the other antigen-binding arm. The modifications can be covalent or non-covalent modifications. Such modifications can be introduced into the antibodies or antigen-binding fragments by, e.g., reacting targeted amino acid residues of the polypeptide with an organic derivatizing agent that is capable of reacting with selected side chains or terminal residues. Suitable sites for modification can be chosen using any of a variety of criteria including, e.g., structural analysis or amino acid sequence analysis of the antibodies or fragments.

The amino acid sequences provided herein are set forth in single-letter amino acid code which can be used interchangeably with three-letter amino acid code. An amino acid refers to any monomer unit that can be incorporated into a peptide, polypeptide, or protein. The twenty natural or genetically encoded alpha-amino acids are as follows: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., *Biochemistry*, $5^{th}$ed., Freeman and Company (2002). The term amino acid also includes unnatural amino acids, modified amino acids (e.g., having modified side chains and/or backbones), and amino acid analogs.

The terms identical or percent identity, in the context of two or more nucleic acids or polypeptide sequences, refer to two or more sequences or subsequences that are the same or have a specified percentage of nucleotides or amino acid residues that are the same (e.g., 90%, or 95% or greater identity over a specified region), when compared and aligned for maximum correspondence over a comparison window, or designated region as measured using one of the following sequence comparison algorithms or by manual alignment and visual inspection.

Identity or similarity with respect to a sequence is defined as the percentage of amino acid residues in the candidate sequence that are identical (i.e., same residue) with the starting amino acid residues, after aligning the sequences and introducing gaps, if necessary, to achieve the maximum percent sequence identity. Methods of alignment of sequences for comparison are well known in the art. Optimal alignment of sequences for comparison can be conducted, for example, by the local homology algorithm of Smith and Waterman (*Adv. Appl. Math.* 2:482, 1970), by the homology alignment algorithm of Needleman and Wunsch (*J. Mol. Biol.* 48:443, 1970), by the search for similarity method of Pearson and Lipman (*Proc. Natl. Acad. Sci. USA* 85:2444, 1988), by computerized implementations of these algorithms (e.g., GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

As with all peptides, polypeptides, and proteins, including fragments thereof, it is understood that additional modifications in the amino acid sequence of the constructs, antibodies or antigen-binding portions thereof described herein, for example, in the heavy chain variable region and/or light chain variable region, can occur that do not alter the nature or function of the antibodies or antigen-binding fragments thereof. Such modifications include conservative amino acids substitutions, such that each recited sequence optionally contains one or more conservative amino acid substitutions. The following groups each contain amino acids that are conservative substitutions for one another. These groups are exemplary as other conservative substitutions are known to those of skill in the art.

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)

By way of example, when an aspartic acid at a specific residue is mentioned, also contemplated is a conservative substitution at the residue, for example, glutamic acid. Nonconservative substitutions, for example, substituting a proline with glycine, are also contemplated.

In some embodiments, the constructs, antibodies or antigen-binding portions thereof can be conjugated to a heterologous moiety. The heterologous moiety can be, e.g., a heterologous polypeptide, a therapeutic agent (e.g., a toxin or a drug), or a detectable label such as, but not limited to, a radioactive label, an enzymatic label, a fluorescent label, a heavy metal label, a luminescent label, or an affinity tag such as biotin or streptavidin. Suitable heterologous polypeptides include, e.g., an antigenic tag (e.g., FLAG (DYKDDDDK) (SEQ ID NO: 117), polyhistidine (6-His; HHHHHH (SEQ ID NO: 118)), hemagglutinin (HA; YPYDVPDYA (SEQ ID NO: 119)), glutathione-S-transferase (GST), or maltose-binding protein (MBP)) for use in purifying the antibodies or fragments. Heterologous polypeptides also include polypeptides (e.g., enzymes) that are useful as diagnostic or detectable markers, for example, luciferase, a fluorescent protein (e.g., green fluorescent protein (GFP)), or chloramphenicol acetyl transferase (CAT). Suitable radioactive labels include, e.g., $^{32}P$, $^{33}P$, $^{14}C$, $^{125}I$, $^{131}I$, $^{35}S$, and $^{3}H$. Suitable fluorescent labels include, without limitation, fluorescein, fluorescein isothiocyanate (FITC), green fluorescent protein (GFP), DYLIGHT™ 488, phycoerythrin (PE), propidium iodide (PI), PerCP, PE-ALEXA FLUOR® 700, Cy5, allophycocyanin, and Cy7. Luminescent labels include, e.g., any of a variety of luminescent lanthanide (e.g., europium or terbium) chelates. For example, suitable europium chelates include the europium chelate of diethylene triamine pentaacetic acid (DTPA) or tetraazacyclododecane-1,4,7,10-tetraacetic acid (DOTA). Enzymatic labels include, e.g., alkaline phosphatase, CAT, luciferase, and horseradish peroxidase.

Two proteins (e.g., an antibody and a heterologous moiety) can be cross-linked using any of a number of known chemical cross linkers. Examples of such cross linkers are those which link two amino acid residues via a linkage that includes a "hindered" disulfide bond. In these linkages, a disulfide bond within the cross-linking unit is protected (by hindering groups on either side of the disulfide bond) from reduction by the action, for example, of reduced glutathione or the enzyme disulfide reductase. One suitable reagent, 4-succinimidyloxycarbonyl-α-methyl-α(2-pyridyldithio)

toluene (SMPT), forms such a linkage between two proteins utilizing a terminal lysine on one of the proteins and a terminal cysteine on the other. Heterobifunctional reagents that cross-link by a different coupling moiety on each protein can also be used. Other useful cross-linkers include, without limitation, reagents which link two amino groups (e.g., N-5-azido-2-nitrobenzoyloxysuccinimide), two sulfhydryl groups (e.g., 1,4-bis-maleimidobutane), an amino group and a sulfhydryl group (e.g., m-maleimidobenzoyl-N-hydroxysuccinimide ester), an amino group and a carboxyl group (e.g., 4-[p-azidosalicylamido]butylamine), and an amino group and a guanidinium group that is present in the side chain of arginine (e.g., p-azidophenyl glyoxal monohydrate).

In some embodiments, a radioactive label can be directly conjugated to the amino acid backbone of the antibody. Alternatively, the radioactive label can be included as part of a larger molecule (e.g., $^{125}$I in meta-[$^{125}$I]iodophenyl-N-hydroxysuccinimide ([$^{125}$I]mIPNHS) which binds to free amino groups to form meta-iodophenyl (mIP) derivatives of relevant proteins (see, e.g., Rogers et al. (1997) *J Nucl Med* 38:1221-1229) or chelate (e.g., to DOTA or DTPA) which is in turn bound to the protein backbone. Methods of conjugating the radioactive labels or larger molecules/chelates containing them to the antibodies or antigen-binding fragments described herein are known in the art. Such methods involve incubating the proteins with the radioactive label under conditions (e.g., pH, salt concentration, and/or temperature) that facilitate binding of the radioactive label or chelate to the protein (see, e.g., U.S. Pat. No. 6,001,329).

Methods for conjugating a fluorescent label (sometimes referred to as a "fluorophore") to a protein (e.g., an antibody) are known in the art of protein chemistry. For example, fluorophores can be conjugated to free amino groups (e.g., of lysines) or sulfhydryl groups (e.g., cysteines) of proteins using succinimidyl (NETS) ester or tetrafluorophenyl (TFP) ester moieties attached to the fluorophores. In some embodiments, the fluorophores can be conjugated to a heterobifunctional cross-linker moiety such as sulfo-SMCC. Suitable conjugation methods involve incubating an antibody protein, or fragment thereof, with the fluorophore under conditions that facilitate binding of the fluorophore to the protein. See, e.g., Welch and Redvanly (2003) "Handbook of Radiopharmaceuticals: Radiochemistry and Applications," John Wiley and Sons (ISBN 0471495603).

In some embodiments, the antibodies or fragments can be modified, e.g., with a moiety that improves the stabilization and/or retention of the antibodies in circulation, e.g., in blood, serum, or other tissues. For example, the antibody or fragment can be PEGylated as described in, e.g., Lee et al. (1999) *Bioconjug Chem* 10(6): 973-8; Kinstler et al. (2002) *Advanced Drug Deliveries Reviews* 54:477-485; and Roberts et al. (2002) *Advanced Drug Delivery Reviews* 54:459-476 or HESylated (Fresenius Kabi, Germany; see, e.g., Pavisić et al. (2010) *Int J Pharm* 387(1-2):110-119). The stabilization moiety can improve the stability, or retention of, the antibody (or fragment) by at least 1.5 (e.g., at least 2, 5, 10, 15, 20, 25, 30, 40, or 50 or more) fold.

In some embodiments, the antibodies or antigen-binding fragments thereof described herein can be glycosylated. In some embodiments, an antibody or antigen-binding fragment thereof described herein can be subjected to enzymatic or chemical treatment, or produced from a cell, such that the antibody or fragment has reduced or absent glycosylation. Methods for producing antibodies with reduced glycosylation are known in the art and described in, e.g., U.S. Pat. No. 6,933,368; Wright et al. (1991) *EMBO J* 10(10):2717-2723; and Co et al. (1993) *Mol Immunol* 30:1361. In some embodiments, the antibodies or antigen-binding fragments thereof are aglycosylated.

G. Pharmaceutical Compositions and Formulations

The present disclosure also provides for a pharmaceutical composition comprising the multispecific antigen-binding constructs of the present disclosure with a pharmaceutically acceptable diluent, carrier, solubilizer, emulsifier, preservative and/or adjuvant to be used with the methods disclosed herein. Such pharmaceutical compositions can be used in a subject having e.g., cancer, as disclosed herein.

In certain embodiments, acceptable formulation materials preferably are nontoxic to recipients at the dosages and concentrations employed. In certain embodiments, the formulation material(s) are for s.c. and/or I.V. administration. In certain embodiments, the pharmaceutical composition can contain formulation materials for modifying, maintaining or preserving, for example, the pH, osmolality, viscosity, clarity, color, isotonicity, odor, sterility, stability, rate of dissolution or release, adsorption or penetration of the composition. In certain embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. (Remington's Pharmaceutical Sciences, 18th Edition, A. R. Gennaro, ed., Mack Publishing Company (1995). In certain embodiments, the formulation comprises PBS; 20 mM NaOAC, pH 5.2, 50 mM NaCl; and/or 10 mM NAOAC, pH 5.2, 9% Sucrose. In certain embodiments, the optimal pharmaceutical composition will be determined by one skilled in the art depending upon, for example, the intended route of administration, delivery format and desired dosage. See, for example, Remington's Pharmaceutical Sciences, supra. In certain embodiments, such compositions may influence the physical state, stability, rate of in vivo release and/or rate of in vivo clearance of the multispecific antigen-binding construct.

In certain embodiments, the primary vehicle or carrier in a pharmaceutical composition can be either aqueous or non-aqueous in nature. For example, in certain embodiments, a suitable vehicle or carrier can be water for injection, physiological saline solution or artificial cerebrospinal fluid, possibly supplemented with other materials common in compositions for parenteral administration. In certain embodiments, the saline comprises isotonic phosphate-buffered saline. In certain embodiments, neutral buffered saline or saline mixed with serum albumin are further exemplary vehicles. In certain embodiments, pharmaceutical compositions comprise Tris buffer of about pH 7.0-8.5, or acetate buffer of about pH 4.0-5.5, which can further include sorbitol or a suitable substitute therefore. In certain embodiments, a composition comprising the multispecific antigen-binding constructs disclosed herein can be prepared for storage by mixing the selected composition having the desired degree of purity with optional formulation agents (Remington's Pharmaceutical Sciences, supra) in the form of a lyophilized cake or an aqueous solution. Further, in certain embodiments, a composition comprising the multispecific antigen-binding construct disclosed herein can be formulated as a lyophilizate using appropriate excipients such as sucrose.

In certain embodiments, the pharmaceutical composition can be selected for parenteral delivery. In certain embodiments, the compositions can be selected for inhalation or for delivery through the digestive tract, such as orally. The preparation of such pharmaceutically acceptable compositions is within the ability of one skilled in the art.

In certain embodiments, the formulation components are present in concentrations that are acceptable to the site of administration. In certain embodiments, buffers are used to maintain the composition at physiological pH or at a slightly lower pH, typically within a pH range of from about 5 to about 8.

In certain embodiments, when parenteral administration is contemplated, a therapeutic composition can be in the form of a pyrogen-free, parenterally acceptable aqueous solution comprising a multispecific antigen-binding construct, in a pharmaceutically acceptable vehicle. In certain embodiments, a vehicle for parenteral injection is sterile distilled water in which a multispecific antigen-binding construct is formulated as a sterile, isotonic solution, and properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that can provide for the controlled or sustained release of the product which can then be delivered via a depot injection. In certain embodiments, hyaluronic acid can also be used, and can have the effect of promoting sustained duration in the circulation. In certain embodiments, implantable drug delivery devices can be used to introduce the desired molecule.

In certain embodiments, a pharmaceutical composition can be formulated for inhalation. In certain embodiments, a multispecific antigen-binding construct can be formulated as a dry powder for inhalation. In certain embodiments, an inhalation solution comprising a multispecific antigen-binding construct can be formulated with a propellant for aerosol delivery. In certain embodiments, solutions can be nebulized. Pulmonary administration is further described in PCT application No. PCT/US94/001875, which describes pulmonary delivery of chemically modified proteins.

In certain embodiments, it is contemplated that formulations can be administered orally. In certain embodiments, a multispecific antigen-binding construct that is administered in this fashion can be formulated with or without those carriers customarily used in the compounding of solid dosage forms such as tablets and capsules. In certain embodiments, a capsule can be designed to release the active portion of the formulation at the point in the gastrointestinal tract when bioavailability is maximized and pre-systemic degradation is minimized. In certain embodiments, at least one additional agent can be included to facilitate absorption of a multispecific antigen-binding construct. In certain embodiments, diluents, flavorings, low melting point waxes, vegetable oils, lubricants, suspending agents, tablet disintegrating agents, and binders can also be employed.

In certain embodiments, a pharmaceutical composition can involve an effective quantity of a multispecific antigen-binding construct in a mixture with non-toxic excipients which are suitable for the manufacture of tablets. In certain embodiments, by dissolving the tablets in sterile water, or another appropriate vehicle, solutions can be prepared in unit-dose form. In certain embodiments, suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving a multispecific antigen-binding construct in sustained- or controlled-delivery formulations. In certain embodiments, techniques for formulating a variety of other sustained- or controlled-delivery means, such as liposome carriers, bio-erodible microparticles or porous beads and depot injections, are also known to those skilled in the art. See for example, PCT Application No. PCT/US93/00829 which describes the controlled release of porous polymeric microparticles for the delivery of pharmaceutical compositions. In certain embodiments, sustained-release preparations can include semipermeable polymer matrices in the form of shaped articles, e.g. films, or microcapsules. Sustained release matrices can include polyesters, hydrogels, polylactides (U.S. Pat. No. 3,773,919 and EP 058,481), copolymers of L-glutamic acid and gamma ethyl-L-glutamate (Sidman et al., Biopolymers, 22:547-556 (1983)), poly (2-hydroxyethyl-methacrylate) (Langer et al., J. Biomed. Mater. Res., 15: 167-277 (1981) and Langer, Chem. Tech., 12:98-105 (1982)), ethylene vinyl acetate (Langer et al., supra) or poly-D(−)-3-hydroxybutyric acid (EP 133,988). In certain embodiments, sustained release compositions can also include liposomes, which can be prepared by any of several methods known in the art. See, e.g., Eppstein et al, Proc. Natl. Acad. Sci. USA, 82:3688-3692 (1985); EP 036,676; EP 088,046 and EP 143,949.

The pharmaceutical composition to be used for in vivo administration typically is sterile. In certain embodiments, this can be accomplished by filtration through sterile filtration membranes. In certain embodiments, where the composition is lyophilized, sterilization using this method can be conducted either prior to or following lyophilization and reconstitution. In certain embodiments, the composition for parenteral administration can be stored in lyophilized form or in a solution. In certain embodiments, parenteral compositions generally are placed into a container having a sterile access port, for example, an intravenous solution bag or vial having a stopper pierceable by a hypodermic injection needle.

In certain embodiments, once the pharmaceutical composition has been formulated, it can be stored in sterile vials as a solution, suspension, gel, emulsion, solid, or as a dehydrated or lyophilized powder. In certain embodiments, such formulations can be stored either in a ready-to-use form or in a form (e.g., lyophilized) that is reconstituted prior to administration.

In certain embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

In certain embodiments, the effective amount of a pharmaceutical composition comprising a multispecific antigen-binding construct to be employed therapeutically will depend, for example, upon the therapeutic context and objectives. One skilled in the art will appreciate that the appropriate dosage levels for treatment, according to certain embodiments, will thus vary depending, in part, upon the molecule delivered, the indication for which a multispecific antigen-binding construct is being used, the route of administration, and the size (body weight, body surface or organ size) and/or condition (the age and general health) of the patient. In certain embodiments, the clinician can titer the dosage and modify the route of administration to obtain the optimal therapeutic effect.

In certain embodiments, the frequency of dosing will take into account the pharmacokinetic parameters of a multispecific antigen-binding construct in the formulation used. In certain embodiments, a clinician will administer the composition until a dosage is reached that achieves the desired effect. In certain embodiments, the composition can therefore be administered as a single dose or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. In certain embodiments, appropriate dosages can be ascertained through use of appropriate dose-response data.

In certain embodiments, the route of administration of the pharmaceutical composition is in accord with known methods, e.g. orally, through injection by intravenous, intraperitoneal, intracerebral (intra-parenchymal), intracerebroventricular, intramuscular, subcutaneously, intra-ocular, intraarterial, intraportal, or intralesional routes; by sustained release systems or by implantation devices. In certain embodiments, the compositions can be administered by bolus injection or continuously by infusion, or by implantation device. In certain embodiments, individual elements of the combination therapy may be administered by different routes.

In certain embodiments, the composition can be administered locally via implantation of a membrane, sponge or another appropriate material onto which the desired molecule has been absorbed or encapsulated. In certain embodiments, where an implantation device is used, the device can be implanted into any suitable tissue or organ, and delivery of the desired molecule can be via diffusion, timed-release bolus, or continuous administration. In certain embodiments, it can be desirable to use a pharmaceutical composition comprising a multispecific antigen-binding construct in an ex vivo manner. In such instances, cells, tissues and/or organs that have been removed from the patient are exposed to a pharmaceutical composition comprising a multispecific antigen-binding construct after which the cells, tissues and/or organs are subsequently implanted back into the patient.

In certain embodiments, a multispecific antigen-binding construct can be delivered by implanting certain cells that have been genetically engineered, using methods such as those described herein, to express and secrete the polypeptides. In certain embodiments, such cells can be animal or human cells, and can be autologous, heterologous, or xenogeneic. In certain embodiments, the cells can be immortalized. In certain embodiments, in order to decrease the chance of an immunological response, the cells can be encapsulated to avoid infiltration of surrounding tissues. In certain embodiments, the encapsulation materials are typically biocompatible, semi-permeable polymeric enclosures or membranes that allow the release of the protein product(s) but prevent the destruction of the cells by the patient's immune system or by other detrimental factors from the surrounding tissues.

H. Methods of Use

As described herein, the present disclosure provides a method of treating a proliferative disorder in a subject in need thereof, comprising administering to the subject a therapeutically effective amount of a multispecific antigen-binding construct of the present disclosure. In some embodiments, the present disclosure provides a method of enhancing an immune response (e.g., enhanced T cell function, such as rescue from T cell functional exhaustion; enhanced T cell-mediated response; increased inflammtary cytokine secretion and/or production, e.g., IFNγ secretion and/or production from T cells; enhanced NK cell function; enhanced macrophage function) in a subject in need thereof, comprising administering to the subject a therapeutically effective amount of a multispecific antigen-binding construct of the present disclosure. As exemplified herein, the enhancement of the immune response is greater upon administration of the multispecific antigen-binding construct disclosed herein as compared to an agent (e.g., antibody) that binds either PD-1 or its ligand (e.g., PD-L1 or PD-L2), or a cocktail comprising an agent (e.g., antibody) that binds PD-1 and an agent (e.g., antibody) that binds its ligand. In some embodiments, the enhancement of the immune response (e.g., enhanced T cell function, such as rescue from T cell functional exhaustion; enhanced T cell-mediated response; increased inflammtary cytokine, IFNγsecretion and/or production from T cells; enhanced NK cell function; enhanced macrophage function) is greater by at least 10%, at least 20%, at least 30%, at least 40%, at least 50%, at least 60%, at least 70%, at least 80%, at least 90%, at least 100%, or more, as compared to an agent (e.g., antibody) that binds either PD-1 or its ligand, or a cocktail comprising an agent (e.g., antibody) that binds PD-1 and an agent (e.g., antibody) that binds its ligand. Also provided herein are methods for treating or delaying progression of a cancer or reducing or inhibiting tumor growth in a subject by administering to the subject an effective amount of a multispecific antigen-binding construct, an antibody or antigen-binding fragment thereof, a pharmaceutical composition, or a protein conjugate as described herein.

The compositions described herein are useful in, inter alia, methods for treating or preventing a variety of cancers in a subject.

The compositions can be administered to a subject, e.g., a human subject, using a variety of methods that depend, in part, on the route of administration. The route can be, e.g., intravenous injection or infusion (IV), subcutaneous injection (SC), intraperitoneal (IP) injection, intramuscular injection (IM), or intrathecal injection (IT). The injection can be in a bolus or a continuous infusion.

As used herein, the term "subject" means a mammalian subject. Exemplary subjects include, but are not limited to humans, monkeys, dogs, cats, mice, rats, cows, horses, camels, goats and sheep. In some embodiments, the subject is a human. In some embodiments, the subject has or is suspected to have a disease or condition that can be treated with a multispecific antigen-binding construct provided herein. In some embodiments, the disease or condition is a cancer. In some embodiments, the subject is a human with a cancer that can be treated with a multispecific antigen-binding construct provided herein. In some embodiments, the subject is a human that is suspected to have cancer that can be treated with a multispecific antigen-binding construct provided herein.

"Treating" or "treatment" of any disease or disorder refers, in some embodiments, to ameliorating a disease or disorder that exists in a subject. In another embodiment, "treating" or "treatment" includes ameliorating at least one physical parameter, which can be indiscernible by the subject. In yet another embodiment, "treating" or "treatment" includes modulating the disease or disorder, either physically (e.g., stabilization of a discernible symptom) or physiologically (e.g., stabilization of a physical parameter) or both. In yet another embodiment, "treating" or "treatment" includes delaying or preventing the onset of the disease or disorder.

As used herein, the term "therapeutically effective amount" or "effective amount" refers to an amount of a multispecific antigen-binding construct that, when administered to a subject, is effective to treat a disease or disorder.

As used herein, "administer" or "administration" refers to the act of injecting or otherwise physically delivering a substance as it exists outside the body (e.g., a multispecific antigen-binding construct provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

Administration can be achieved by, e.g., local infusion, injection, or by means of an implant. The implant can be of a porous, non-porous, or gelatinous material, including membranes, such as sialastic membranes, or fibers. The implant can be configured for sustained or periodic release of the composition to the subject. See, e.g., U.S. Patent Application Publication No. 20080241223; U.S. Pat. Nos. 5,501,856; 4,863,457; and 3,710,795; EP488401; and EP 430539, the disclosures of each of which are incorporated herein by reference in their entirety. The composition can be delivered to the subject by way of an implantable device based on, e.g., diffusive, erodible, or convective systems, e.g., osmotic pumps, biodegradable implants, electrodiffusion systems, electroosmosis systems, vapor pressure pumps, electrolytic pumps, effervescent pumps, piezoelectric pumps, erosion-based systems, or electromechanical systems.

In some embodiments, a multispecific antigen-binding construct of the present disclosure is therapeutically delivered to a subject by way of local administration.

As used herein, the term "enhanced T cell function" or "activation of T cells" refers to a cellular process in which mature T cells, which express antigen-specific T cell receptors on their surfaces, recognize their cognate antigens and respond by entering the cell cycle, secreting cytokines or lytic enzymes, and initiating or becoming competent to perform cell-based effector functions. T cell activation requires at least two signals to become fully activated. The first occurs after engagement of the T cell antigen-specific receptor (TCR) by the antigen-major histocompatibility complex (MEW), and the second by subsequent engagement of co-stimulatory molecules (e.g., CD28). These signals are transmitted to the nucleus and result in clonal expansion of T cells, upregulation of activation markers on the cell surface, differentiation into effector cells, induction of cytotoxicity or cytokine secretion, induction of apoptosis, or a combination thereof. In some embodiments, "enhanced T cell function" also encompasses enhanced survival and/or enhanced proliferation of the T cell. Methods for measuring such activities are routine and known in the art. In some embodiments, "enhanced T cell function" also encompasses rescue of a T cell from an exhausted phenotype, so that restoration of or an increase in one or more T cell functions is achieved. As known in the art, the state of T cell exhaustion is characterized by sequential loss of T cell effector functions, such as inflammtory cytokine production, proliferative abilities, metabolic fitness, in addition to sustained upregulation of a wide array of co-inhibitory receptors, and unique transcriptional and epigenetic signatures. T cell exhaustion and alterations thereof can be measured using techniques known in the art, and described herein, for example, the in vitro nonspecific T cell+K562-PD-L1 tumor target cell assay.

As used herein, the term T cell-mediated response refers to any response mediated by T cells, including, but not limited to, effector T cells (e.g., $CD8^+$ cells, effector $\gamma\delta$ T cells) and helper T cells (e.g., $CD4^+$ cells, including subbsets thereof, such as $T_H1$, $T_H2$, $T_H3$, $T_H17$, $T_H9$, and $T_{FH}$ cells). T cell-mediated responses include, for example, T cell cytotoxicity, T cell cytokine secretion, and proliferation. A suitable dose of an antibody or fragment thereof described herein, which dose is capable of treating or preventing cancer in a subject, can depend on a variety of factors including, e.g., the age, sex, and weight of a subject to be treated and the particular inhibitor compound used. For example, a different dose of a whole multispecific antigen-binding construct may be required to treat a subject with cancer as compared to the dose of a fragment of the multispecific antigen-binding construct (e.g., Fab' antibody fragment) required to treat the same subject. Other factors affecting the dose administered to the subject include, e.g., the type or severity of the cancer. For example, a subject having metastatic melanoma may require administration of a different dosage of multispecific antigen-binding construct than a subject with glioblastoma. Other factors can include, e.g., other medical disorders concurrently or previously affecting the subject, the general health of the subject, the genetic disposition of the subject, diet, time of administration, rate of excretion, drug combination, and any other additional therapeutics that are administered to the subject. It should also be understood that a specific dosage and treatment regimen for any particular subject will also depend upon the judgment of the treating medical practitioner (e.g., doctor or nurse). Suitable dosages are described herein. In some embodiments, the multispecific antigen-binding construct described herein are effective at both high and low doses.

A pharmaceutical composition can include a therapeutically effective amount multispecific antigen-binding construct described herein. Such effective amounts can be readily determined by one of ordinary skill in the art based, in part, on the effect of the administered antibody, or the combinatorial effect of the antibody and one or more additional active agents, if more than one agent is used. A therapeutically effective amount of an antibody or fragment thereof described herein can also vary according to factors such as the disease state, age, sex, and weight of the individual, and the ability of the antibody (and one or more additional active agents) to elicit a desired response in the individual, e.g., reduction in tumor growth. For example, a therapeutically effective amount of multispecific antigen-binding construct can inhibit (lessen the severity of or eliminate the occurrence of) and/or prevent a particular disorder, and/or any one of the symptoms of the particular disorder known in the art or described herein. A therapeutically effective amount is also one in which any toxic or detrimental effects of the composition are outweighed by the therapeutically beneficial effects.

Suitable human doses of any of the multispecific antigen-binding construct described herein can further be evaluated in, e.g., Phase I dose escalation studies. See, e.g., van Gurp et al. (2008) *Am J Transplantation* 8(8):1711-1718; Hanouska et al. (2007) *Clin Cancer Res* 13(2, part 1):523-531; and Hetherington et al. (2006) *Antimicrobial Agents and Chemotherapy* 50(10): 3499-3500.

Toxicity and therapeutic efficacy of such compositions can be determined by known pharmaceutical procedures in cell cultures or experimental animals (e.g., animal models of any of the cancers described herein). These procedures can be used, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. An antibody or antigen-binding fragment thereof that exhibits a high therapeutic index is preferred. While compositions that exhibit toxic side effects may be used, care should be taken to design a delivery system that targets such compounds to the site of affected tissue and to minimize potential damage to normal cells and, thereby, reduce side effects.

The data obtained from the cell culture assays and animal studies can be used in formulating a range of dosage for use in humans. The dosage of such antibodies or antigen-binding fragments thereof lies generally within a range of circulating concentrations of the antibodies or fragments that include the $ED_{50}$ with little or no toxicity. The dosage may vary within this range depending upon the dosage form employed and the route of administration utilized. For multispecific antigen-binding construct described herein, the therapeutically effective dose can be estimated initially from cell culture assays. A dose can be formulated in animal models to achieve a circulating plasma concentration range that includes the $EC_{50}$ (i.e., the concentration of the construct—e.g., antibody—which achieves a half-maximal inhibition of symptoms) as determined in cell culture. Such information can be used to more accurately determine useful doses in humans. Levels in plasma may be measured, for example, by high performance liquid chromatography. In some embodiments, e.g., where local administration (e.g., to the eye or a joint) is desired, cell culture or animal modeling can be used to determine a dose required to achieve a therapeutically effective concentration within the local site.

In some embodiments, the methods can be performed in conjunction with other therapies for cancer. For example, the composition can be administered to a subject at the same time, prior to, or after, radiation, surgery, targeted or cytotoxic chemotherapy, chemoradiotherapy, hormone therapy, immunotherapy, gene therapy, cell transplant therapy, precision medicine, genome editing therapy, or other pharmacotherapy.

As described above, the multispecific antigen-binding construct described herein be used to treat a variety of cancers selected from the group consisting of a hematological cancer, a lymphoma, a myeloma, a leukemia, a neurological cancer, skin cancer, breast cancer, a prostate cancer, a colorectal cancer, lung cancer, head and neck cancer, a gastrointestinal cancer, liver cancer, pancreatic cancer, a genitourinary cancer, a bone cancer, renal cancer, and a vascular cancer. Optionally, the cancer is selected from the group consisting of Kaposi's sarcoma, leukemia, acute lymphocytic leukemia (etv6, aml1, cyclophilin b), acute myelocytic leukemia, myeloblasts promyelocyte myelomonocytic monocytic erythroleukemia, chronic leukemia, chronic myelocytic (granulocytic) leukemia, chronic lymphocytic leukemia (cyclophilin b), mantle cell lymphoma, primary central nervous system lymphoma, Burkitt's lymphoma, marginal zone B cell lymphoma (Ig-idiotype), Polycythemia vera Lymphoma, Hodgkin's disease (Imp-1, EBNA-1), non-Hodgkin's disease, mycloma (MUC family, p21ras), multiple myeloma, Waldenstrom's macroglobulinemia, heavy chain disease, solid tumors, sarcoma, carcinoma, fibrosarcoma, myxosarcoma, liposarcoma, chrondrosarcoma, osteogenic sarcoma, osteosarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon sarcoma, colon carcinoma (p21ras, HER2/neu, c-erbB-2, MUC family), pancreatic cancer, breast cancer (MUC family, HER2/neu, c-erbB-2), ovarian cancer, prostate cancer (Prostate Specific Antigen (PSA) and its antigenic epitopes PSA-1, PSA-2, and PSA-3, PSMA, HER2/neu, c-erbB-2, ga733 glycoprotein), squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma (HER2/neu, c-erbB-2), hepatoma, hepatocellular cancer (a-fetoprotein), bile duct carcinoma, choriocarcinoma, seminoma, embryonal carcinoma, Wilm's tumor, cervical cancer, uterine cancer, testicular tumor (NY-ESO-1), lung carcinoma, small cell lung carcinoma, non-small cell lung carcinoma (HER2/neu, c-erbB-2), bladder carcinoma, epithelial carcinoma, glioma (E-cadherin, α-catenin, β-catenin, γ-catenin, p120ctn), astrocytoma, medulloblastoma, craniopharyngioma, ependymoma, pinealoma, hemangioblastoma, acoustic neuroma, oligodendroglioma, menangioma, melanoma (p5 protein, gp75, oncofetal antigen, GM2 and GD2 gangliosides, Melan-A/MART-1, cdc27, MAGE-3, p21ras, gp100), neuroblastoma, retinoblastoma, nasopharyngeal carcinoma (Imp-1, EBNA-1), esophageal carcinoma, basal cell carcinoma, biliary tract cancer (p21ras), bladder cancer (p21ras), bone cancer, brain and central nervous system (CNS) cancer, cervical carcinoma (p53, p21ras), choriocarcinoma (CEA), colorectal cancers (colorectal associated antigen (CRC)-0017-1A/GA733, APC), connective tissue cancer, cancer of the digestive system, endometrial cancer, esophageal cancer, eye cancer, head and neck cancer, gastric cancer (HER2/neu, c-erbB-2, ga733 glycoprotein), epithelial cell cancer (cyclophilin b), intraepithelial neoplasm, kidney cancer, larynx cancer, liver cancer, lung cancer (small cell, large cell) (CEA, MAGE-3, NY-ESO-1), oral cavity cancer (for example lip, tongue, mouth, and pharynx cancers), ovarian cancer (MUC family, HER2/neu, c-erbB-2), pancreatic cancer, rectal cancer, cancer of the respiratory system, skin cancer, thyroid cancer, and cancer of the urinary system.

In some embodiments, a multispecific antigen-binding construct described herein can be administered to a subject as a monotherapy. Alternatively, as described above, the antibody or fragment thereof can be administered to a subject as a combination therapy with another treatment, e.g., another treatment for a cancer. For example, the combination therapy can include administering to the subject (e.g., a human patient) one or more additional agents that provide a therapeutic benefit to a subject who has, or is at risk of developing, cancer. Chemotherapeutic agents suitable for co-administration with compositions of the present invention include, for example: taxol, cytochalasin B, gramicidin D, ethidium bromide, emetine, mitomycin, etoposide, tenoposide, vincristine, vinblastine, colchicin, doxorubicin, daunorubicin, dihydroxyanthrancindione, mitoxantrone, mithramycin, actinomycin D, 1-dehydrotestosterone, glucocorticoids, procaine, tetracaine, lidocaine, propranolol, and puromycin and analogs or homologs thereof. Further agents include, for example, antimetabolites (e.g., methotrexate, 6-mercaptopurine, 6-thioguanine, cytarabine, 5-fluorouracil decarbazine), alkylating agents (e.g. mechlorethamine, thioTEPA, chlorambucil, melphalan, carmustine (BSNU), lomustine (CCNU), cyclophosphamide, busulfan, dibromomannitol, streptozotocin, mitomycin C, cis-dichlordiamine platinum (II)(DDP), procarbazine, altretamine, cisplatin, carboplatin, oxaliplatin, nedaplatin, satraplatin, or triplatin tetranitrate), anthracycline (e.g. daunorubicin (formerly daunomycin) and doxorubicin), antibiotics (e.g. dactinomcin (formerly actinomycin), bleomycin, mithramycin, and anthramycin (AMC)), and antimitotic agents (e.g. vincristine and vinblastine) and temozolomide. In some embodiments, the multispecific antigen-binding construct and the one or more additional active agents are administered at the same time. In other embodiments, the multispecific antigen-binding construct is administered first in time and the one or more additional active agents are administered second in time. In some embodiments, the one or more additional active agents are administered first in time and the multispecific antigen-binding construct is administered second in time.

A multispecific antigen-binding construct described herein can replace or augment a previously or currently administered therapy. For example, upon treating with a multispecific antigen-binding construct, administration of the one or more additional active agents can cease or diminish, e.g., be administered at lower levels or dosages. In some embodiments, administration of the previous therapy can be maintained. In some embodiments, a previous therapy will be maintained until the level of the multispecific antigen-binding construct reaches a level sufficient to provide a therapeutic effect. The two therapies can be administered in combination.

Monitoring a subject (e.g., a human patient) for an improvement in a cancer, as defined herein, means evaluating the subject for a change in a disease parameter, e.g., a reduction in tumor growth. In some embodiments, the evaluation is performed at least one (1) hour, e.g., at least 2, 4, 6, 8, 12, 24, or 48 hours, or at least 1 day, 2 days, 4 days, 10 days, 13 days, 20 days or more, or at least 1 week, 2 weeks, 4 weeks, 10 weeks, 13 weeks, 20 weeks or more, after an administration. The subject can be evaluated in one or more of the following periods: prior to beginning of treatment; during the treatment; or after one or more elements of the treatment have been administered. Evaluation can include evaluating the need for further treatment, e.g., evaluating whether a dosage, frequency of administration, or duration of treatment should be altered. It can also include evaluating the need to add or drop a selected therapeutic modality, e.g., adding or dropping any of the treatments for a cancer described herein.

In some embodiments, a multispecific antigen-binding construct described herein is administered to modulate a T-cell response in a patient, for example, by increasing T-cell activation and/or proliferation. Blocking the interaction between PD-1 expressed by an immune cell and its ligand strongly enhances T cell proliferation, IFNγ production and secretion, and the cytolytic activity of T cells. Bridging an immune cell that expresses PD-1 with a second cell (e.g., another immune cells, or a tumor cell) that expresses a PD-1 ligand (e.g., PD-L1 or PD-L2) can strongly enhance T cell proliferation, IFNγ production and secretion, and the cytolytic activity of T cells. Accordingly, in some embodiments, the multispecific antigen-binding construct of the present disclosure is administered to a patient in need thereof to induce or increase T-cell activation, enhance T cell proliferation, induce the production and/or secretion of IFNγ, and/or induce a cytolytic T cell response.

EXAMPLES

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the disclosure.

Example 1: Induction of Interferon-Gamma (IFNγ) in T Cells

Figure 4:
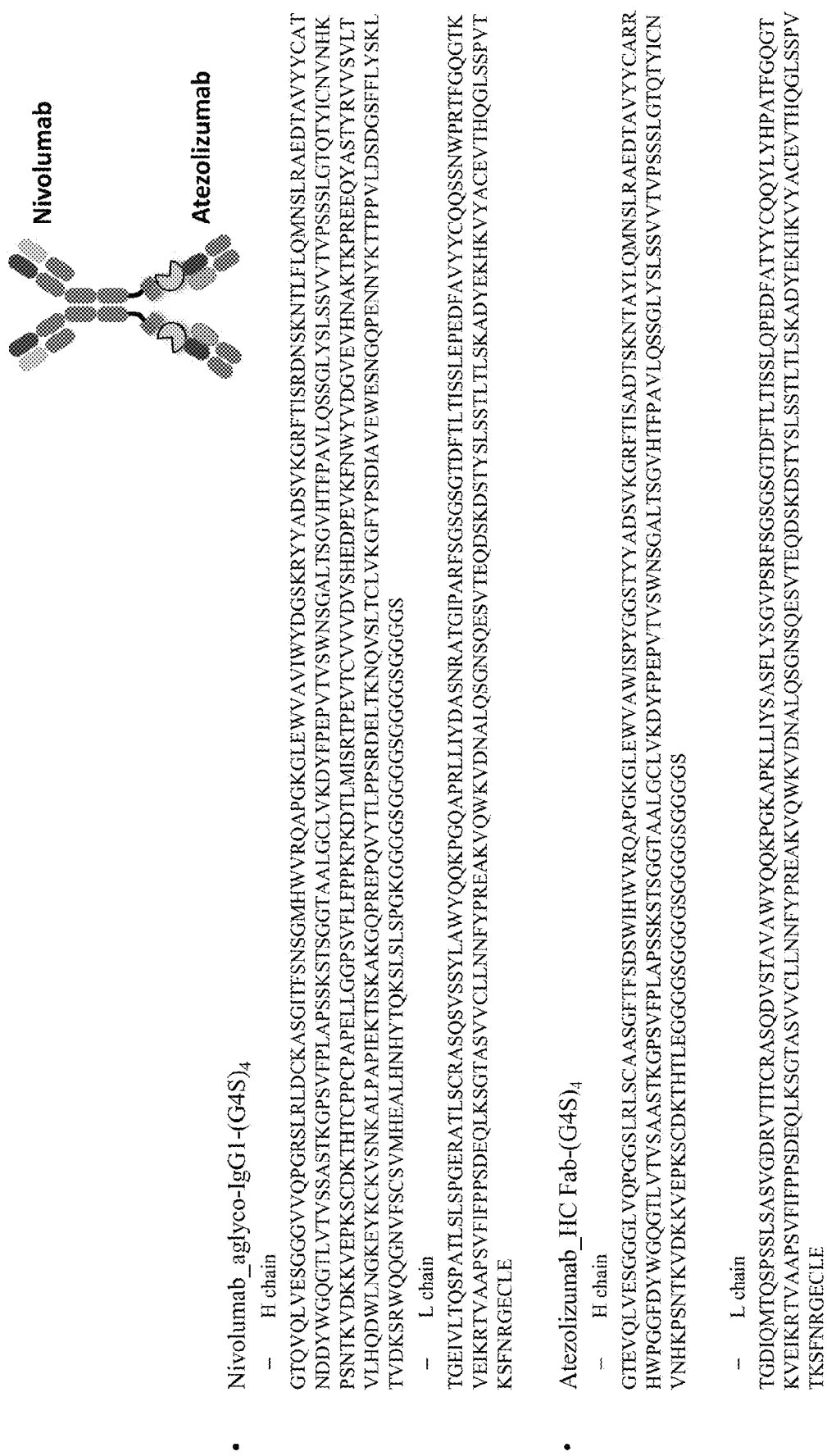
FIG. 4 shows a schematic and amino acid sequence for a NivolumabxAtezolizumab bispecific. Separate sequences are given for the Nivolumab aglyco-IgG1-(G4S)$_4$ heavy chain (H chain; SEQ ID NO: 108) and light chain (L chain; SEQ ID NO: 109) and for the Atezolizumab FabH-(G4S)$_4$ heavy chain (H chain; SEQ ID NO: 106) and light chain (L chain; SEQ ID NO: 107).
Figure 5:
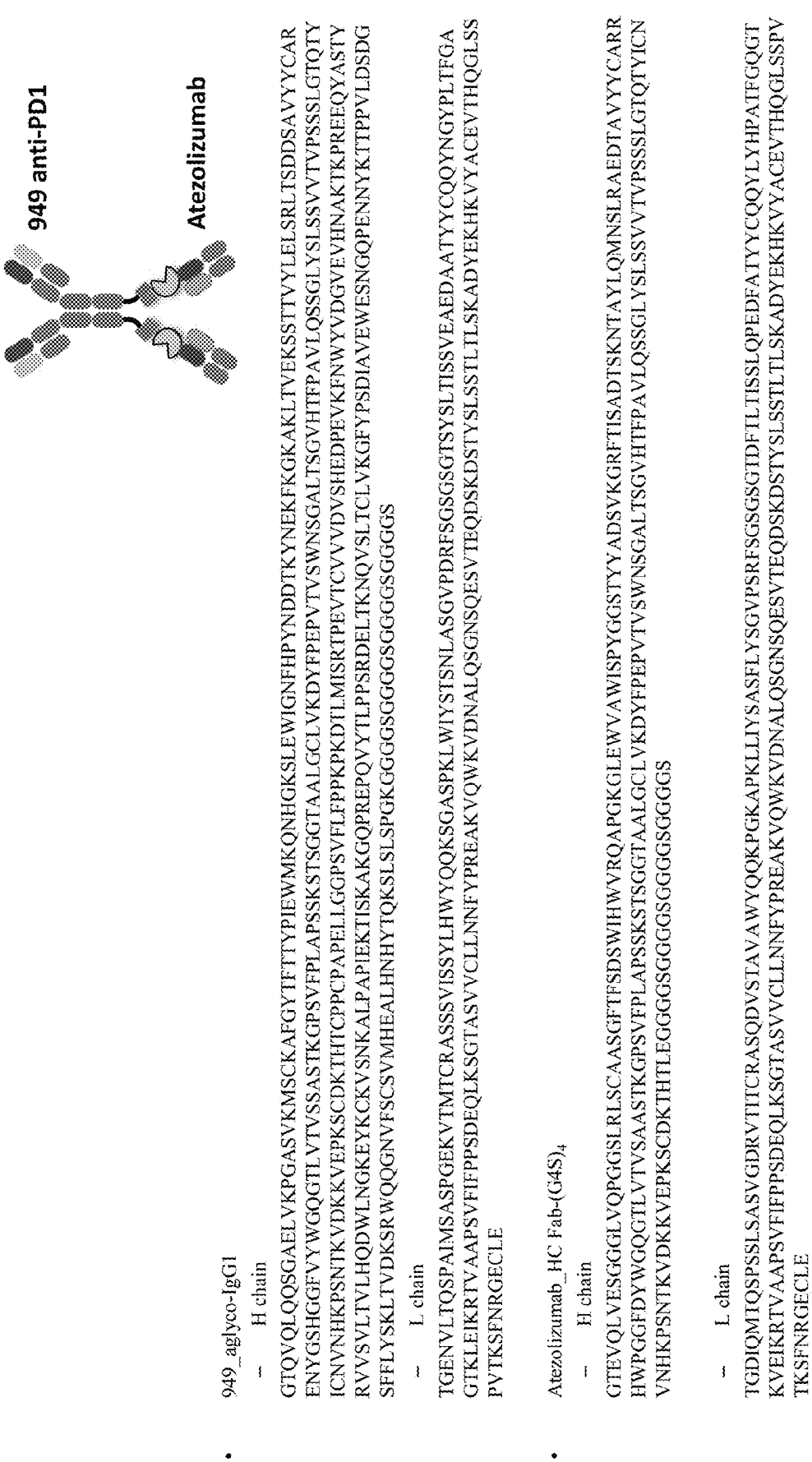
FIG. 5 shows a schematic and amino acid sequence for a 949 aglyco-IgG1xAtezolizumab bispecific. Separate sequences are given for the 949_aglyco-IgG1-(G4S)$_4$ heavy chain (H chain; SEQ ID NO: 110) and light chain (L chain; SEQ ID NO: 111) and for the Atezolizumab_FabH-(G4S)$_4$ heavy chain (H chain; SEQ ID NO: 106) and light chain (L chain; SEQ ID NO: 107).

To assess the effect of PD1/PDL1 bispecific antibody on T-cell activation, IFNγ production was analyzed in a mixed lymphocyte reaction (MLR). Aglycosylated bispecific antibodies combining binding domains of NivolumabxAtezolizumab, 949×Atezolizumab, J43×Atezolizumab, PidilizumabxAtezolizumab, AtezolizumabxNivolumab, or DurvalumabxNivolumab were tested. The antibody 949 refers to a PD-1 antibody as disclosed in U.S. Pat. No. 9,102,728. Antibody J43 refers to an anti-murine PD-1 antibody. KEYTRUDA, a humanized antibody that blocks PD-1 (Merck) and is known to induce IFNγ production, was used as a comparator. A schematic and amino acid sequence for NivolumabxAtezolizumab, 949 xAtezolizumab, and AtezolizumabxNivolumab are shown in FIGS. 4-6, respectively. Each of the bispecific formats exemplified and tested herein were generated using known methods in the art. For example, as shown, in FIG. 4, the heavy chain portion of the Atezolizumab Fab was crosslinked to the heavy chain Fc portion of Nivolumab using methods known in the art. Suitable methods for crosslinking two proteins, such as the heavy chain of a Fab and the heavy chain of IgG molecule, with or without linker sequences, are described herein. This study demonstrated that various concentrations of bispecific antibodies described above can induce an IFNγ response in T cells.

Peripheral blood mononuclear cells (PBMCs) were isolated from leukopaks (HemaCare, Van Nuys, Calif.) derived from three independent human donors (D985, D7603, and D5004). Total T cells were enriched from PBMC by negative selection using immunomagnetic cell separation (EASYSEP™; Stemcell Technologies, Vancouver BC). Monocytes were isolated from PBMCs using immunomagnetic cell separation (EASYSEP™; Stemcell Technologies, Vancouver BC). T cells were resuspended in complete RPMI at $1 \times 10^6$ cells/ml concentration and monocytes were adjusted to $5 \times 10^5$ cells/ml respectively. In a 96-well plate, 100 μl of media containing T cells were plated at 1×10$^5$ cells/well density followed by adding 100 μl of monocyte cell suspension (E:T ratio 2:1). Next, 50 μl of media containing various dilutions of antibodies was added to reach a final concentration of 0 nM, 0.5 nM, 5 nM, or 50 nM. Plates were incubated at 37° C. in a CO$_2$ incubator for five days. At the end of incubation period, culture supernatants were collected and IFNγ levels were analyzed by MSD assay (Mesoscale Diagnostics, Rockville, Md.).

Example 2: Induction of Interferon-Gamma (IFNγ) in T Cells Treated with a Pembrolizumab/Atezolizumab Bispecific Antibody To assess the effect of PD1/PDL1 bispecific antibody on T-cell activation, IFNγ production was analyzed in a mixed lymphocyte reaction (MLR). A PembrolizumabxAtezolizumab bispecific, Pembrolizumab mAb, Atezolizumab Fab, a mix of KEYTRUDA and Atezolizumab Fab, and KEYTRUDA, a humanized antibody that blocks PD-1 (Merck) and is known to induce IFN-γ production, were used as comparators. A schematic and amino acid sequence for the PembrolizumabxAtezolizumab bispecific antibody is shown in FIG. 3. As similarly described for the other bispecific formats exemplified and tested herein, the bispecific format shown in FIG. 3 was generated using known methods in the art. As shown in FIG. 3, the heavy chain portion of the Atezolizumab Fab was crosslinked to the c-terminus of the heavy chain Fc portion of Pembrolizumab using methods known in the art. Suitable methods for crosslinking two proteins, such as the heavy chain of a Fab and the heavy chain of IgG molecule, with or without linker sequences, are described herein. These results indicate that PembrolizumabxAtezolizumab, a bispecific antibody targeting PD-1 and PD-L1, induces an IFNγ response in T cells comparable to Pembrolizumab, Atezolizumab Fab, or KEYTRUDA treatments alone.

T cells were prepared as described above. A volume of 50 μl of media containing various dilutions of antibodies was added to reach a final concentration of 0 nM, 0.5 nM, 5 nM, or 50 nM. Plates were incubated at 37° C. in a CO$_2$ incubator for five days. At the end of incubation period, culture supernatants were collected and IFN-γ levels were analyzed by MSD assay (Mesoscale Diagnostics, Rockville, Md.).

Example 3: Comparison of Interferon-Gamma (IFNγ) Induction in T Cells Treated with a Bispecific Antibody Targeting PD-1 and PD-L1 or Cocktail of Monoclonal Antibodies Targeting PD-1/PD-L1

To assess the effect of PD-1xPD-L1 or PD-L1xPD-L1 bispecific antibodies on T-cell activation, IFN-γ production was analyzed in a mixed lymphocyte reaction (MLR). A PembrolizumabxAtezolizumab bispecific antibody, NivolumabxAtezolizumab bispecific antibody, a cocktail of KEYTRUDA and Atezolizumab, a cocktail of Nivolumab and Atezolizumab were tested and KEYTRUDA alone, a humanized antibody that blocks PD-1 (Merck) and is known to induce IFN-γ production, was used as a comparator.

T cells were prepared as described above. A volume of 50 μl of media containing various dilutions of antibodies was added to reach a final concentration of 0 nM, 0.01 nM, 0.001 nM, or 0.0001 nM. Plates were incubated at 37° C. in a CO$_2$ incubator for five days. At the end of incubation period, culture supernatants were collected and IFNγ levels were analyzed by MSD assay (Mesoscale Diagnostics, Rockville, Md.).

FIG. 1 shows the concentration of IFN-γ as pg/mL at the final concentrations of antibodies tested, as indicated. These results indicate that bispecific PD-1xPD-L1 antibodies, such as PembrolizumabxAtezolizumab or the PDL1/PDL1 bispecific antibody Nivolumab/Atezolizumab, induce a higher IFNγ response in T cells than a cocktail of PD1 and PDL1 specific antibodies, or a PD-1 antibody (KEYTRUDA) alone.

Example 4: Comparison of Interferon-Gamma (IFNγ) Induction in T Cells Treated with a Bispecific Antibody Targeting PD-1/PDL-1 or Monoclonal Antibodies Targeting PD-1 or PD-L1

To assess the effect of a PD-1xPD-L1 or PD-L1xPD-L1 bispecific antibody on T-cell activation, IFNγ production was analyzed in a mixed lymphocyte reaction (MLR). PembrolizumabxNivolumab bispecific antibody, AtezolizumabxAtezolizumab tetravalent, monospecific antibody were tested and Nivolumab alone, Atezolizumab alone, and KEYTRUDA (Pembrolizumab), a humanized antibody that blocks PD-1 (Merck) and is known to induce IFN-γ production, were used as comparators.

T cells were prepared as described above. A volume of 50 μl of media containing various dilutions of antibodies was added to reach a final concentration of 0 nM, 0.01 nM, 0.001 nM, or 0.0001 nM. Plates were incubated at 37° C. in a CO$_2$ incubator for five days. At the end of incubation period, culture supernatants were collected and IFN-γ levels were analyzed by MSD assay (Mesoscale Diagnostics, Rockville, Md.).

Figure 2:
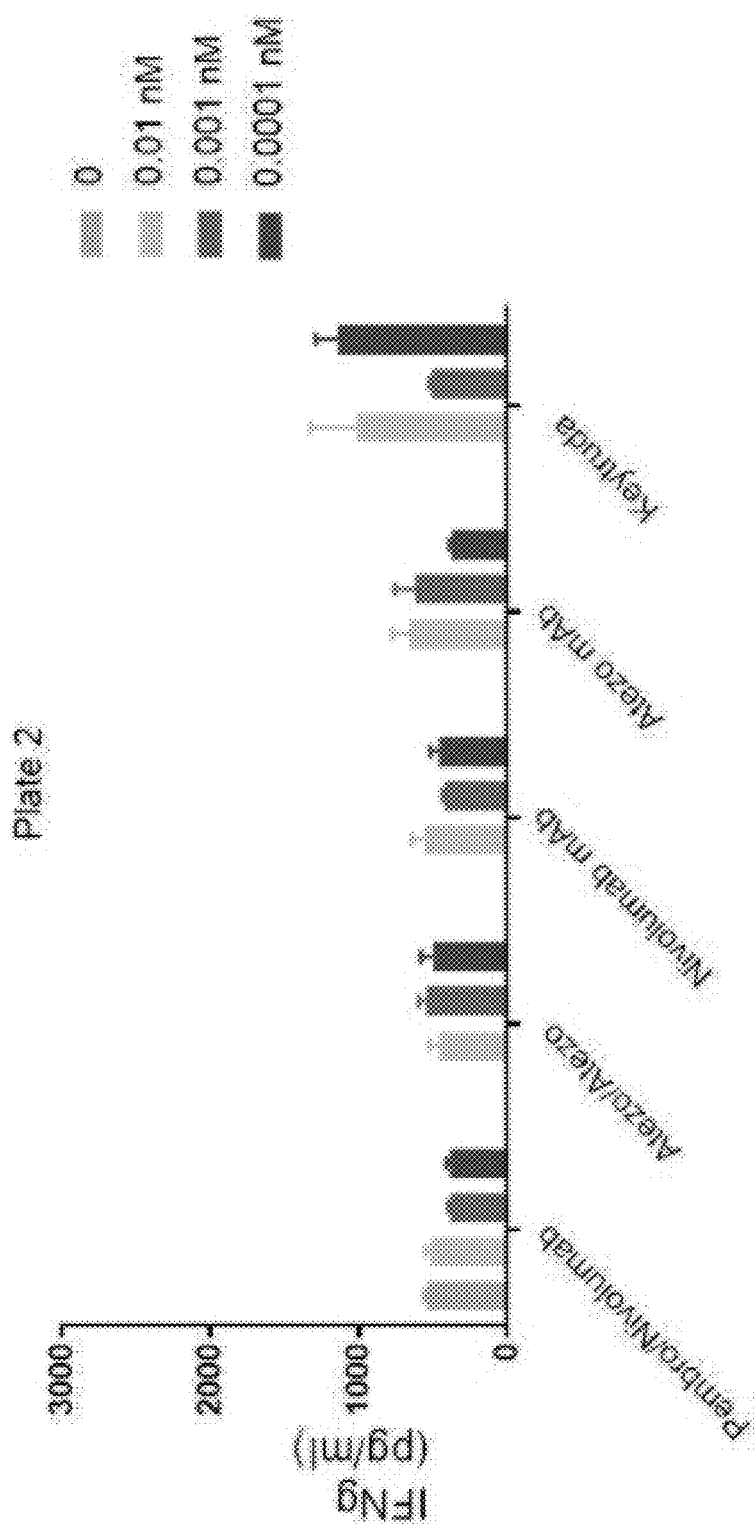
FIG. 2 shows the induction of interferon-gamma (IFNγ) in mixed lymphocyte reaction (MLR) assay treated with various monoclonal and bispecific antibodies including a PembrolizumabxNivolumab bispecific, AtezolizumabxAtezolizumab tetravalent fusion, Nivolumab, and Atezolizumab, as compared to KEYTRUDA alone. The results show the concentration of IFNγ as pg/mL at the final concentrations of antibodies tested, as indicated.

FIG. 2 shows the concentration of IFN-γ as pg/mL at the final concentrations of antibodies tested, in PBS, as indicated. These results indicate that bispecific PD1xPDL1 (PembrolizumabxNivolumab) or PD-L1xPD-L1 antibodies (AtezolizumabxAtezolizumab) induce a similar IFN-γ response in T cells as PD-1 (Atezolizumab or KEYTRUDA) or PD-L1 (Nivolumab) specific antibodies alone.

Figure 7:
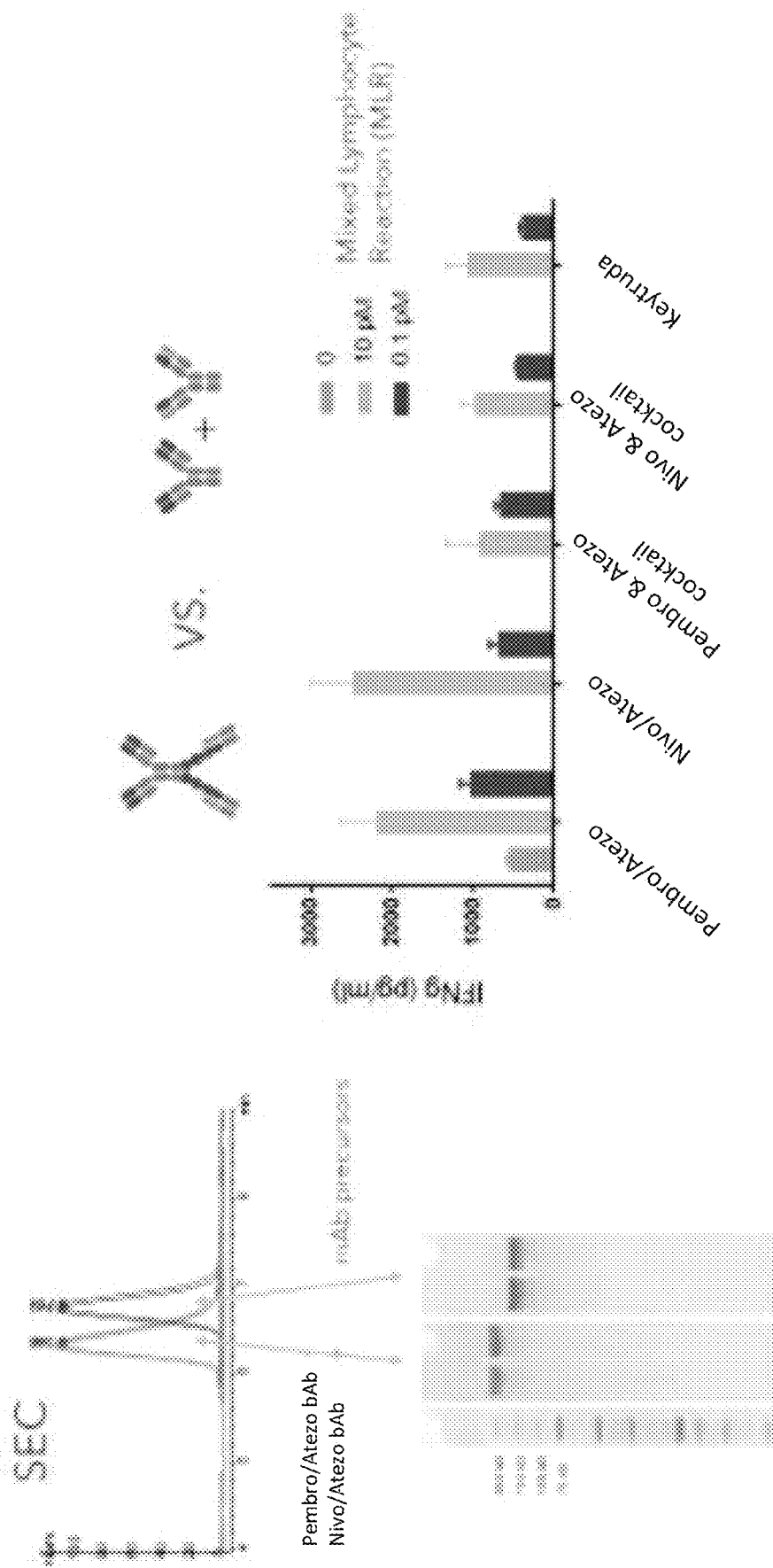
FIG. 7 shows IFN-γ release, in pg/mL, in a mixed lymphocyte reaction (MLR) assay as a function of antibodies tested at various concentrations (right panel). These results indicate that bispecific antibodies PD-1xPD-L1 (Pembrolizumabx Atezolizumab) or (NivolumabxAtezolizumab) in multispecific format induce a greater IFN-γ response at femtomolar concentrations, as compared to a cocktail of Pembrolizumab and Atezolizumab or Nivolumab and Atezolizumab. Size exclusion chromatography of the bispecific formats against mAb precursors is shown (left panel).

FIG. 7 shows the concentration of IFN-γ as pg/mL at the final concentrations of antibodies tested, in PBS, as indicated. These results indicate that bispecific antibodies PD-1x PD-L1 (PembrolizumabxAtezolizumab) or (NivolumabxAtezolizumab) in a multispecific format induce a greater IFN-γ response at femtomolar concentrations in a mixed lymphocyte reaction (MLR) as compared to a cocktail of Pembrolizumab and Atezolizumab or Nivolumab and Atezolizumab. These results suggest a synergistic effect that results from a multispecific format.

Figure 8:
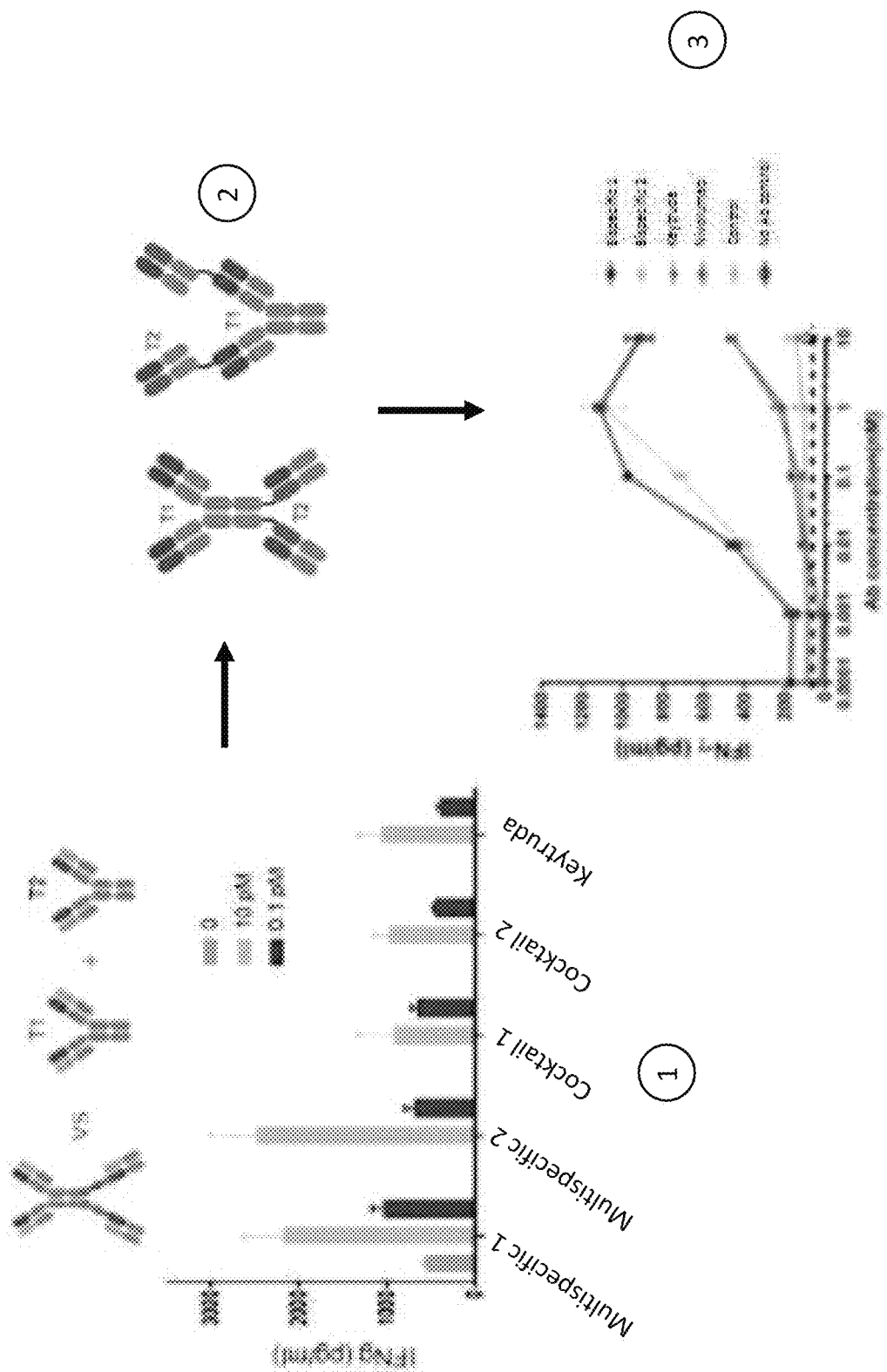
FIG. 8 shows an example of a workflow for identifying multispecific (e.g., bispecific) antibodies that demonstrate synergy. The process includes an unbiased screen of checkpoint blocker combinations in a mixed lymphocyte reaction (MLR) assay, which measures IFN-γ release, in pg/mL, at various concentrations. In the second step of the illustrated workflow, common light chain bispecifics were generated to further test their efficacy; here, various bispecific formats are depicted. The identified bispecific formats outperform known PD-1 blockers in a T-cell activation assay.

FIG. 8 shows an exemplary workflow for identifying multispecific (e.g., bispecific) antibodies that demonstrate synergy. The process includes an unbiased screen of checkpoint blocker combinations in mixed lymphocyte reaction (MLR), which measures IFNγ release, in pg/mL, at various concentrations, as described elsewhere herein (see, for example, the section below entitled Nonspecific T cell+ K562-PD-L1 tumor target cell assay). In the second step of the illustrated workflow, common light chain bispecifics were generated to further test their efficacy and various exemplary common light chain bispecific formats are depicted. The identified common light chain bispecific formats outperform known PD-1 blockers in a T-cell activation assay.

Example 5: Generation and Characterization of Anti-PD-1 and Anti-PD-L1 Antibody Constructs and Multispecific Antigen-Binding Molecules Affinity Maturation of Anti-PD-L1 Antibodies Affinity matured anti-PD-L1 antibodies derived from PD-L1 antibody mAb24 were generated via construction of a mutant library, mammalian display sorting, and screening of monoclonal IgG. The library contained mutations in the heavy chain, where synthetic diversity in CDRH1, CDRH2, and CDRH3 was introduced, while the light chain sequence was held constant, except in some cases, to maintain compatibility with single light chain constructs. The library went through 3 rounds of mammalian display sorting aimed at increasing affinity for human PD-L1 and maintaining mouse cross-reactivity. In each round, an off-rate competition step was employed after initial binding to biotinylated antigens (i.e., 1 hour incubation with excess unlabeled antigen or parental IgG). After the final round of sorting, clones were picked, their sequences analyzed, and unique clones were assayed via Wasatch SPR binding kinetics and cell-binding equilibrium assays to identify lead candidates.

The resulting anti-PD-L1 antibodies from different selection rounds were plotted on $k_d/k_a$ double log plots. Apparent association and dissociation kinetic rate constants ($k_a$ and $k_d$ values) were determined on an SPRi reader (MX96, Carterra, Salt Lake City, Utah)) in a running buffer of PBS-Tween 0.01%. Anti-human PD-L1 antibodies were covalently conjugated on a Carboxymethyldextran hydrogel 50 L chip (XanTec bioanalytics GmbH, Dusseldorf, Germany) on a CFM (Carterra). Freshly mixed activating reagents (150 ul of 0.4 M EDC and 150 ul of 0.1 M sulfo-NHS in 5 ml of H2O) were used to activate the surface of the SPR substrate for 7 minutes. Antibodies at 10 mg/ml, in acetic acid buffer pH 4.5, were used for printing for 15 minutes. The printed chip was then quenched on an SPRi reader (MX96, Carterra) with 1 M ethanolamine for 15 minutes. For kinetics analysis, purified recombinant His tagged human PD-L1 (0, 2.05, 5.12, 12.8, 32, 80, 200, 500 nM) was injected sequentially. For each concentration, there was 5 minutes of association followed by 10 minutes of dissociation. Data were processed and analyzed in SPR Inspection Tool and Scrubber softwares (Biosensor Tools LLC, Salt Lake City, Utah). The kinetic data were referenced with the interstitial reference spots and double-referenced to a buffer cycle, and then fit globally to a 1:1 binding model to determine their parent association and dissociation kinetic rate constants ($k_a$ and $k_d$ values). The ratio $k_d/k_a$ was used to derive the $K_D$ value of each antigen/mAb interaction, i.e. $K_D=k_d/k_a$.

Affinity Maturation of Anti-PD-1 Antibodies

Affinity matured anti-PD-1 antibodies derived from PD-1 antibody mAb25 were generated via construction of a mutant library, phage display panning, and screening of monoclonal antibodies. The library contained mutations in the heavy chain, where synthetic diversity in CDRH1, CDRH2, and CDRH3 was introduced, while the light chain sequence was held constant to maintain compatibility with single light chain constructs. The library went through 4 rounds of phage display panning rounds aimed at increasing affinity for human PD-1 and gaining mouse cross-reactivity. In each round, an off-rate competition step was employed after initial binding to biotinylated antigens (i.e., 1 hour incubation with excess unlabeled antigen or parental IgG). After the final round of panning, clones were picked, their sequences analyzed, and unique Fab clones were assayed via Octet SPR binding kinetics and cell-binding equilibrium assays to identify lead candidates. Lead candidates were converted from Fab to human IgG and further characterized.

The resulting anti-PD-1 antibodies from different selection rounds were plotted on $k_d/k_a$ double log plots. Apparent association and dissociation kinetic rate constants ($k_a$ and $k_d$ values) were determined on an SPRi reader (MX96, Carterra, Salt Lake City, Utah)) in a running buffer of PBS-Tween 0.01%. Anti-human PD-1 antibodies were covalently conjugated on a Carboxymethyldextran hydrogel 50 L chip (XanTec bioanalytics GmbH, Dusseldorf, Germany) on a CFM (Carterra). Freshly mixed activating reagents (150 ul of 0.4 M EDC and 150 ul of 0.1 M sulfo-NHS in 5 ml of H2O) were used to activate the surface of the SPR substrate for 7 minutes. Antibodies at 10 mg/ml, in acetic acid buffer pH 4.5, were used for printing for 15 minutes. The printed chip was then quenched on an SPRi reader (MX96, Carterra) with 1 M ethanolamine for 15 minutes. For kinetics analysis, purified recombinant His tagged human PD-1 (0, 2.05, 5.12, 12.8, 32, 80, 200, 500 nM) was injected sequentially. For each concentration, there was 5 minutes of association followed by 10 minutes of dissociation. Data were processed and analyzed in SPR Inspection Tool and Scrubber softwares (Biosensor Tools LLC, Salt Lake City, Utah). The kinetic data were referenced with the interstitial reference spots and double-referenced to a buffer cycle, and then fit globally to a 1:1 binding model to determine their apparent association and dissociation kinetic rate constants ($k_a$ and $k_d$ values). The ratio $k_d/k_a$ was used to derive the $K_D$ value of each antigen/mAb interaction, i.e. $K_D=k_d/k_a$.

Nonspecific T Cell+K562-PD-L1 Tumor Target Cell Assay

Figure 9A:
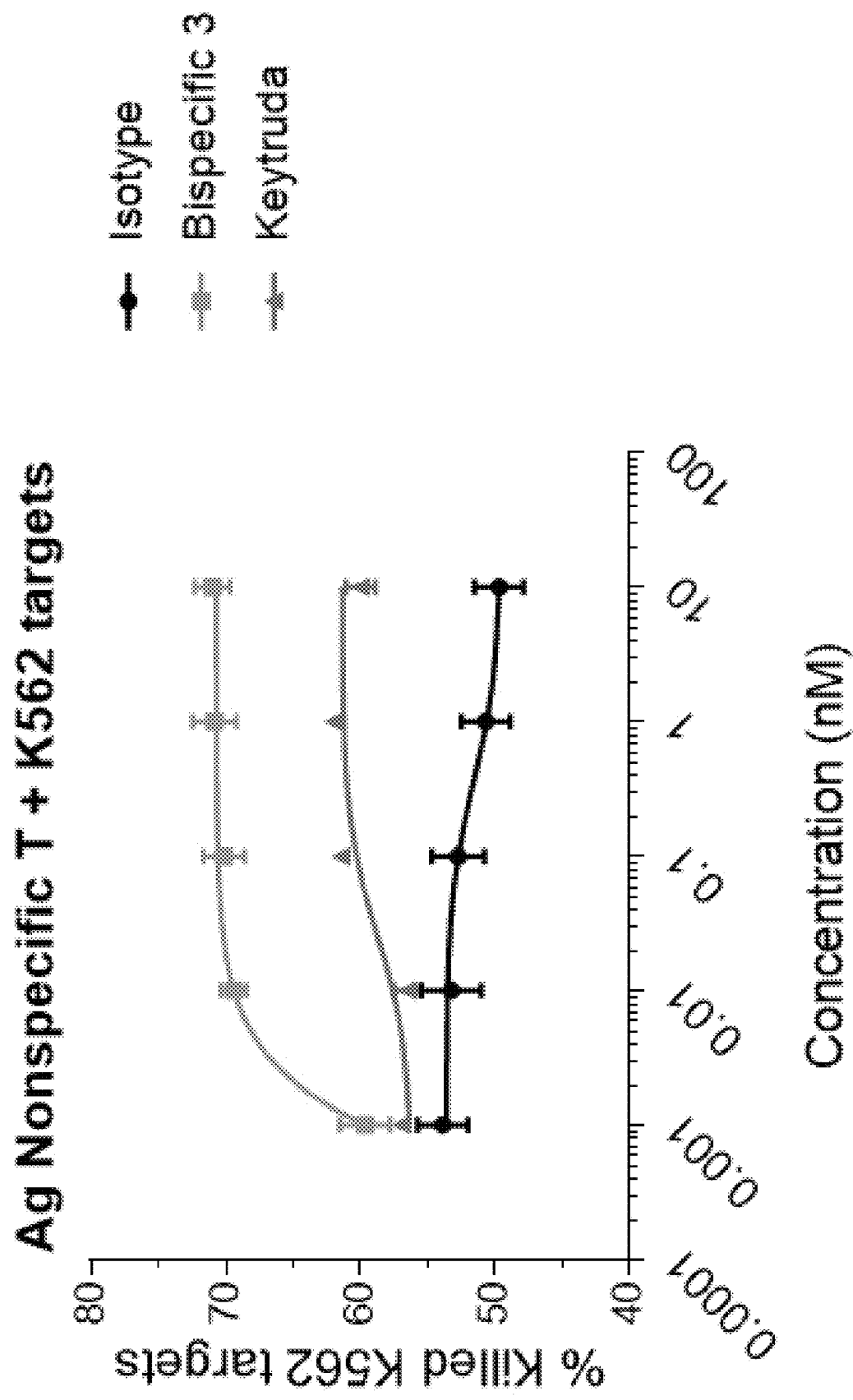
FIGS. 9A-9B show that Bispecific 3 induced higher killing of K562-CD32-PDL1 target cells (FIG. 9A) and increased IFNγ production (FIG. 9B) by CD3/CD28 expanded T-cells in an antigen non-specific T cell assay, as compared to both an isotype control antibody and KEYTRUDA. This increased killing by Bispecific 3 was seen even at low concentrations of 0.01 nM.
Figure 9B:
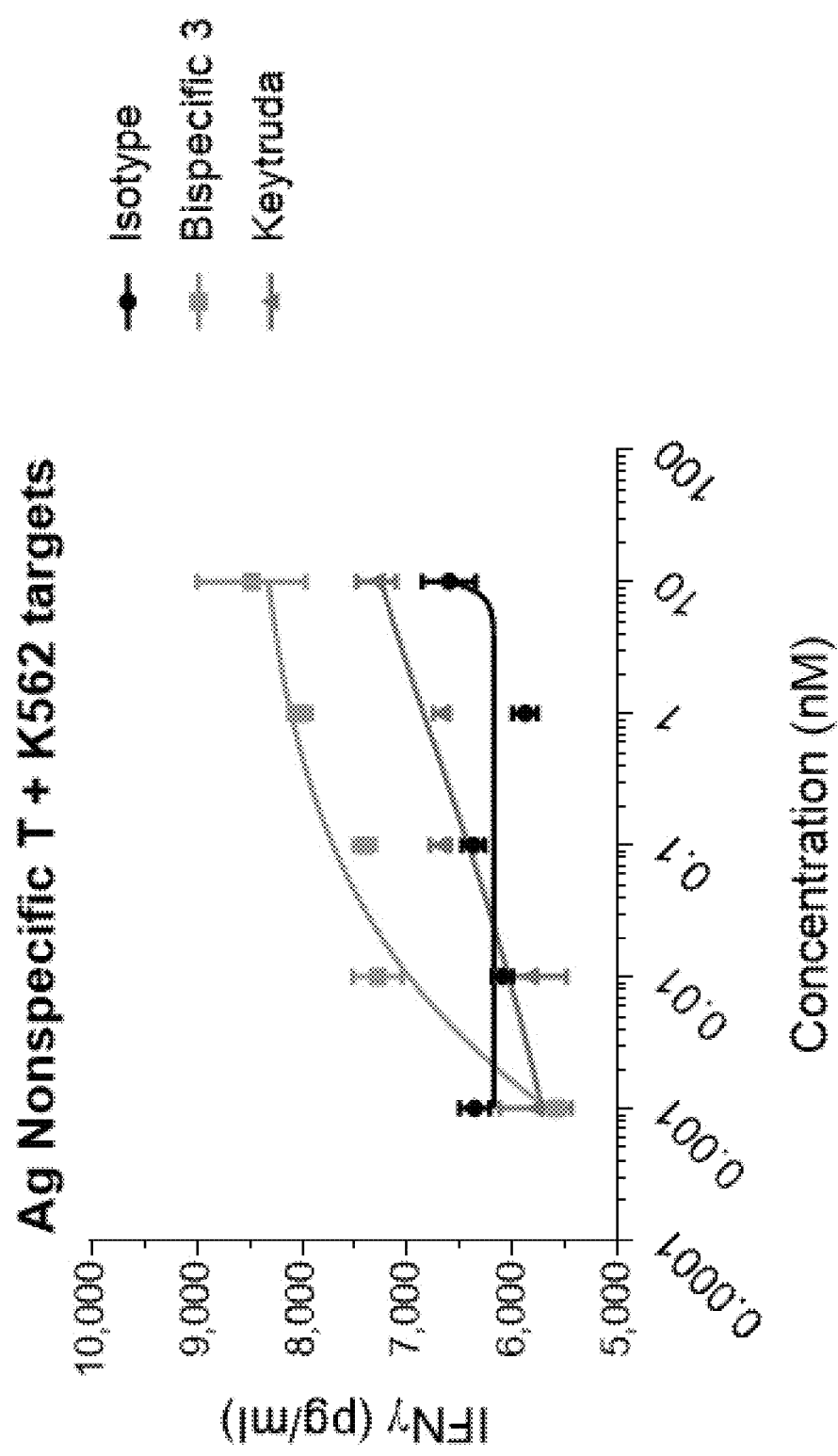

T cells were isolated from previously frozen PBMCs (peripheral blood mononuclear cells) using a negative selection kit and activated using IMMUNOCULT™ anti-CD3/CD28 T cell activator in X-VIVO 15 media supplemented with 10% FBS ("X-10"). After 3 days, the cells were switched to X-10 media containing 5 ng/ml IL-2 and 2.5 ng/ml IL-7 ("hX-10"). Every 2-3 days the cells were fed fresh hX-10. After 10 days of activation, the IMMUNOCULT™-expanded T cells were CELLTRACE™ Violet-labeled and co-cultured with K562 cells that were stably transduced to express human CD32B and PD-L1 ("K32P") in 96 well round-bottom plates with 50,000 T cells and 25,000 K32P cells per well. Antibodies (Bispecific 3, KEYTRUDA, and an isotype control) were added at final concentrations between 10 and 0.001 nM done in 10-fold dilutions along with 0.25 µg/ml anti-CD3 (clone OKT3). After 3 days, supernatants were collected for measuring IFNγ cytokine production via MSD plates, and cells were stained for flow cytometry, and then run on a BD LSR-FORTESSA™ cytometer to look at T cell activation and target cell killing. Target cell killing is measured by counting the number of live K32P targets in the experimental wells compared to the number of K32P targets in a set of no CD3 control wells. All data was then analyzed in GraphPad Prism. As shown in FIGS. 9A-9B, Bispecific 3 induced higher amounts of IFNγ and killing of K32P target cells as compared to both the isotype control antibody and KEYTRUDA.

Figure 10A:
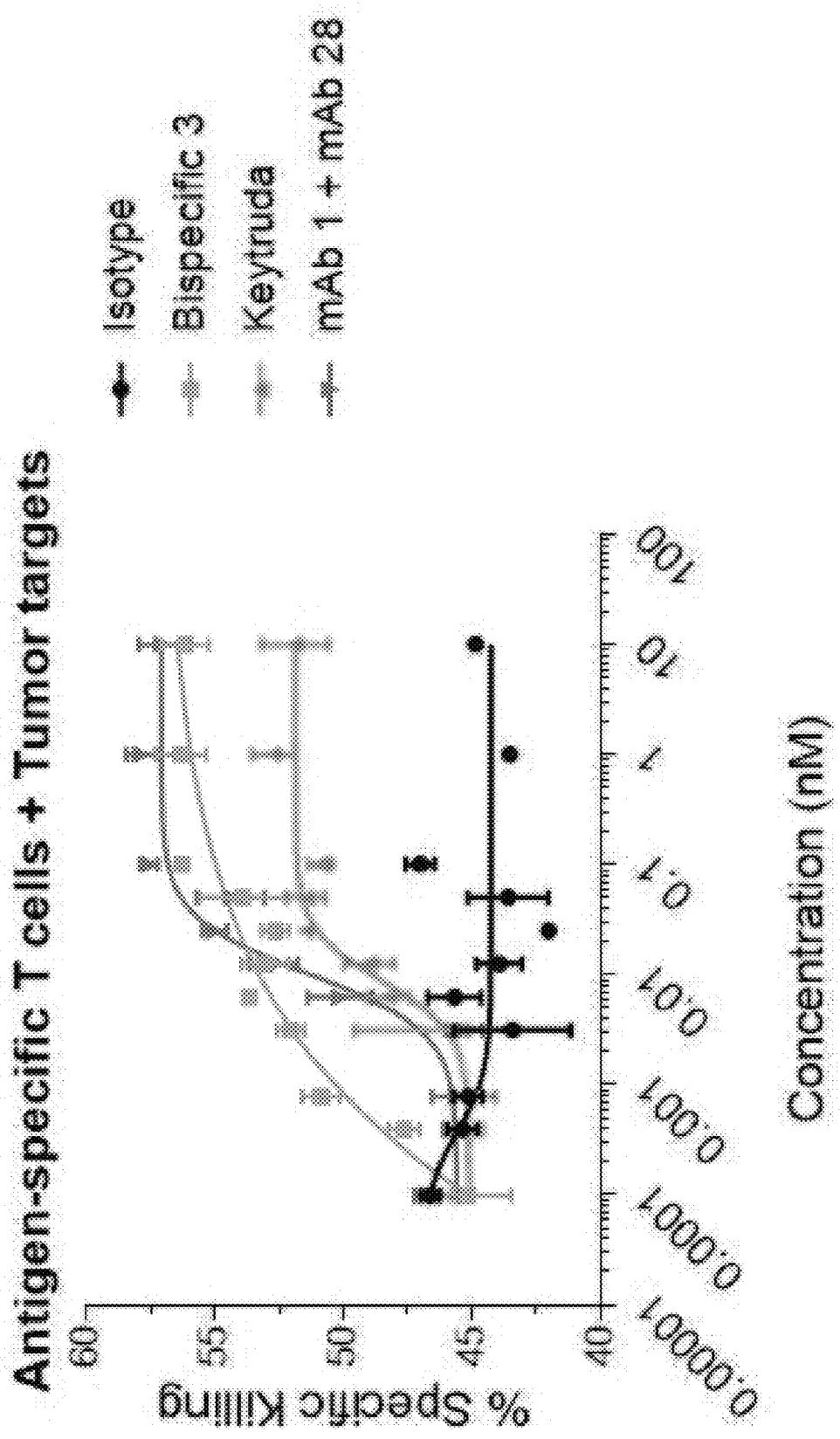
FIGS. 10A-10B show an effect of Bispecific 3 on tumor cell killing.

CMV Antigen Recall Assay Day 12 expanded CMV antigen specific CD8+ T cells, from an HLA A02:01 donor, were thawed and rested overnight in hX-10 media containing 2 ug/ml DNase I. The following day, the cells were collected, and dead cells were removed using Ficoll-separation. The remaining cells were then co-cultured with K562 cells expressing HLA-A02:01, CMV protein pp65-IRES-GFP, and PD-L1 ("KACP", GFP+) and K562 cells expressing HLA-A02:01 ("KA", GFP-) in 96 well round-bottom plates with 25,000 CMV T cells, 50,000 KACP cells, and 50,000 KA cells per well. Antibodies (Bispecific 3, KEYTRUDA, a combination of mAb1 and mAb28, and an isotype control) were added at final concentrations between 10 and 0.0001 nM. This dosing included 10-fold dilutions between 10 and 0.1 nM and then 2-fold dilutions until 0.0001 nM. After 2 days of co-culture, specific killing of KACP tumor targets via flow cytometry were analyzed. Specific killing is defined ratiometrically as the ratio of live GFP+ KACP cells to GFP-KA cells, normalized to the ratio of these cells when no T cells are present. As shown in FIG. 10A, Bispecific 3 increased the specific killing of tumor antigen target cells. The increase mediated by Bispecific 3 was always higher than what was seen for KEYTRUDA, while at high doses the combination of mAb1 and mAb28 killed an equal number of KACP cells. Critically, at the low doses of antibody (0.001 through 0.01 nM) Bispecific 3 showed an increase in killing of KACP cells as compared to both KEYTRUDA and the combination of mAb1 and mAb28, indicating that Bispecific 3 can be used to mediate antigen-specific killing of target cells at lower doses.

Figure 10B:
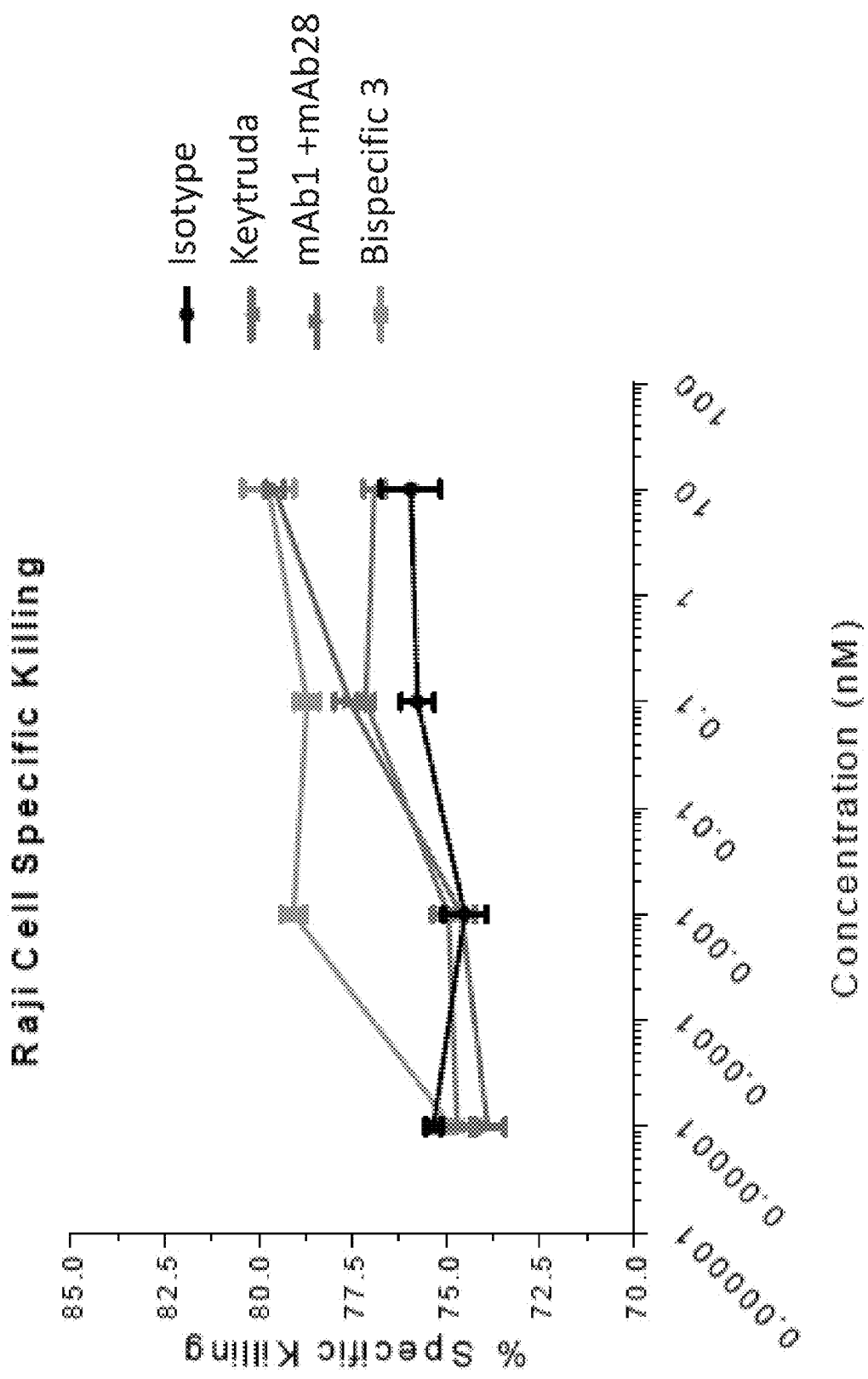

In a separate experiment, the effect of Bispecific 3 on Raji cell-specific killing was examined in a manner similar to that outlined above for K562 cell-specific killing assay. Briefly, CMV antigen specific CD8+ T cells were co-cultured with Raji cells expressing HLA-A02:01, CMV protein pp65-IRES-GFP, and PD-L1 ("RACP", GFP+) and Raji cells expressing HLA-A02:01 ("RA", GFP-) in 96 well round-bottom plates with 25,000 CMV T cells, 50,000 RACP cells, and 50,000 RA cells per well. Antibodies (Bispecific 3, KEYTRUDA, a combination of mAb1 and mAb28, and an isotype control) were added at final concentrations between 10 and 0.0001 nM. This dosing included 10-fold dilutions between 10 and 0.1 nM and then 2-fold dilutions until 0.0001 nM. After 2 days of co-culture, specific killing of RACP tumor targets via flow cytometry were analyzed. Specific killing is defined ratiometrically as the ratio of live GFP+ RACP cells to GFP− RA cells, normalized to the ratio of these cells when no T cells are present. As shown in FIG. 10B, Bispecific 3 increased the specific killing of tumor antigen target cells. The increase mediated by Bispecific 3 was noticeably higher at 0.001 nM than what was seen for either KEYTRUDA or the combination of mAb1 and mAb28, while at high doses Bispecific 3 and the combination of mAb1 and mAb28 caused comparable killing of target cells. These data indicate that Bispecific 3 can be used to mediate antigen-specific killing of target cells at lower doses.

*Staphylococcus aureus* Enterotoxin A ("SEA") Assay

Figure 11:
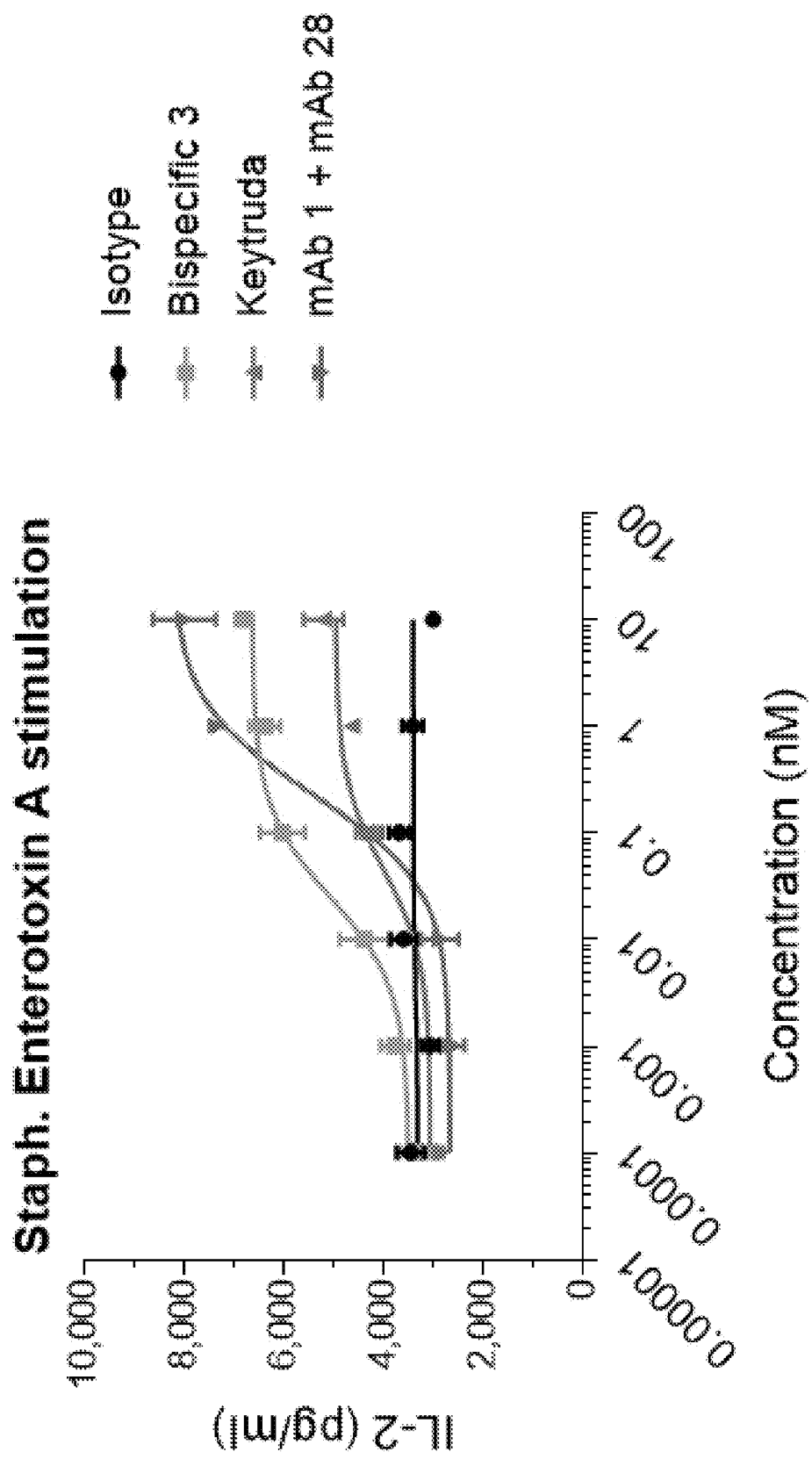
FIG. 11 shows that Bispecific 3 induced more IL-2 than KEYTRUDA at all tested doses in an SEA stimulation assay. Importantly, Bispecific 3 induced increased IL-2 production starting at lower concentrations of antibody as compared to both KEYTRUDA and mAb1 and mAb28.

Previously frozen PBMCs were thawed and incubated with 0.1 mg/ml DNase I in PBS for 15 minutes, passed through a 40 μm nylon mesh filter, and then plated in X-10 media at 100,000 cells per well of a 96 well round-bottom plate. Antibodies (Bispecific 3, KEYTRUDA, a combination of mAb1 and mAb28, and an isotype control) were added at final concentrations between 10 and 0.0001 nM, along with 10 ng/ml SEA. After 3 days of co-culture, IL-2 cytokine production was analyzed. As shown in FIG. 11, Bispecific 3 induced more IL-2 than KEYTRUDA at all tested doses. Importantly, Bispecific 3 induced increased IL-2 production starting at lower concentrations of antibody as compared to both KEYTRUDA and the combination of mAb1 and mAb28.

PD-1 Expression Determination Assays

Figure 12A:
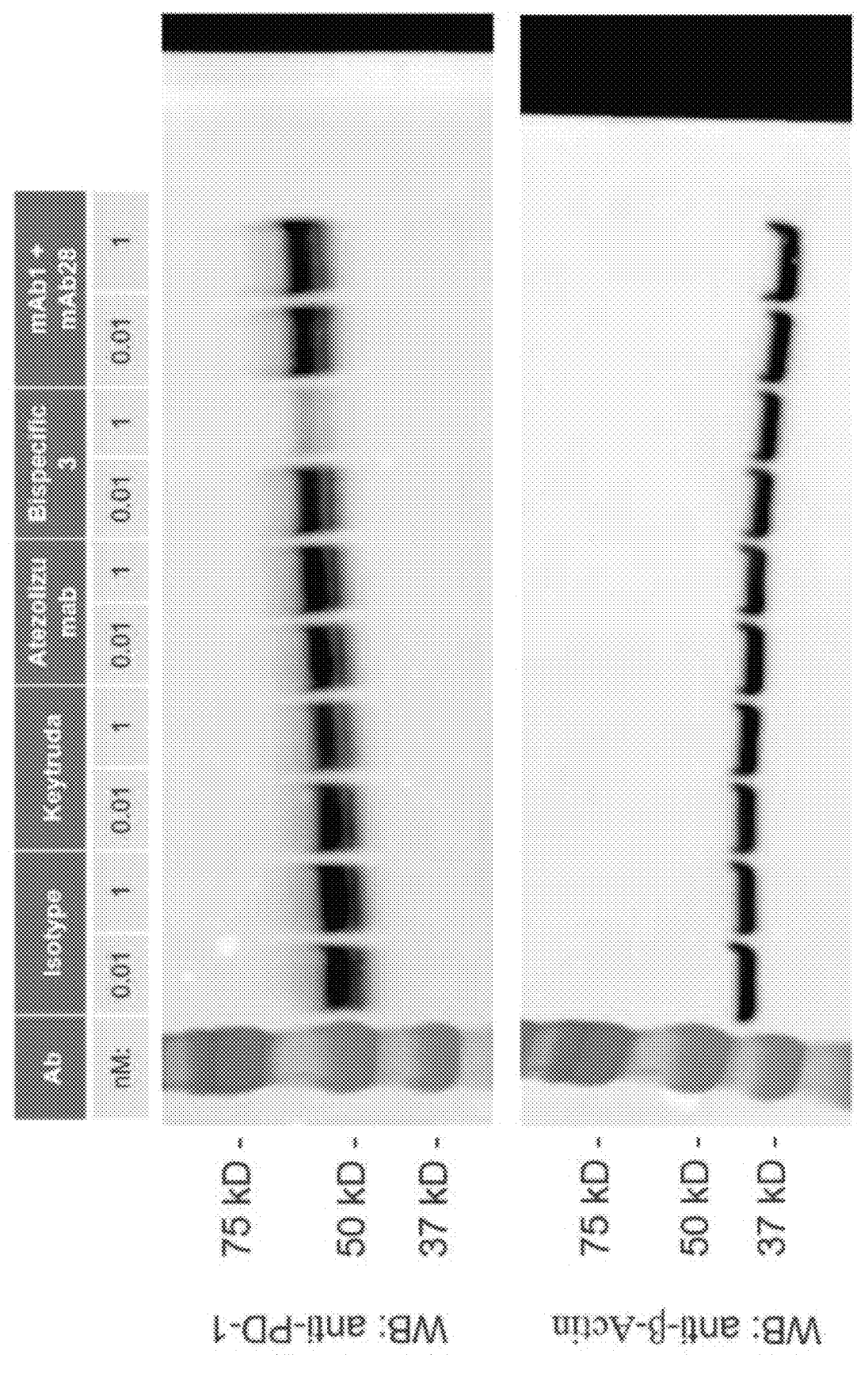
FIGS. 12A-12G demonstrate that Bispecific 3 has a unique ability to cause the internalization and subsequent degradation or loss of expression of PD-1, and that this property is dependent on engagement of both the PD-1 and PD-L1 targeting arms of the molecule.

Previously frozen PBMCs were thawed and incubated with 0.1 mg/ml DNase I in PBS for 15 minutes, passed through a filter, and then plated at $1 \times 10^6$ cells/ml in hX-10 with 0.25 μg/ml anti-CD3 (clone OKT3) and 0.25 μg/ml anti-CD28 (clone CD28.2) for 3 days. After 3 days, the cells were adjusted to $2 \times 10^6$ cells/ml in hX-10 by spinning down the cells and removing excess media. The cells were then resuspended and plated at $1 \times 10^6$ cells/well (0.5 ml) in a 48 well plate. Antibodies (Bispecific 3, KEYTRUDA, a combination of mAb1 and mAb28, Atezolizumab, or isotype control) were then added to each well to get a final volume of 1 ml/well hX-10, with final concentrations of 0.01 nM or 1 nM antibody. After an overnight culture, the cells were collected into 1.5 ml Eppendorf tubes and lysed in 100 ul of Lysis buffer containing a protease inhibitor cocktail. After spinning to clear the supernatants of particulates, cleared supernatant was stored at −80° C. until use for western blots. For Western blots, samples were adjusted to include 1×LDS sample buffer and 1× reducing agent, heated at 70° C. for 10 minutes, then 20 ul per well was loaded onto 4-12% Bis-Tris gels. After the gel ran, it was transferred to nitrocellulose membrane, blocked with TBS-0.1% Tween-20 (TBST) containing 5% dry milk for 1 hour at room temperature, washed in TBST, and then incubated overnight at 4° C. with anti-PD-1 (clone D4W2J, Cell Signaling Technologies) or anti-β-Actin (Clone 13E5, Cell Signaling Technologies) antibodies in TBST containing 5% bovine serum albumin. The following day, the membranes were washed in TBST, incubated with a HRP-conjugated anti-Rabbit IgG antibody, washed in TBST, then developed with SUPERSIGNAL™ Pico substrate. Chemiluminescent and white light images were collected on the Amersham Imager 600 and superimposed to generate the images shown. As shown in FIG. 12A, Bispecific 3 is unique in its ability to cause the loss of cellular PD-1 expression by internalization and/or subsequent degradation of PD-1 and/or shedding.

Figure 12B:
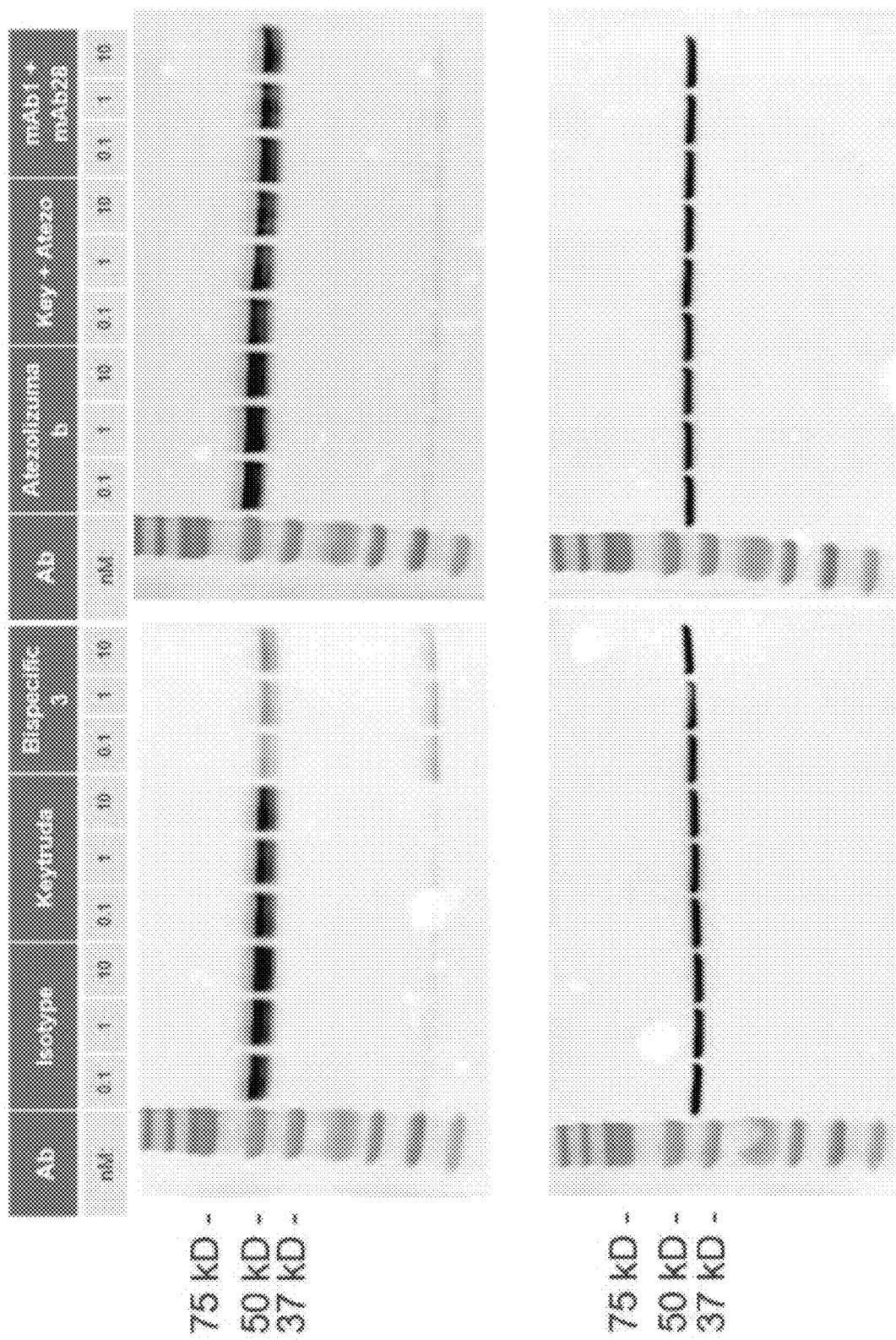
Figure 12C:
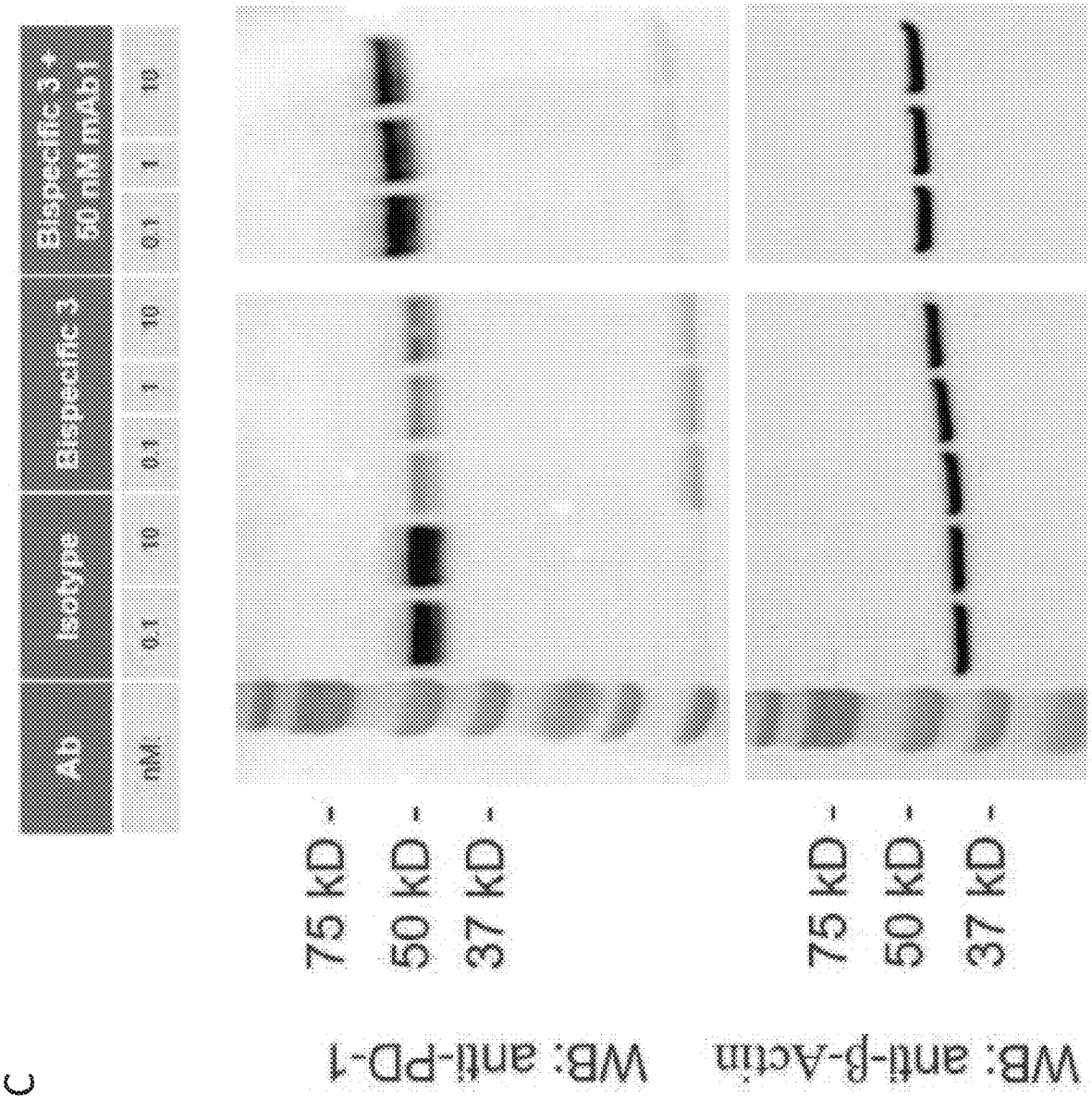

In a subsequent assay, previously frozen PBMCs were thawed and incubated with 0.1 mg/ml DNase I in PBS for 15 minutes, passed through a filter, and then plated at $1 \times 10^6$ cells/ml in hX-10 with 0.25 μg/ml anti-CD3 (clone OKT3) and 0.25 μg/ml anti-CD28 (clone CD28.2) for 3 days. After 3 days, the cells were adjusted to $2 \times 10^6$ cells/ml in hX-10 by spinning down the cells and removing excess media. The cells were then resuspended and plated at $1 \times 10^6$ cells/well (0.5 ml) in a 48 well plate. Antibodies (Bispecific 3, KEYTRUDA, a combination of mAb1 and mAb 28, Atezolizumab, Atezolizumab and KEYTRUDA, Bispecific 3 with 50 nM mAb 1, or isotype control) were then added to each well to get a final volume of 1 ml/well hX-10 with final concentration of 0.1 nM, 1 nM, or 10 nM antibody. After an overnight culture, the cells were collected into 1.5 ml Eppendorf tubes and lysed in 100 ul of Lysis buffer containing a protease inhibitor cocktail. After spinning to clear the supernatants of particulates, cleared supernatant was stored at −80° C. until use for western blots. For western blots, samples were adjusted to include 1×LDS sample buffer and 1× reducing agent, heated at 70° C. for 10 minutes, then 10 ul per well was loaded onto 4-12% Bis-Tris gels. After the gel ran, it was transferred to nitrocellulose membrane, blocked with TBS-0.1% Tween-20 (TBST) containing 5% dry milk for 1 hour at room temperature, washed in TBST, and then incubated overnight at 4 C with anti-PD-1 (clone D4W2J, Cell Signaling Technologies) or anti-β-Actin (Clone 13E5, Cell Signaling Technologies) antibodies TBST containing 5% bovine serum albumin. The following day, the membranes were washed in TBST, incubated with a HRP-conjugated anti-Rabbit IgG antibody, washed in TBST, then developed with SUPERSIGNAL™ Pico substrate. Chemiluminescent and white light images were collected on the Amersham Imager 600 and superimposed to generate the images shown. As shown in FIGS. 12B-12C, Bispecific 3 is unique in its ability to cause the loss of cell-surface PD-1 expression through internalization and/or subsequent degradation of PD-1 and/or shedding of PD-1. Additionally, when the anti-PD-L1 antibody, mAb1, was added at 50 nM to wells containing Bispecific 3, the ability of Bispecific 3 to drive loss of cell-surface PD-1 expression by PD-1 internalization and/or subsequent degradation of PD-1 and/or shedding was lost. This suggests that both arms of Bispecific 3 should be engaged to drive loss of cell-surface PD-1 expression by internalization and/or degradation of PD-1 and/or shedding.

Figure 12D:
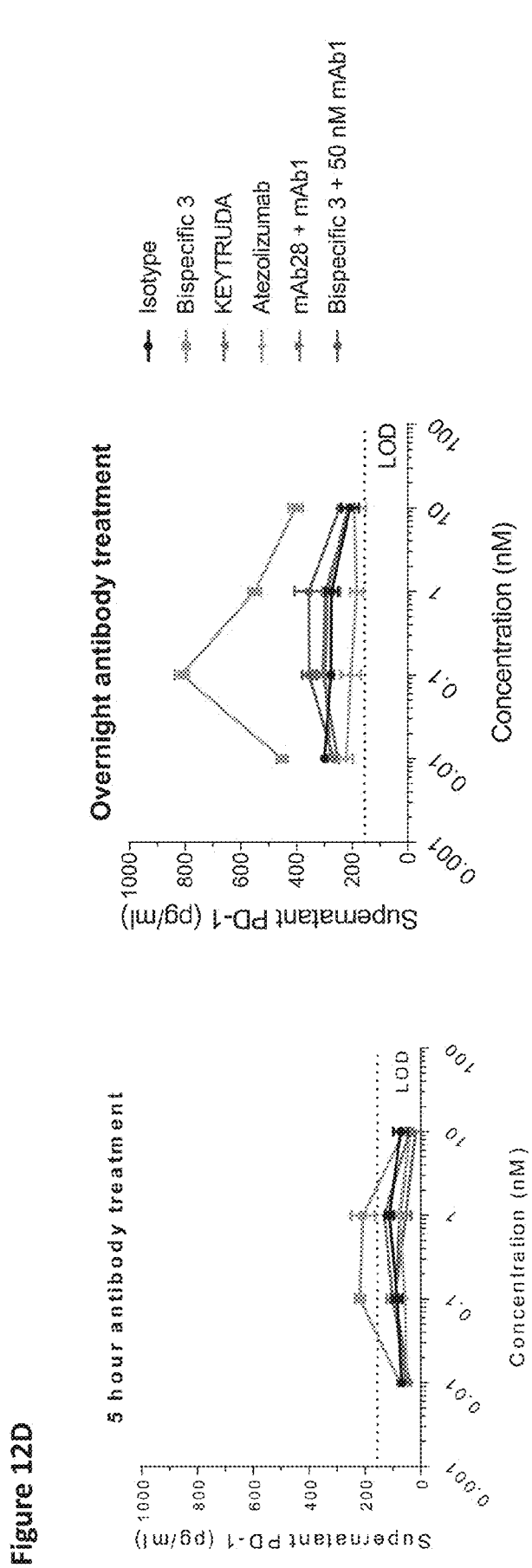

FIG. 12D shows that treatment with Bispecific 3 increases the amount of PD-1 in the supernatant when both binding arms of the bispecific are engaged concurrently. This effect is lost when the PD-L1 targeting arm is blocked by mAb1, the parent PD-L1 arm antibody. This suggests that Bispecific 3 increases shedding of PD-1 into the supernatant.

The effect of valency versus the sequence of the binding arms was next investigated. A new bispecific was generated (Bispecific 5) having a first N-terminal Fab that binds PD-L1 derived from the VH and VL sequences of mAb1, and a second N-terminal Fab that binds PD-1 derived from the VH and VL sequences of mAb28. In other words, while they share the same VH and VL sequences for binding to PD-1 and PD-L1, Bispecific 5 has one monovalent arm binding PD-L1 and one movalent arm binding PD-1, as compared to Bispecific 3, which has bivalent arms binding PD-L1 and bivalent arms binding PD-1.

Figure 12E:
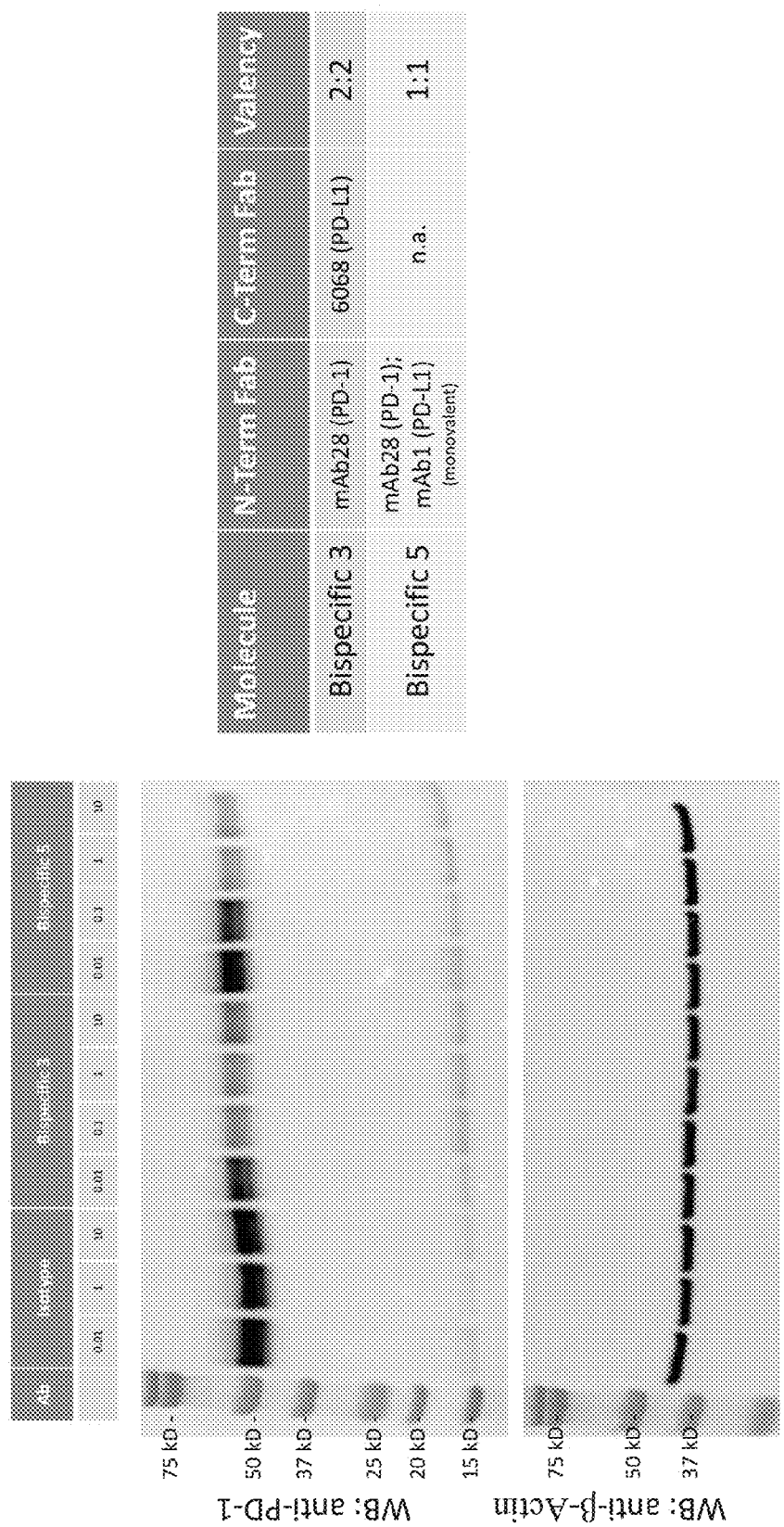

$40 \times 10^6$ PBMCs were treated with 0.25 µg/ml anti-CD3 and 0.25 µg/ml anti-CD28 for 3 days in a T75 flask in hX-10 media containing IL-2 and IL-7. Cells were incubated for 3 days in the flask with no manipulation. On Day 3, the cells were collected without washing away any of the old media. Cells were plated in wells of a 48-well plate, at a final volume of 1 ml, with $1 \times 10^6$ cells/well and antibodies at 0.01 nM, 0.1 nM, 1 nM, and 10 nM. After an overnight incubation, cells were collected into 1.5 ml tubes, with a wash to collect all cells from the well, then lysed and used for western blotting. Western blots were run for PD-1 and Actin. FIG. 12E demonstrates that the valency of the binding arms influences the degree of the loss of PD-1 expression. As shown, loss of PD-1 expression starts to occur at higher doses of Bispecific 5 (monovalent binding arms, total valency=2 or bivalent) versus Bispecific 3 (bivalent binding arms, total valency=4 or tetravalent), suggesting that the increased valency of Bispecific 3 is responsible for this difference.

Figure 12F:
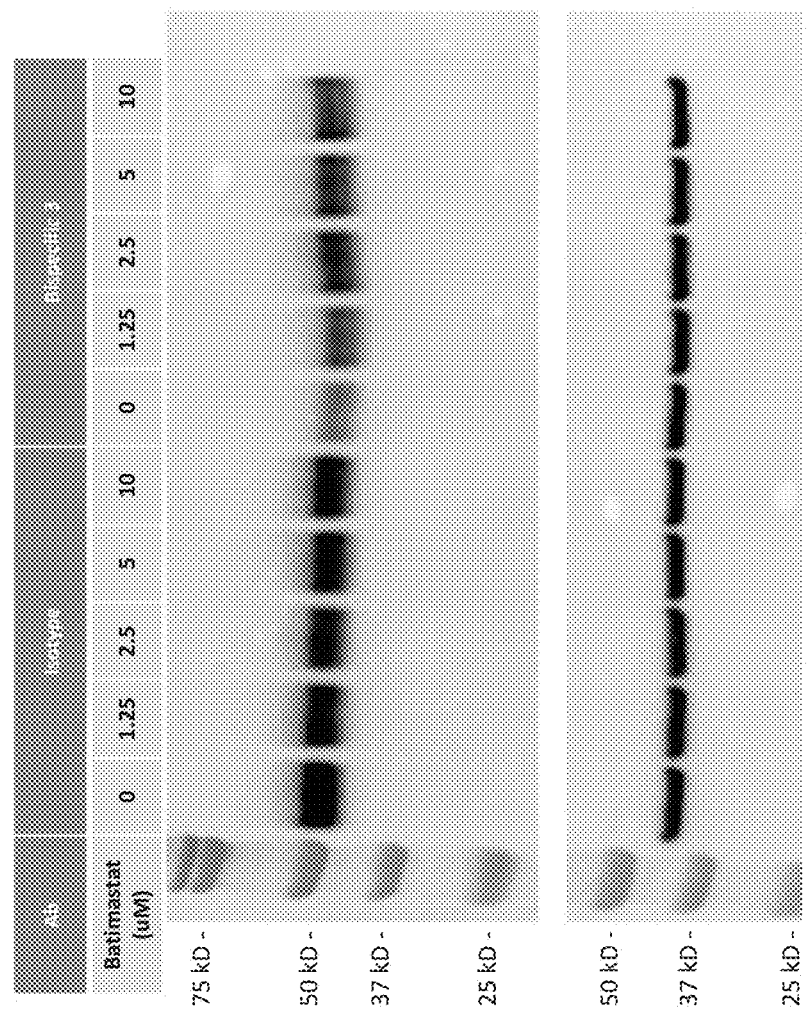
Figure 12G:
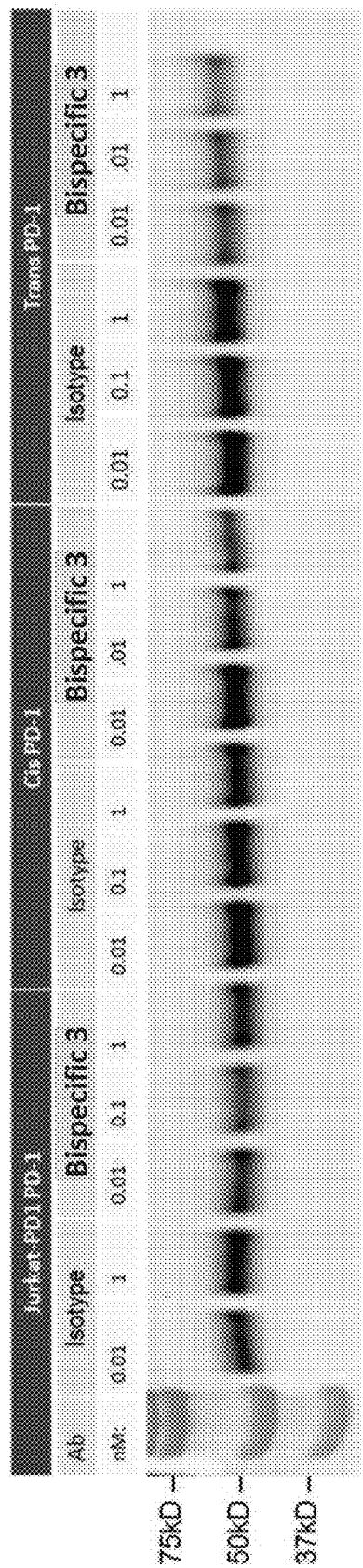

Next, the effect(s) of ADAM/MMP inhibition was examined using Batimastat, a broad-spectrum inhibitor of multiple MMPs and ADAMs, which are sheddases or proteases responsible for cleaving proteins off the plasma membrane of cells. Briefly, $40 \times 10^6$ PBMCs were treated with 0.25 µg/ml anti-CD3 and 0.25 µg/ml anti-CD28 for 3 days in a T75 flask in hX-10 media containing IL-2 and IL-7. Cells were incubated for 3 days in the flask with no manipulation. On Day 3, the cells were collected without washing away any of the old media. Cells were plated in wells of a 48-well plate, at a final volume of 1 ml, with $1 \times 10^6$ cells/well. At least ½ hour before antibody addition, Batimastat or DMSO vehicle were added at increasing concentrations of 0 µM, 1.25 µM, 2.5 µM, 5 µM, and 10 µM and pre-incubated at 37 C to look at the consequence of ADAM/MMP inhibition. Isotype control and Bispecific 3 were then added at 1 nM. After an overnight incubation, cells were collected into 1.5 ml tubes, with a wash to collect all cells from the well, then lysed and used for western blotting. Western blots were run for PD-1 and Actin. FIG. 12F demonstrates that pretreatment with Batimastat, a broad-spectrum inhibitor of multiple MMPs and ADAMs, greatly reduces the amount of cell-associated PD-1 loss, suggesting that PD-1 loss or shedding is due to cleavage by an MMP or ADAM protease. FIG. 12G suggests that Bispecific 3 drives loss of cell-surface PD-1 expression primarily when it binds to PD-1 and PD-L1 that are in the trans configuration, i.e., are being expressed by different cells. Given that PD-1 and PD-L1 can be expressed on the same cell, it was investigated whether Bispecific 3 binding to PD-1 and PD-L1 in cis results in loss of PD-1 expression or PD-1 shedding, or whether the binding by Bispecific 3 needs to be in trans, with Bispecific 3 bridging a first cell, such as a tumor cell expressing PD-L1, and a second cell, such as aT effector cell expressing PD-1. Jurkat cells expressing only PD-1, only PD-L1, or both PD-1 and PD-L1 were used in experiments. Briefly, a total of $0.5 \times 10^6$ Jurkat cells expressing PD-1, Jurkat cells expressing PD-1 and PD-L1, or a 1:1 mix of PD-1-only or PD-L1 only-expressing Jurkat cells were treated with isotype control or Bispecific 3 at 0.01, 0.1 and 1 nM. After an overnight incubation, cells were collected into 1.5 ml tubes, with a wash to collect all cells from the well, then lysed and used for western blotting. Western blots were run to determine PD-1 and Actin levels.

In Vivo Function of Bispecific 3

Figure 13A:
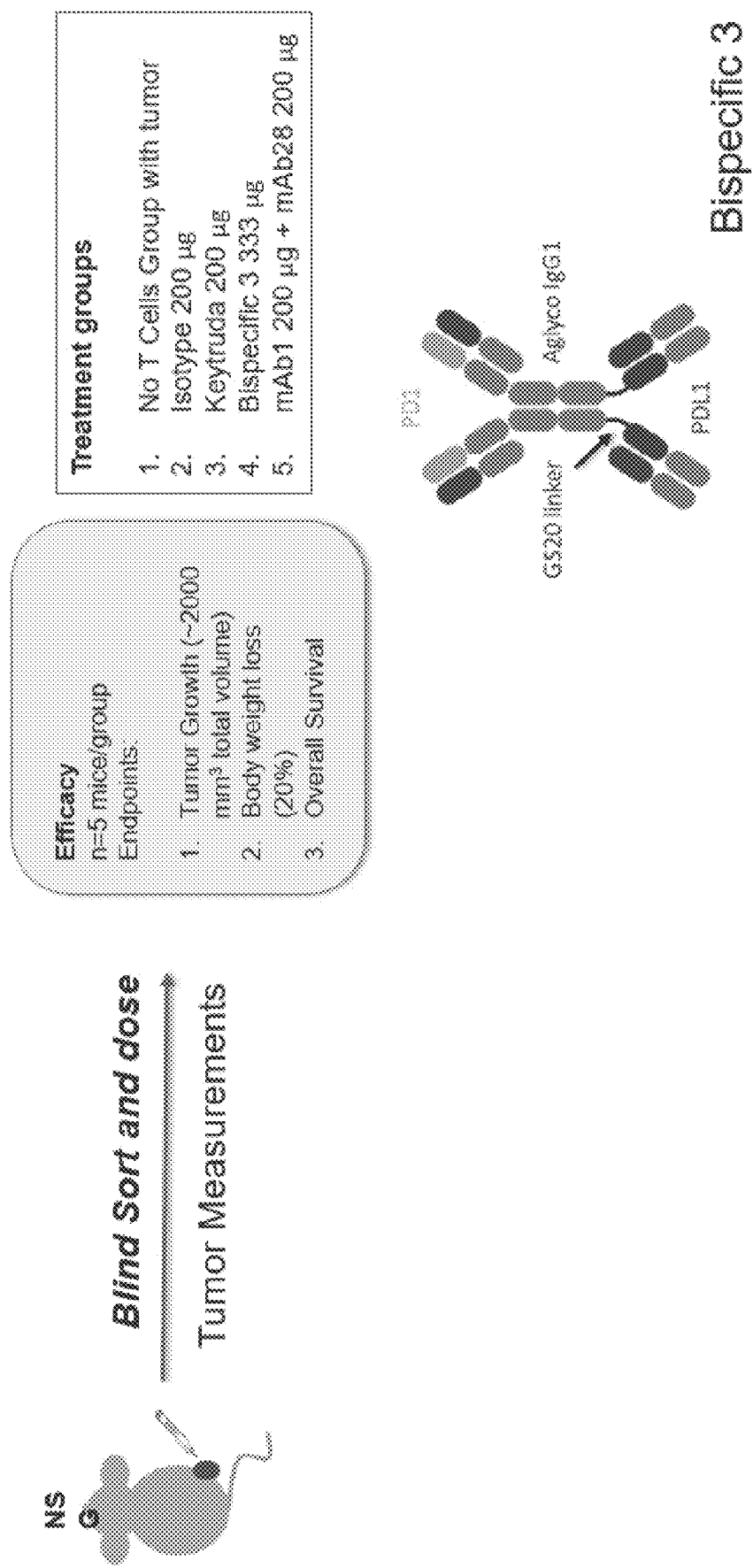
FIGS. 13A-13B shows in vivo results using Bispecific 3.
Figure 13B:
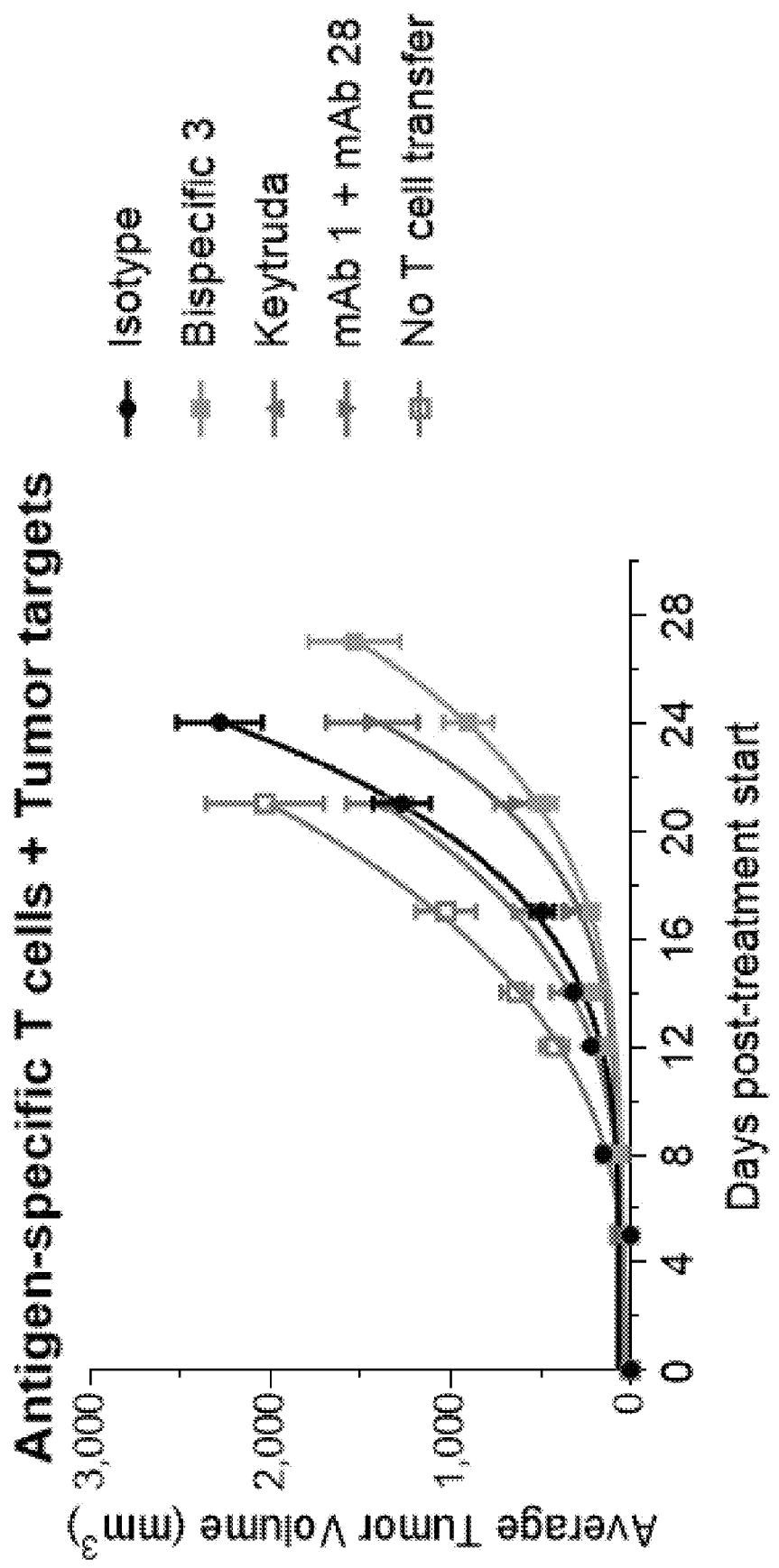

Day 13 expanded CMV antigen specific CD8+ T cells from an HLA A02:01 donor were collected and then mixed with K562 cells expressing HLA-A02:01, CMV protein pp65-IRES-GFP, and PD-L1 ("KACP") at a ratio of 2:1 KACP:CMV T cell and Matrigel such that 100 µl included 1× Matrigel, $5 \times 10^6$ KACP cells, and $2.5 \times 10^6$ CMV T cells. NSG mice were implanted subcutaneously on their flank with 100 ul of prepared Matrigel-KACP-CMV T cell mixture per mouse. Antibody dosing with was started on the day of implantation and given at equimolar amounts (200 µg for each monoclonal, 333 µg for Bispecific 3) and mice were re-dosed with antibody every 3 days. Treatment groups included a control group that was given KACP tumor cells in Matrigel alone ("No T cell transfer"), and groups given isotype, KEYTRUDA, mAb1 and mAb28 (mAb1+mAb28), or Bispecific 3. There were 5 mice per group, and mice were monitored daily, with tumors measured twice a week. The protocol is schematically depicted in FIG. 13A. As shown in FIG. 13B, the No T cell transfer group had tumors that grew more aggressively than any group containing T cells. In this model, KEYTRUDA gave no benefit in delaying KACP tumor growth as compared to the isotype control. Both Bispecific 3 and the combination mAb1 and mAb28 groups had significant delays in tumor growth as compared to both the isotype and KEYTRUDA groups. At day 24, there was a significant divergence between the Bispecific 3 group and the group treated with a combination of mAb1 and mAb28, with Bispecific 3 causing a delay in tumor growth as compared to the combination.

Example 6: In Vivo Studies for Pharmacological Investigation of Bispecific 3

Figure 14A:
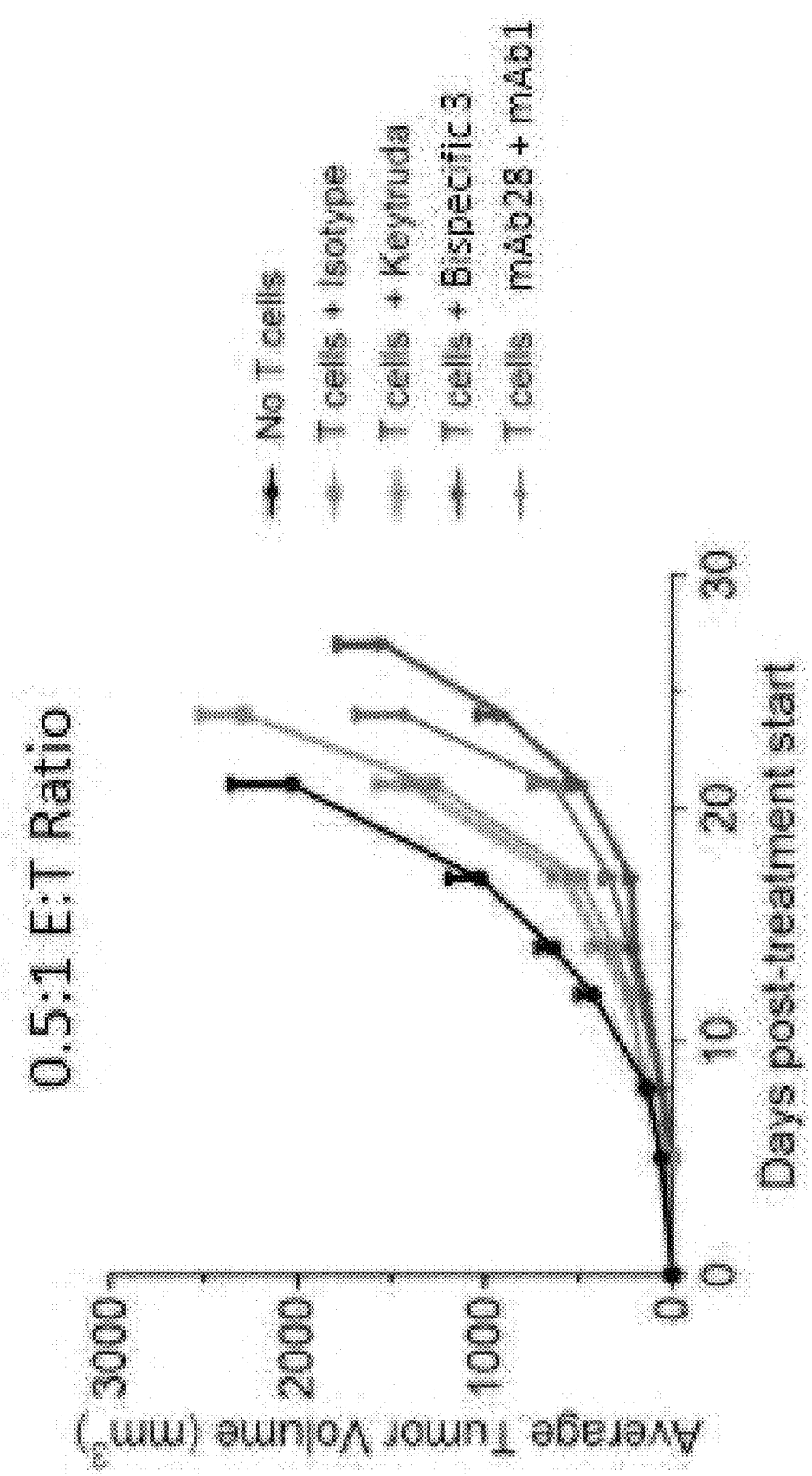
FIGS. 14A-14B shows in vivo results using Bispecific 3 in a K562-A2-CMV-PD-L1 tumor mouse model.
Figure 14B:
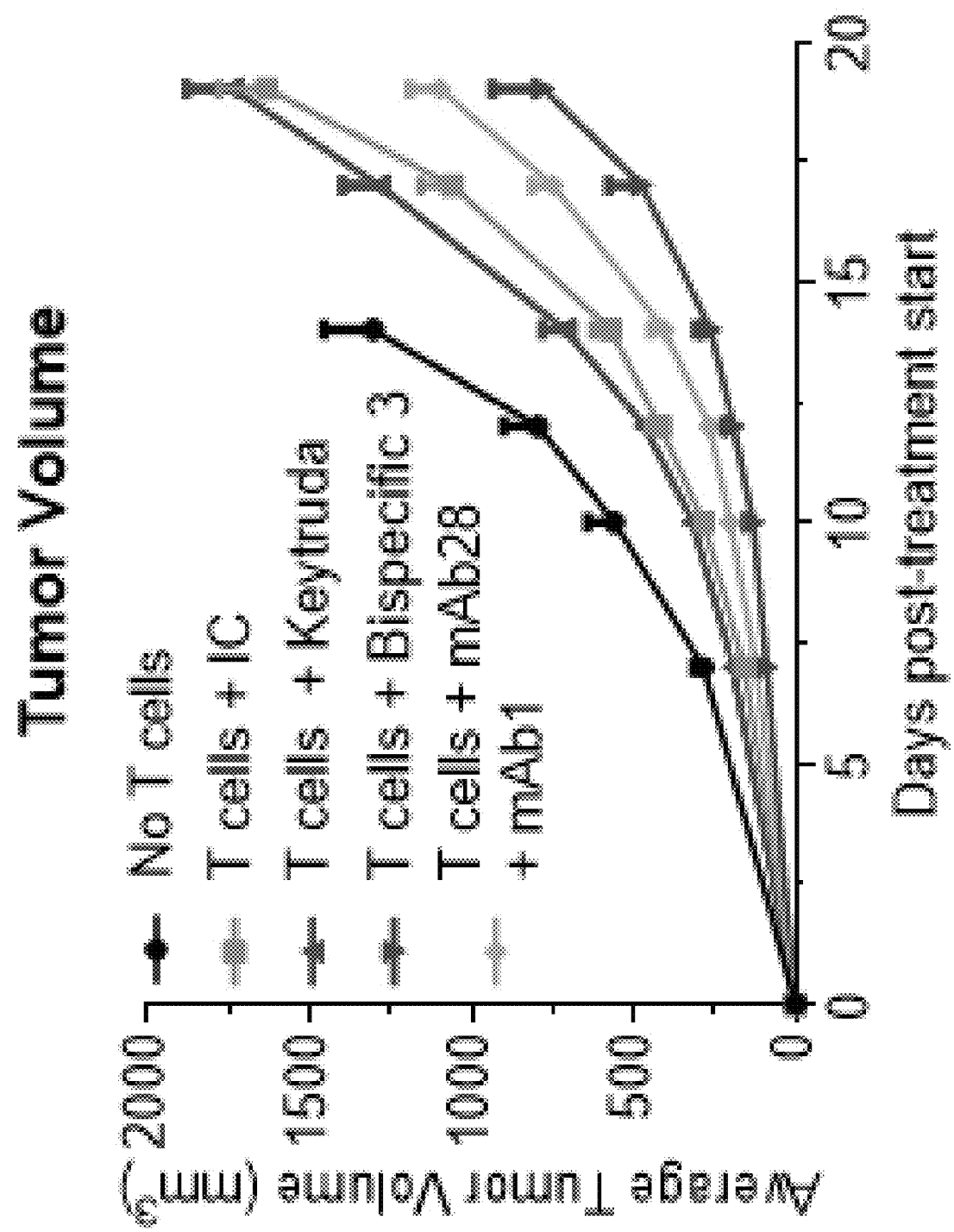

Co-Inoculation Model of K562-A2-CMV-PD-L1 Target Cells and CMV T-Cells in NSG Mice In two separate studies with the protocol schematically depicted in FIG. 13A, NSG female mice were co-injected subcutaneously (s.c.) with 100 µL Matrigel containing $5 \times 10^6$ K562-A2-CMV-PD-L1 ("KACP") cells and either $2.5 \times 10^6$ (FIGS. 13B and 14A; effector: target ratio=0.5:1) or 5×10⁶ (FIG. 14B; effector: target ratio=1:1) CMV-specific T cells expanded in vitro from the same donor. Mice were blind-grouped the day of inoculation in 5 groups of 5 mice per group, or 10 mice per group respectively. To determine the anti-tumor activity of the human T cells, in both studies the first group of mice were injected only with tumor cells. The second group received human IgG1 isotype control antibodies (0.2 mg Q3D×5). The third group received KEYTRUDA (0.2 mg Q3D×5), the fourth group was treated with Bispecific 3 (0.333 mg Q3D×5), and the fifth group received a combination of the anti-PD-1 (mAb28) and anti-PD-L1 (mAb1) antibodies (0.2 mg each Q3D×5). All antibodies were injected i.p. and dosing started on implantation day. Anti-tumor activity was determined by tumor growth monitored by tumor volume measurements, body weight loss, and overall survival. Tumor size and body weight were measured 2-3 times per week, with mice euthanized when tumors were approaching 2000 mm³ or mice lost 20% of body weight. Data was analyzed and graphed using Graph Pad Prism software. As illustrated in FIGS. 14A and 14B, Bispecific 3 displayed increased anti-tumor efficacy as compared to the different monoclonal antibodies tested.

Transplantable Syngeneic Mouse Models

Breast cancer EMT-6 cells (5×10⁴/mouse) were implanted in the mammary fat pad of BALB/c female mice. When tumors were established (tumor vol approximately 50 mm³), mice were grouped (n=8) and treated with human IgG1 isotype control (0.2 mg Q3D×3) or Bispecific 3 (0.333 mg Q3D×3). Antibodies were delivered by i.p. injections.

Using a similar study design, bladder cancer MB-49 cells (5×10⁵/mouse) were injected s.c. in female C57BL/6 mice. When tumors were established (tumor volume approximately 75 mm³) mice were grouped (n=8) and treated with human IgG1 isotype control (0.2 mg Q3D×3) or Bispecific 3 (0.333 mg Q3D×3). Antibodies were delivered by i.p. injections.

Figure 15A:
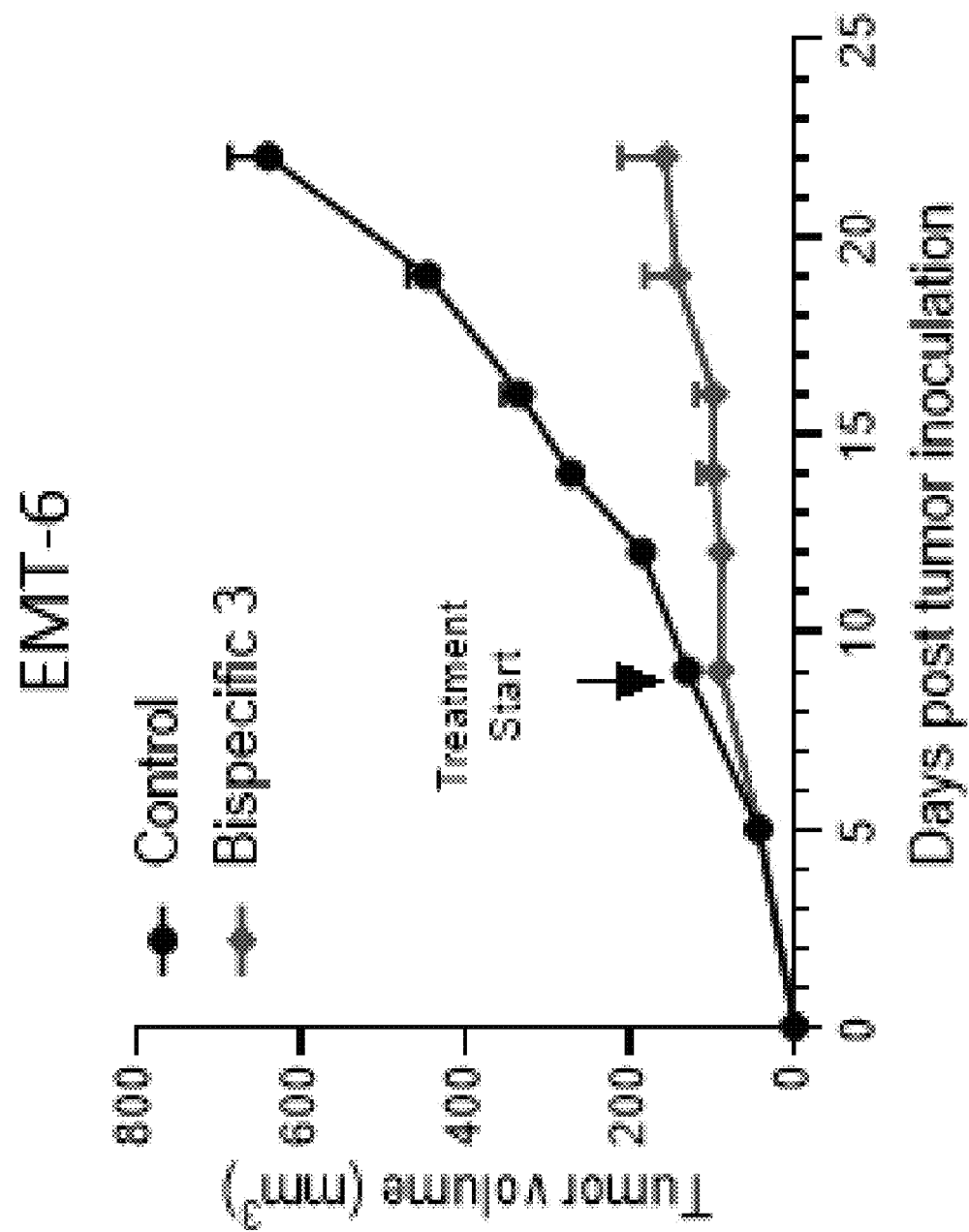
FIGS. 15A-15B illustrate in vivo results using Bispecific 3 in several syngeneic tumor models.
Figure 15B:
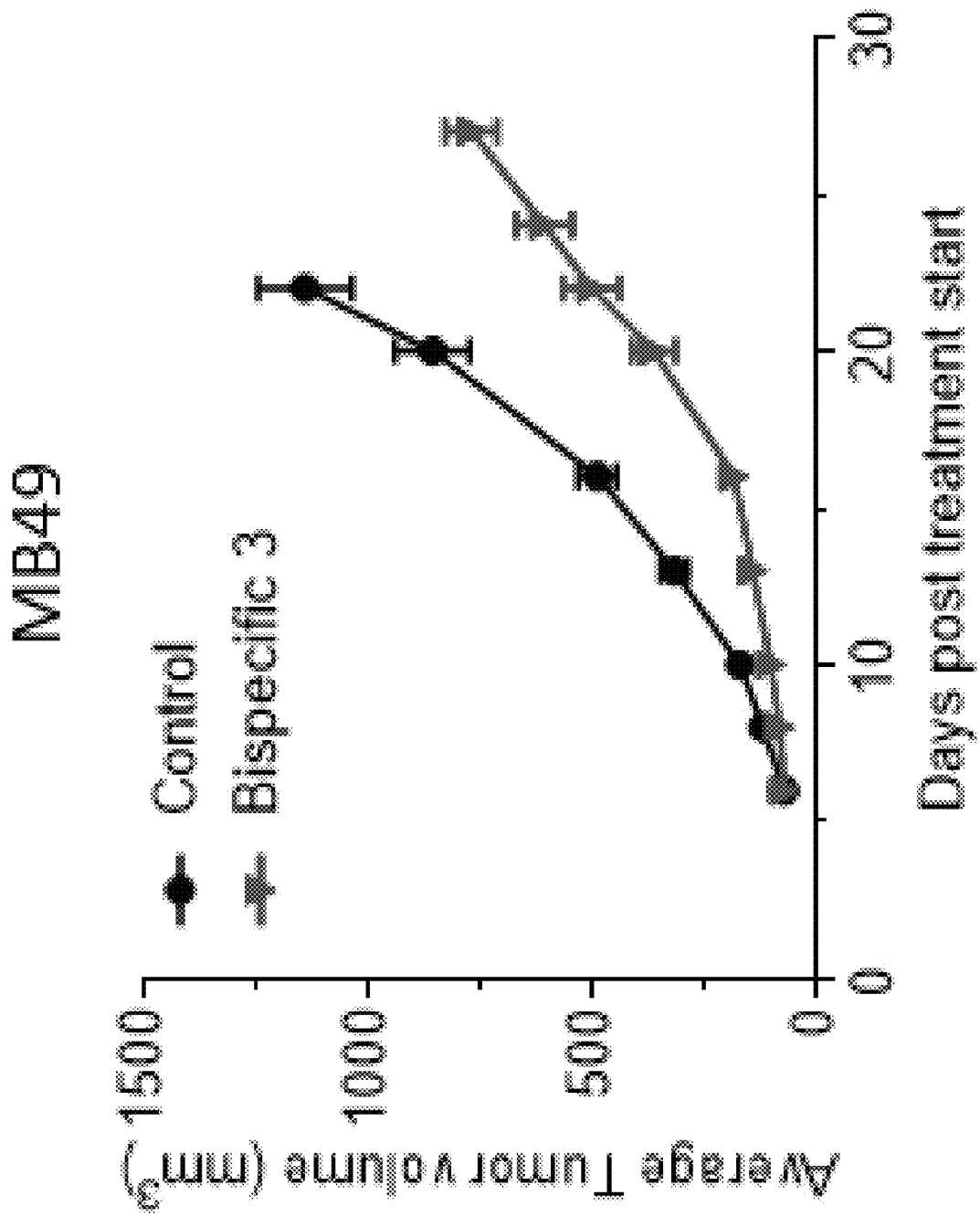

For both studies, tumor size and body weight were measured 2-3 times per week, with mice euthanized when tumors were approaching 2000 mm³ or mice lost 20% of body weight. Results were plotted, graphed, and analyzed by Graph Pad Prism software. Bispecific 3 showed greater anti-tumor efficacy in the EMT-6 breast cancer cell model (FIG. 15A) and in the MB-49 cell model (FIG. 15B) as compared to the isotype control-treatment.

Engineered Transplantable Syngeneic Models in Transgenic Mice

Figure 16A:
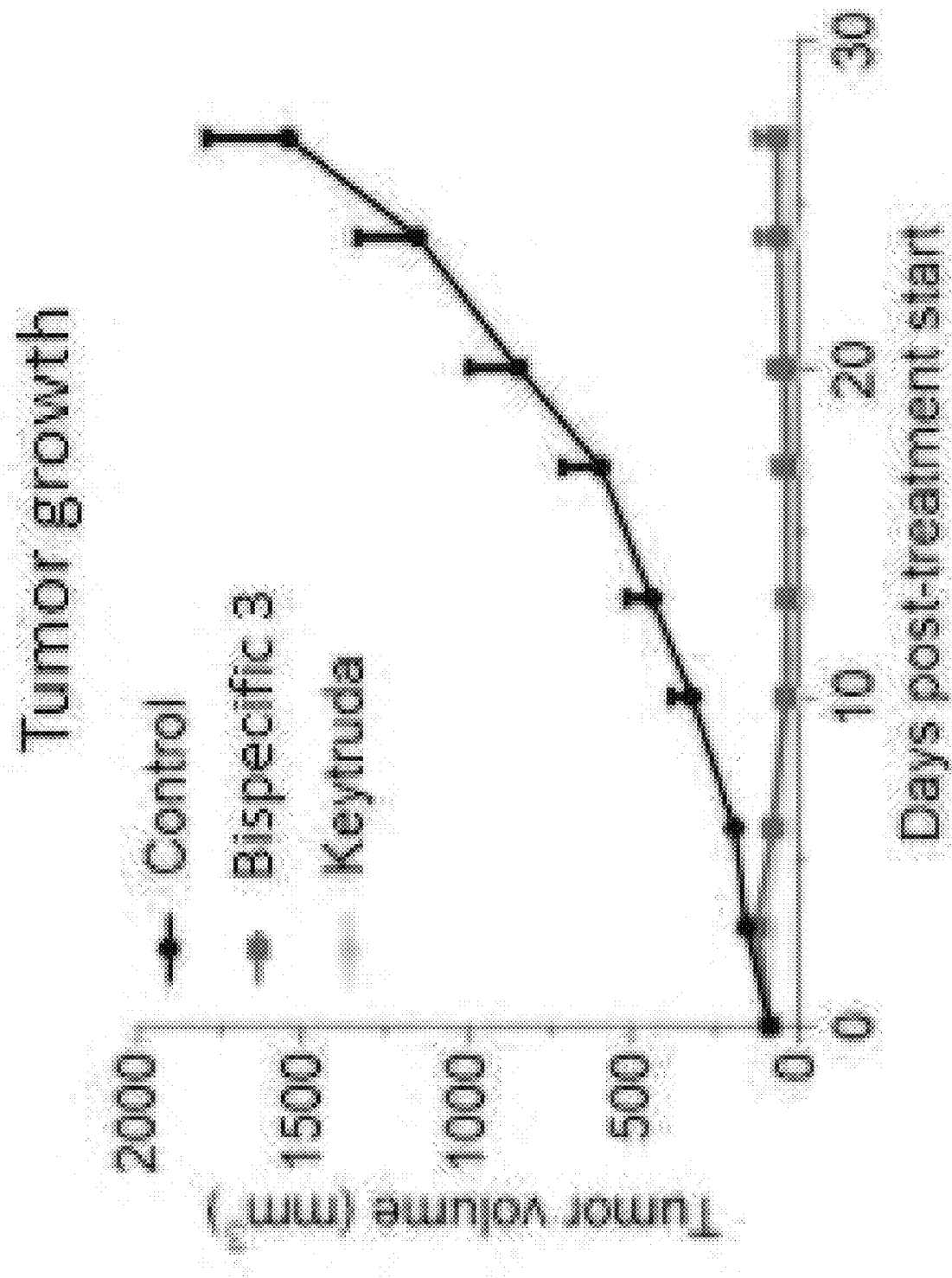
FIGS. 16A-16B show in vivo results using Bispecific 1 in an MC38-hPD-L1 model in humanized PD-1/PD-L1 transgenic mice.
Figure 16B:
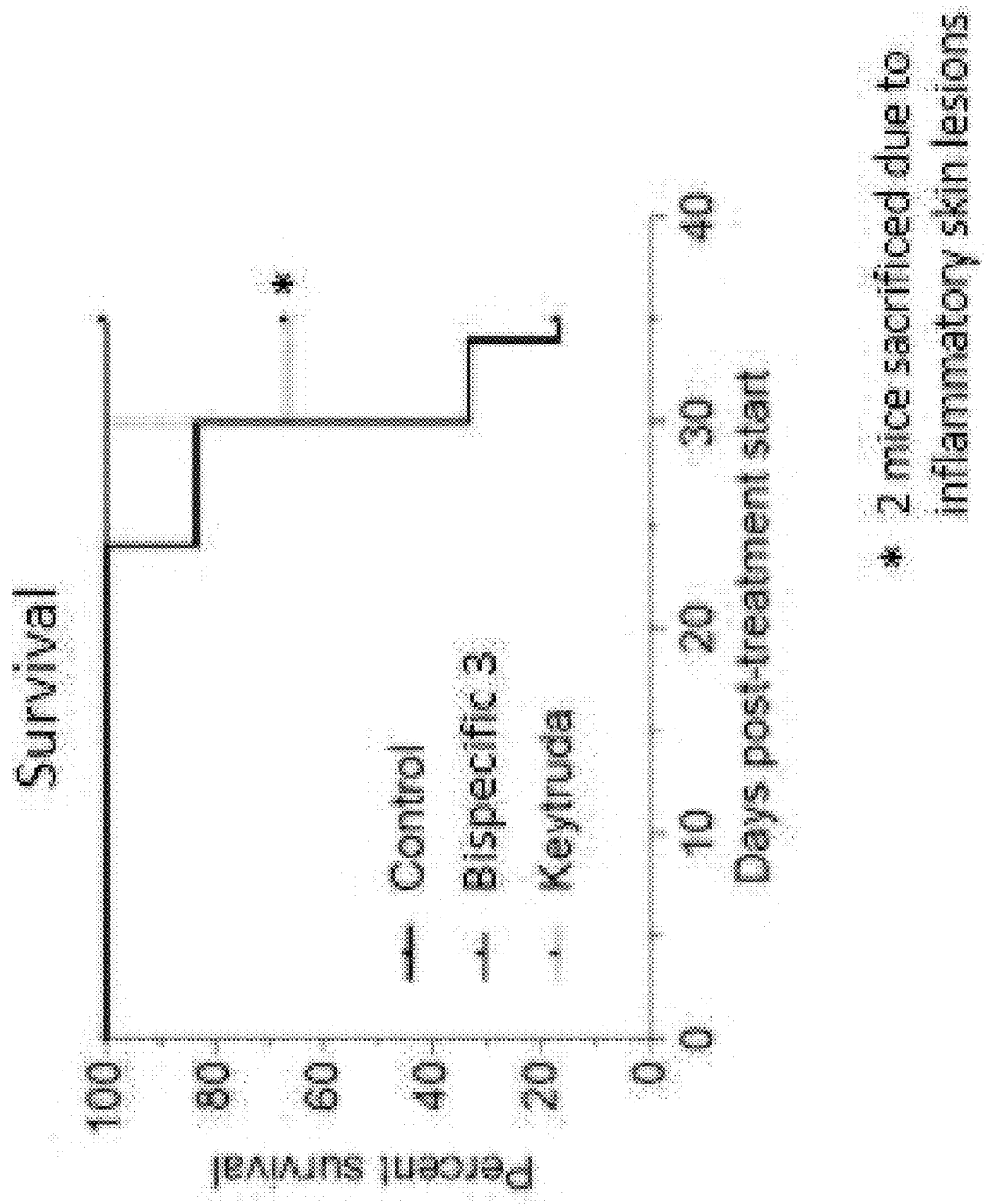

Mouse colon cancer MC-38 cells engineered to express human PD-L1 (MC-38-hPD-L1) were injected s.c. in C57BL/6 female mice in which the extracellular domains of PD-1 and PD-L1 were replaced with human PD-1 and PD-L1, while the transmembrane and signaling domains of the receptor-ligand pair were not modified. The genetic knock-in of human PD-1 and PD-L1 allowed for testing our bispecific PD-1×PD-L1 antibodies head to head with KEYTRUDA, which does not interact with mouse PD-1, and thus, cannot be evaluated in syngeneic mouse models. Mice with established MC-38-hPD-L1 tumors were grouped (n=8) and treated i.p. with isotype control (0.2 mg Q3D×3), KEYTRUDA (0.2 mg Q3D×3), or Bispecific 3 (0.333 mg Q3D×3). Treatment with Bispecific 3 controlled MC-38-hPD-L1 tumor growth significantly better than isotype control- or KEYTRUDA treatments (FIG. 16A). In addition, Bispecific 3 treatment resulted in an increase in survival in the MC-38-hPD-L1 tumor mice as compared to the isotype control- or KEYTRUDA-treated mice (FIG. 16B).

Figure 17A:
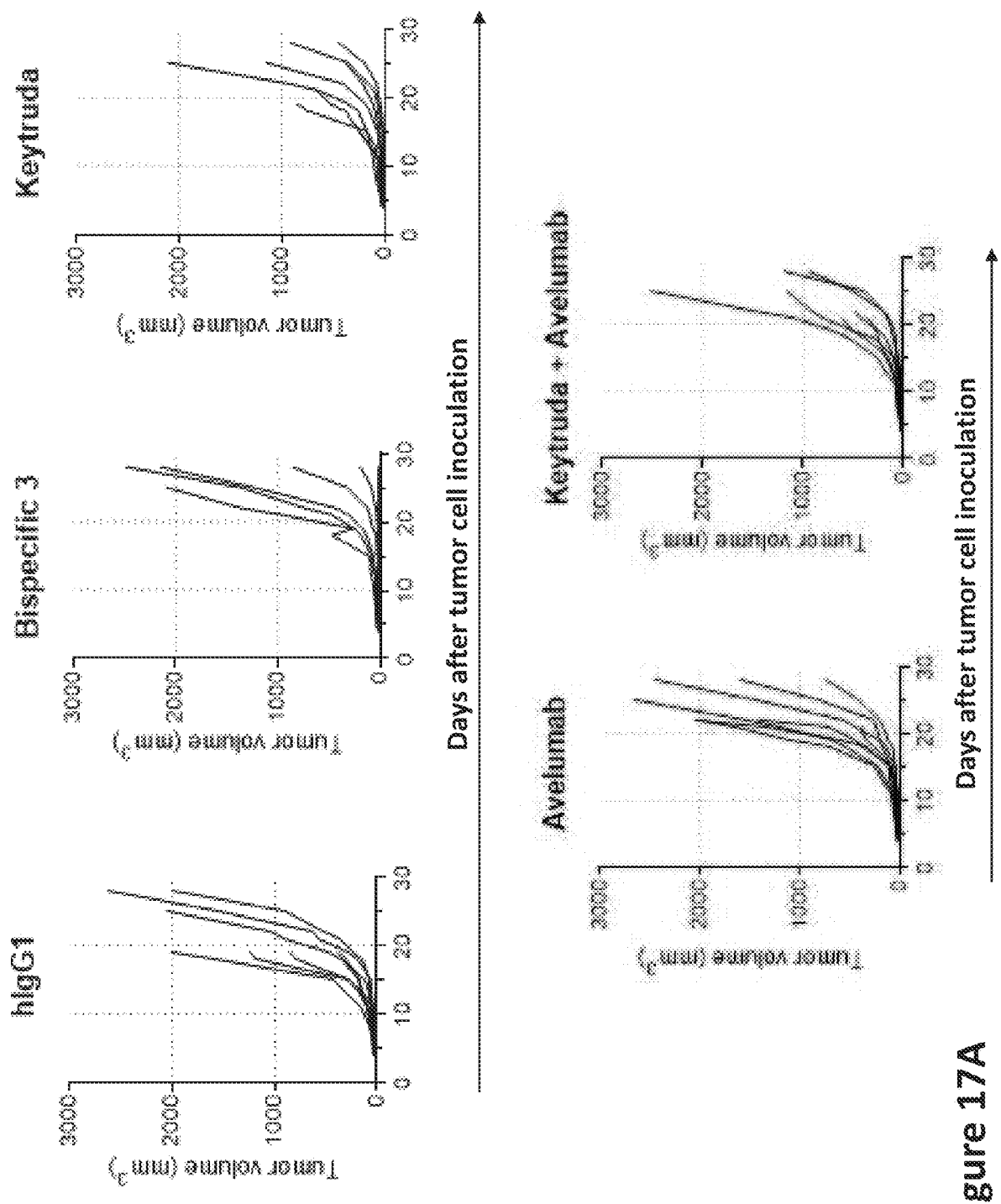
Figure 17B:
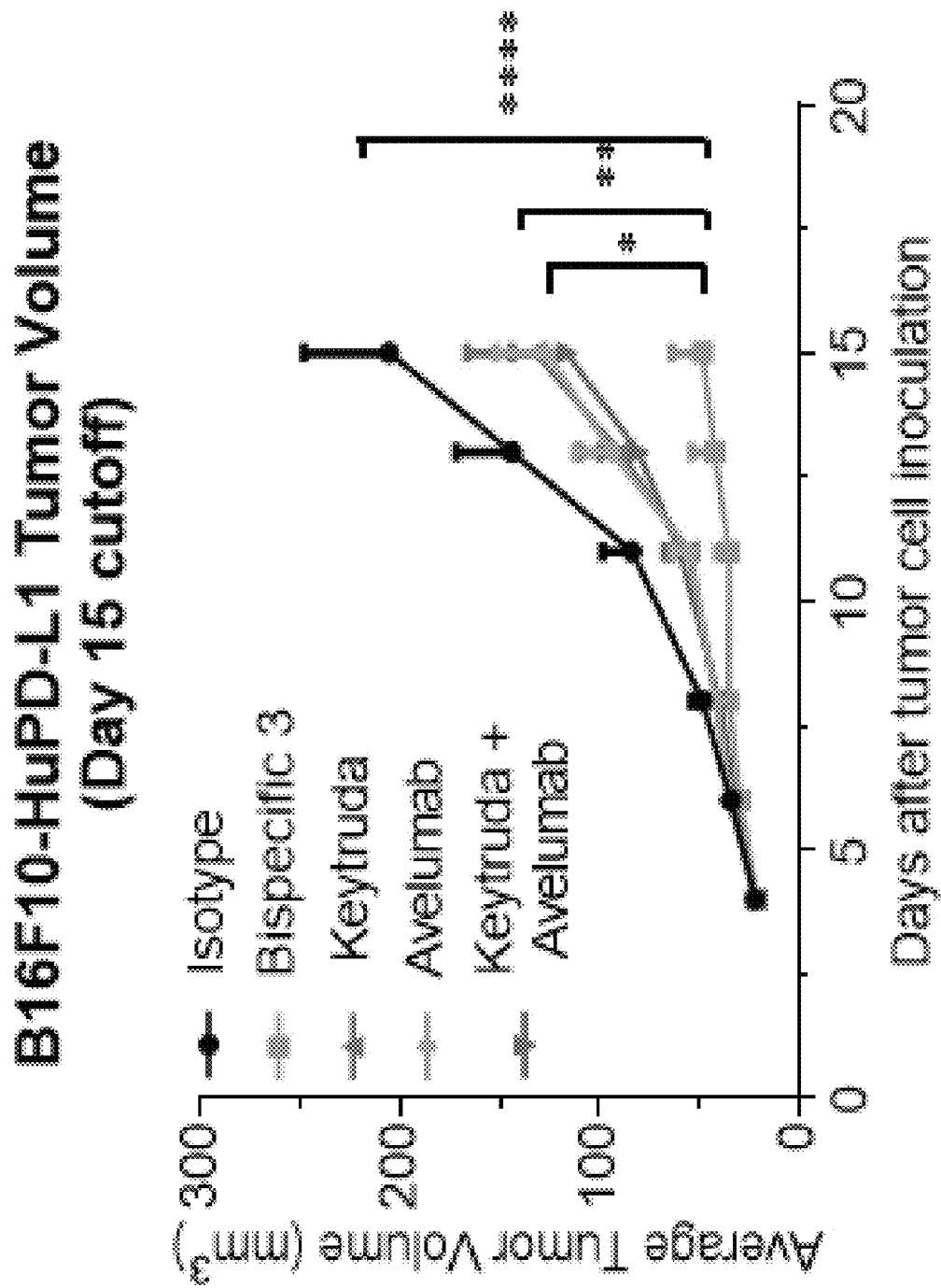
Figure 17C:
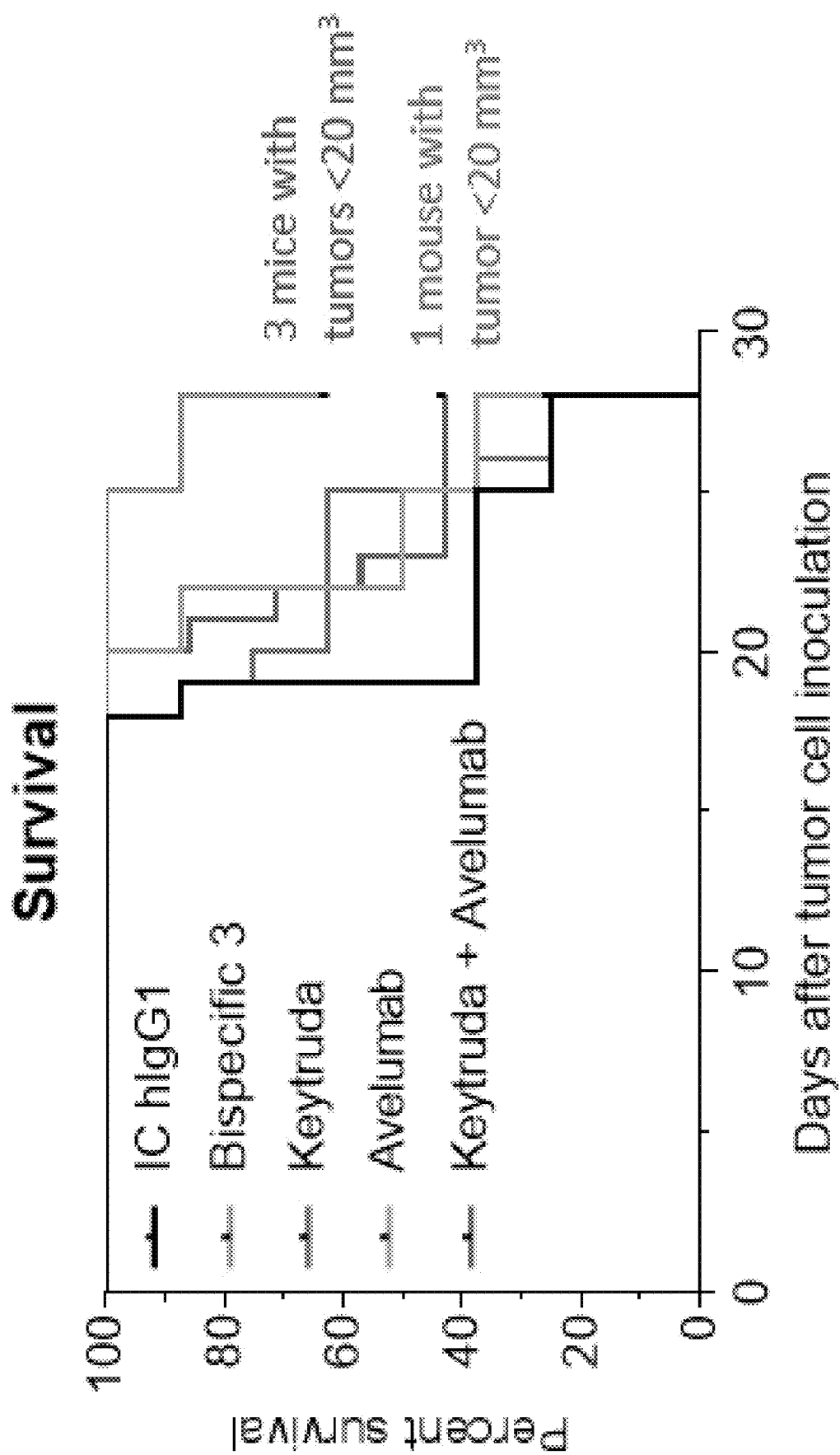

In a separate study, C57BL/6 human PD-1/PD-L1 transgenic female mice were injected s.c. with 1×10⁵ B16F10-hPD-L1 cells, an extremely aggressive mouse melanoma cell line. Mice were grouped (n=8) as soon as the melanoma was visible (day 4 after tumor cell inoculation) in 5 groups which received the following treatment. Group 1 received isotype control human IgG1 (0.2 mg Q3D×3), group 2 Avelumab (0.2 mg Q3D×3), group 3 KEYTRUDA (0.2 mg Q3D×3), group 4 Bispecific 3 (0.333 Q3D×3), and group 5 combination of KEYTRUDA and Avelumab (0.2 mg each Q3D×3). For both studies tumor size and body weight were measured 2-3 times per week, and mice euthanized when tumors were approaching 2000 mm³ or mice lost 20% of body weight. Survival was recorded and analyzed. Data were plotted, graphed, and analyzed by Graph Pad Prism software. As illustrated in FIGS. 17A and 17B, Bispecific 3 was significantly more effective in delaying tumor growth in the B16F10-hPD-L1 mice as compared to the other treatment groups tested. In addition, B16F10-hPD-L1 mice treated with Bispecific 3 survived longer on average than mice receiving the other tested treatments (FIG. 17C and FIG. 17E).

Example 7: Bispecific 3 has Monoclonal-Like DLP's and Parental-Like Binding

Figure 18D:
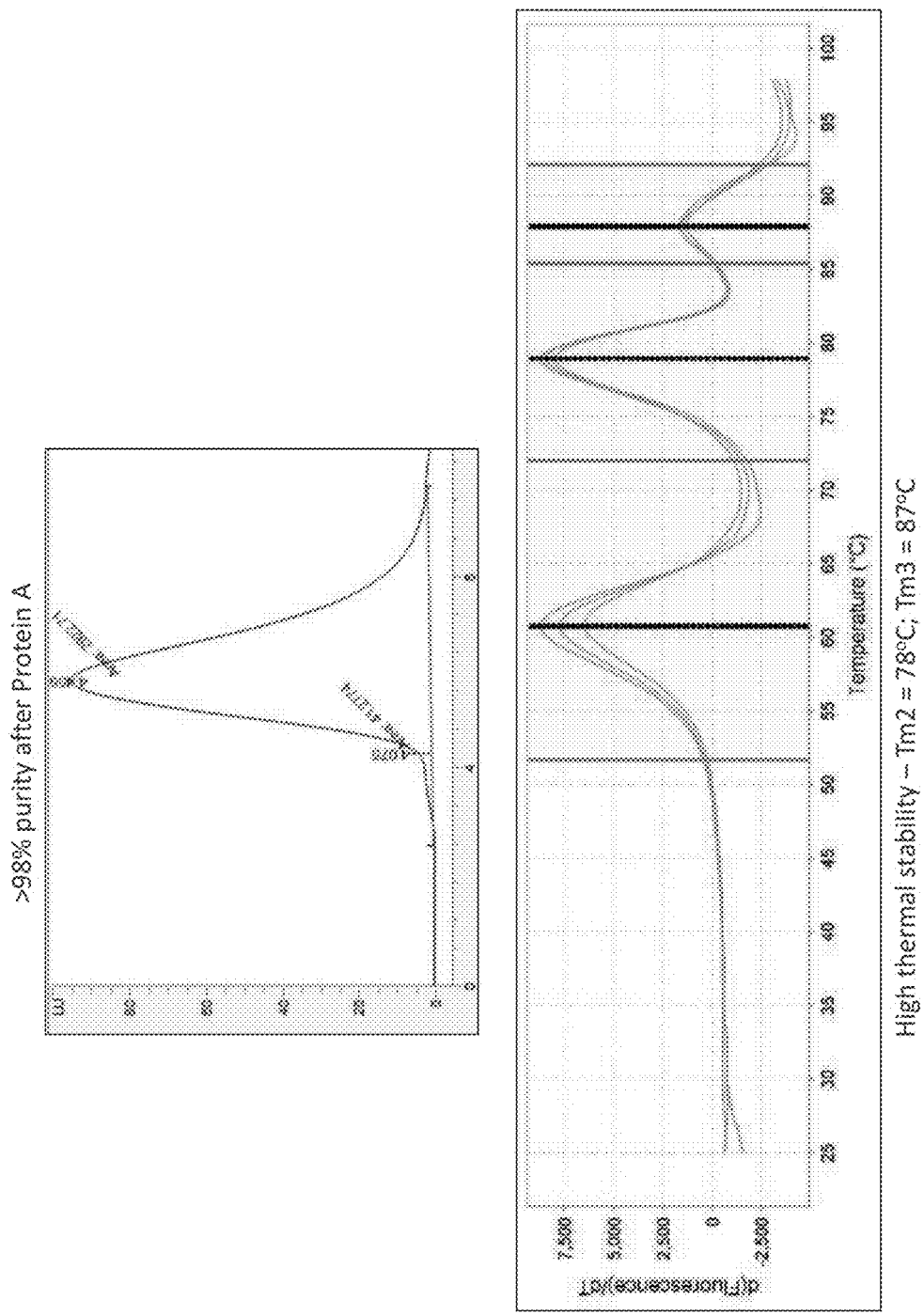

FIGS. 18A-18D demonstrate that Bispecific 3 has drug-like properties (DLP's) similar to a well-behaved monoclonal antibody and maintains parental PD-1 and PD-L1 binding. FIG. 18A shows that Bispecific 3 shows similar binding to CHO cells expressing human PD-1 as parental clone mAb28 (top), and to CHO cells expressing human PD-L1 as parental clone mAb1 (bottom). FIG. 18B shows that Bispecific 3 shows similar binding to CHO cells expressing cynomolgus PD-1 as parental clone mAb28 (top), and to CHO cells expressing cynomolgus PD-L 1 as parental clone mAb1 (bottom). FIG. 18C shows that Bispecific 3 shows similar binding to CHO cells expressing mouse PD-1 as parental clone mAb28 (top), and to CHO cells expressing mouse PD-L1 as parental clone mAb1 (bottom). FIG. 18D shows a size-exclusion chromatography trace of Bispecific 3 after Protein A chromatography (top) demonstrating a single peak with greater than 98% purity and a differential scanning fluorimetry (DSF) trace of Bispecific 3 (bottom) demonstrating that the molecule has high thermal stability.

We claim:

1. A multispecific antigen-binding construct comprising at least two antigen-binding arms, wherein:
   a first arm binds PD-1 and comprises a heavy chain variable region and a light chain variable region, the heavy chain variable region of the first arm comprising a CDRH1 of SEQ ID NO: 77, a CDRH2 of SEQ ID NO: 71, and a CDRH3 of SEQ ID NO: 75, and
   a second arm binds a PD-1 ligand and comprises a heavy chain variable region and a light chain variable region, the heavy chain variable region of the second arm comprising a CDRH1 of SEQ ID NO: 1, a CDRH2 of SEQ ID NO: 7, and a CDRH3 of SEQ ID NO: 8;
   wherein the light chain variable region of the first arm and the light chain variable region of the second arm each comprise a CDRL1 of SEQ ID NO: 9, a CDRL2 of SEQ ID NO: 5, and a CDRL3 of SEQ ID NO: 10; and
   wherein the multispecific antigen-binding construct blocks the interaction of PD-1 and the PD-1 ligand.

2. The multispecific antigen-binding construct of claim 1, wherein the heavy chain variable region of the first arm comprises an amino acid sequence that is at least 85% identical to the amino acid sequence of SEQ ID NO: 90.

3. The multispecific antigen-binding construct of claim 1, wherein the heavy chain variable region of the first arm comprises an amino acid sequence that is at least 90% identical to the amino acid sequence of SEQ ID NO: 90.

4. The multispecific antigen-binding construct of claim 1, wherein the heavy chain variable region of the second arm comprises an amino acid sequence that is at least 85% identical to the amino acid sequence of SEQ ID NO: 55.

5. The multispecific antigen-binding construct of claim 1, wherein the heavy chain variable region of the second arm comprises an amino acid sequence that is at least 90% identical to the amino acid sequence of SEQ ID NO: 55.

6. The multispecific antigen-binding construct of claim 1, wherein the first and the second antigen-binding arms each comprise a common light chain variable region.

7. The multispecific antigen-binding construct of claim 1, wherein the construct comprises at least two arms that bind PD-1 and at least two arms that bind PD-L1.

8. The multispecific antigen-binding construct of claim 1, wherein the construct comprises a bivalent antibody specific for PD-1, and a bivalent antibody specific for PD-L1, wherein the bivalent antibody specific for PD-1 and the bivalent antibody specific for PD-L1 are linked.

9. The multispecific antigen-binding construct of claim 1, wherein the heavy chain of the first arm has an amino acid sequence that is at least 85% identical to the amino acid sequence of SEQ ID NO: 100; and wherein the light chain of the first arm and the second arm has an amino acid sequence that is at least 85% identical to the amino acid sequence of SEQ ID NO: 101.

10. The multispecific antigen-binding construct of claim 1, wherein the heavy chain of the first arm has an amino acid sequence that is at least 90% identical to the amino acid sequence of SEQ ID NO: 100, and wherein the light chain of the first arm and the second arm have an amino acid sequence that is at least 90% identical to the amino acid sequence of SEQ ID NO: 101.

11. The multispecific antigen-binding construct of claim 1, wherein the heavy chain of the first arm has an amino acid sequence of SEQ ID NO: 100, and wherein the light chain of the first arm and the second arm have an amino acid sequence of SEQ ID NO: 101.

12. The multispecific antigen-binding construct of claim 1, wherein the heavy chain variable region of the first arm comprises an amino acid sequence that is at least 95% identical to the amino acid sequence of SEQ ID NO: 90.

13. The multispecific antigen-binding construct of claim 1, wherein the heavy chain variable region of the first arm comprises an amino acid sequence that is at least 99% identical to the amino acid sequence of SEQ ID NO: 90.

14. The multispecific antigen-binding construct of claim 1, wherein the heavy chain variable region of the first arm comprises the amino acid sequence of SEQ ID NO: 90.

15. The multispecific antigen-binding construct of claim 1, wherein the heavy chain variable region of the second arm comprises an amino acid sequence that is at least 95% identical to the amino acid sequence of SEQ ID NO: 55.

16. The multispecific antigen-binding construct of claim 1, wherein the heavy chain variable region of the second arm comprises an amino acid sequence that is at least 99% identical to the amino acid sequence of SEQ ID NO: 55.

17. The multispecific antigen-binding construct of claim 1, wherein the heavy chain variable region of the second arm comprises the amino acid sequence of SEQ ID NO: 55.

18. The multispecific antigen-binding construct of claim 1, wherein the heavy chain of the first arm has an amino acid sequence that is at least 95% identical to the amino acid sequence of SEQ ID NO: 100, and wherein the light chain of the first arm and the second arm have an amino acid sequence that is at least 90% identical to the amino acid sequence of SEQ ID NO: 101.

19. The multispecific antigen-binding construct of claim 1, wherein the heavy chain of the first arm has an amino acid sequence that is at least 99% identical to the amino acid sequence of SEQ ID NO: 100, and wherein the light chain of the first arm and the second arm have an amino acid sequence that is at least 99% identical to the amino acid sequence of SEQ ID NO: 101.

20. The multispecific antigen-binding construct of claim 1, wherein the first arm binds PD-1 expressed by an immune cell.

21. The multispecific antigen-binding construct of claim 1, wherein the second arm binds a PD-1 ligand expressed by a second cell.

22. The multispecific antigen-binding construct of claim 21, wherein the second cell is a tumor cell and the PD-1 ligand is PD-L1.

* * * * *